US012618828B2

(12) United States Patent
Lazar et al.

(10) Patent No.: US 12,618,828 B2
(45) Date of Patent: May 5, 2026

(54) PROBE AND METHOD FOR DETECTING MEMBRANE-ASSOCIATED MOLECULES IN LIVING CELLS

(71) Applicant: Josef Lazar, Ceske Budejovice (CZ)

(72) Inventors: Josef Lazar, Pribram (CZ); Alexey Bondar, Ceske Budejovice (CZ)

(73) Assignee: Josef Lazar, Ceske Budejovice (CZ)

( * ) Notice: Subject to any disclaimer, the term of this patent is extended or adjusted under 35 U.S.C. 154(b) by 673 days.

(21) Appl. No.: 18/057,629

(22) Filed: Nov. 21, 2022

(65) Prior Publication Data

US 2023/0194503 A1     Jun. 22, 2023

(30) Foreign Application Priority Data

Nov. 22, 2021    (EP) .................................... 21209717

(51) Int. Cl.
| | |
|---|---|
| *G01N 33/50* | (2006.01) |
| *C07K 14/47* | (2006.01) |
| *G01N 33/58* | (2006.01) |

(52) U.S. Cl.
CPC ..... *G01N 33/5035* (2013.01); *C07K 14/4705* (2013.01); *C07K 14/4706* (2013.01); *G01N 33/582* (2013.01); *C07K 2319/03* (2013.01); *C07K 2319/60* (2013.01); *G01N 2333/726* (2013.01)

(58) Field of Classification Search
None
See application file for complete search history.

(56) References Cited

FOREIGN PATENT DOCUMENTS

WO    WO-2007068313 A2 *  6/2007   ........... G01N 33/566

OTHER PUBLICATIONS

Govarts et al. Frameshifting in the p6 cDNA phage display system. Molecules. Dec. 20, 2010;15(12):9380-90 (Year: 2010).*
Stolz et al. Fluorescence-based ATG8 sensors monitor localization and function of LC3/GABARAP proteins. EMBO J. Feb. 15, 2017;36(4):549-564. (Year: 2017).*
(Continued)

*Primary Examiner* — Bao-Thuy L Nguyen
*Assistant Examiner* — Alexander Alexandrovic Volkov
(74) *Attorney, Agent, or Firm* — Notaro, Michaolos & Zaccaria P.C.

(57)    ABSTRACT

A protein-based probe for detecting the presence of one of two distinct states of a target membrane-associated molecule by means of polarization microscopy is disclosed. The probe contains an anchoring moiety consisting of at least one lipidated peptide and/or at least one transmembrane α-helical peptide, a peptide linker moiety having the length of at least 5 amino acids, wherein at least 50% of the amino acids forming the linker are selected from glycine, serine, and threonine, a fluorescent moiety, and an affinity binding moiety capable of binding the target membrane-associated molecule. The moieties are arranged in the order a-b-c-d or d-c-b-a in the direction from the N-terminus to the C-terminus. Methods of detecting presence or absence of the target molecule, detecting activated or inactive forms of the target molecule, and detecting the activation of the target molecule are also described.

21 Claims, 6 Drawing Sheets

Specification includes a Sequence Listing.

In absence of a target molecule                In presence of a target molecule

(56) References Cited

OTHER PUBLICATIONS

Bondar A, Lazar J. The G protein Gi1 exhibits basal coupling but not preassembly with G protein-coupled receptors. J Biol Chem. Jun. 9, 2017;292(23):9690-9698. (Year: 2017).*

Natwick et al. Optimized iLID Membrane Anchors for Local Optogenetic Protein Recruitment. ACS Synth Biol. May 21, 2021;10(5):1009-1023. (Year: 2021).*

* cited by examiner

In absence of a target molecule          In presence of a target molecule

A)        Ex. 1

B)    Ex. 2

C)    Ex. 3

D)    Ex. 4

E)    Ex. 5

Fig. 2 – continued
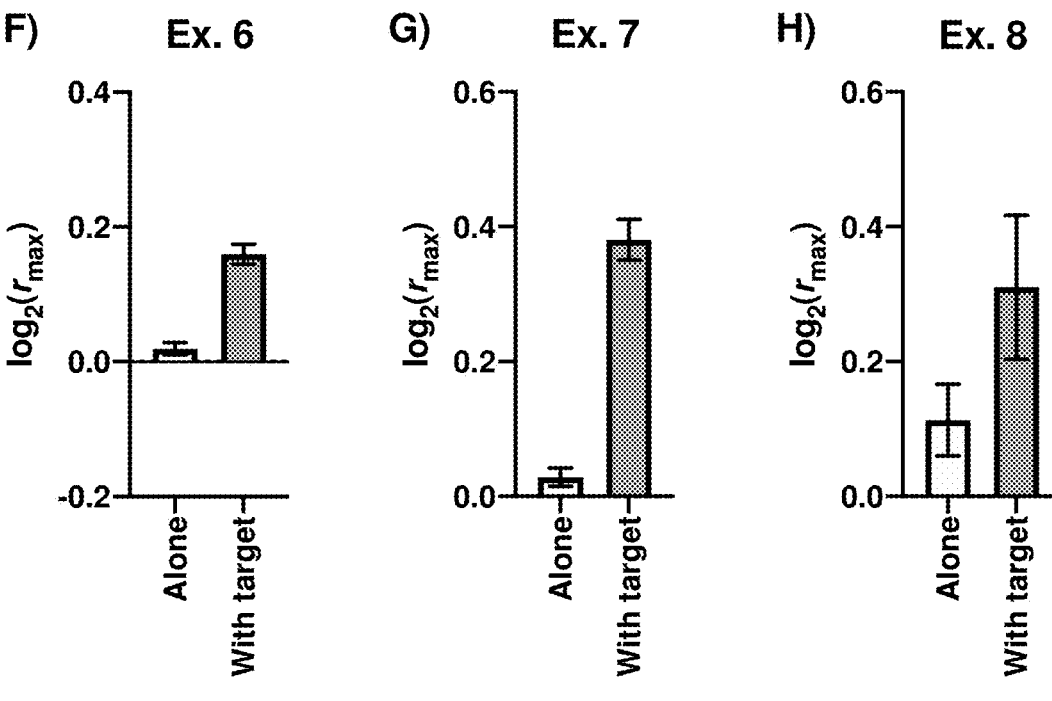
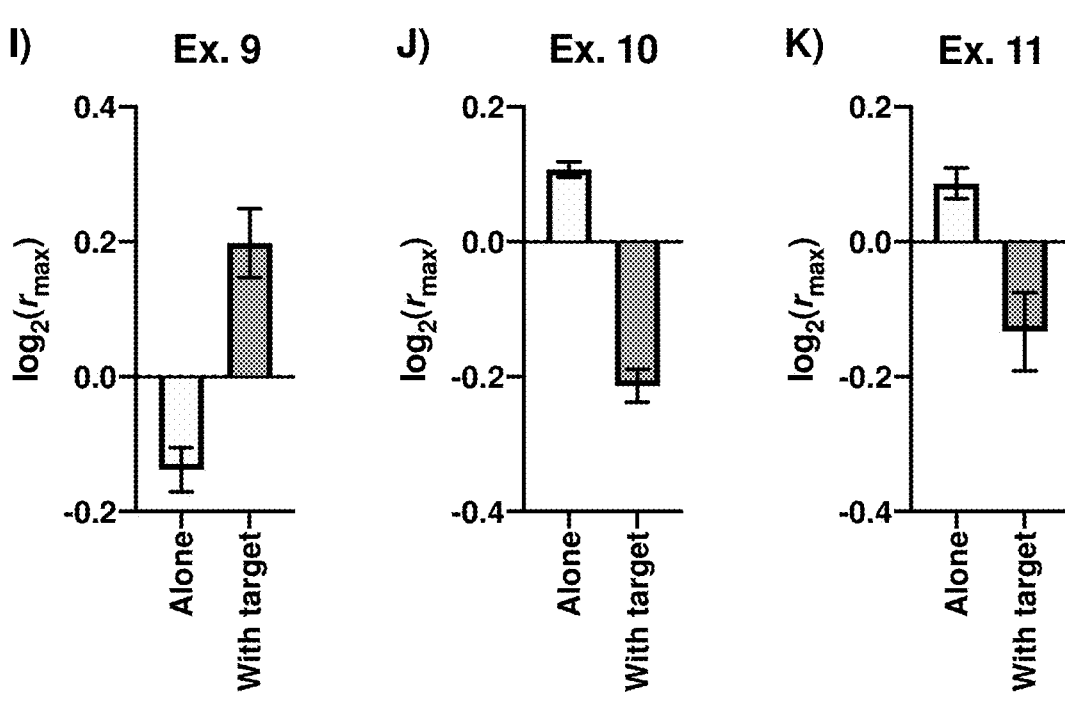

Fig. 2 – continued
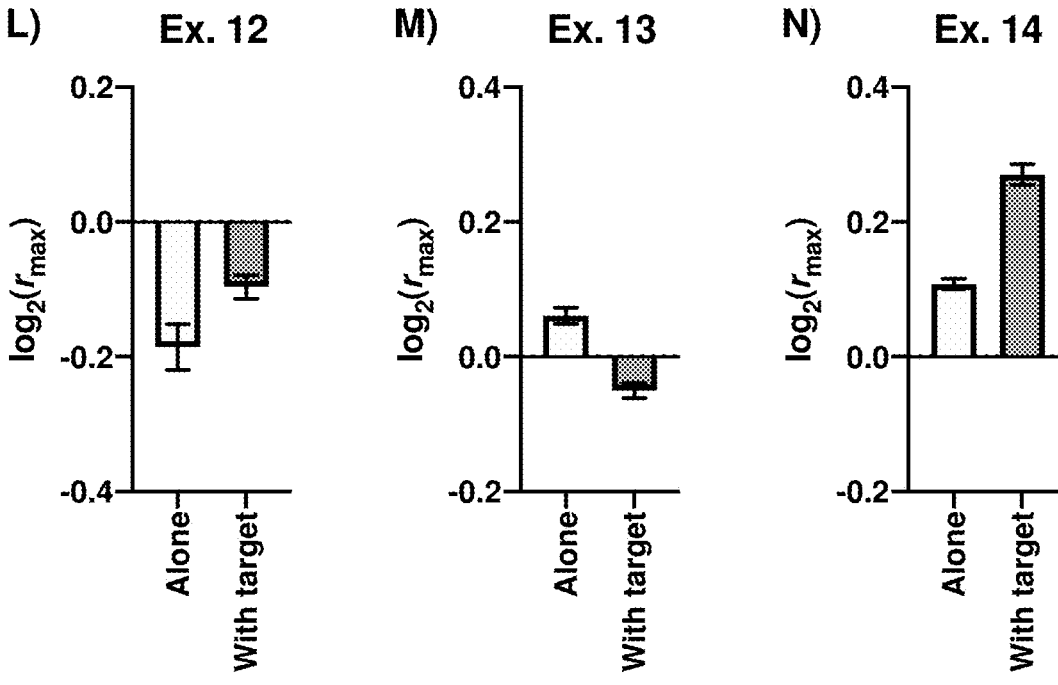
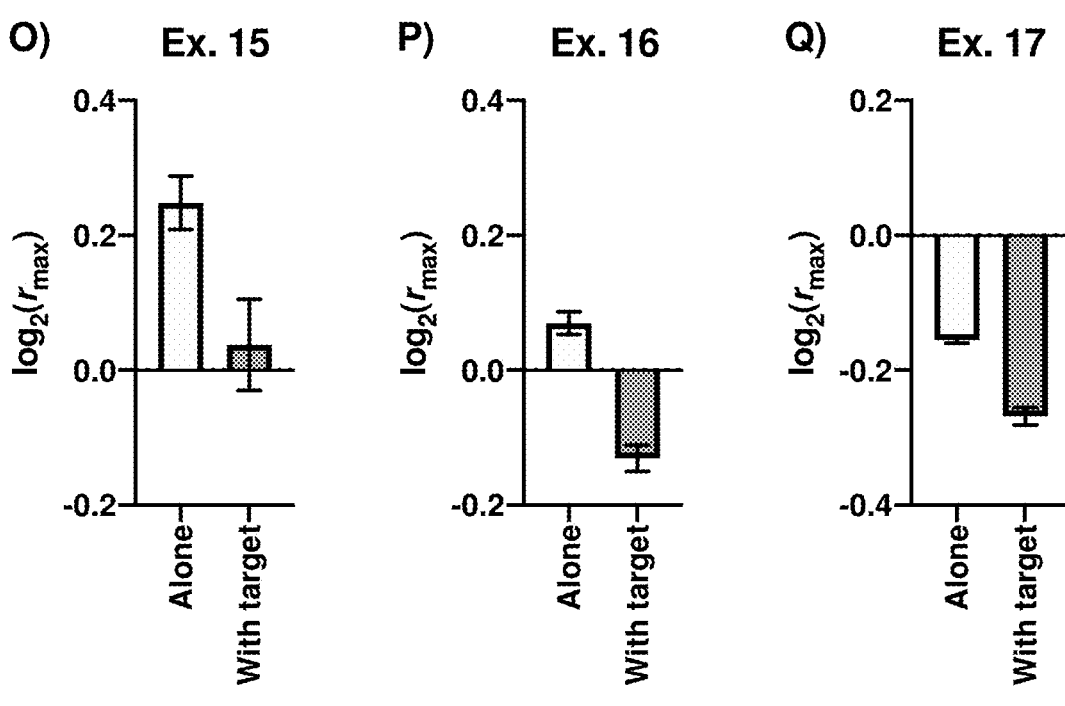

Fig. 2 – continued
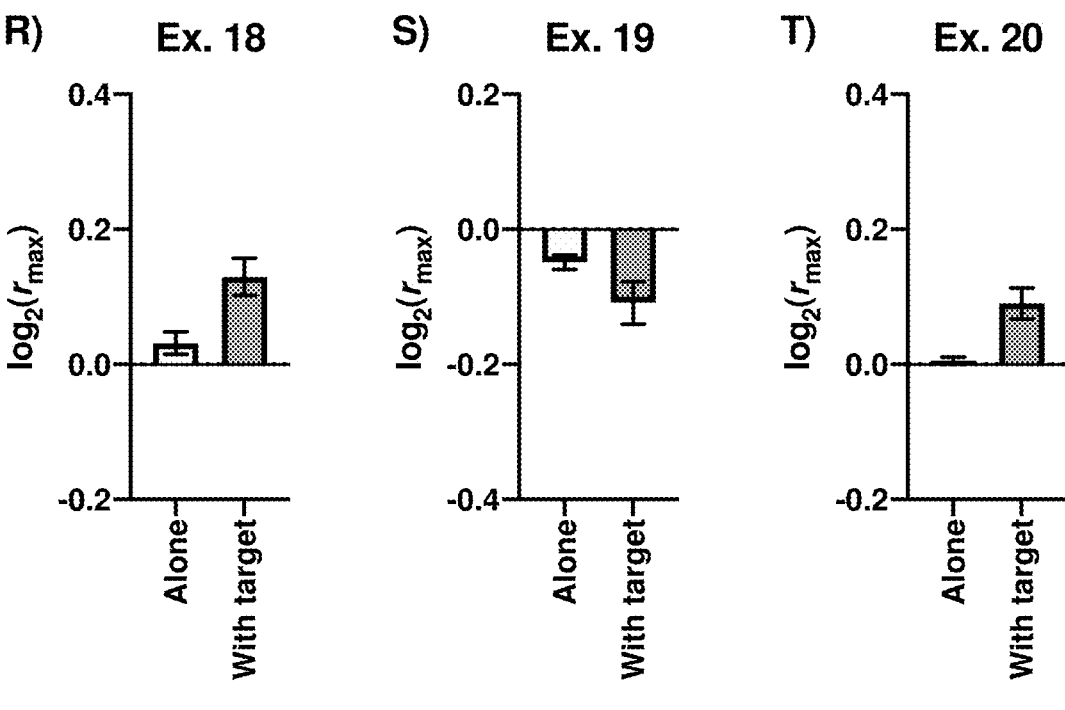
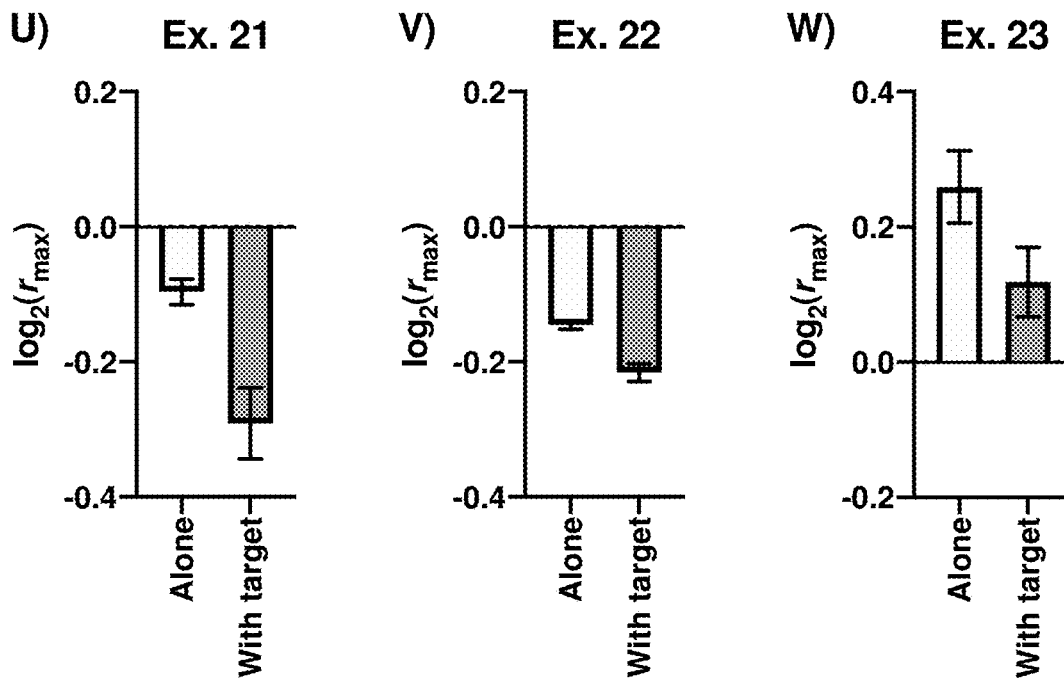

Fig. 2 – continued
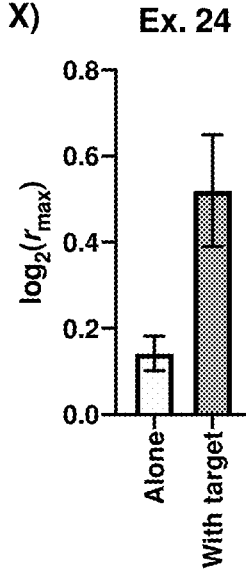
X)     Ex. 24

SEQUENCE LISTING

Sequence total quantity: 75
SEQ ID NO: 1          moltype = AA  length = 7
FEATURE               Location/Qualifiers -continued

```
REGION                  1..7
                        note = linker
source                  1..7
                        mol_type = protein
                        organism = synthetic construct
SEQUENCE: 1
GSGGSGG                                                                      7

SEQ ID NO: 2            moltype = AA   length = 8
FEATURE                 Location/Qualifiers
REGION                  1..8
                        note = linker
source                  1..8
                        mol_type = protein
                        organism = synthetic construct
SEQUENCE: 2
SSGSSGTG                                                                     8

SEQ ID NO: 3            moltype = AA   length = 27
FEATURE                 Location/Qualifiers
REGION                  1..27
                        note = linker
source                  1..27
                        mol_type = protein
                        organism = synthetic construct
SEQUENCE: 3
GSKSSGSGSE SKSTGKSTGS GTETGGS                                                27

SEQ ID NO: 4            moltype = AA   length = 6
FEATURE                 Location/Qualifiers
REGION                  1..6
                        note = motif
source                  1..6
                        mol_type = protein
                        organism = synthetic construct
SEQUENCE: 4
GGVWLG                                                                       6

SEQ ID NO: 5            moltype = AA   length = 273
FEATURE                 Location/Qualifiers
REGION                  1..273
                        note = KB1753-meGFP-GSGGSGG-hRas
source                  1..273
                        mol_type = protein
                        organism = synthetic construct
SEQUENCE: 5
MSSRGYYHGI WVGEEGRLSR GKGEELFTGV VPILVELDGD VNGHKFSVSG EGEGDATYGK   60
LTLKFICTTG KLPVPWPTLV TTLTYGVQCF SRYPDHMKRH DFFKSAMPEG YVQERTIFFK   120
DDGNYKTRAE VKFEGDTLVN RIELKGIDFK EDGNILGHKL EYNYNSHNVY IMADKQKNGI   180
KANFKIRHNI ESGGVQLADH YQQNTPIGDG PVLLPDNHYL STQSKLSKDP NEKRDHMVLK   240
ERVTAAGITH GMDELYKGSG GSGGCMSCKC VLS                                273

SEQ ID NO: 6            moltype = DNA   length = 6229
FEATURE                 Location/Qualifiers
misc_feature            1..6229
                        note = KB1753-meGFP- GSGGSGG-hRas-pcDNA3.1+
source                  1..6229
                        mol_type = other DNA
                        organism = synthetic construct
SEQUENCE: 6
gacggatcgg gagatctccc gatcccctat ggtgcactct cagtacaatc tgctctgatg   60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggag tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta acaactccgc cccattgacg caaatgggcg   780
gtaggcgtgt acggtgggag gtctatataa gcagagctct ctggctaact agagaaccca   840
ctgcttactg gcttatcgaa attaatacga ctcactatag ggagacccaa gctggctagc   900
ggtaccgagc tcggatcact agtccagtgt ggtggaattc acgcggacca tgtcttctag   960
aggttactac catggtattt gggtgggtga agaaggtcga cttttctcgag gtaaaggaga   1020
agaacttttc actggagttg tcccaattct tgttgaatta gatggtgatg ttaatgggca   1080
caaattttct gtcagtggag agggtgaagg tgatgcaaca tacggaaaac ttacccttaa   1140
```

-continued

```
atttatttgc actactggaa aactacctgt tccttggcca acacttgtca ctactttaac   1200
ttatggtgtt caatgctttt caagataccc agatcatatg aaacggcatg acttttttcaa  1260
gagtgccatg cccgaaggtt atgtacagga aagaactata ttttttcaaag atgacgggaa  1320
ctacaagaca cgtgctgaag tcaagtttga aggtgatacc cttgttaata gaatcgagtt   1380
aaaaggtatt gattttaaag aagatgggaaa cattcttgga cacaaattgg aatacaacta  1440
taactcacac aatgtataca tcatggcaga caaacaaaag aatggaatca aagctaactt   1500
caaaattaga cacaacattg agtccggagg cgttcaacta gcagaccatt atcaacaaaa   1560
tactccaatt ggcgatggcc ctgtccttt accagacaac cattacctgt ccacacaatc    1620
taagctttcg aaagatccca acgaaaagag agaccacatg gtccttaaag agagggtaac   1680
agctgctggg attacacatg gcatggacga gctgtacaag ggatccggtg gaagtggagg   1740
ctgcatgagc tgcaagtgtg tgctgtccta atgagcggcc gcactagagg gcccgggccc   1800
gtttaaaccc gctgatcagc ctcgactgtg ccttctagtt gccagccatc tgttgtttgc   1860
ccctcccccg tgccttcctt gaccctggaa ggtgccactc ccactgtcct ttcctaataa   1920
aatgaggaaa ttgcatcgca ttgtctgagt aggtgtcatt ctattctgag gggtggggtg   1980
gggcaggaca gcaagggga ggattgggaa gacaatagca ggcatgctgg ggatgcggtg    2040
ggctctatgg cttctgaggc ggaaagaacc agctggggct ctaggggta tccccacgcg    2100
ccctgtagcg gcgcattaag cgcggcgggt gtggtggtta cgcgcagcgt gaccgctaca    2160
cttgccagcg ccctagcgcc cgctccttc gctttcttcc cttcctttct cgccacgttc    2220
gccggctttc cccgtcaagc tctaaatcgg gggctccctt tagggttccg atttagtgct    2280
ttacggcacc tcgaccccaa aaaacttgat taggtgatg gttcacgtag tgggccatcg     2340
ccctgataga cggttttcg ccctttgacg ttggagtcca cgttctttaa tagtggactc     2400
ttgttccaaa ctggaacaac actcaaccct atctcggtct attctttttga tttataaggg   2460
attttgccga tttcggccta ttggttaaaa aatgagctga tttaacaaaa atttaacgcg    2520
aattaattct gtggaatgtg tgtcagttag ggtgtggaaa gtccccaggc tccccagcag    2580
gcagaagtat gcaaagcatg catctcaatt agtcagcaac caggtgtgga aagtccccag     2640
gctccccagc aggcagaagt atgcaaagca tgcatctcaa ttagtcagca accatagtcc     2700
cgccctaac tccgcccatc ccgccctaa ctccgcccag ttcgcccat tctccgcccc        2760
atggctgact aattttttttt atttatgcag aggccgaggc cgcctctgcc tctgagctat    2820
tccagaagta gtgaggaggc tttttttggag gcctaggctt ttgcaaaaag ctcccgggag     2880
cttgtatatc cattttcgga tctgatcaag agacaggatg aggatcgttt cgcatgattg      2940
aacaagatgg attgcacgca ggttctccgg ccgcttgggt ggagaggcta ttcggctatg      3000
actgggcaca acagacaatc ggctgctctg atgccgccgt gttccggctg tcagcgcagg      3060
ggcgcccggt tctttttgtc aagaccgacc tgtccggtgc cctgaatgaa ctgcaggacg      3120
aggcagcgcg gctatcgtgg ctggccacga cgggcgttcc ttgcgcagct gtgctcgacg      3180
ttgtcactga agcgggaagg gactggctgc tattggcgaa gtgccgggg caggatctcc       3240
tgtcatctca ccttgctcct gccgagaaag tatccatcat ggctgatgca atgcggcggc      3300
tgcatacgct tgatccggct acctgcccat tcgaccacca agcgaaacat cgcatcgagc      3360
gagcacgtac tcggatggaa gccggtcttg tcgatcagga tgatctggac gaagagcatc       3420
aggggctcgc gccagccgaa ctgttcgcca ggctcaaggc gcatgatgcc cgacggcgagg       3480
atctcgtcgt gacccatggc gatgcctgct tgccgaatat catggtggaa aatggccgct       3540
tttctggatt catcgactgt ggccggctgg gtgtggcgga ccgctatcag gacatagcgt       3600
tggctacccg tgatattgct gaagagcttg gcggcgaatg ggctgaccgc ttcctcgtgc       3660
tttacggtat cgccgctccc gattcgcagc gcatcgcctt ctatcgcctt cttgacgagt       3720
tcttctgagc gggactctgg ggttcgaaat gaccgaccaa gcgacgccca acctgccatc       3780
acgagatttc gattccaccg ccgccttcta tgaaaggttg ggcttcggaa tcgttttccg       3840
ggacgccggc tggatgatcc tccagcgcgg ggatctcatg ctggagttct tcgcccaccc        3900
caacttgttt attgcagctt ataatggtta caaataaagc aatagcatca caaatttcac        3960
aaataaagca tttttttcac tgcattctag ttgtggtttg tccaaactca tcaatgtatc        4020
ttatcatgtc tgtataccgt cgacctctag ctagagcttg gcgtaatcat ggtcatagct        4080
gtttcctgtg tgaaattgtt atccgctcac aattccacac aacatacgag ccggaagcat        4140
aaagtgtaaa gcctggggtg cctaatgagt gagctaactc acattaattg cgttgcgctc        4200
actgcccgct ttccagtcgg gaaacctgtc gtgccagctg cattaatgaa tcggccaacg        4260
cgcggggaga ggcggtttgc gtattgggcg ctcttccgct tcctcgctca ctgactcgct        4320
gcgctcggtc gttcggctgc ggcgagcggt atcagctcac tcaaaggcgg taatacggtt        4380
atccacagaa tcaggggata acgcaggaaa gaacatgtga gcaaaaggcc agcaaaaggc         4440
caggaaccgt aaaaaggccg cgttgctggc gtttttccat aggctccgcc ccctgacga         4500
gcatcacaaa aatcgacgct caagtcagag gtggcgaaac ccgacaggac tataaagata         4560
ccaggcgttt ccccctggaa gctccctcgt gcgctctcct gttccgaccc tgccgcttac         4620
cggatacctg tccgcctttc tcccttcggg aagcgtggcg ctttctcata gctcacgctg          4680
taggtatctc agttcggtgt aggtcgttcg ctccaagctg ggctgtgtgc acgaacccc           4740
cgttcagccc gaccgctgcg ccttatccgg taactatcgt cttgagtcca acccggtaag           4800
acacgactta tcgccactgg cagcagccac tggtaacagg attagcagag cgaggtatgt           4860
aggcggtgct acagagttct tgaagtggtg gcctaactac ggctacacta gaagaacagt           4920
atttggtatc tgcgctctgc tgaagccagt taccttcgga aaaagagttg gtagctcttg           4980
atccggcaaa caaaccaccg ctggtagcgg tggtttttttt gtttgcaagc agcagattac          5040
gcgcagaaaa aaaggatctc aagaagatcc tttgatcttt tctacggggt ctgacgctca           5100
gtggaacgaa aactcacgtt aagggatttt ggtcatgaga ttatcaaaaa ggatcttcac           5160
ctagatcctt ttaaattaaa aatgaagttt taaatcaatc taaagtatat atgagtaaac           5220
ttggtctgac agttaccaat gcttaatcag tgaggcacct atctcagcga tctgtctatt          5280
tcgttcatcc atagttgcct gactccccgt cgtgtagata actacgatac gggagggctt          5340
accatctggc cccagtgctg caatgatacc gcgagaccca cgctcaccgg ctccagattt          5400
atcagcaata aaccagccag ccggaagggc cgagcgcaga agtggtcctg caactttatc          5460
cgcctccatc cagtctatta attgttgccg ggaagctaga gtaagtagtt cgccagttaa          5520
tagtttgcgc aacgttgttg ccattgctac aggcatcgtg gtgtcacgct cgtcgtttgg          5580
tatggcttca ttcagctccg gttcccaacg atcaaggcga gttacatgat ccccccatgtt         5640
gtgcaaaaaa gcggttagct ccttcggtcc tccgatcgtt gtcagaagta agttggccgc           5700
agtgttatca ctcatggtta tggcagcact gcataattct cttactgtca tgccatccgt           5760
aagatgcttt tctgtgactg gtgagtactc aaccaagtca ttctgagaat agtgtatgcg          5820
gcgaccgagt tgctcttgcc cggcgtcaat acgggataat accgcgccac atagcagaac          5880
```

```
tttaaaagtg ctcatcattg gaaaacgttc ttcggggcga aaactctcaa ggatcttacc   5940
gctgttgaga tccagttcga tgtaacccac tcgtgcaccc aactgatctt cagcatcttt   6000
tactttcacc agcgtttctg ggtgagcaaa aacaggaagg caaaatgccg caaaaaaggg   6060
aataagggcg acacggaaat gttgaatact catactcttc cttttttcaat attattgaag   6120
catttatcag ggttattgtc tcatgagcgg atacatattt gaatgtattt agaaaaataa   6180
acaaataggg gttccgcgca catttccccg aaaagtgcca cctgacgtc               6229
```

```
SEQ ID NO: 7              moltype = AA  length = 354
FEATURE                   Location/Qualifiers
REGION                    1..354
                          note = G i1(Q204L)
source                    1..354
                          mol_type = protein
                          organism = synthetic construct
SEQUENCE: 7
MGCTLSAEDK AAVERSKMID RNLREDGEKA AREVKLLLLG AGESGKSTIV KQMKIIHEAG   60
YSEEECKQYK AVVYSNTIQS IIAIIRAMGR LKIDFGDSAR ADDARQLFVL AGAAEEGFMT   120
AELAGVIKRL WKDSGVQACF NRSREYQLND SAAYYLNDLD RIAQPNYIPT QQDVLRTRVK   180
TTGIVETHFT FKDLHFKMFD VGGLRSERKK WIHCFEGVTA IIFCVALSDY DLVLAEDEEM   240
NRMHESMKLF DSICNNKWFT DTSIILFLNK KDLFEEKIKK SPLTICYPEY AGSNTYEEAA   300
AYIQCQFEDL NKRKDTKEIY THFTCATDTK NVQFVFDAVT DVIIKNNLKD CGLF         354
```

```
SEQ ID NO: 8              moltype = DNA  length = 7111
FEATURE                   Location/Qualifiers
misc_feature              1..7111
                          note = Galfa-i1(Q204L)-pcDNA3.1
source                    1..7111
                          mol_type = other DNA
                          organism = synthetic construct
SEQUENCE: 8
tagttattaa tagtaatcaa ttacggggtc attagttcat agcccatata tggagttccg   60
cgttacataa cttacggtaa atggcccgcc tggctgaccg cccaacgacc cccgcccatt   120
gacgtcaata atgacgtatg ttcccatagt aacgccaata gggactttcc attgacgtca   180
atgggtggag tatttacggt aaactgccca cttggcagta tcatatgcc atcatatgcc     240
aagtacgccc cctattgacg tcaatgacgg taaatggccc gcctggcatt atgcccagta   300
catgacctta tgggactttc ctacttggca gtacatctac gtattagtca tcgctattac   360
catggtgatg cggttttggc agtacatcaa tgggcgtgga tagcggtttg actcacgggg   420
atttccaagt ctccacccca ttgacgtcaa tgggagtttg ttttggcacc aaaatcaacg   480
ggactttcca aaatgtcgta acaactccgc cccattgacg caaatgggcg gtaggcgtgt   540
acggtgggag gtctatataa gcagagctgg tttagtgaac cgtcagatcc gctagcctcg   600
acttgagctc tctggctaac tagagaaccc actgcttact ggcttatcga aattaatacg   660
actcactata gggagaccca agctggctag cgtttaaact taagcttggt accaccatgg   720
gctgcacgct gagcgccgag gacaaggcgg cggtggagcg gagtaagatg atcgaccgca   780
acctccgtga ggacggcgag aaggcggcgc gcgaggtcaa gctgctgctg ctcggtgctg   840
gtgaatctgg taaaagtaca attgtgaagc agatgaaaat tatccatgaa gctggttatt   900
cagaagagga gtgtaaacaa tacaaagcag tggtctacag taacaccatc cagtcaatta   960
ttgctatcat tagggctatg gggaggttga agatagactt tggtgactca gcccgggcgg   1020
atgatgcacg ccaactcttt gtgctagctg gagctgctga agaaggcttt atgactgcag   1080
aacttgctgg agttataaag agattgtgga aagatagtgg tgtacaagcc tgtttcaaca   1140
gatcccgaga gtaccagctt aatgattctg cagcatacta tttgaatgac ttggacagaa   1200
tagctcaacc aaattacatc ccgactcaac aagatgttct cagaactaga gtgaaaacta   1260
caggaattgt tgaaacccat tttactttca aagatcttca ttttaaaatg tttgatgtgg   1320
gaggtctgag atctgagcgg aagaagtgga ttcattgctt cgaaggagtg acggcgatca   1380
tcttctgtgt agcactgagt gactacgacc tggttctagc tgaagatgaa gaaatgaacc   1440
gaatgcatga aagcatgaaa ttgtttgaca gcatatgtaa caacaagtgg tttacagata   1500
catccattat acttttttcta aacaagaagg atctctttga agaaaaaatc aaaaagagcc   1560
ctctcactat atgctatcca gaatatgcag atcaaacac atatgaagag gcagctgcat    1620
atattcaatg tcagtttgaa gacctcaata aagaaaagga cacaaaggaa atatacaccc   1680
acttcacatg tgccacagat actaagaatg tgcagtttgt ttttgatgct gtaacagatg   1740
tcatcataaa aaataatcta aaagattgtg gtctctttta actcgagtct agaactagtt   1800
tgagtcgagc cgcggcaatt ccgccccccc cccccccccct ctccctcccc cccccctaac   1860
gttactggcc gaagccgctt ggaataaggc cggtgtgcgt ttgtctatat gttatttttcc   1920
accatattgc cgtcttttgg caatgtgagg gcccggaaac ctggccctgt cttcttgacg   1980
agcattccta ggggtcttttc ccctctcgcc aaaggaatgc aaggtctgtt gaatgtcgtg   2040
aaggaagcag ttcctctgga agcttcttga agacaaacaa cgtctgtagc gaccctttgc   2100
aggcagcgga accccccacc tggcaacagt gcctctgcg gccaaaagcc acgtgtataa    2160
gatacacctg caaaggcggc acaacccccag tgccacgttg tgagttggat agttgtggaa   2220
agagtcaaat ggctctcctc aagcgtattc aacaaggggc tgaaggatgc ccagaaggta   2280
ccccattgta tgggatctga tctgtgggcct cggtgaccat gcttacatg tgtttagtcg   2340
aggttaaaaa aacgtctagg ccccccgaac cacggggacg tggttttcct ttgaaaaaca   2400
cgatgataat atggtgagca agggcgagga ggataacatg gccatcatca aggagttcat   2460
gcgcttcaag gtgcacatgg agggctccgt gaacggccac gagttcgaga tcgagggcga   2520
gggcgagggc cgcccctacg agggcaccca gaccgccaag ctgaaggtga ccaagggtgg   2580
ccccctgccc ttcgcctggg acatcctgtc ccctcagttc atgtacggct ccaaggccta   2640
cgtgaagcac cccgccgaca tccccgacta cttgaagctg tccttcccccg agggcttcaa   2700
gtgggagcgc gtgatgaact tcgaggacgg cggcgtggtg accgtgaccc aggactcctc   2760
cctgcaggac ggcgagttca tctacaaggt gaagctgcgc ggcaccaact cccctccga   2820
cggccccgta atgcagaaga gaccatgggc ctggaggc cctccgagc ggatgtaccc     2880
cgaggacggc gccctgaagg gcgagatcaa gcagaggctg aagctgaagg acggcggcca   2940
```

-continued

```
ctacgacgct gaggtcaaga ccacctacaa ggccaagaag cccgtgcagc tgcccggcgc    3000
ctacaacgtc aacatcaagt tggacatcac ctcccacaac gaggactaca ccatcgtgga    3060
acagtacgaa cgcgccgagg gccgccactc caccggcggc atggacgagc tgtacaagta    3120
accgcggtcg acggtaccgc gggcccggga tctaagctta tcgataatca acctctggat    3180
tacaaaattt gtgaaagatt gactggtatt cttaactatg ttgctccttt tacgctatgt    3240
ggatacgctg ctttaatgcc tttgtatcat gctattgctt cccgtatggc tttcattttc    3300
tcctccttgt ataaatcctg gttgctgtct ctttatgagg agttgtggcc cgttgtcagg    3360
caacgtggcg tggtgtgcac tgtgtttgct gacgcaaccc ccactggttg gggcattgcc    3420
accacctgtc agctcctttc cgggactttc gctttccccc tccctattgc cacggcggaa    3480
ctcatcgccg cctgccttgc ccgctgctgg acaggggctc ggctgttggg cactgacaat    3540
tccgtggtgt tgtcggggaa atcatcgtcc tttccttggc tgctcgcctg tgttgccacc    3600
tggattctgc gcgggacgtc cttctgctac gtcccttcgg ccctcaatcc agcggacctt    3660
ccttcccgcg gcctgctgcc ggctctgcgg cctcttccgc gtcttcgcct tcgccctcag    3720
acgagtcgga tctccctttg ggccgcctcc cgcatcgat accgtggatc gatccaccgg    3780
atctagataa ctgatcataa tcagccatac cacatttgta gaggttttac ttgctttaaa    3840
aaacctccca cacctccccc tgaacctgaa acataaaatg aatgcaattg ttgttgttaa    3900
cttgtttatt gcagcttata atggttacaa ataaagcaat agcatcacaa atttcacaaa    3960
taaagcattt ttttcactgc attctagttg tggtttgtcc aaactcatca atgtatctta    4020
acgcgtaaat tgtaagcgtt aatattttgt taaaattcgc gttaaatttt tgttaaatca    4080
gctcattttt taaccaatag gccgaaatcg gcaaaatccc ttataaatca aaagaataga    4140
ccgagatagg gttgagtgtt gttccagttt ggaacaagag tccactatta agaacgtgg    4200
actccaacgt caaagggcga aaaaccgtct atcagggcga tggcccacta cgtgaaccat    4260
caccctaatc aagttttttg gggtcgaggt gccgtaaagc actaaatcgg aaccctaaag    4320
ggagcccccg atttagagct tgacggggaa agccggcgaa cgtggcgaga aaggaaggga    4380
agaaagcgaa aggagcgggc gctagggcgc tggcaagtgt agcggtcacg ctgcgcgtaa    4440
ccaccacacc cgccgcgctt aatgcgccgc tacagggcgc gtcaggtgtc acttttcggg    4500
gaaatgtgcg cggaacccct atttgtttat ttttctaaat acattcaaat atgtatccgc    4560
tcatgagaca ataaccctga taaatgcttc aataatattg aaaaaggaag agtcctgagg    4620
cggaaagaac cagctgtgga atgtgtgtca gttagggtgt ggaaagtccc caggctcccc    4680
agcaggcaga agtatgcaaa gcatgcatct caattagtca gcaaccaggt gtggaaagtc    4740
cccaggctcc ccagcaggca gaagtatgca aagcatgcat ctcaattagt cagcaaccat    4800
agtcccgccc ctaactccgc ccatcccgcc cctaactccg cccagttccg cccattctcc    4860
gccccatggc tgactaattt tttttattta tgcagaggcc gaggccgcct cggcctctga    4920
gctattccag aagtagtgag gaggcttttt tggaggccta ggcttttgca aagatcgatc    4980
aagagacagg atgaggatcg tttcgcatga ttgaacaaga tggattgcac gcaggttctc    5040
cggccgcttg ggtggagagg ctattcggct atgactgggc acaacagaca atcggctgct    5100
ctgatgccgc cgtgttccgg ctgtcagcgc aggggcgccc ggttcttttt gtcaagaccg    5160
acctgtccgg tgccctgaat gaactgcaag acgaggcagc gcggctatcg tggctggcca    5220
cgacggcgt tccttgcgca gctgtgctcg acgttgtcac tgaagcggga agggactggc    5280
tgctattggg cgaagtgccg gggcaggatc tcctgtcatc tcaccttgct cctgccgaga    5340
aagtatccat catggctgat gcaatgcggc ggctgcatac gcttgatccg gctacctgcc    5400
cattcgacca ccaagcgaaa catcgcatcg agcgagcacg tactcggatg gaagccggtc    5460
ttgtcgatca ggatgatctg gacgaagagc atcaggggct cgcgccagcc gaactgttcg    5520
ccaggctcaa ggcgagcatg cccgacggcg aggatctcgt cgtgacccat ggcgatgcct    5580
gcttgccgaa tatcatggtg gaaaatggcc gcttttctgg attcatcgac tgtggccggc    5640
tgggtgtggc ggaccgctat caggacatag cgttggctac ccgtgatatt gctgaagagc    5700
ttggcggcga atgggctgac cgcttcctcg tgctttacgg tatcgccgct cccgattcgc    5760
agcgcatcgc cttctatcgc cttcttgacg agttcttctg agcgggactc tggggttcga    5820
aatgaccgac caagcgacgc ccaacctgcc atcacgagat ttcgattcca ccgccgcctt    5880
ctatgaaagg ttgggcttcg gaatcgtttt ccgggacgcc ggctggatga tcctccagcg    5940
cggggatctc atgctggagt tcttcgccca ccctagggg aggctaactg aaacacggaa    6000
ggagacaata ccggaaggaa cccgcgctat gacggcaata aaaagacaga ataaaacgca    6060
cggtgttggg tcgtttgttc ataaacgcgg ggttcggtcc cagggctggc actctgtcga    6120
taccccaccg agacccccatt ggggccaata cgcccgcgtt tcttcctttt ccccacccca    6180
cccccaagt tcgggtgaag gcccagggct cgcagccaac gtcggggcgg caggccctgc    6240
catagcctca ggttactcat atatacttta gattgattta aaacttcatt tttaatttaa    6300
aaggatctag gtgaagatcc tttttgataa tctcatgacc aaaatccctt aacgtgagtt    6360
ttcgttccac tgagcgtcag accccgtaga aaagatcaaa ggatcttctt gagatccttt    6420
ttttctgcgc gtaatctgct gcttgcaaac aaaaaaacca ccgctaccag cggtggtttg    6480
tttgccggat caagagctac caactctttt tccgaaggta actggcttca gcagagcgca    6540
gataccaaat actgtccttc tagtgtagcc gtagttaggc caccacttca agaactctgt    6600
agcaccgcct acatacctcg ctctgctaat cctgttacca gtggctgctg ccagtggcga    6660
taagtcgtgt cttaccgggt tggactcaag acgatagtta ccggataagg cgcagcggtc    6720
gggctgaacg gggggttcgt gcacacagcc cagcttggag cgaacgacct acaccgaact    6780
gagatacccta cagcgtgagc tatgagaaag cgccacgctt cccgaaggga gaaaggcgga    6840
caggtatccg gtaagcggca gggtcggaac aggagagcgc acgagggagc ttccaggggg    6900
aaacgcctgg tatctttata gtcctgtcgg gtttcgccac ctctgacttg agcgtcgatt    6960
tttgtgatgc tcgtcagggg ggcggagcct atggaaaaac gccagcaacg cggccttttt    7020
acggttcctg gccttttgct ggccttttgc tcacatgttc tttcctgcgt tatcccctga    7080
ttctgtggat aaccgtatta ccgccatgca t                                  7111
```

SEQ ID NO: 9　　　　　moltype = AA　length = 278
FEATURE　　　　　　　Location/Qualifiers
REGION　　　　　　　1..278
　　　　　　　　　　note = KB1753-meGFP-GSGGSGG-kRas
source　　　　　　　1..278
　　　　　　　　　　mol_type = protein
　　　　　　　　　　organism = synthetic construct
SEQUENCE: 9

```
MSSRGYYHGI WVGEEGRLSR GKGEELFTGV VPILVELDGD VNGHKFSVSG EGEGDATYGK  60
LTLKFICTTG KLPVPWPTLV TTLTYGVQCF SRYPDHMKRH DFFKSAMPEG YVQERTIFFK  120
DDGNYKTRAE VKFEGDTLVN RIELKGIDFK EDGNILGHKL EYNYNSHNVY IMADKQKNGI  180
KANFKIRHNI ESGGVQLADH YQQNTPIGDG PVLLPDNHYL STQSKLSKDP NEKRDHMVLK  240
ERVTAAGITH GMDELYKGSG GSGGKKKKKK SKTKCVIM  278

SEQ ID NO: 10        moltype = DNA  length = 6244
FEATURE              Location/Qualifiers
misc_feature         1..6244
                     note = KB1753-meGFP-GSGGSGG-kRas
source               1..6244
                     mol_type = other DNA
                     organism = synthetic construct
SEQUENCE: 10
gacggatcgg gagatctccc gatccctat ggtgcactct cagtacaatc tgctctgatg   60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagaccca gctggctagc  900
ggtaccgagc tcggatcact agtccagtgt ggtggaattc acgcggacca tgtcttctag  960
aggttactac catggtattt gggtgggtga agaaggtcga ctttctcgag gtaaaggaga  1020
agaactttc actggagttg tcccaattct tgttgaatta gatggtgatg ttaatgggca  1080
caaattttct gtcagtggag agggtgaagg tgatgcaaca tacggaaaac ttaccctaa  1140
atttatttgc actactggaa aactacctgt tccttggcca aacttgtca ctactttaac  1200
ttatggtgtt caatgctttt caagataccc agatcatatg aaacggcatg acttttcaa  1260
gagtgccatg cccgaaggtt atgtacagga agaactata tttttcaaag atgacgggaa  1320
ctacaagaca cgtgctgaag tcaagtttga aggtgatacc cttgttaata gaatcgagtt  1380
aaaaggtatt gattttaaag aagatggaaa cattcttgga cacaaattgg aatacaacta  1440
taactcacac aatgtataca tcatggcaga caaacaaag aatggaatca aagctaactt  1500
caaaattaga cacaacattg agtccggagg cgttcaacta gcagaccatt atcaacaaa  1560
tactccaatt ggcgatggcc ctgtcctttt accagacaac cattacctgt ccacacaatc  1620
taagctttcg aaagatccca acgaaaagag agaccacatg gtccttaaag agagggtaac  1680
agctgctggg attacacatg gcatggacga gctgtacaag ggatccggtg gaagtggagg  1740
caagaaaaag aaaaagaaga gcaaaactaa gtgtgtaatc atgtaatgag cggccgcact  1800
agagggcccg ggcccgttta aacccgctga tcagcctcga ctgtgccttc tagttgccag  1860
ccatctgttg tttgcccctc ccccgtgcct tccttgaccc tggaaggtgc cactcccact  1920
gtcctttcct aataaaatga ggaaattgca tcgcattgtc tgagtaggtg tcattctatt  1980
ctggggggtg gggtggggca ggacagcaag ggggaggatt gggaagacaa tagcaggcat  2040
gctggggatg cggtgggctc tatggcttct gaggcggaaa gaaccagctg gggctctagg  2100
gggtatcccc acgcgccctg tagcggcgca ttaagcgcgg cgggtgtggt ggttacgcgc  2160
agcgtgaccg ctacacttgc cagcgcccta gcgcccgctc ctttcgcttt cttcccttcc  2220
tttctcgcca cgttcgccgg ctttccccgt caagctctaa atcggggct ccctttaggg  2280
ttccgattta gtgctttacg gcacctcgac cccaaaaac ttgattaggg tgatggttca  2340
cgtagtgggc catcgccctg atagacggtt tttcgccctt tgacgttgga gtccacgttc  2400
tttaatagtg gactcttgtt ccaaactgga acaacactca accctatctc ggtctattct  2460
tttgatttat aagggatttt gccgatttcg gcctattggt taaaaaatga gctgatttaa  2520
caaaaattta acgcgaatta attctgtgga atgtgtgtca gttagggtgt ggaaagtccc  2580
caggctcccc agcaggcaga agtatgcaaa gcatgcatct caattagtca gcaaccaggt  2640
gtggaaagtc cccaggctcc ccagcaggca gaagtatgca aagcatgcat ctcaattagt  2700
cagcaaccat agtcccgccc ctaactccgc ccatcccgcc cctaagtccg cccagttccg  2760
cccattctcc gccccatggc tgactaattt ttttatttta tgcagaggcc gaggccgcct  2820
ctgcctctga gctattccag aagtagtgag gaggcttttt tggaggccta ggcttttgca  2880
aaaagctccc gggagcttgt atatccattt tcggatctga tcaagagaca ggatgaggat  2940
cgtttcgcat gattgaacaa gatggattgc acgcaggttc tccggccgct tgggtgggaa  3000
ggctattcgg ctatgactgg gcacaacaga caatcggctg ctctgatgcc gccgtgttcc  3060
ggctgtcagc gcaggggcgc ccggttcttt ttgtcaagac cgacctgtcc ggtgccctga  3120
atgaactgca ggacgaggca gcgcggctat cgtggctggc cacgacgggc gttccttgcg  3180
cagctgtgct cgacgttgtc actgaagcgg gaagggactg gctgctattg ggcgaagtgc  3240
cggggcagga tctcctgtca tctcaccttg ctcctgccga aaagtatccat catggctgat  3300
atgcaatgcg gcggctgcat acgcttgatc cggctacctg cccattcgac caccaagcga  3360
aacatcgcat cgagcgagca cgtactcgga tggaagccgg tcttgtcgat caggatgatc  3420
tggacgaaga gcatcagggg ctcgcgccag ccgaactgtt cgccaggctc aaggcgcgca  3480
tgcccgacgg cgaggatctc gtcgtgaccc atggcgatgc ctgcttgccg aatatcatgg  3540
tggaaaatgg ccgcttttct ggattcatcg actgtggccg gctgggtgtg gcggaccgct  3600
atcaggacat agcgttggct acccgtgata ttgctgaaga gcttggcggc gaatgggctg  3660
accgcttcct cgtgctttac ggtatcgccg ctcccgattc gcagcgcatc gccttctatc  3720
gccttcttga cgagttcttc tgagcgggac tctggggttc gaaatgaccg accaagcgac  3780
gcccaacctg ccatcacgag atttcgattc caccgccgcc ttctatgaaa ggttgggctt  3840
cggaatcgtt ttccgggacg ccggctggat gatcctccag cgcggggatc tcatgctgga  3900
```

```
gttcttcgcc caccccaact tgtttattgc agcttataat ggttacaaat aaagcaatag   3960
catcacaaat ttcacaaata aagcatttt ttcactgcat tctagttgtg gtttgtccaa    4020
actcatcaat gtatcttatc atgtctgtat accgtcgacc tctagctaga gcttggcgta   4080
atcatggtca tagctgtttc ctgtgtgaaa ttgttatccg ctcacaattc cacacaacat   4140
acgagccgga agcataaagt gtaaagcctg gggtgcctaa tgagtgagct aactcacatt   4200
aattgcgttg cgctcactgc ccgctttcca gtcgggaaac ctgtcgtgcc agctgcatta   4260
atgaatcggc caacgcgcgg ggagaggcgg tttgcgtatt gggcgctctt ccgcttcctc   4320
gctcactgac tcgctgcgct cggtcgttcg gctgcggcga gcggtatcag ctcactcaaa   4380
ggcggtaata cggttatcca cagaatcagg ggataacgca ggaaagaaca tgtgagcaaa   4440
aggccagcaa aaggccagga accgtaaaaa ggccgcgttg ctggcgtttt tccataggct   4500
ccgcccccct gacgagcatc acaaaaatcg acgctcaagt cagaggtggc gaaacccgac   4560
aggactataa agataccagg cgtttccccc tggaagctcc ctcgtgcgct ctcctgttcc   4620
gaccctgccg cttaccggat acctgtccgc ctttctccct tcgggaagcg tggcgctttc   4680
tcatagctca cgctgtaggt atctcagttc ggtgtaggtc gttcgctcca agctgggctg   4740
tgtgcacgaa ccccccgttc agcccgaccg ctgcgcctta tccggtaact atcgtcttga   4800
gtccaacccg gtaagacacg acttatcgcc actggcagca gccactggta acaggattag   4860
cagagcgagg tatgtaggcg gtgctacaga gttcttgaag tggtggccta actacggcta   4920
cactagaaga acagtatttg gtatctgcgc tctgctgaag ccagttacct tcggaaaaag   4980
agttggtagc tcttgatccg gcaaacaaac caccgctggt agcggtggtt tttttgtttg   5040
caagcagcag attacgcgca gaaaaaaagg atctcaagaa gatcctttga tcttttctac   5100
ggggtctgac gctcagtgga acgaaaactc acgttaaggg attttggtca tgagattatc   5160
aaaaaggatc ttcacctaga tccttttaaa ttaaaaatga agttttaaat caatctaaag   5220
tatatatgag taaacttggt ctgacagtta ccaatgctta atcagtgagg cacctatctc   5280
agcgatctgt ctatttcgtt catccatagt tgcctgactc cccgtcgtgt agataactac   5340
gatacgggag ggcttaccat ctggccccag tgctgcaatg ataccgcgag acccacgctc   5400
accggctcca gatttatcag caataaacca gccagccgga agggccgagc gcagaagtgg   5460
tcctgcaact ttatccgcct ccatccagtc tattaattgt tgccgggaag ctagagtaag   5520
tagttcgcca gttaatagtt tgcgcaacgt tgttgccatt gctacaggca tcgtggtgtc   5580
acgctcgtcg tttggtatgg cttcattcag ctccggttcc caacgatcaa ggcgagttac   5640
atgatccccc atgttgtgca aaaaagcggt tagctccttc ggtcctccga tcgttgtcag   5700
aagtaagttg gccgcagtgt tatcactcat ggttatggca gcactgcata attctcttac   5760
tgtcatgcca tccgtaagat gcttttctgt gactggtgag tactcaacca agtcattctg   5820
agaatagtgt atgcggcgac cgagttgctc ttgcccggcg tcaatacggg ataataccgc   5880
gccacatagc agaactttaa aagtgctcat cattggaaaa cgttcttcgg ggcgaaaact   5940
ctcaaggatc ttaccgctgt tgagatccag ttcgatgtaa cccactcgtg cacccaactg   6000
atcttcagca tcttttactt tcaccagcgt ttctgggtga gcaaaaacag gaaggcaaaa   6060
tgccgcaaaa aagggaataa gggcgacacg gaaatgttga atactcatac tcttcctttt   6120
tcaatattat tgaagcattt atcagggtta ttgtctcatg agcggataca tatttgaatg   6180
tatttagaaa aataaacaaa tagggggtcc gcgcacattt ccccgaaaag tgccacctga   6240
cgtc                                                               6244
```

```
SEQ ID NO: 11           moltype = AA   length = 285
FEATURE                 Location/Qualifiers
REGION                  1..285
                        note = GAP43-SSGSSGTG-meGFP-KB1753
source                  1..285
                        mol_type = protein
                        organism = synthetic construct
SEQUENCE: 11
MLCCMRRTKQ VEKNDEDQNS SGSSGTGSKG EELFTGVVPI LVELDGDVNG HKFSVSGEGE    60
GDATYGKLTL KFICTTGKLP VPWPTLVTTL TYGVQCFSRY PDHMKRHDFF KSAMPEGYVQ   120
ERTIFFKDDG NYKTRAEVKF EGDTLVNRIE LKGIDFKEDG NILGHKLEYN YNSHNVYIMA   180
DKQKNGIKAN FKIRHNIESG GVQLADHYQQ NTPIGDGPVL LPDNHYLSTQ SKLSKDPNEK   240
RDHMVLKERV TAAGITHGMD ELYKGSSRGY YHGIWVGEEG RLSRG               285
```

```
SEQ ID NO: 12           moltype = DNA   length = 6250
FEATURE                 Location/Qualifiers
misc_feature            1..6250
                        note = GAP43-SSGSSGTG-meGFP-KB1753
source                  1..6250
                        mol_type = other DNA
                        organism = synthetic construct
SEQUENCE: 12
gacggatcgg gagatctccc gatcccctat ggtgcactct cagtacaatc tgctctgatg    60
ccgcatagtt aagccagtat ctgctccctg cttgtgtgtt ggaggtcgct gagtagtgcg   120
cgagcaaaat ttaagctaca caaggcaag gcttgaccga caattgcatg aagaatctgc    180
ttaggggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggag tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta acaactccgc cccattgacg caaatgggcg   780
gtaggcgtgt acggtgggag gtctatataa gcagagctct ctggctaact agagaaccca   840
ctgcttactg gcttatcgaa attaatacga ctcactatag gagacccaa gctggctagc    900
gtttaaactt aagcttggta ccgacggacc atgctgtgct gtatgagaag aaccaaacag   960
```

-continued

```
gttgaaaaga atgatgagga ccagaattcc tccggatcgt ctggaaccgg ttctaaagga   1020
gaagaacttt tcactggagt tgtcccaatt cttgttgaat tagatggtga tgttaatggg   1080
cacaaatttt ctgtcagtgg agagggtgaa ggtgatgcaa catacggaaa acttaccctt   1140
aaatttattt gcactactgg aaaactacct gttccttggc caacacttgt cactacttta   1200
acttatggtg ttcaatgctt ttcaagatac ccagatcata tgaaacggca tgactttttc   1260
aagagtgcca tgcccgaagg ttatgtacag gaaagaacta tattttttcaa agatgacggg   1320
aactacaaga cacgtgctga agtcaagttt gaaggtgata cccttgttaa tagaatcgag   1380
ttaaaaggta ttgattttaa agaagatgga aacattcttg gacacaaatt ggaatacaac   1440
tataactcac acaatgtata catcatggca gacaaacaaa agaatggaat caaagctaac   1500
ttcaaaatta gacacaacat tgagtccgga ggcgttcaac tagcagacca ttatcaacaa   1560
aatactccaa ttggcgatgg ccctgtcctt ttaccagaca accattacct gtccacacaa   1620
tctaagcttt cgaaagatcc caacgaaaag agagaccaca tggtccttaa agagagggta   1680
acagctgctg ggattacaca tggcatggac gagctgtaca agggatcctc tagaggttac   1740
taccatggta tttgggtggg tgaagaaggt cgactttctc gaggataatg aaggtggcgg   1800
ccgctcgaaa ctagagggcc cgtttaaacc cgctgatcag cctcgactgt gccttctagt   1860
tgccagccat ctgttgtttg cccctccccc gtgccttcct tgaccctgga aggtgccact   1920
cccactgtcc tttcctaata aaatgaggaa attgcatcgc attgtctgag taggtgtcat   1980
tctattctgg ggggtggggt ggggcaggac agcaaggggg aggattggga agacaatagc   2040
aggcatgctg gggatgcggt gggctctatg gcttctgagg cggaaagaac cagctggggc   2100
tctaggggggg atccccacgc gccctgtagc ggcgcattaa gcgcggcggg tgtggtggtt   2160
acgcgcagcg tgaccgctac acttgccagc gccctagcgc ccgctccttt cgctttcttc   2220
ccttcctttc tcgccacgtt cgccggcttt ccccgtcaag ctctaaatcg ggggctccct   2280
ttagggttcc gatttagtgc tttacggcac ctcgacccca aaaaacttga ttagggtgat   2340
ggttcacgta gtgggccatc gccctgatag acggtttttc gccctttgac gttggagtcc   2400
acgttcttta atagtggact cttgttccaa actggaacaa cactcaaccc tatctcggtc   2460
tattcttttg atttataagg gattttgccg atttcggcct attggttaaa aaatgagctg   2520
atttaacaaa aatttaacgc gaattaattc tgtggaatgt gtgtcagtta gggtgtggaa   2580
agtccccagg ctccccagca ggcagaagta tgcaaagcat gcatctcaat tagtcagcaa   2640
ccaggtgtgg aaagtcccca ggctccccag caggcagaag tatgcaaagc atgcatctca   2700
attagtcagc aaccatagtc ccgcccctaa ctccgcccat cccgccccta actccgccca   2760
gttccgccca ttctccgccc catggctgac taattttttt tatttatgca gaggccgagg   2820
ccgcctctgc ctctgagcta ttccagaagt agtgaggagg cttttttgga ggcctaggct   2880
tttgcaaaaa gctcccggga gcttgtatat ccattttcgg atctgatcaa gagacaggat   2940
gaggatcgtt tcgcatgatt gaacaagatg gattgcacgc aggttctccg gccgcttggg   3000
tggagaggct attcggctat gactgggcac aacagacaat cggctgctct gatgccgccg   3060
tgttccggct gtcagcgcag gggcgcccgg ttctttttgt caagaccgac ctgtccggtg   3120
ccctgaatga actgcaggac gaggcagcgc ggctatcgtg gctggccacg acgggcgttc   3180
cttgcgcagc tgtgctcgac gttgtcactg aagcgggaag ggactggctg ctattgggcg   3240
aagtgccggg gcaggatctc ctgtcatctc accttgctcc tgccgagaaa gtatccatca   3300
tggctgatgc aatgcggcgg ctgcatacgc ttgatccggc tacctgccca ttcgaccacc   3360
aagcgaaaca tcgcatcgag cgagcacgta ctcggatgga agccggtctt gtcgatcagg   3420
atgatctgga cgaagagcat caggggctcg cgccagccga actgttcgcc aggctcaagg   3480
cgcgcatgcc cgacggcgag gatctcgtcg tgacccatgg cgatgcctgc ttgccgaata   3540
tcatggtgga aaatggccgc ttttctggat tcatcgactg tggccggctg ggtgtggcgg   3600
accgctatca ggacatagcg ttggctaccg tgatattgc tgaagagctt ggcggcgaat   3660
gggctgaccg cttcctcgtg ctttacggta tcgccgctcc cgattcgcag cgcatcgcct   3720
tctatcgcct tcttgacgag ttcttctgag cgggactctg gggttcgaaa tgaccgacca   3780
agcgacgccc aacctgccat cacgagattt cgattccacc gccgccttct atgaaaggtt   3840
gggcttcgga atcgttttcc gggacgccgg ctggatgatc ctccagcgcg gggatctcat   3900
gctggagttc ttcgcccacc ccaacttgtt tattgcagct tataatggtt acaaataaag   3960
caatagcatc acaaatttca caaataaagc atttttttca ctgcattcta gttgtggttt   4020
gtccaaactc atcaatgtat cttatcatgt ctgtataccg tcgacctcta gctagagctt   4080
ggcgtaatca tggtcatagc tgtttcctgt gtgaaattgt tatccgctca caattccaca   4140
caacatacga gccggaagca taaagtgtaa agcctggggt gcctaatgag tgagctaact   4200
cacattaatt gcgttgcgct cactgcccgc tttccagtcg ggaaacctgt cgtgccagct   4260
gcattaatga atcggccaac gcgcggggag aggcggtttg cgtattgggc gctcttccgc   4320
ttcctcgctc actgactcgc tgcgctcggt cgttcggctg cggcgagcgg tatcagctca   4380
ctcaaaggcg gtaatacggt tatccacaga atcaggggat aacgcaggaa agaacatgtg   4440
agcaaaaggc cagcaaaagg ccaggaaccg taaaaaggcc gcgttgctgg cgtttttcca   4500
taggctccgc cccctgacg agcatcacaa aaatcgacgc tcaagtcaga ggtggcgaaa   4560
cccgacagga ctataaagat accaggcgtt tcccctgga agctccctcg tgcgctctcc   4620
tgttccgacc ctgccgctta ccggatacct gtccgccttt ctcccttcgg gaagcgtggc   4680
gctttctcat agctcacgct gtaggtatct cagttcggtg taggtcgttc gctccaagct   4740
gggctgtgtg cacgaacccc ccgttcagcc cgaccgctgc gccttatccg gtaactatcg   4800
tcttgagtcc aacccggtaa gacacgactt atcgccactg gcagcagcca ctggtaacag   4860
gattagcaga gcgaggtatg taggcggtgc tacagagttc ttgaagtggt ggcctaacta   4920
cggctacact agaagaacag tatttggtat ctgcgctctg ctgaagccag ttaccttcgg   4980
aaaaagagtt ggtagctctt gatccggcaa acaaaccacc gctggtagcg gtggtttttt   5040
tgtttgcaag cagcagatta cgcgcagaaa aaaaggatct caagaagatc ctttgatctt   5100
ttctacgggg tctgacgctc agtggaacga aaactcacgt taagggattt tggtcatgag   5160
attatcaaaa aggatcttca cctagatcct tttaaattaa aaatgaagtt ttaaatcaat   5220
ctaaagtata tatgagtaaa cttggtctga cagttaccaa tgcttaatca gtgaggcacc   5280
tatctcagcg atctgtctat ttcgttcatc catagttgcc tgactccccg tcgtgtagat   5340
aactacgata cgggagggct taccatctgg ccccagtgct gcaatgatac cgcgagaccc   5400
acgctcaccg gctccagatt tatcagcaat aaaccagcca gccggaaggg ccgagcgcag   5460
aagtggtcct gcaactttat ccgcctccat ccagtctatt aattgttgcc gggaagctag   5520
agtaagtagt tcgccagtta atagtttgcg caacgttgtt gccattgcta caggcatcgt   5580
ggtgtcacgc tcgtcgtttg gtatggcttc attcagctcc ggttcccaac gatcaaggcg   5640
agttacatga tcccccatgt tgtgcaaaaa agcggttagc tccttcggtc ctccgatcgt   5700
```

```
tgtcagaagt aagttggccg cagtgttatc actcatggtt atggcagcac tgcataattc   5760
tcttactgtc atgccatccg taagatgctt ttctgtgact ggtgagtact caaccaagtc   5820
attctgagaa tagtgtatgc ggcgaccgag ttgctcttgc ccggcgtcaa tacgggataa   5880
taccgcgcca catagcagaa ctttaaaagt gctcatcatt ggaaaacgtt cttcgggggcg   5940
aaaactctca aggatcttac cgctgttgag atccagttcg atgtaaccca ctcgtgcacc   6000
caactgatct tcagcatctt ttactttcac cagcgtttct gggtgagcaa aaacaggaag   6060
gcaaaatgcc gcaaaaaagg gaataagggc gacacggaaa tgttgaatac tcatactctt   6120
cctttttcaa tattattgaa gcatttatca gggttattgt ctcatgagcg gatacatatt   6180
tgaatgtatt tagaaaaata aacaaatagg ggttccgcgc acatttcccc gaaaagtgcc   6240
acctgacgtc                                                            6250
```

```
SEQ ID NO: 13               moltype = AA   length = 341
FEATURE                     Location/Qualifiers
REGION                      1..341
                            note = IL4R-SSGSSGTG-meGFP-KB1753
source                      1..341
                            mol_type = protein
                            organism = synthetic construct
SEQUENCE: 13
MAAGPRTSLL LAFALLCLPW TNGGVAFPAM SSDPDGTDTE QHLLLGVSVS CIVILAVCLL   60
CYVSITVEKN DEDQNSSGSS GTGSKGEELF TGVVPILVEL DGDVNGHKFS VSGEGEGDAT   120
YGKLTLKFIC TTGKLPVPWP TLVTTLTYGV QCFSRYPDHM KRHDFFKSAM PEGYVQERTI   180
FFKDDGNYKT RAEVKFEGDT LVNRIELKGI DFKEDGNILG HKLEYNYNSH NVYIMADKQK   240
NGIKANFKIR HNIESGGVQL ADHYQQNTPI GDGPVLLPDN HYLSTQSKLS KDPNEKRDHM   300
VLKERVTAAG ITHGMDELYK GSSRGYYHGI WVGEEGRLSR G                        341
```

```
SEQ ID NO: 14               moltype = DNA   length = 6418
FEATURE                     Location/Qualifiers
misc_feature                1..6418
                            note = IL4R-SSGSSGTG-meGFP-KB1753
source                      1..6418
                            mol_type = other DNA
                            organism = synthetic construct
SEQUENCE: 14
gacggatcgg gagatctccc gatccctat ggtgcactct cagtacaatc tgctctgatg   60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgtttttgcg ctgcttcgcg atgtacgggc cagatatacg cgttgacatt   240
gattattgac tagttattaa tagtaatcaa ttacgggatc attagttcat agccccatata   300
tggagttccg cgttacataa cttacggtaa atggcccgcc tggctgaccg cccaacgacc   360
cccgcccatt gacgtcaata atgacggtatg ttcccatagt aacgccaata gggactttcc   420
attgacgtca atgggtggag tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aatgtcgta acaactccgc cccattgacg caaatgggcg   780
gtaggcgtgt acggtgggag gtctatataa gcagagctct ctggctaact agagaaccca   840
ctgcttactg gcttatcgaa attaatacga ctcactatag ggagacccaa gctggctagc   900
gtttaaactt aagcttggta ccgacggacc atggccgccg gccccaggac cagcctgctg   960
ctggccttcg ccctgctgtg cctgccctgg accaacggcg gcgtggcctt ccccgccatg   1020
agcagcgacc ccgacggcac cgacaccgag cagcacctgc tgctgggcgt gagcgtgagc   1080
tgcatcgtga tcctggccgt gtgcctgctg tgctacgtga gcatcaccgt ggagaagaac   1140
gacgaggacc agaattcctc cggatcgtct ggaaccggtt ctaaaggaga agaacttttc   1200
actggagttg tcccaattct tgttgaatta gatggtgatg ttaatgggca caaattttc   1260
gtcagtggag agggtgaagg tgatgcaaca tacggaaaac ttacccttaa atttatttgc   1320
actactggaa aactacctgt tccttggcca cacttgtca ctactttaac ttatggtgtt   1380
caatgctttt caagataccc agatcatatg aaacggcatg acttttttcaa gagtgccatg   1440
cccgaaggtt atgtacagga agaactata ttttttcaaga atgacgggaa ctacaagaca   1500
cgtgctgaag tcaagtttga aggtgatacc cttgttaata gaatcgagtt aaaaggtatt   1560
gattttaaag aagatggaaa cattcttgga cacaaattgg aatacaacta taactcacac   1620
aatgtataca tcatggcaga caaacaaaag aatggaatca agctaacttt caaaattaga   1680
cacaacattg agtccggagg cgttcaacta gcagaccatt atcaacaaaa tactccaatt   1740
ggcgatggcc ctgtcctttt accagacaac cattacctgt ccacacaatc taagctttcg   1800
aaagatccca cgaaaagag agaccacatg gtccttaaag agagggtaac agctgctggg   1860
attacacatg gcatggacga gctgtacaag ggatcctcta gaggttacta ccatggtatt   1920
tgggtgggtg aagaaggtcg actttctcga ggataatgaa ggtggcggcc gctcgaaact   1980
agagggcccg tttaaacccg ctgatcagcc tcgactgtgc cttctagttg ccagccatct   2040
gttgtttgcc cctcccccgt gccttccttg accctggaag gtgccactcc cactgtcctt   2100
tcctaataaa atgaggaaat tgcatcgcat tgtctgagta ggtgtcattc tattctgggg   2160
ggtggggtgg ggcaggacag caagggggag gattgggaag acaatagcag gcatgctggg   2220
gatgcggtgg gctctatggc ttctgaggcg aaagaacca gctggggctc tagggggtat   2280
ccccacgcgc cctgtagcgg cgcattaagc gcggcgggtg tggtggttac gcgcagcgtg   2340
accgctacac ttgccagcgc cctagcgccc gctcctttcg ctttcttccc ttcctttctc   2400
gccacgttcg ccggctttcc ccgtcaagct ctaaatcggg gctcccttt agggttccga   2460
tttagtgctt tacggcacct cgaccccaaa aaacttgatt agggtgatgg ttcacgtagt   2520
gggccatcgc cctgatagac ggtttttcgc cctttgacgt tggagtccac gttctttaat   2580
agtggactct tgttccaaac tggaacaaca ctcaacccta tctcggtcta ttcttttgat   2640
ttataaggga ttttgccgat ttcggcctat tggttaaaaa atgagctgat ttaacaaaaa   2700
```

-continued

```
tttaacgcga attaattctg tggaatgtgt gtcagttagg gtgtggaaag tccccaggct   2760
ccccagcagg cagaagtatg caaagcatgc atctcaatta gtcagcaacc aggtgtggaa   2820
agtccccagg ctccccagca ggcagaagta tgcaaagcat gcatctcaat tagtcagcaa   2880
ccatagtccc gcccctaact ccgcccatcc cgcccctaac tccgcccagt tccgcccatt   2940
ctccgcccca tggctgacta atttttttta tttatgcaga ggccgaggcc gcctctgcct   3000
ctgagctatt ccagaagtag tgaggaggct ttttttggagg cctaggcttt tgcaaaaagc   3060
tcccgggagc ttgtatatcc attttcggat ctgatcaaga gacaggatga ggatcgtttc   3120
gcatgattga acaagatgga ttgcacgcag gttctccggc cgcttgggtg gagaggctat   3180
tcggctatga ctgggcacaa cagacaatcg gctgctctga tgccgccgtg ttccggctgt   3240
cagcgcaggg gcgcccggtt ctttttgtca agaccgacct gtccggtgcc ctgaatgaac   3300
tgcaggacga ggcagcgcgg ctatcgtggc tggccacgac gggcgttcct tgcgcagctg   3360
tgctcgacgt tgtcactgaa gcgggaaggg actggctgct attgggcgaa gtgccggggc   3420
aggatctcct gtcatctcac cttgctcctg ccgagaaagt atccatcatg gctgatgcaa   3480
tgcggcggct gcatacgctt gatccggcta cctgcccatt cgaccaccaa gcgaaacatc   3540
gcatcgagcg agcacgtact cggatggaag ccggtcttgt cgatcaggat gatctggacg   3600
aagagcatca ggggctcgcg ccagccgaac tgttcgccag gctcaaggcg cgcatgcccg   3660
acggcgagga tctcgtcgtg acccatggcg atgcctgctt gccgaatatc atggtggaaa   3720
atggccgctt ttctggattc atcgactgtg gccggctggg tgtggcggac cgctatcagg   3780
acatagcgtt ggctacccgt gatattgctg aagagcttgg cggcgaatgg gctgaccgct   3840
tcctcgtgct ttacggtatc gccgctcccg attcgcagcg catcgccttc tatcgccttc   3900
ttgacgagtt cttctgagcg ggactctggg gttcgaaatg accgaccaag cgacgcccaa   3960
cctgccatca cgagatttcg attccaccgc cgccttctat gaaaggttgg cgtcggaat   4020
cgttttccgg gacgccggct ggatgatcct ccagcgcggg gatctcatgc tggagttctt   4080
cgcccacccc aacttgttta ttgcagctta taatggttac aaataaagca atagcatcac   4140
aaatttcaca aataaagcat ttttttcact gcattctagt tgtggtttgt ccaaactcat   4200
caatgtatct tatcatgtct gtataccgtc gacctctaga tagagcttgg cgtaatcatg   4260
gtcatagctg tttcctgtgt gaaattgtta tccgctcaca attccacaca acatacgagc   4320
cggaagcata aagtgtaaag cctggggtgc ctaatgagtg agctaactca cattaattgc   4380
gttgcgctca ctgcccgctt tccagtcggg aaacctgtcg tgccagctgc attaatgaat   4440
cggccaacgc gcggggagag gcggtttgcg tattgggcgc tcttccgctt cctcgctcac   4500
tgactcgctg cgctcggtcg ttcggctgcg gcgagcggta tcagctcact caaaggcggt   4560
aatacggtta tccacagaat caggggataa cgcaggaaag aacatgtgag caaaaggcca   4620
gcaaaaggcc aggaaccgta aaaaggccgc gttgctggcg tttttccata ggctccgccc   4680
ccctgacgag catcacaaaa atcgacgctc aagtcagagg tggcgaaacc cgacaggact   4740
ataaagatac caggcgtttc ccccctggaag ctccctcgtg cgctctcctg ttccgacccct   4800
gccgcttacc ggatacctgt ccgcctttct cccttcggga agcgtggcgc tttctcatag   4860
ctcacgctgt aggtatctca gttcggtgta ggtcgttcgc tccaagctgg gctgtgtgca   4920
cgaacccccc gttcagcccg accgctgcgc cttatccggt aactatcgtc ttgagtccaa   4980
cccggtaaga cacgacttat cgccactggc agcagccact ggtaacagga ttagcagagc   5040
gaggtatgta ggcggtgcta cagagttctt gaagtggtgg cctaactacg gctacactag   5100
aagaacagta tttggtatct gcgctctgct gaagccagtt accttcggaa aaagagttgg   5160
tagctcttga tccggcaaac aaaccaccgc tggtagcggt ggtttttttg tttgcaagca   5220
gcagattacg cgcagaaaaa aaggatctca agaagatcct ttgatctttt ctacgggget   5280
tgacgctcag tggaacgaaa actcacgtta agggattttg gtcatgagat tatcaaaaag   5340
gatcttcacc tagatccttt taaattaaaa atgaagtttt aaatcaatct aaagtatata   5400
tgagtaaact tggtctgaca gttaccaatg cttaatcagt gaggcaccta tctcagcgat   5460
ctgtctattt cgttcatcca tagttgcctg actccccgtc gtgtagataa ctacgatacg   5520
ggagggctta ccatctggcc ccagtgctgc aatgataccg cgagacccac gctcaccggc   5580
tccagattta tcagcaataa accagccagc cggaagggcc gagcgcagaa gtggtcctgc   5640
aactttatcc gcctccatcc agtctattaa ttgttgccgg gaagctagag taagtagttc   5700
gccagttaat agtttgcgca acgttgttgc cattgctaca ggcatcgtgg tgtcacgctc   5760
gtcgtttggt atggcttcat tcagctccgg ttcccaacga tcaaggcgag ttacatgatc   5820
ccccatgttg tgcaaaaaag cggttagctc cttcggtcct ccgatcgttg tcagaagtaa   5880
gttggccgca gtgttatcac tcatggttat ggcagcactg cataattctc ttactgtcat   5940
gccatccgta agatgctttt ctgtgactgg tgagtactca accaagtcat tctgagaata   6000
gtgtatgcgg cgaccgagtt gctcttgccc ggcgtcaata cgggataata ccgcgccaca   6060
tagcagaact ttaaaagtgc tcatcattgg aaaacgttct tcggggcgaa aactctcaag   6120
gatcttaccg ctgttgagat ccagttcgat gtaacccact cgtgcaccca actgatcttc   6180
agcatctttt actttcacca gcgtttctgg gtgagcaaaa acaggaaggc aaaatgccgc   6240
aaaaaaggga ataagggcga cacggaaatg ttgaatactc atactcttcc tttttcaata   6300
ttattgaagc atttatcagg gttattgtct catgagcgga tacatatttg aatgtattta   6360
gaaaaataaa caaataggggg ttccgcgcac atttccccga aaagtgccac ctgacgtc     6418
```

```
SEQ ID NO: 15          moltype = AA  length = 293
FEATURE                Location/Qualifiers
REGION                 1..293
                       note = KB1753-meGFP-GS24-hRas
source                 1..293
                       mol_type = protein
                       organism = synthetic construct
SEQUENCE: 15
MSSRGYYHGI WVGEEGRLSR GKGEELFTGV VPILVELDGD VNGHKFSVSG EGEGDATYGK   60
LTLKFICTTG KLPVPWPTLV TTLTYGVQCF SRYPDHMKRH DFFKSAMPEG YVQERTIFFK   120
DDGNYKTRAE VKFEGDTLVN RIELKGIDFK EDGNILGHKL EYNYNSHNVY IMADKQKNGI   180
KANFKIRHNI ESGGVQLADH YQQNTPIGDG PVLLPDNHYL STQSKLSKDP NEKRDHMVLK   240
ERVTAAGITH GMDELYKGSK SSGSGSESKS TGKSTGSGTE TGGSCMSCKC VLS           293

SEQ ID NO: 16          moltype = DNA  length = 6289
FEATURE                Location/Qualifiers
```

-continued

```
misc_feature          1..6289
                      note = KB1753-meGFP-GS24-hRas
source                1..6289
                      mol_type = other DNA
                      organism = synthetic construct
SEQUENCE: 16
gacggatcgg gagatctccc gatcccctat ggtgcactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgtttgcg ctgcttcgcg atgtacgggc cagatatacg cgttgacatt    240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggag tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta acaactccgc cccattgacg caaatgggcg   780
gtaggcgtgt acggtgggag gtctatataa gcagagctct ctggctaact agagaaccca   840
ctgcttactg gcttatcgaa attaatacga ctcactatag ggagacccaa gctggctagc   900
ggtaccgagc tcggatcact agtccagtgt ggtggaattc tgcagatatc gcgttcttctag   960
aggttactac catggtattt gggtgggtga agaaggtcga ctttctcgag gtaaaggaga  1020
agaacttttc actggagttg tcccaattct tgttgaatta gatggtgatg ttaatgggca  1080
caaattttct gtcagtggag agggtgaagg tgatgcaaca tacggaaaac ttaccctaa   1140
atttatttgc actactggaa aactacctgt tccttggcca cacttgtca ctactttaac   1200
ttatggtgtt caatgctttt caagataccc agatcatatg aaacggcatg acttttcaa   1260
gagtgccatg cccgaaggtt atgtacagga agaactatat tttttcaaag atgacgggaa  1320
ctacaagaca cgtgctgaag tcaagtttga aggtgatacc cttgttaata gaatcgagtt  1380
aaaaggtatt gattttaaag aagatggaaa cattcttgga cacaaattgg aatacaacta  1440
taactcacac aatgtataca tcatggcaga caaacaaaag aatggaatca aagctaactt  1500
caaaattaga cacaacattg agtcaggagg cgttcaacta gcagaccatt atcaacaaaa  1560
tactccaatt ggcgatggcc ctgtcctttt accagacaac cattacctgt ccacacaatc  1620
taagctttcg aaagatccca acgaaaagag agaccacatg gtccttaaag agagggtaac  1680
agctgctggg attacacatg gcatggacga gctgtacaag ggatccaagt cttccggaag  1740
cgggagcgag tctaaatcaa caggcaagag cacaggttcc gggaccgaga cgggtggatc  1800
ctgcatgagc tgcaagtgtg tgctgtccta atgagcggcc gcactagagg cccgggccc    1860
gtttaaaccc gctgatcagc ctcgactgtg ccttctagtt gccagccatc tgttgtttgc  1920
ccctccccg tgccttcctt gaccctggaa ggtgccactc ccactgtcct ttcctaataa  1980
aatgaggaaa ttgcatcgca ttgtctgagt aggtgtcatt ctattctggg gggtgggggtg  2040
gggcaggaca gcaagggga ggattgggaa gacaatagca ggcatgctgg ggatgcggtg   2100
ggctctatgg cttctgaggc ggaaagaacc agctggggct ctagggggta tccccacgcg  2160
ccctgtagcg gcgcattaag cgcggcgggt gtggtggtta cgcgcagcgt gaccgctaca  2220
cttgccagcg ccctagcgcc cgctcctttc gctttcttcc cttcctttct cgccacgttc  2280
gccggctttc cccgtcaagc tctaaatcgg gggctccctt tagggttccg atttagtgct  2340
ttacggcacc tcgaccccaa aaaacttgat tagggtgatg gttcacgtag tgggccatcg  2400
ccctgataga cggtttttcg ccctttgacg ttggagtcca cgttctttaa tagtggactc  2460
ttgttccaaa ctggaacaac actcaaccct atctcggtct attcttttga tttataaggg  2520
attttgccga tttcggccta ttggttaaaa aatgagctga tttaacaaaa atttaacgcg  2580
aattaattct gtggaatgtg tgtcagttag ggtgtggaaa gtccccaggc tccccagcag  2640
gcagaagtat gcaaagcatg catctcaatt agtcagcaac caggtgtgga aagtccccag  2700
gctcccagc aggcagaagt atgcaaagca tgcatctcaa ttagtcagca accatagtcc   2760
cgcccctaac tccgcccatc ccgcccctaa ctccgcccag ttccgcccat tctccgcccc  2820
atggctgact aatttttttt atttatgcag aggccgaggc cgcctctgcc tctgagctat  2880
tccagaagta gtgaggaggc tttttttggag gcctaggctt ttgcaaaaag ctcccgggag  2940
cttgtatatc cattttcgga tctgatcaag agacaggatg aggatcgttt cgcatgattg  3000
aacaagatgg attgcacgca ggttctccgg ccgcttgggt ggagaggcta ttcggctatg  3060
actgggcaca acagacaatc ggctgctctg atgccgccgt gttccggctg tcagcgcagg  3120
ggcgcccggt tctttttgtc aagaccgacc tgtccggtgc cctgaatgaa ctgcaggacg  3180
aggcagcgcg gctatcgtgg ctggccacga cgggcgttcc ttgcgcagct gtgctcgacg  3240
ttgtcactga gcgggaagg gactggctgc tattgggcga agtgccgggg caggatctcc  3300
tgtcatctca ccttgctcct gccgagaaag tatccatcat ggctgatgca atgcggcggc  3360
tgcatacgct tgatccggct acctgcccat tcgaccacca agcgaaacat cgcatcgagc  3420
gagcacgtac tcggatggaa gccggtcttg tcgatcagga tgatctggac gaagagcatc  3480
aggggctcgc gccagccgaa ctgttcgcca ggctcaaggc gcgcatgccc gacggcgagg  3540
atctcgtcgt gacccatggc gatgcctgct tgccgaatat catggtggaa aatggccgct  3600
tttctggatt catcgactgt ggccggctgg gtgtggcgga ccgctatcag gacatagcgt  3660
tggctacccg tgatattgct gaagagcttg gcggcgaatg ggctgaccgc ttcctcgtgc  3720
tttacggtat cgccgctccc gattgcgagc gcatcgcctt ctatcgcctt cttgacgagt  3780
tcttctgagc gggactctgg ggttcgaaat gaccgaccaa gcgacgccca acctgccatc  3840
acgagatttc gattccaccg ccgccttcta tgaaaggttg ggcttcggaa tcgttttccg  3900
ggacgccggc tggatgatcc tccagcgcgg ggatctcatg ctggagttct tcgcccaccc  3960
caacttgttt attgcagctt ataatggtta caaataaagc aatagcatca caaatttcac  4020
aaataaagca tttttttcac tgcattctag ttgtggtttg tccaaactca tcaatgtatc  4080
ttatcatgtc tgtataccgt cgacctctag ctagagcttg gcgtaatcat ggtcatagct  4140
gtttcctgtg tgaaattgtt atccgctcac aattccacac aacatacgag ccggaagcat  4200
aaagtgtaaa gcctggggtg cctaatgagt gagctaactc acattaattg cgttgcgctc  4260
actgcccgct ttccagtcgg gaaacctgtc gtgccagctg cattaatgaa tcggccaacg  4320
cgcggggaga ggcggtttgc gtattgggcg ctcttccgct tcctcgctca ctgactcgct  4380
```

```
gcgctcggtc gttcggctgc ggcgagcggt atcagctcac tcaaaggcgg taatacggtt   4440
atccacagaa tcaggggata acgcaggaaa gaacatgtga gcaaaaggcc agcaaaaggc   4500
caggaaccgt aaaaaggccg cgttgctggc gtttttccat aggctccgcc ccctgacga    4560
gcatcacaaa aatcgacgct caagtcagag gtggcgaaac ccgacaggac tataaagata   4620
ccaggcgttt cccctggaa gctccctcgt gcgctctct gttccgaccc tgccgcttac     4680
cggatacctg tccgcctttc tcccttcggg aagcgtggcg ctttctcata gctcacgctg    4740
taggtatctc agttcggtgt aggtcgttcg ctccaagctg ggctgtgtgc acgaaccccc   4800
cgttcagccc gaccgctgcg ccttatccgg taactatcgt cttgagtcca acccggtaag   4860
acacgactta tcgccactgg cagcagccac tggtaacagg attagcagag cgaggtatgt   4920
aggcggtgct acagagttct tgaagtggtg gcctaactac ggctacacta gaagaacagt   4980
atttggtatc tgcgctctgc tgaagccagt taccttcgga aaaagagttg gtagctcttg   5040
atccggcaaa caaaccaccg ctggtagcgg tggttttttt gtttgcaagc agcagattac   5100
gcgcagaaaa aaaggatctc aagaagatcc tttgatcttt tctacggggt ctgacgctca   5160
gtggaacgaa aactcacgtt aagggatttt ggtcatgaga ttatcaaaaa ggatcttcac   5220
ctagatcctt ttaaattaaa aatgaagttt taaatcaatc taaagtatat atgagtaaac   5280
ttggtctgac agttaccaat gcttaatcag tgaggcacct atctcagcga tctgtctatt   5340
tcgttcatcc atagttgcct gactccccgt cgtgtagata actacgatac gggagggctt   5400
accatctggc cccagtgctg caatgatacc gcgagaccca cgctcaccgg ctccagattt   5460
atcagcaata aaccagccag ccggaagggc cgagcgcaga agtggtcctg caactttatc   5520
cgcctccatc cagtctatta attgttgccg ggaagctaga gtaagtagtt cgccagttaa   5580
tagtttcgc aacgttgttg ccattgctac aggcatcgtg gtgtcacgct cgtcgtttgg   5640
tatggcttca ttcagctccg gttcccaacg atcaaggcga gttacatgat cccccatgtt   5700
gtgcaaaaaa gcggttagct ccttcggtcc tccgatcgtt gtcagaagta agttggccgc   5760
agtgttatca ctcatggtta tggcagcact gcataattct cttactgtca tgccatccgt   5820
aagatgcttt tctgtgactg gtgagtactc aaccaagtca ttctgagaat agtgtatgcg   5880
gcgaccgagt tgctcttgcc cggcgtcaat acgggataat accgcgccac atagcagaac   5940
tttaaaagtg ctcatcattg gaaaacgttc ttcggggcga aaactctcaa ggatcttacc   6000
gctgttgaga tccagttcga tgtaacccac tcgtgcaccc aactgatctt cagcatcttt   6060
tactttcacc agcgtttctg ggtgagcaaa aacaggaagg caaaatgccg caaaaaaggg   6120
aataagggcg acacggaaat gttgaatact catactcttc ctttttcaat attattgaag   6180
catttatcag ggttattgtc tcatgagcgg atacatattt gaatgtattt agaaaaataa   6240
acaaataggg gttccgcgca catttccccg aaaagtgcca cctgacgtc               6289
```

```
SEQ ID NO: 17         moltype = AA  length = 267
FEATURE               Location/Qualifiers
REGION                1..267
                      note = KB1753-mScarlet-GSGGSGG-hRas
source                1..267
                      mol_type = protein
                      organism = synthetic construct
SEQUENCE: 17
MSSRGYYHGI WVGEEGRLSR VSKGEAVIKE FMRFKVHMEG SMNGHEFEIE GEGEGRPYEG    60
TQTAKLKVTK GGPLPFSWDI LSPQFMYGSR AFTKHPADIP DYYKQSFPEG FKWERVMNFE   120
DGGAVTVTQD TSLEDGTLIY KVKLRGTNFP PDGPVMQKKT MGWEASTERL YPEDGVLKGD   180
IKMALRLKDG GRYLADFKTT YKAKKPVQMP GAYNVDRKLD ITSHNEDYTV VEQYERSEGR   240
HSTGGMDELY KGSGGSGGCM SCKCVLS                                       267
```

```
SEQ ID NO: 18         moltype = DNA  length = 6211
FEATURE               Location/Qualifiers
misc_feature          1..6211
                      note = KB1753-mScarlet-GSGGSGG-hRas
source                1..6211
                      mol_type = other DNA
                      organism = synthetic construct
SEQUENCE: 18
gacggatcgg gagatctccc gatccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttaggggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc     360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagaccaa gctggctagc     900
ggtaccgagc tcggatcact agtccagtgt ggtggaattc acgcggacca tgtcttctag    960
aggttactac catggtattt gggtgggtga agaaggtcga ctttctcgag tgagcaaggg   1020
cgaggcagtg atcaaggagt tcatgcgttt caaggtgcac atggagggct ccatgaacgg   1080
ccacgagttc gagatcgagg gcgaggggcga gggccgcccc tacgagggca ccagaccgc    1140
caagctgaag gtgaccaagg gtggccccct gccttctcc tgggacatcc tgtcccctca    1200
gttcatgtac ggctccaggg ccttcaccaa gcaccccgcc gacatccccg actactataa   1260
gcagtccttc cccgagggct tcaagtggga gcgcgtgatg aacttcgagg acggcggcgc   1320
cgtgaccgtg acccaggaca cctccctgga ggacggcacc ctgatctaca aggtgaagct   1380
ccgcggcacc aacttccctc ctgacggccc cgtaatgcag aagaagacaa tgggctggga   1440
```

```
agcgtccacc gagcggttgt accccgagga cggcgtgctg aagggcgaca ttaagatggc   1500
cctgcgcctg aaggacggcg gccgctacct ggcggacttc aagaccacct acaaggccaa   1560
gaagcccgtg cagatgcccg cgcgcctacaa cgtcgaccgc aagttggaca tcacctccca   1620
caacgaggac tacaccgtgg tggaacagta cgaacgctcc gagggccgcc actccaccgg   1680
cggcatggac gagctgtaca agggatccgg tggaagtgga ggctgcatga gctgcaagtg   1740
tgtgctgtcc taatgagcgg ccgcactaga gggcccgggc ccgtttaaac ccgctgatca   1800
gcctcgactg tgccttctag ttgccagcca tctgttgttt gcccctcccc cgtgccttcc   1860
ttgacccctgg aaggtgccac tcccactgtc ctttcctaat aaaatgagga aattgcatcg   1920
cattgtctga gtaggtgtca ttctattctg gggggtgggg tggggcagga cagcaagggg   1980
gaggattggg aagacaatag caggcatgct ggggatgcgg tgggctctat ggcttctgag   2040
gcggaaagaa ccagctgggg ctctagggggg tatccccacg cgccctgtag cggcgcatta   2100
agcgcggcgg gtgtggtggt tacgcgcagc gtgaccgcta cacttgccag cgccctagcg   2160
cccgctcctt tcgctttctt cccttccttt ctcgccacgt tcgccggctt tccccgtcaa   2220
gctctaaatc gggggctccc tttagggttc cgatttagtg ctttacggca cctcgacccc   2280
aaaaaacttg attagggtga tggttcacgt agtgggccat cgccctgata gacggttttt   2340
cgcccttga cgttggagtc cacgttcttt aatagtggac tcttgttcca aactggaaca   2400
acactcaacc ctatctcggt ctattctttt gatttataag ggattttgcc gatttcggcc   2460
tattggttaa aaaatgagct gatttaacaa aaatttaacg cgaattaatt ctgtggaatg   2520
tgtgtcagtt agggtgtgga aagtccccag gctccccagc aggcagaagt atgcaaagca   2580
tgcatctcaa ttagtcagca accaggtgtg gaaagtcccc aggctcccca gcaggcagaa   2640
gtatgcaaag catgcatctc aattagtcag caaccatagt cccgccccta actccgccca   2700
tcccgcccct aactccgccc attctccgcc ccatggctga ctaattttttt   2760
ttatttatgc agaggccgag gccgcctctg cctctgagct attccagaag tagtgaggag   2820
gcttttttgg aggcctaggc ttttgcaaaa agctcccggg agcttgtata tccatttttcg   2880
gatctgatca agagacagga tgaggatcgt ttcgcatgat tgaacaagat ggattgcacg   2940
caggttctcc ggccgcttgg gtgggagaggc tattcggcta tgactgggca caacagacaa   3000
tcggctgctc tgatgccgcc gtgttccggc tgtcagcgca ggggcgcccg gttcttttttg   3060
tcaagaccga cctgtccggt gccctgaatg aactgcagga cgaggcagcg cggctatcgt   3120
ggctggccac gacgggcgtt ccttgcgcag ctgtgctcga cgttgtcact gaagcgggaa   3180
gggactggct gctattgggc gaagtgccgg ggcaggatct cctgtcatct caccttgctc   3240
ctgccgagaa agtatccatc atggctgatg caatgcggcg gctgcatacg cttgatccgg   3300
ctacctgccc attcgaccac caagcgaaac atcgcatcga gcgagcacgt actcggatgg   3360
aagccggtct tgtcgatcag gatgatctgg acgaagagca tcaggggctc gcgccagccg   3420
aactgttcgc caggctcaag gcgcgcatgc ccgacgcgcga ggatctcgtc gtgacccatg   3480
gcgatgcctg cttgccgaat atcatggtgg aaaatggccg cttttctgga ttcatcgact   3540
gtggccggct gggtgtggcg gaccgctatc aggacatagc gttggctacc cgtgatattg   3600
ctgaagagct tggcggcgaa tgggctgacc gcttcctcgt gctttacggt atcgccgctc   3660
ccgattcgca gcgcatcgcc ttctatcgcc ttcttgacga gttcttctga gcgggactct   3720
ggggttcgaa atgaccgacc aagcgacgcc caacctgcca tcacgagatt tcgattccac   3780
cgccgccttc tatgaaaggt tgggcttcgg aatcgttttc cgggacgccg gctggatgat   3840
cctccagcgc ggggatctca tgctggagtt cttcgcccac cccaacttgt ttattgcagc   3900
ttataatggt tacaaataaa gcaatagcat cacaaatttc acaaataaag catttttttc   3960
actgcattct agttgtggtt tgtccaaact catcaatgta tcttatcatg tctgtatacc   4020
gtcgacctct agctagagct tggcgtaatc atggtcatag ctgtttcctg tgtgaaattg   4080
ttatccgctc acaattccac acaacatacg agccggaagc ataaagtgta aagcctgggg   4140
tgcctaatga gtgagctaac tcacattaat tgcgttgcgc tcactgcccg ctttccagtc   4200
gggaaacctg tcgtgccagc tgcattaatg aatcggccaa cgcgcgggga gaggcggttt   4260
gcgtattggg cgctcttccg cttcctcgct cactgactcg ctgcgctcgg tcgttcggct   4320
gcggcgagcg gtatcagctc actcaaaggc ggtaatacgg ttatccacag aatcaggggga   4380
taacgcagga aagaacatgt gagcaaaagg ccagcaaaag gccaggaacc gtaaaaaggc   4440
cgcgttgctg gcgtttttcc ataggctccg ccccccctgac gagcatcaca aaatcgacgc   4500
ctcaagtcag aggtggcgaa acccgacagg actataaaga taccaggcgt ttccccctgg   4560
aagctccctc gtgcgctctc ctgttccgac cctgccgctt accggatacc tgtccgcctt   4620
tctcccttcg ggaagcgtgg cgctttctca tagctcacgc tgtaggtatc tcagttcggt   4680
gtaggtcgtt cgctccaagc tgggctgtgt gcacgaaccc cccgttcagc ccgaccgctg   4740
cgccttatcc ggtaactatc gtcttgagtc caacccggta agacacgact tatcgccact   4800
ggcagcagcc actggtaaca ggattagcag agcgaggtat gtaggcggtg ctacagagtt   4860
cttgaagtgg tggcctaact acggctacac tagaagaaca gtatttggta tctgcgctct   4920
gctgaagcca gttaccttcg gaaaaagagt tggtagctct tgatccggca aacaaaccac   4980
cgctggtagc ggtggttttt ttgtttgcaa gcagcagatt acgcgcagaa aaaaaggatc   5040
tcaagaagat cctttgatct tttctacggg gtctgacgct cagtggaacg aaaactcacg   5100
ttaagggatt ttggtcatga gattatcaaa aaggatcttc acctagatcc ttttaaatta   5160
aaaatgaagt tttaaatcaa tctaaagtat atatgagtaa acttggtctg acagttacca   5220
atgcttaatc agtgaggcac ctatctcagc gatctgtcta tttcgttcat ccatagttgc   5280
ctgactcccc gtcgtgtaga taactacgat acgggagggc ttaccatctg gccccagtgc   5340
tgcaatgata ccgcgagacc cacgctcacc ggctccagat ttatcagcaa taaaccagcc   5400
agccggaagg gccgagcgca gaagtggtcc tgcaacttta tccgcctcca tccagtctat   5460
taattgttgc cgggaagcta gagtaagtag ttcgccagtt aatagtttgc gcaacgttgt   5520
tgccattgct acaggcatcg tggtgtcacg ctcgtcgttt ggtatggctt cattcagctc   5580
cggttcccaa cgatcaaggc gagttacatg atcccccatg ttgtgcaaaa aagcggttag   5640
ctccttcggt cctccgatcg ttgtcagaag taagttggcc gcagtgttat cactcatggt   5700
tatggcagca ctgcataatt ctcttactgt catgccatcc gtaagatgct tttctgtgac   5760
tggtgagtac tcaaccaagt cattctgaga atagtgtatg cggcgaccga gttgctcttg   5820
cccggcgtca atacgggata ataccgcgcc acatagcaga actttaaaag tgctcatcat   5880
tggaaaacgt tcttcggggc gaaaactctc aaggatctta ccgctgttga atccagttc    5940
gatgtaaccc actcgtgcac ccaactgatc ttcagcatct tttactttca ccagcgtttc   6000
tgggtgagca aaaacaggaa ggcaaaatgc cgcaaaaaag gaataaggg cgacacggaa    6060
atgttgaata ctcatactct ccttttttca atattattga agcatttatc agggttattg   6120
tctcatgagc ggatacatat ttgaatgtat ttagaaaaat aaacaaatag gggttccgcg   6180
```

-continued

```
cacatttccc cgaaaagtgc cacctgacgt c                                    6211

SEQ ID NO: 19              moltype = AA   length = 279
FEATURE                    Location/Qualifiers
REGION                     1..279
                           note = KB1753-cpmTurquoise2-GSGGSGG-hRas
source                     1..279
                           mol_type = protein
                           organism = synthetic construct
SEQUENCE: 19
MSSRGYYHGI WVGEEGRLSR VPVPWPTLVT TLSWGVQCFA RYPDHMKQHD FFKSAMPEGY    60
VQERTISFKD DGTYKTRAEV KFEGDTLVNR IELKGIDFKE DGNILGHKLE YNYFSDNVYI    120
TADKQKNGIK ANFKIRHNVE DGGVQLADHY QQNTPIGDGP VLLPDNHYLS TQSKLSKDPN    180
EKRDHMVLLE FVTAAGITLG MDELYKGGGS GSKGEELFTG VVPILVELDG DVNGHKFSVR    240
GEGEGDATNG KLTLKFICTT GKLGSGGSGG CMSCKCVLS                           279

SEQ ID NO: 20              moltype = DNA   length = 6247
FEATURE                    Location/Qualifiers
misc_feature               1..6247
                           note = KB1753-cpmTurquoise2-GSGGSGG-hRas
source                     1..6247
                           mol_type = other DNA
                           organism = synthetic construct
SEQUENCE: 20
gacggatcgg gagatctccc gatccctat ggtgcactct cagtacaatc tgctctgatg    60
ccgcatagtt aagccagtat ctgctccctg cttgtgtgct ggaggtcgct gagtagtgcg    120
cgagcaaaat ttaagctaca caaggcaag gcttgaccga caattgcatg aagaatctgc     180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
ggtaccgagc tcggatcact agtccagtgt ggtggaattc acgcggacca tgtcttctag    960
aggttactac catggtattt gggtgggtga agaaggtcga cttttctcgag tgccagtgcc    1020
ttggccaacc ctcgtgacca ccctgtcctg gggcgtgcag tgcttcgccc gctacccccga   1080
ccacatgaag cagcacgact tcttcaagtc cgccatgccc gaaggctacg tccaggacga    1140
caccatcagc ttcaaggacg acggcacata caagacccgc gccgaggtga agttcgaggg    1200
cgacaccctg gtgaaccgca tcgagctgaa gggcatcgac ttcaaggagg acggcaacat    1260
cctggggcac aagctggagt acaactactt tagcgacaac gtctatatca ccgccgacaa    1320
gcagaagaac ggcatcaagg ccaacttcaa gatccgccac aacgtggagg acggcggcgt    1380
gcagctcgcc gaccactacc agcagaacac ccccatcggc gacggccccg tgctgctgcc    1440
cgacaaccac tacctgagca cccagtccaa gctgagcaaa gaccccaacg agaagcgcga    1500
tcacatggtc ctgctggagt tcgtgaccgc cgccgggatc actctcggca tggacgagct    1560
gtacaagggc ggtggcagcg ggagcaaggg cgaggagctg ttcaccgggg tggtgcccat    1620
cctggtcgag ctggacggcg acgtaaacgg ccacaagttc agcgtgcgcg gcgagggcga    1680
gggcgatgcc accaatggca agctgaccct gaagttcatc tgcaccaccg gcaagctggg    1740
atccggtgga agtggaggct gcatgagctg caagtgtgtg ctgtcctaat gagcggccgc    1800
actagaggg ccggcccgt ttaaacccgc tgatcagcct cgactgtgcc ttctagttgc     1860
cagccatctg ttgtttgccc ctcccccgtg ccttccttga ccctggaagg tgccactccc    1920
actgtccttt cctaataaaa tgaggaaatt gcatcgcatt gtctgagtag gtgtcattct    1980
attctgggg gtggggtggg gcaggacagc aagggggagg attgggaaga caatagcagg    2040
catgctgggg atgcggtggg ctctatggct tctgaggcgg aaagaaccag ctggggctct    2100
aggggggtatc cccacgcgcc ctgtagcggc gcattaagcg cggcgggtgt ggtggttacg    2160
cgcagcgtga ccgctacact tgccagcgcc ctagcgcccg ctcctttcgc tttcttccct    2220
tcctttctcg ccacgttcgc cggctttccc cgtcaagctc taaatcgggg ctccctttagg   2280
gggttccgat ttagtgcttt acggcacctc gaccccaaaa aacttgatta gggtgatggt    2340
tcacgtagtg ggccatcgcc ctgatagacg gtttttcgcc ctttgacgtt ggagtccacg    2400
ttctttaata gtggactctt gttccaaact ggaacaacac tcaacccctat ctcggtctat    2460
tcttttgatt tataagggat tttgccgatt tcggcctatt ggttaaaaaa tgagctgatt    2520
taacaaaaat ttaacgcgaa ttaattctgt ggaatgtgtg tcagttaggg tgtggaaagt    2580
ccccaggctc cccagcaggc agaagtatgc aaagcatgca tctcaattag tcagcaacca    2640
ggtgtggaaa gtcccaggc tccccagcag gcagaagcat gcatctcaatt catctcaatt   2700
agtcagcaac catagtcccg cccctaactc cgcccatccc gcccctaact ccgcccagtt    2760
ccgcccattc tccgccccat ggctgactaa tttttttat ttatgcagag gccgaggccg     2820
cctctgcctc tgagctattc cagaagtagt gaggaggctt ttttggaggc ctaggctttt    2880
gcaaaaagct cccgggagct gtatatcca ttttcggatc tgatcaagag acaggatgag     2940
gatcgtttcg catgattgaa caagatggat tgcacgcagg ttctccggcc gcttgggtgg    3000
agaggctatt cggctatgac tgggcacaac agacaatcgg ctgctctgat gccgccgtgt    3060
tccggctgtc agcgcagggg cgcccggttc tttttgtcaa gaccgacctg tccggtgccc    3120
tgaatgaact gcaggacgag gcagcgcggc tatcgtggct ggccacgacg ggcgttcctt    3180
gcgcagctgt gctcgacgtt gtcactgaag cgggaaggga ctggctgcta ttgggcgaag    3240
tgccggggca ggatctcctg tcatctcacc ttgctcctgc cgagaaagta tccatcatgg    3300
```

```
ctgatgcaat gcggcggctg catacgcttg atccggctac ctgcccattc gaccaccaag    3360
cgaaacatcg catcgagcga gcacgtactc ggatggaagc cggtcttgtc gatcaggatg    3420
atctggacga agagcatcag gggctcgcgc cagccgaact gttcgccagg ctcaaggcgc    3480
gcatgcccga cggcgaggat ctcgtcgtga cccatggcga tgcctgcttg ccgaatatca    3540
tggtggaaaa tggccgcttt tctggattca tcgactggtg ccggctgggt gtggcggacc    3600
gctatcagga catagcgttg gctacccgtg atattgctga agagcttggc ggcgaatggg    3660
ctgaccgctt cctcgtgctt tacggtatcg ccgctcccga ttcgcagcgc atcgccttct    3720
atcgccttct tgacgagttc ttctgagcgg gactctgggg ttcgaaatga ccgaccaagc    3780
gacgcccaac ctgccatcac gagatttcga ttccaccgcc gccttctatg aaaggttggg    3840
cttcggaatc gttttccggg acgccggctg gatgatcctc cagcgcgggg atctcatgct    3900
ggagttcttc gcccaccccca acttgtttat tgcagcttat aatggttaca aataaagcaa    3960
tagcatcaca aatttcacaa ataaagcatt ttttcactg cattctagtt gtggtttgtc     4020
caaactcatc aatgtatctt atcatgtctg tataccgtcg acctctagct agagcttggc    4080
gtaatcatgg tcatagctgt ttcctgtgtg aaattgttat ccgctcacaa ttccacacaa    4140
catacgagcc ggaagcataa agtgtaaagc ctggggtgcc taatgagtga gctaactcac    4200
attaattgcg ttgcgctcac tgcccgcttt ccagtcggga aacctgtcgt gccagctgca    4260
ttaatgaatc ggccaacgcg cggggagagg cggtttgcgt attgggcgct cttccgcttc    4320
ctcgctcact gactcgctgc gctcggtcgt tcggctgcgg cgagcggtat cagctcactc    4380
aaaggcggta atacggttat ccacagaatc aggggataac gcaggaaaga acatgtgagc    4440
aaaaggccag caaaaggcca ggaaccgtaa aaaggccgcg ttgctggcgt ttttccatag    4500
gctccgcccc cctgacgagc atcacaaaaa tcgacgctca agtcagaggt ggcgaaaccc    4560
gacaggacta taaagatacc aggcgtttcc ccctggaagc tccctcgtgc gctctcctgt    4620
tccgaccctg ccgcttaccg gatacctgtc cgcctttctc ccttcgggaa gcgtggcgct    4680
ttctcatagc tcacgctgta ggtatctcag ttcggtgtag gtcgttcgct ccaagctggg    4740
ctgtgtgcac gaacccccccg ttcagcccga ccgctgcgcc ttatccggta actatcgtct    4800
tgagtccaac ccggtaagac acgacttatc gccactggca gcagccactg gtaacaggat    4860
tagcagagcg aggtatgtag gcggtgctac agagttcttg aagtggtggc ctaactacgg    4920
ctacactaga agaacagtat ttggtatctg cgctctgctg aagccagtta ccttcggaaa    4980
aagagttggt agctcttgat ccggcaaaca aaccaccgct ggtagcggtg gtttttttgt     5040
ttgcaagcag cagattacgc gcagaaaaaa aggatctcaa gatatcctt gatcttttc       5100
tacgggtct gacgctcagt ggaacgaaaa ctcacgttaa gggattttgg tcatgagatt       5160
atcaaaaagg atcttcacct agatcctttt aaattaaaaa tgaagtttta aatcaatcta     5220
aagtatatat gagtaaactt ggtctgacag ttaccaatgc ttaatcagtg aggcacctat    5280
ctcagcgatc tgtctatttc gttcatccat agttgcctga ctccccgtcg tgtagataac    5340
tacgatacgg gagggcttac catctggccc cagtgctgca atgataccgc gagacccacg    5400
ctcaccggct ccagatttat cagcaataaa ccagccagcc ggaagggccg agcgcagaag    5460
tggtcctgca actttatccg cctccatcca gtctattaat tgttgccggg aagctagagt     5520
aagtagttcg ccagttaata gtttgcgcaa cgttgttgcc attgctacag gcatcgtggt    5580
gtcacgctcg tcgtttggta tggcttcatt cagctccggt tcccaacgat caaggcgagt    5640
tacatgatcc cccatgttgt gcaaaaaagc ggttagctcc ttcggtcctc cgatcgttgt    5700
cagaagtaag ttggccgcag tgttatcact catggttatg gcagcactgc ataattctct    5760
tactgtcatg ccatccgtaa gatgcttttc tgtgactggt gagtactcaa ccaagtcatt    5820
ctgagaatag tgtatgcggc gaccgagttg ctcttgcccg gcgtcaatac gggataatac    5880
cgcgccacat agcagaactt taaaagtgct catcattgga aaacgttctt cggggcgaaa    5940
actctcaagg atcttaccgc tgttgagatc cagttcgatg taacccactc gtgcacccaa    6000
ctgatcttca gcatctttta ctttcaccag cgtttctggg tgagcaaaaa caggaaggca    6060
aaatgccgca aaaaagggaa taagggcgac acggaaatgt tgaatactca tactcttcct    6120
ttttcaatat tattgaagca tttatcaggg ttattgtctc atgagcggat acatatttga    6180
atgtatttag aaaaataaac aaataggggt tccgcgcaca tttccccgaa aagtgccacc    6240
tgacgtc                                                              6247
```

SEQ ID NO: 21          moltype = AA   length = 332
FEATURE                Location/Qualifiers
REGION                 1..332
                       note = KB1753-HALO-GSGGSGG-hRas
source                 1..332
                       mol_type = protein
                       organism = synthetic construct
SEQUENCE: 21
MSSRGYYHGI WVGEEGRLSR AEIGTGFPFD PHYVEVLGER MHYVDVGPRD GTPVLFLHGN    60
PTSSYVWRNI IPHVAPTHRC IAPDLIGMGK SDKPDLGYFF DDHVRFMDAF IEALGLEEVV    120
LVIHDWGSAL GFHWAKRNPE RVKGIAFMEF IRPIPTWDEW PEFARETFQA FRTTDVGRKL    180
IIDQNVFIEG TLPMGVVRPL TEVEMDHYRE PFLNPVDREP LWRFPNELPI AGEPANIVAL    240
VEEYMDWLHQ SPVPKLLFWG TPGVLIPPAE AARLAKSLPN CKAVDIGPGL NLLQEDNPDL    300
IGSEIARWLS TLEISGGSGG SGGCMSCKCV LS                                 332

SEQ ID NO: 22          moltype = DNA   length = 6406
FEATURE                Location/Qualifiers
misc_feature           1..6406
                       note = KB1753-HALO-GSGGSGG-hRas
source                 1..6406
                       mol_type = other DNA
                       organism = synthetic construct
SEQUENCE: 22
gacggatcgg gagatctccc gatccctat ggtgcactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
```

-continued

```
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggag tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta acaactccgc cccattgacg caaatgggcg   780
gtaggcgtgt acggtgggag gtctatataa gcagagctct ctggctaact agagaaccca   840
ctgcttactg gcttatcgaa attaatacga ctcactatag ggagacccaa gctggctagc   900
ggtaccgagc tcgatcact  agtccagtgt ggtggaattc acgcggacca tgtcttctag   960
aggttactac catggtattt gggtgggtga agaaggtcga ctttctcgag cagaaatcgg  1020
tactggcttt ccattcgacc cccattatgt ggaagtcctg ggcgagcgca tgcactacgt  1080
cgatgttggt ccgcgcgatg gcaccccctgt gctgttcctg cacggtaacc cgacctcctc  1140
ctacgtgtgg cgcaacatca tcccgcatgt tgcaccgacc catcgctgca ttgctccaga  1200
cctgatcggt atgggcaaat ccgacaaacc agacctgggt tatttcttcg acgaccacgt  1260
ccgcttcatg gatgccttca tcgaagccct gggtctggaa gaggtcgtcc tggtcattca  1320
cgactggggc tccgctctgg gtttccactg ggccaagcgc aatccagagc cgtcaaagg   1380
tattgcattt atggagttca tccgccctat cccgacctgg gacgaatggc cagaatttgc  1440
ccgcgagacc ttccaggcct tccgcaccac cgacgtcggc cgcaagctga tcatcgatca  1500
gaacgttttt atcgagggta cgctgccgat gggtgtcgtc cgcccgctga ctgaagtcga  1560
gatggaccat taccgcgagc cgttcctgaa tcctgttgac cgtggcgctt  1620
cccaaacgag ctgccaatcg ccggtgagcc agcgaacatc gtcgcgctgg tcgaagaata  1680
catggactgg ctgcaccagt cccctgtccc gaagctgctg ttctgggca ccccaggcgt  1740
tctgatccca ccggccgaag ccgctcgcct ggccaaaagc ctgcctaact gcaaggctgt  1800
ggacatcggc ccgggtctga atctgctgca agaagacaac ccggacctga tcggcagcga  1860
gatcgcgcgc tggctgtcga cgctcgaaat ttccggcgga tccggtggaa gtggaggctg  1920
catgagctgc aagtgtgtgc tgtcctaatg agcggccgca ctagagggcc cgggcccgtt  1980
taaacccgct gatcagcctc gactgtgcct tctagttgcc agccatctgt tgtttgcccc  2040
tccccgtga cttccttgac cctggaaggt gccactcca ctgtcctttc ctaataaaat  2100
gaggaaattg catcgcattg tctgagtagg tgtcattcta ttctgggggg tggggtgggg  2160
caggacagca aggggaggga ttgggaagac aatagcaggc atgctgggga tgcggtgggc  2220
tctatggctt ctgaggcgga aagaaccagc tggggctcta gggggtatcc ccacgcgccc  2280
tgtagcggcg cattaagcgc ggcgggtgtg gtggttacgc gcagcgtgac cgctacactt  2340
gccagcgccc tagcgcccgc tcctttcgct ttcttccctt cctttctcgc cacgttcgcc  2400
ggctttcccc gtcaagctct aaatcggggg ctccctttag ggttccgatt tagtgcttta  2460
cggcacctcg accccaaaaa acttgattag ggtgatggtt cacgtagtgg gccatcgccc  2520
tgatagacgg ttttttcgcc ctttgacgtt ggagtccacg tctttaatag tggactcttg  2580
ttccaaactg gaacaacact caacctatc tcggtctatt ctttttgattt ataagggatt  2640
ttgccgattt cggcctattg gttaaaaaat gagctgattt aacaaaaatt taacgcgaat  2700
taattctgtg gaatgtgtgt cagttagggt gtggaaagtc cccaggctcc ccagcaggca  2760
gaagtatgca aagcatgcat ctcaattagt cagcaaccag gtgtggaaag tccccaggct  2820
ccccagcagg cagaagtatg caaagcatgc atctcaatta cagtgtcaacc atagtcccgc  2880
ccctaactcc gcccatcccg cccctaactc cgcccagttc cgcccattct ccgccccatg  2940
gctgactaat ttttttttatt tatgcagagg ccgaggccgc ctctgcctct gagctattcc  3000
agaagtagtg aggaggcttt tttggaggcc taggcttttg caaaaagctc ccgggagctt  3060
gtatatccat tttcggatct gatcaagaga caggatgagg atcgtttcgc atgattgaac  3120
aagatggatt gcacgcaggt tctccggccg cttgggtgga gaggctattc ggctatgact  3180
gggcacaaca gacaatcggc tgctctgatg ccgccgtgtt ccggctgtca gcgcaggggc  3240
gcccggttct ttttgtcaag accgacctgt ccggtgccct gaatgaactg caggacgagg  3300
cagcgcggct atcgtggctg gccacgacgg cgttccttgc gcagctgtgt ctcgacgtt  3360
tcactgaagc gggaagggac tggctgctat tgggcgaagt gccggggcag gatctcctgt  3420
catctcacct tgctcctgcc gagaaagtat ccatcatggc tgatgcaatg cggcggctgc  3480
atacgcttga tccggctacc tgcccattcg accaccaagc gaaacatcgc atcgagcgag  3540
cacgtactcg gatggaagcc ggtcttgtcg atcaggatga tctggacgaa gagcatcagg  3600
ggctcgcgcc agccgaactg ttcgccaggc tcaaggcgcg catgcccgac ggcgaggatc  3660
tcgtcgtgac ccatggcgat gcctgcttgc cgaatatcat ggtggaaaat ggccgctttt  3720
ctggattcat cgactgtggc cggctgggtg tggcggaccg ctatcaggac atagcgttgg  3780
ctacccgtga tattgctgaa gagcttggcg gcgaatgggc tgaccgcttc ctcgtgcttt  3840
acggtatcgc cgctcccgat tcgcagcgca tcgccttcta tcgccttctt gacgagttct  3900
tctgagcggg actctggggt tcgaaatgac cgaccaagcg acgcccaacc tgccatcacg  3960
agatttcgat tccaccgccg ccttctatga aaggttgggc ttcggaatcg ttttccggga  4020
cgccggctgg atgatcctcc agcgcgggga tctcatgctg gagttcttcg cccaccccaa  4080
cttgtttatt gcagcttata atggttacaa ataaagcaat agcatcacaa atttcacaaa  4140
taaagcattt ttttcactgc attctagttg tggtttgtcc aaactcatca atgtatctta  4200
tcatgtctgt ataccgtcga cctctagcta gagcttggcg taatcatggt catagctgtt  4260
tcctgtgtga aattgttatc cgctcacaat tccacacaac atacgagccg gaagcataaa  4320
gtgtaaagcc tggggtgcct aatgagtgag ctaactcaca ttaattgcgt tgcgctcact  4380
gcccgctttc cagtcgggaa acctgtcgtg ccagctgcat taatgaatcg gccaacgcgc  4440
ggggagaggc ggtttgcgta ttgggcgctc ttccgcttcc tcgctcactg actcgctgcg  4500
ctcggtcgtt cggctgcggc gagcggtatc agctcactca aaggcggtaa tacggttatc  4560
cacagaatca ggggataacg caggaaagaa catgtgagca aaaggccagc aaaaggccag  4620
gaaccgtaaa aaggccgcgt tgctggcgtt tttccatagg ctccgccccc ctgacgagca  4680
tcacaaaaat cgacgctcaa gtcagaggtg gcgaaacccg acaggactat aaagatacca  4740
ggcgtttccc cctggaagct ccctcgtgcg ctctcctgtt ccgaccctgc cgcttaccgg  4800
atacctgtcc gcctttctcc cttcgggaag cgtggcgctt tctcatagct cacgctgtag  4860
gtatctcagt tcggtgtagg tcgttcgctc caagctgggc tgtgtgcacg aaccccccgt  4920
tcagcccgac cgctgcgcct tatccggtaa ctatcgtctt gagtccaacc cggtaagaca  4980
cgacttatcg ccactggcag cagccactgg taacaggatt agcagagcga ggtatgtagg  5040
```

-continued

```
cggtgctaca gagttcttga agtggtggcc taactacggc tacactagaa gaacagtatt   5100
tggtatctgc gctctgctga agccagttac cttcggaaaa agagttggta gctcttgatc   5160
cggcaaacaa accaccgctg gtagcggtgg ttttttttgtt tgcaagcagc agattacgcg   5220
cagaaaaaaa ggatctcaag aagatccttt gatcttttct acggggtctg acgctcagtg   5280
gaacgaaaac tcacgttaag ggattttggt catgagatta tcaaaaagga tcttcaccta   5340
gatccttta aattaaaaat gaagttttaa atcaatctaa agtatatatg agtaaacttg   5400
gtctgacagt taccaatgct taatcagtga ggcacctatc tcagcgatct gtctatttcg   5460
ttcatccata gttgcctgac tccccgtcgt gtagataact acgatacggg agggcttacc   5520
atctggcccc agtgctgcaa tgataccgcg agacccacgc tcaccggctc cagatttatc   5580
agcaataaac cagccagccg gaagggccga gcgcagaagt ggtcctgcaa ctttatccgc   5640
ctccatccag tctattaatt gttgccggga agctagagta agtagttcgc cagttaatag   5700
tttgcgcaac gttgttgcca ttgctacagg catcgtggtg tcacgctcgt cgtttggtat   5760
ggcttcattc agctccggtt cccaacgatc aaggcgagt acatgatccc ccatgttgtg   5820
caaaaaagcg gttagctcct tcggtcctcc gatcgttgtc agaagtaagt tggccgcagt   5880
gttatcactc atggttatgg cagcactgca taattctctt actgtcatgc catccgtaag   5940
atgcttttct gtgactggtg agtactcaac caagtcattc tgagaatagt gtatgcggcg   6000
accgagttgc tcttgcccgg cgtcaatacg ggataatacc gcgccacata gcagaacttt   6060
aaaagtgctc atcattggaa aacgttcttc ggggcgaaaa ctctcaagga tcttaccgct   6120
gttgagatcc agttcgatgt aacccactcg tgcacccaac tgatcttcag catcttttac   6180
tttcaccagc gtttctgggt gagcaaaaac aggaaggcaa aatgccgcaa aaaagggaat   6240
aagggcgaca cggaaatgtt gaatactcat actcttcctt tttcaatatt attgaagcat   6300
ttatcagggt tattgtctca tgagcggata catatttgaa tgtatttaga aaaataaaca   6360
aataggggtt ccgcgcacat ttccccgaaa agtgccacct gacgtc                  6406
```

```
SEQ ID NO: 23              moltype = AA   length = 216
FEATURE                    Location/Qualifiers
REGION                     1..216
                           note = KB1753-SNAP-GSGGSGG-hRas
source                     1..216
                           mol_type = protein
                           organism = synthetic construct
SEQUENCE: 23
MSSRGYYHGI WVGEEGRLSR DKDCEMKRTT LDSPLGKLEL SGCEQGLHRI IFLGKGTSAA   60
DAVEVPAPAA VLGGPEPLMQ ATAWLNAYFH QPEAIEEFPV PALHHPVFQQ ESFTRQVLWK   120
LLKVVKFGEV ISYSHLAALA GNPAATAAVK TALSGNPVPI LIPCHRVVQG DLDVGGYEGG   180
LAVKEWLLAH EGHRLGKPGL GSGGSGGCMS CKCVLS                             216
```

```
SEQ ID NO: 24              moltype = DNA   length = 6058
FEATURE                    Location/Qualifiers
misc_feature               1..6058
                           note = KB1753-SNAP-GSGGSGG-hRas
source                     1..6058
                           mol_type = other DNA
                           organism = synthetic construct
SEQUENCE: 24
gacggatcgg gagatctccc gatccctat ggtgcactct cagtacaatc tgctctgatg   60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggag tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta acaactccgc cccattgacg caaatgggcg   780
gtaggcgtgt acggtgggag gtctatataa gcagagctct ctggctaact agagaaccca   840
ctgcttactg gcttatcgaa attaatacga ctcactatag ggagacccaa gctggctagc   900
ggtaccgagc tcggatcact agtccagtgt ggtggaattc acgcggacca tgtcttctag   960
aggttactac catggtattt gggtgggtga agaaggtcga ctttctcgag acaaagactg   1020
cgaaatgaag cgcaccaccc tggatagccc tctgggcaag ctggaactgt ctgggtgcga   1080
acagggcctg caccgtatca tcttcctggg caaaggaaca tctgccgcca acgtacgacc   1140
agtgcctgcc ccagccgccg tgctgggcgg accagagcca ctgatgcagg ccaccgcctg   1200
gctcaacgcc tactttcacc agcctgaggc catcgaggag ttccctgtgc cagccctgca   1260
ccacccagtg ttccagcagg agagctttac ccgccaggtg ctgtggaaac tgctgaaagt   1320
ggtgaagttc ggagaggtca tcagctacag ccacctggcc gccctggccg gcaatcccgc   1380
cgccaccgcc gccgtgaaaa ccgccctgag cggaaatccc gtgcccattc tgatccctg   1440
ccacggggtg gtgcagggcg acctggacgt ggggggctac gagggcggc tcgccgtgaa   1500
agagtggctg ctggcccacg agggccacag actgggcaag cctgggctgg atccggtgg   1560
aagtggaggc tgcatgagct gcaagtgtgt gctgtcctaa tgagcggccg cactagaggg   1620
cccgggccc tttaaacccg ctgatcagcc tcgactgtgc cttctagttg ccagccatct   1680
gttgtttgcc cctccccgt gccttccttg accctggaag gtgccactcc cactgtcctt   1740
tcctaataaa atgaggaaat tgcatcgcat tgtctgagta ggtgtcattc tattctgggg   1800
ggtggggtgg ggcaggacag caagggggag gattgggaag acaatagcag gcatgctggg   1860
gatgcggtgg gctctatggc ttctgaggcg gaaagaacca gctgggggctc tagggggtat   1920
ccccacgcgc cctgtagcgg cgcattaagc gcggcgggtg tggtggttac gcgcagcgtg   1980
accgctacac ttgccagcgc cctagcgccc gctcctttcg ctttcttccc ttcctttctc   2040
```

-continued

```
gccacgttcg ccggctttcc ccgtcaagct ctaaatcggg ggctcccttt agggttccga   2100
tttagtgctt tacggcacct cgaccccaaa aaacttgatt agggtgatgg ttcacggtagt  2160
gggccatcgc cctgatagac ggttttttcgc cctttgacgt tggagtccac gttctttaat  2220
agtggactct tgttccaaac tggaacaaca ctcaacccta tctcggtcta ttcttttgat   2280
ttataaggga ttttgccgat ttcggcctat tggttaaaaa atgagctgat ttaacaaaaa   2340
tttaacgcga attaattctg tggaatgtgt gtcagttagg gtgtggaaag tccccaggct   2400
ccccagcagg cagaagtatg caaagcatgc atctcaatta gtcagcaacc aggtgtggaa   2460
agtccccagg ctccccagca ggcagaagta tgcaaagcat gcatctcaat tagtcagcaa   2520
ccatagtccc gcccctaact ccgcccatcc cgcccctagt tccgcccagt tccgcccatt   2580
ctccgcccca tggctgacta attttttta tttatgcaga ggccgaggcc gcctctgcct   2640
ctgagctatt ccagaagtag tgaggaggct ttttttggagg cctaggcttt tgcaaaaagc   2700
tcccgggagc ttgtatatcc attttcggat ctgatcaaga acaggatga ggatcgtttc   2760
gcatgattga acaagatgga ttgcacgcag gttctccggc cgcttgggtg gagaggctat   2820
tcggctatga ctgggcacaa cagacaatcg gctgctctga tgccgccgtg ttccggctgt   2880
cagcgcaggg gcgcccggtt cttttttgtca agaccgacct gtccggtgcc ctgaatgaac   2940
tgcaggacga ggcagcgcgg ctatcgtggc tggccacgac gggcgttcct tgcgcagctg   3000
tgctcgacgt tgtcactgaa gcgggaaggg actggctgct attgggcgaa gtgccggggc   3060
aggatctcct gtcatctcac cttgctcctg ccgagaaagt atccatcatg gctgatgcaa   3120
tgcggcggct gcatacgctt gatccggcta cctgcccatt cgaccaccaa gcgaaacatc   3180
gcatcgagcg agcacgtact cggatggaag ccggtcttgt cgatcaggat gatctggacg   3240
aagagcatca ggggctcgcg ccagccgaac tgttcgccag gctcaaggcg cgcatgcccg   3300
acggcgagga tctcgtcgtg acccatggcg atgcctgctt gccgaatatc atggtggaaa   3360
atggccgctt ttctggattc atcgactgtg gccggctggg tgtggcggac cgctatcagg   3420
acatagcgtt ggctacccgt gatattgctg aagagcttgg cggcgaatgg gctgaccgct   3480
tcctcgtgct ttacggtatc gccgctcccg attcgcagcg catcgccttc tatcgccttc   3540
ttgacgagtt cttctgagcg ggactctggg gttcgaaatg accgaccaag cgacgcccaa   3600
cctgccatca cgagatttcg attccaccgc cgccttctat gaaaggttgg gcttcggaat   3660
cgttttccgg gacgccggct ggatgatcct ccagcgcggg gatctcatgc tggagttctt   3720
cgcccacccc aacttgttta ttgcagctta taatggttac aaataaagca atagcatcac   3780
aaatttcaca aataaagcat ttttttcact gcattctagt tgtggtttgt ccaaactcat   3840
caatgtatct tatcatgtct gtataccgtc gacctctagc tagagcttgg cgtaatcatg   3900
gtcatagctg tttcctgtgt gaaattgtta tccgctcaca attccacaca acatacgagc   3960
cggaagcata aagtgtaaag cctggggtgc ctaatgagtg agctaactca cattaattgc   4020
gttgcgctca ctgcccgctt tccagtcggg aaacctgtcg tgccagctgc attaatgaat   4080
cggccaacgc gcggggagag gcggtttgcg tattgggcgc tcttccgctt cctcgctcac   4140
tgactcgctg cgctcggtcg ttcggctgcg gcgagcggta tcagctcact caaaggcggt   4200
aatacggtta tccacagaat caggggataa cgcaggaaag aacatgtgag caaaaggcca   4260
gcaaaaggcc aggaaccgta aaaaggccgc gttgctggcg tttttccata ggctccgccc   4320
ccctgacgag catcacaaaa atcgacgctc aagtcagagg tggcgaaacc cgacaggact   4380
ataaagatac caggcgtttc cccctggaag ctccctcgtg cgctctcctg ttccgaccct   4440
gccgcttacc ggatacctgt ccgcctttct cccttcggga agcgtggcgc tttctcatag   4500
ctcacgctgt aggtatctca gttcggtgta ggtcgttcgc tccaagctgg gctgtgtgca   4560
cgaacccccc gttcagcccg accgctgcgc cttatccggt aactatcgtc ttgagtccaa   4620
cccggtaaga cacgacttat cgccactggc agcagccact ggtaacagga ttagcagagc   4680
gaggtatgta ggcggtgcta cagagttctt gaagtggtgg cctaactacg gctacactag   4740
aagaacagta tttggtatct gcgctctgct gaagccagtt accttcggaa aaagagttgg   4800
tagctcttga tccggcaaac aaaccaccgc tggtagcggt ggtttttttg tttgcaagca   4860
gcagattacg cgcagaaaaa aaggatctca agaagatcct ttgatctttt ctacggggtc   4920
tgacgctcag tggaacgaaa actcacgtta agggattttg gtcatgagat tatcaaaaag   4980
gatcttcacc tagatccttt taaattaaaa atgaagtttt aaatcaatct aaagtatata   5040
tgagtaaact tggtctgaca gttaccaatg cttaatcagt gaggcaccta tctcagcgat   5100
ctgtctattt cgttcatcca tagttgcctg actccccgtc gtgtagataa ctacgatacg   5160
ggagggctta ccatctggcc ccagtgctgc aatgataccg cgagacccac gctcaccggc   5220
tccagattta tcagcaataa accagccagc cggaagggcc gagcgcagaa gtggtcctgc   5280
aactttatcc gcctccatcc agtctattaa ttgttgccgg gaagctagag taagtagttc   5340
gccagttaat agtttgcgca acgttgttgc cattgctaca ggcatcgtgg tgtcacgctc   5400
gtcgtttggt atggcttcat tcagctccgg ttcccaacga tcaaggcgag ttacatgatc   5460
ccccatgttg tgcaaaaaag cggttagctc cttcggtcct ccgatcgttg tcagaagtaa   5520
gttggccgca gtgttatcac tcatggttat ggcagcactg cataattctc ttactgtcat   5580
gccatccgta agatgctttt ctgtgactgg tgagtactca accaagtcat tctgagaata   5640
gtgtatgcgg cgaccgagtt gctcttgccc ggcgtcaata cgggataata ccgcgccaca   5700
tagcagaact ttaaaagtgc tcatcattgg aaaacgttct cggggcgaa aactctcaag   5760
gatcttaccg ctgttgagat ccagttcgat gtaacccact cgtgcaccca actgatcttc   5820
agcatctttt actttcacca gcgtttctgg gtgagcaaaa acaggaaggc aaaatgccgc   5880
aaaaaaggga ataagggcga cacggaaatg ttgaatactc atactcttcc tttttcaata   5940
ttattgaagc atttatcagg gttattgtct catgagcgga tacatatttg aatgtattta   6000
gaaaaataaa caaataggggg ttccgcgcac atttccccga aaagtgccac ctgacgtc    6058
```

SEQ ID NO: 25         moltype = AA  length = 379
FEATURE               Location/Qualifiers
REGION                1..379
                        note = NB80-meGFP-GSGGSGG-hRas
source                1..379
                        mol_type = protein
                        organism = synthetic construct
SEQUENCE: 25
```
MSSRGQVQLQ ESGGGLVQAG GSLRLSCAAS GSIFSINTMG WYRQAPGKQR ELVAAIHSGG   60
STNYANSVKG RFTISRDNAA NTVYLQMNSL KPEDTAVYYC NVKDYGAVLY EYDYWGQGTQ   120
VTVSSRGKGE ELFTGVVPIL VELDGDVNGH KFSVSGEGEG DATYGKLTLK FICTTGKLPV   180
```

```
PWPTLVTTLT YGVQCFSRYP DHMKRHDFFK SAMPEGYVQE RTIFFKDDGN YKTRAEVKFE  240
GDTLVNRIEL KGIDFKEDGN ILGHKLEYNY NSHNVYIMAD KQKNGIKANF KIRHNIESGG  300
VQLADHYQQN TPIGDGPVLL PDNHYLSTQS KLSKDPNEKR DHMVLKERVT AAGITHGMDE  360
LYKGSGGSGG CMSCKCVLS                                                379

SEQ ID NO: 26          moltype = DNA  length = 6547
FEATURE                Location/Qualifiers
misc_feature           1..6547
                       note = NB80-meGFP-GSGGSGG-hRas
source                 1..6547
                       mol_type = other DNA
                       organism = synthetic construct
SEQUENCE: 26
gacggatcgg gagatctccc gatccctat ggtgcactct cagtacaatc tgctctgatg   60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttaggggttag gcgttttgcg ctgcttcgcg atgtacgggc cagatatacg cgttgacatt  240
gattattgac tagttattaa tagtaatcaa ttacgggtc attagttcat agcccatata  300
tggagttccg cgttacataa cttacggtaa atggcccgcc tggctgaccg cccaacgacc  360
cccgcccatt gacgtcaata atgacggtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacga taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
ggtaccgagc tcggatcact agtccagtgt ggtggaattc acgcggacca tgtcttctag  960
aggacaggtg cagctgcagg agtctggggg aggcttggtg caggctgggg ggtctctgag 1020
actctcctgt gcagcctctg gaagcatctt cagtatcaat accatgggct ggtaccgcca 1080
ggctccaggg aagcagcgcg agttggtcgc agctattcat agtggtggta gcacaaaacta 1140
tgccaactcc gtgaagggcc gattcaccat ctccagagac aatgccgcga acacggtgta 1200
tctgcaaatg aacagcctga aacctgagga cacggccgtc tattactgta atgtaaagga 1260
ctacggggcg gtcctatatg agtatgacta ctggggccag gggacccagg tcaccgtctc 1320
ctctcgaggt aaaggagaag aacttttcac tggagttgtc ccaattcttg ttgaattaga 1380
tggtgatgtt aatgggcaca aattttctgt cagtggagag ggtgaaggtg atgcaacata 1440
cggaaaactt acccttaaat ttatttgcac tactggaaaa ctacctcgttc cttggccaac 1500
acttgtcact actttaactt atggtgttca atgcttttca agatacccag atcatatgaa 1560
acggcatgac tttttcaaga gtgccatgcc cgaaggttat gtacaggaaa gaactatatt 1620
tttcaaagat gacgggaact acaagacacg tgctgaagtc aagtttgaag gtgatacect 1680
tgttaataga atcgagttaa aaggtattga ttttaaagaa gatggaaaca ttcttggaca 1740
caaattggaa tacaactata actcacacaa tgtatacatc atggcagaca acaaaaagaa 1800
tggaatcaaa gctaacttca aaattagaca caacattgag tccggaggcg ttcaactagc 1860
agaccattat caacaaaata ctccaattgg cgatggccct gtcctttttac cagacaacca 1920
ttacctgtcc acacaatcta agctttcgaa agatcccaac gaaaagagag accacatggt 1980
ccttaaagag agggtaacag ctgctgggat tacacatggc atggacgagc tgtacaaggg 2040
atccggtgga agtggaggct gcatgagctg caagtgtgtg ctgtcctaat gagcggccgc 2100
actagggc ccgggcccgt ttaaacccgc tgatcagcct cgactgtgcc ttctagttgc 2160
cagccatctg ttgtttgccc ctcccccgtg ccttccttga ccctggaagg tgccactccc 2220
actgtccttt cctaataaaa tgaggaaatt gcatcgcatt gtctgagtag gtgtcattct 2280
attctggggg gtggggtggg gcaggacagc aaggggagg attgggaaga caatagcagg 2340
catgctgggg atgcggtggg ctctatggct tctgaggcgg aaagaaccag ctggggctct 2400
agggggtatc cccacgcgcc ctgtagcggc gcattaagcg cggcgggtgt ggtggttacg 2460
cgcagcgtga ccgctacact gccagcgcc ctagcgcccg ctcctttcgc tttcttccct 2520
tcctttctcg ccacgttcgc cggctttccc cgtcaagctc taaatcgggg gctccctta 2580
gggttccgat ttagtgcttt acggcacctc gaccccaaaa aacttgattta gggtgatggt 2640
tcacgtagtg ggccatcgcc ctgatagacg gtttttcgcc ctttgacgtt ggagtccacg 2700
ttctttaata gtggactctt gttccaaact ggaacaacac tcaacccctat tcggtctat 2760
tcttttgatt tataagggat tttgccgatt tcggcctatt ggttaaaaaa tgagctgatt 2820
taacaaaaat ttaacgcgaa ttaattctgt ggaatgtgtg tcagttaggg tgtgaaagt 2880
ccccaggctc cccagcaggc agaagtatgc aaagcatgca tctcaattag tcagcaacca 2940
ggtgtggaaa gtcccaggc tccccagcag gcagaagtat gcaaagcatg catctcaatt 3000
agtcagcaac catagtcccg cccctaactc cgcccatccc gcccctaact ccgcccagtt 3060
ccgcccattc tccgccccat ggctgactaa ttttttttat ttatgcagag gccgaggccg 3120
cctctgcctc tgagctattc cagaagtagt gaggaggctt ttttggaggc ctaggctttt 3180
gcaaaaagct cccgggagct gtatatcca ttttcggatc tgatcaagag acaggatgag 3240
gatcgtttcg catgattgaa caagatggat tgcacgcagg ttctccggcc gcttgggtgg 3300
agaggctatt cggctatgac tgggcacaac agacaatcgg ctgctctgat gccgccgtgt 3360
tccggctgtc agcgcagggg cgcccggttc tttttgtcaa gaccgacctg tccggtgccc 3420
tgaatgaact gcaggacgag gcagcgcggc tatcgtggct ggccacgacg ggcgttcctt 3480
gcgcagctgt gctcgacgtt gtcactgaag cgggaaggga ctggctgcta ttgggcgaag 3540
tgccggggca ggatctcctg tcatctcacc ttgctcctgc cgagaaagta tccatcatgg 3600
ctgatgcaat gcggcggctg catacgcttg atccggctac ctgcccattc gaccaccaag 3660
cgaaacatcg catcgagcga gcacgtactc ggatggaagc cggtcttgtc gatcaggatg 3720
atctggacga gagcatcag gggctcgcgc cagccgaact gttcgccagg ctcaaggcgc 3780
gcatgcccga cggcgaggat ctcgtcgtga cccatggcga tgcctgcttg ccgaatatca 3840
tggtggaaaa tggccgcttt tctggattca tcgactgtgg ccggctgggt gtggcggacc 3900
gctatcagga catagcgttg gctacccgtg atattgctga agagcttggc ggcgaatggg 3960
```

```
ctgaccgctt cctcgtgctt tacggtatcg ccgctcccga ttcgcagcgc atcgccttct   4020
atcgccttct tgacgagttc ttctgagcgg gactctgggg ttcgaaatga ccgaccaagc   4080
gacgcccaac ctgccatcac gagatttcga ttccaccgcc gccttctatg aaaggttggg   4140
cttcggaatc gtttttccgg acgccggctg gatgatcctc cagcgcgggg atctcatgct   4200
ggagttcttc gcccacccca acttgtttat tgcagcttat aatggttaca aataaagcaa   4260
tagcatcaca aatttcacaa ataaagcatt ttttttcactg cattctagtt gtggtttgtc   4320
caaactcatc aatgtatctt atcatgtctg tataccgtcg acctctagct agagcttggc   4380
gtaatcatgg tcatagctgt ttcctgtgtg aaattgttat ccgctcacaa ttccacacaa   4440
catacgagcc ggaagcataa agtgtaaagc ctggggtgcc taatgagtga gctaactcac   4500
attaattgcg ttgcgctcac tgcccgcttt ccagtcggga aacctgtcgt gccagctgca   4560
ttaatgaatc ggccaacgcg cggggagagg cggtttgcgt attgggcgct cttccgcttc   4620
ctcgctcact gactcgctgc gctcggtcgt tcggctgcgg cgagcggtat cagctcactc   4680
aaaggcggta atacggttat ccacagaatc aggggataac gcaggaaaga acatgtgagc   4740
aaaaggccag caaaaggcca ggaaccgtaa aaaggccgcg ttgctggcgt ttttccatag   4800
gctccgcccc cctgacgagc atcacaaaaa tcgacgctca agtcagaggt ggcgaaaccc   4860
gacaggacta taaagatacc aggcgtttcc ccctggaagc tccctcgtgc gctctcctgt   4920
tccgaccctg ccgcttaccg gatacctgtc cgcctttctc ccttcgggaa gcgtggcgct   4980
ttctcatagc tcacgctgta ggtatctcag ttcggtgtag gtcgttcgct ccaagctggg   5040
ctgtgtgcac gaaccccccg ttcagcccga ccgctgcgcc ttatccggta actatcgtct   5100
tgagtccaac ccggtaagac acgacttatc gccactggca gcagccactg gtaacaggat   5160
tagcagagcg aggtatgtag gcggtgctac agagttcttg aagtggtggc ctaactacgg   5220
ctacactaga agaacagtat ttggtatctg cgctctgctg aagccagtta ccttcggaaa   5280
aagagttggt agctcttgat ccggcaaaca aaccaccgct ggtagcggtg gtttttttgt   5340
ttgcaagcag cagattacgc gcagaaaaaa aggatctcaa gaagatcctt tgatcttttc   5400
tacggggtct gacgctcagt ggaacgaaaa ctcacgttaa gggattttgg tcatgagatt   5460
atcaaaaagg atcttcacct agatcctttt aaattaaaaa tgaagtttta aatcaatcta   5520
aagtatatat gagtaaactt ggtctgacag ttaccaatgc ttaatcagtg aggcacctat   5580
ctcagcgatc tgtctatttc gttcatccat agttgcctga ctccccgtcg tgtagataac   5640
tacgatacgg gagggcttac catctggccc cagtgctgca atgataccgc gagacccacg   5700
ctcaccggct ccagatttat cagcaataaa ccagccagcc ggaagggccg agcgcagaag   5760
tggtcctgca actttatccg cctccatcca gtctattaat tgttgccggg aagctagagt   5820
aagtagttcg ccagttaata gtttgcgcaa cgttgttgcc attgctacag gcatcgtggt   5880
gtcacgctcg tcgtttggta tggcttcatt cagctccggt tcccaacgat caaggcgagt   5940
tacatgatcc cccatgttgt gcaaaaaagc ggttagctcc ttcggtcctc cgatcgttgt   6000
cagaagtaag ttggccgcag tgttatcact catggttatg gcagcactgc ataattctct   6060
tactgtcatg ccatccgtaa gatgcttttc tgtgactggt gagtactcaa ccaagtcatt   6120
ctgagaatag tgtatgcggc gaccgagttg ctcttgcccg gcgtcaatac gggataatac   6180
cgcgccacat agcagaactt taaaagtgct catcattgga aaacgttctt cggggcgaaa   6240
actctcaagg atcttaccgc tgttgagatc cagttcgatg taacccactc gtgcacccaa   6300
ctgatcttca gcatctttta ctttcaccag cgtttctggg tgagcaaaaa caggaaggca   6360
aaatgccgca aaaaagggaa taagggcgac acggaaatgt tgaatactca tactcttcct   6420
ttttcaatat tattgaagca tttatcaggg ttattgtctc atgagcggat acatatttga   6480
atgtatttag aaaaataaac aaataggggt tccgcgcaca tttccccgaa aagtgccacc   6540
tgacgtc                                                              6547
```

```
SEQ ID NO: 27            moltype = AA   length = 413
FEATURE                  Location/Qualifiers
REGION                   1..413
                         note = beta2-adrenergic receptor
source                   1..413
                         mol_type = protein
                         organism = synthetic construct
SEQUENCE: 27
MGQPGNGSAF LLAPNRSHAP DHDVTQQRDE VWVVGMGIVM SLIVLAIVFG NVLVITAIAK   60
FERLQTVTNY FITSLACADL VMGLAVVPFG AAHILMKMWT FGNFWCEFWT SIDVLCVTAS   120
IETLCVIAVD RYFAITSPFK YQSLLTKNKA RVIILMVWIV SGLTSFLPIQ MHWYRATHQE   180
AINCYANETC CDFFTNQAYA IASSIVSFYV PLVIMVFVYS RVFQEAKRQL QKIDKSEGRF   240
HVQNLSQVEQ DGRTGHGLRR SSKFCLKEHK ALKTLGIIMG TFTLCWLPFF IVNIVHVIQD   300
NLIRKEVYIL LNWIGYVNSG FNPLIYCRSP DFRIAFQELL CLRRSSLKAY GNGYSSNGNT   360
GEQSGYHVEQ EKENKLLCED LPGTEDFVGH QGTVPSDNID SQGRNCSTND SLL          413

SEQ ID NO: 28            moltype = DNA   length = 7211
FEATURE                  Location/Qualifiers
misc_feature             1..7211
                         note = beta2-adrenergic receptor-IRES-mCherry
source                   1..7211
                         mol_type = other DNA
                         organism = synthetic construct
SEQUENCE: 28
tagttattaa tagtaatcaa ttacggggtc attagttcat agcccatata tggagttccg   60
cgttacataa cttacggtaa atggcccgcc tggctgaccg cccaacgacc cccgcccatt   120
gacgtcaata atgacgtatg ttcccatagt aacgccaata gggactttcc attgacgtca   180
atgggtggag tatttacggt aaactgccca cttggcagta catcaagtgt atcatatgcc   240
aagtacgccc cctattgacg tcaatgacgg taaatggccc gcctggcatt atgcccagta   300
catgacctta tgggactttc ctacttggca gtacatctac gtattagtca tcgctattac   360
catggtgatg cggttttggc agtacatcaa tgggcgtgga tagcggtttg actcacgggg   420
atttccaagt ctccacccca ttgacgtcaa tgggagtttg ttttggcacc aaaatcaacg   480
ggactttcca aaatgtcgta acaactccgc cccattgacg caaatgggcg gtaggcgtgt   540
acggtgggag gtctatataa gcagagctgg tttagtgaac cgtcagatcc gctagcctcg   600
```

-continued

```
acttgagctc ggatccacgg tggaattcga ttatccacca tggggcaacc cgggaacggc    660
agcgccttct tgctggcacc caatagaagc catgcgccgg accacgacgt cacgcagcaa    720
agggacgagg tgtgggtggt gggcatgggc atcgtcatgt ctctcatcgt cctggccatc    780
gtgtttggca atgtgctggt catcacagcc attgccaagt tcgagcgtct gcagacggtc    840
accaactact tcatcacttc actggcctgt gctgatctgt tcatgggcct ggcagtggtg    900
ccctttgggg ccgcccatat tcttatgaaa atgtggactt ttggcaactt ctggtgcgag    960
ttttggactt ccattgatgt gctgtgcgtc acggccagca ttgagaccct gtgcgtgatc   1020
gcagtggatc gctactttgc cattacttca cctttcaagt accagagcct gctgaccaag   1080
aataaggccc gggtgatcat tctgatggtg tggattgtgt caggccttac ctccttcttg   1140
cccattcaga tgcactggta ccgggccacc caccaggaag ccatcaactg ctatgccaat   1200
gagacctgct gtgacttctt cacgaaccaa gcctatgcca ttgcctcttc catcgtgtcc   1260
ttctacgttc ccctggtgat catggtcttc gtctactcca gggtctttca ggaggccaaa   1320
aggcagctcc agaagattga caaatctgag ggccgcttcc atgtccagaa ccttagccag   1380
gtggagcagg atgggcggac ggggcatgga ctccgcagat cttccaagtt ctgcttgaag   1440
gagcacaaag ccctcaagac gttaggcatc atcatgggca ctttcaccct ctgctggctg   1500
cccttcttca tcgttaacat tgtgcatgtg atccaggata acctcatccg taaggaagtt   1560
tacatcctcc taaattggat aggctatgtc aattctggtt tcaatcccct tatctactgc   1620
cggagcccag atttcaggat tgccttccag gagcttctgt gcctgcgcag gtcttctttg   1680
aaggcctatg ggaatggcta ctccagcaac ggcaacacag gggagcagag tggatatcac   1740
gtggaacagg agaagaaaa taaactgctg tgtgaagacc tcccaggcac ggaagacttt   1800
gtgggccatc aaggtactgt gcctagcgat aacattgatt cacaagggag gaattgtagt   1860
acaaatgact cactgctgta actcgagtct agaactagtt tgagtcgagc gcggcaatt   1920
ccgcccccc ccccccct ctccctcccc cccccctaac gttactggcc gaagccgctt   1980
ggaataaggc cggtgtgcgt ttgtctatat gttattttcc accatattgc cgtcttttgg   2040
caatgtgagg gcccggaaac ctggccctgt cttcttgacg agcattccta ggggtctttc   2100
ccctctcgcc aaaggaatgc aaggtctgtt gaatgtcgtg aaggaagcag ttcctctgga   2160
agcttcttga agacaaacaa cgtctgtagc gaccctttgc aggcagcgga acccccacc   2220
tggcaacagg tgcctctgcg gccaaaagcc acgtgtataa gatacacctg caaaggcggc   2280
acaacccag tgccacgttg tgagttggat agttgtggaa agagtcaaat ggctctcctc   2340
aagcgtattc aacaagggc tgaaggatgc ccagaagta cccccattgta tgggatctga   2400
tctgggccct cggtgcacat gctttacatg tgtttagtcg aggttaaaaa aacgtctagg   2460
ccccccgaac cacggggacg tggttttcct ttgaaaaaca cgatgataat atggtgagca   2520
agggcgagga ggataacatg gccatcatca aggagttcat gcgcttcaag gtgcacatgg   2580
agggctccgt gaacggccac gagttcgaga tcgagggcga gggcgagggc cgcccctacg   2640
agggcaccca gaccgccaag ctgaaggtga ccaagggtgg ccccctgccc ttcgcctggg   2700
acatcctgtc ccctcagttc atgtacggct ccaaggccta cgtgaagcac cccgccgaca   2760
tccccgacta cttgaagctg tccttccccg agggcttcaa gtgggagcgc gtgatgaact   2820
tcgaggacgg cggcgtggtg accgtgaccc aggactcctc cctgcaggac ggcgagttca   2880
tctacaaggt gaagctgcgc ggcaccaact tccctccga tgccccgta atgcagaaga   2940
agaccatggg ctgggaggcc tcctccgagc ggatgtaccc cgaggacggc gccctgaagg   3000
gcgagatcaa gcagaggctg aagctgaagg acggcggcca ctacgacgct gaggtcaaga   3060
ccacctacaa ggccaagaag cccgtgcagc tgcccggcgc ctacaacgtc aacatcaagt   3120
tggacatcac ctcccacaac gaggactaca ccatcgtgga acagtacgaa cgcgccgagg   3180
gccgccactc caccggcggc atggacgagc tgtacaagta accgcggtcg acggtaccgc   3240
gggcccggga tctaagctta tcgataatca acctctggat tacaaaattt gtgaaagatt   3300
gactggtatt cttaactatg ttgctccttt tacgctatgt ggatacgctg ctttaatgcc   3360
tttgtatcat gctatttgctt cccgtatggc tttcattttc tcctccttgt ataaatcctg   3420
gttgctgtct ctttatgagg agttgtggc cgttgtcagg caacgtggcg tggtgtgcac   3480
tgtgtttgct gacgcaaccc ccactggttg gggcattgcc accacctgtc agctcctttc   3540
cgggactttc gctttccccc tccctattgc cacggcggaa ctcatcgccg cctgccttgc   3600
ccgctgctgg acaggggctc ggctgttggg cactgacaat tccgtggtgt tgtcggggaa   3660
atcatcgtcc tttccttggc tgctcgcctg tgttgccacc tggattctgc gcgggacgtc   3720
cttctgctac gtcccttcgg ccctcaatcc agcggacctt ccttcccgcg gcctgctgcc   3780
ggctctgcgg cctcttccgc gtcttcgcct tcgccctcag acgagtcgga tctccctttg   3840
ggccgcctcc ccgcatcgat accgtcggatc gatccaccgg atctagataa ctgatcataa   3900
tcagccatac cacatttgta gaggttttac ttgctttaaa aaacctccca cacctcccc   3960
tgaacctgaa acataaaatg aatgcaattg ttgttgttaa cttgtttatt gcagcttata   4020
atggttacaa ataaagcaat agcatcacaa atttcacaaa taaagcattt ttttcactgc   4080
attctagttg tggtttgtcc aaactcatca atgtatctta acgcgtaaat tgtaagcgtt   4140
aatattttgt taaaattcgc gttaaatttt tgttaaatca gctcattttt taaccaatag   4200
gccgaaatcg gcaaaatccc ttataaatca aagaataga ccgagatagg gttgagtgtt   4260
gttccagttt ggaacaagag tccactatta agaacgtgg actccaacgt caaagggcga   4320
aaaaccgtct atcagggcga tggcccacta cgtgaaccat cacctaatc aagttttttg   4380
gggtcgaggt gccgtaaagc actaaatcgg aaccctaaag ggagcccccg atttagagct   4440
tgacggggaa agccgcgaa cgtggcgaga aggaaggga agaaagcgaa aggagcgggc   4500
gctaggcgc tggcaagtgt agcggtcacg ctgcgcgtaa ccaccacacc cgccgcgctt   4560
aatgcgccgc tacagggcgc gtcaggtggc acttttcggg gaaatgtgcg cggaacccct   4620
atttgtttat ttttctaaat acattcaaat atgtatccgc tcatgagaca ataaccctga   4680
taaatgcttc aataatattg aaaaaggag agtcctgagg cggaaagaac cagctgtgga   4740
atgtgtgtca gttagggtgt ggaaagtccc caggctcccc agcaggcaga agtatgcaaa   4800
gcatgcatct caattagtca gcaaccaggt gtggaaagtc cccaggctcc ccagcaggca   4860
gaagtatgca aagcatgcat ctcaattagt cagcaaccat agtcccgccc ctaactccgc   4920
ccatcccgcc cctaactccg cccagttccg cccattctcc gccccatggc tgactaattt   4980
ttttatttat gcagaggccg aggccgcctc ggcctctga gctattccag aagtagtgag   5040
gaggctttttt ggaggcctta ggcttttgca aagatcgatc aagagacagg atgaggatcg   5100
tttcgcatga ttgaacaaga tggattgcac gcaggttctc cggccgcttg ggtggagagg   5160
ctattcggct atgactgggc acaacagaca atcggctgct ctgatgccgc cgtgttccgg   5220
ctgtcagcgc aggggcgccc ggttctttt gtcaagaccg acctgtccgg tgccctgaat   5280
gaactgcaag acgaggcagc gcggctatcg tggctggcca cgacgggcgt tccttgcgca   5340
```

-continued

```
gctgtgctcg acgttgtcac tgaagcggga agggactggc tgctattggg cgaagtgccg   5400
gggcaggatc tcctgtcatc tcaccttgct cctgccgaga aagtatccat catggctgat   5460
gcaatgcggc ggctgcatac gcttgatccg gctacctgcc cattcgacca ccaagcgaaa   5520
catcgcatcg agcgagcacg tactcggatg gaagccggtc ttgtcgatca ggatgatctg   5580
gacgaagagc atcaggggct cgcgccagcc gaactgttcg ccaggctcaa ggcgagcatg   5640
cccgacgcg aggatctcgt cgtgacccat ggcgatgcct gcttgccgaa tatcatggtg   5700
gaaaatggcc gcttttctgg attcatcgac tgtggccggc tgggtgtggc ggaccgctat   5760
caggacatag cgttggctac ccgtgatatt gctgaagagc ttggcggcga atgggctgac   5820
cgcttcctcg tgctttacgg tatcgccgct cccgattcgc agcgcatcgc cttcatcgac   5880
cttcttgacg agttcttctg agcgggactc tggggttcga aatgaccgac caagcgacgc   5940
ccaacctgcc atcacgagat ttcgattcca ccgccgcctt ctatgaaagg ttgggcttcg   6000
gaatcgtttt ccgggacgcc ggctggatga tcctccagcg cggggatctc atgctggagt   6060
tcttcgccca ccctaggggg aggctaactg aaacacggaa ggagacaata ccggaaggaa   6120
cccgcgctat gacggcaata aaaagacaga ataaacgca cggtgttggg tcgtttgttc   6180
ataaacgcgg ggttcggtcc cagggctggc actctgtcga taccccaccg agaccccatt   6240
ggggccaata cgcccgcgtt tcttcctttt ccccaccca cccccaagt tcgggtgaag   6300
gcccagggct cgcagccaac gtcggggcgg caggccctgc catagcctca ggttactcat   6360
atatacttta gattgattta aaacttcatt tttaattaa aaggatctag gtgaagatcc   6420
ttttgataa tctcatgacc aaaatcccctt aacgtgagtt ttcgttccac tgagcgtcag   6480
accccgtaga aagatcaaa ggatcttctt gagatccttt ttttctgcgc gtaatctgct   6540
gcttgcaaac aaaaaaacca ccgctaccag cggtggtttg tttgccggat caagagctac   6600
caactctttt tccgaaggta actggcttca gcagagcgca gataccaaat actgtccttc   6660
tagtgtagcc gtagttaggc caccacttca agaactctgt agcaccgcct acatacctcg   6720
ctctgctaat cctgttacca gtggctgctg ccagtggcga taagtcgtgt cttaccgggt   6780
tggactcaag acgatagtta ccggataagg cgcagcggtc gggctgaacg ggggggttcgt   6840
gcacacagcc cagcttggag cgaacgacct acaccgaact gagataccta cagcgtgagc   6900
tatgagaaag cgccacgctt cccgaaggga gaaaggcgga caggtatccg gtaagcggca   6960
gggtcggaac aggagagcgc acgagggagc ttccaggggg aaacgcctgg tatctttata   7020
gtcctgtcgg gtttcgccac ctctgacttg agcgtcgatt tttgtgatgc tcgtcagggg   7080
ggcggagcct atggaaaaac gccagcaacg cggcctttt acggttcctg ccttttgct   7140
ggccttttgc tcacatgttc tttcctgcgt tatccctga ttctgtggat aaccgtatta   7200
ccgccatgca t                                                        7211
```

```
SEQ ID NO: 29              moltype = AA   length = 782
FEATURE                    Location/Qualifiers
REGION                     1..782
                           note = beta2AR-SSGSSGTG-meGFP-NB80
source                     1..782
                           mol_type = protein
                           organism = synthetic construct
SEQUENCE: 29
MGQPGNGSAF LLAPNRSHAP DHDVTQQRDE VWVVGMGIVM SLIVLAIVFG NVLVITAIAK   60
FERLQTVTNY FITSLACADL VMGLAVVPFG AAHILMKMWT FGNFWCEFWT SIDVLCVTAS   120
IETLCVIAVD RYFAITSPFK YQSLLTKNKA RVIILMVWIV SGLTSFLPIQ MHWYRATHQE   180
AINCYANETC CDFFTNQAYA IASSIVSFYV PLVIMVFVYS RVFQEAKRQL QKIDKSEGRF   240
HVQNLSQVEQ DGRTGHGLRR SSKFCLKEHK ALKTLGIIMG TFTLCWLPFF IVNIVHVIQD   300
NLIRKEVYIL LNWIGYVNSG FNPLIYCRSP DFRIAFQELL CLRRSSLKAY GNGYSSNGNT   360
GEQSGYHVEQ EKENKLLCED LPGTEDFVGH QGTVPSDNID SQGRNCSTND SLLSSGSSGT   420
GSKGEELFTG VVPILVELDG DVNGHKFSVS GEGEGDATYG KLTLKFICTT GKLPVPWPTL   480
VTTLTYGVQC FSRYPDHMKR HDFFKSAMPE GYVQERTIFF KDDGNYKTRA EVKFEGDTLV   540
NRIELKGIDF KEDGNILGHK LEYNYNSHNV YIMADKQKNG IKANFKIRHN IESGGVQLAD   600
HYQQNTPIGD GPVLLPDNHY LSTQSKLSKD PNEKRDHMVL KERVTAAGIT HGMDELYKGS   660
SRGQVQLQES GGGLVQAGGS LRLSCAASGS IFSINTMGWY RQAPGKQREL VAAIHSGGST   720
NYANSVKGRF TISRDNAANT VYLQMNSLKP EDTAVYYCNV KDYGAVLYEY DYWGQGTQVT   780
VS                                                                 782
```

```
SEQ ID NO: 30              moltype = DNA   length = 7750
FEATURE                    Location/Qualifiers
misc_feature               1..7750
                           note = b2AR-SSGSSGTG-meGFP-NB80
source                     1..7750
                           mol_type = other DNA
                           organism = synthetic construct
SEQUENCE: 30
gacggatcgg gagatctccc gatccctat ggtgcactct cagtacaatc tgctctgatg   60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacggtatg ttcccatagt aacgccaata gggactttcc   420
attgacgtca atgggtggag tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta acaactccgc cccattgacg caaatgggcg   780
gtaggcgtgt acggtgggag gtctatataa gcagagctct ctggctaact agagaaccca   840
ctgcttactg gcttatcgaa attaatacga ctcactatag ggagacccaa gctggctagc   900
```

-continued

```
gtttaaactt aagcttggta ccgacggacc atggggcaac ccgggaacgg cagcgccttc  960
ttgctggcac ccaatagaag ccatgcgccg gaccacgacg tcacgcagca aagggacgag 1020
gtgtgggtgg tgggcatggg catcgtcatg tctctcatcg tcctggccat cgtgtttggc 1080
aatgtgctgc tcatcacagc cattgccaag ttcgagcgtc tgcagacggt caccaactac 1140
ttcatcactt cactggcctg tgctgatctg gtcatgggcc tgcagtggt gccctttggg 1200
gccgcccata ttcttatgaa aatgtggact tttggcaact tctggtgcga gttttggact 1260
tccattgatg tgctgtgcgt cacggccagc attgagaccc tgtgcgtgat cgcagtggat 1320
cgctactttg ccattacttc accttttcaag taccagagcc tgctgaccaa gaataaggcc 1380
cgggtgatca ttctgatggt gtggattgtg tcaggcctta cctccttctt gcccattcag 1440
atgcactggt atcgggccac ccaccaggaa gccatcaact gctatgccaa tgagacctgc 1500
tgtgacttct tcacgaacca agcctatgcc attgcctctt ccatcgtgtc cttctacgtt 1560
cccctggtga tcatggtctt cgtctactcc agggtctttc aggaggccaa aaggcagctc 1620
cagaagattg acaaatctga gggccgcttc catgtccaga accttagcca ggtggagcag 1680
gatgggcgga cggggcatgg actccgcaga tcttccaagt tctgcttgaa ggagcacaaa 1740
gccctcaaga cgttaggcat catcatgggc actttcaccc tctgctggct gcccttcttc 1800
atcgttaaca ttgtgcatgt gatccaggat aacctcatcc gtaaggaagt ttacatcctc 1860
ctaaattgga taggctatgt caattctggt ttcaatcccc ttatctactg ccggagccca 1920
gatttcagga ttgccttcca ggagcttctg tgcctgcgca ggtcttcttt gaaggcctat 1980
gggaatggct actccagcaa cggcaacaca ggggagcaga gtggatatca cgtggaacag 2040
gagaaagaaa ataaactgct gtgtgaagac ctcccaggca cggaagactt tgtgggccat 2100
caaggtactg tgcctagcga taacattgat tcacaaggga ggaattgtag tacaaatgac 2160
tcactgctgt cctccggatc gtctggaacc ggttctaaag gagaagaact tttcactgga 2220
gttgtcccaa ttcttgttga attagatggt gatgttaatg ggcacaaatt ttctgtcagt 2280
ggagagggtg aaggtgatgc aacatacgga aaacttaccc ttaaatttat ttgcactact 2340
ggaaaactac ctgttccttg gccaacactt gtcactactt taacttatgg tgttcaatgc 2400
ttttcaagat acccagatca tatgaaacgg catgactttt tcaagagtgc catgcccgaa 2460
ggttatgtac aggaaagaac tatattttc aaagatgacg ggaactacaa gacacgtgct 2520
gaagtcaagt ttgaaggtga tacccttgtt aatagaatcg agttaaaagg tattgatttt 2580
aaagaagatg gaaacattct tggacacaaa ttggaataca actataactc acacaatgta 2640
tacatcatgg cagacaaaca aaagaatgga atcaaagcta acttcaaaat tagacacaac 2700
attgagtccg gaggcgttca actagcagac cattatcaac aaaatactcc aattggcgat 2760
ggccctgtcc ttttaccaga caaccattac ctgtccacac aatctaagct ttcgaaagat 2820
cccaacgaaa agagagacca catggtcctt aaagagaggg taacagctgc tgggattaca 2880
catggcatgg acgagctgta caagggatcc tctagaggac aggtgcagct gcaggagtct 2940
gggggaggct tggtgcaggc tggggggtct ctgagactct cctgtgcagc ctctggaagc 3000
atcttcagta tcaataccat gggctggtac cgccaggctc cagggaagca gcgcgagttg 3060
gtcgcagcta ttcatagtgg tggtagcaca aactatgcca actccgtgaa gggccgattc 3120
accatctcca gagacaatgc cgcgaacacg gtgtatctgc aaatgaacag cctgaaacct 3180
gaggacacgg ccgtctatta ctgtaatgta aaggactacg ggcggtcct atatgagtat 3240
gactactggg gccaggggac ccaggtcacc gtctcctctc gaggataatg aaggtggcgg 3300
ccgctcgaaa ctagagggcc cgtttaaacc cgctgatcag cctcgactgt gccttctagt 3360
tgccagccat ctgttgtttg cccctcccc gtgccttcct gaccctgga aggtgccact 3420
cccactgtcc tttcctaata aaatgaggaa attgcatcgc attgtctgag taggtgtcat 3480
tctattctgg ggggtggggt ggggcaggac agcaagggg aggattggga agacaatagc 3540
aggcatgctg gggatgcggt gggctctatg gcttctgagg cggaaagaac cagctggggc 3600
tctaggggg atccccacgc gccctgtagc ggcgcattaa gcgcggcggg tgtggtggtt 3660
acgcgcagcg tgaccgctac acttgccagc gccctagcgc ccgctccttt cgctttcttc 3720
ccttcctttc tcgccacgtt cgccggcttt ccccgtcaag ctctaaatcg ggggctccct 3780
ttagggttcc gatttagtgc tttacggcac ctcgacccca aaaaacttga ttagggtgat 3840
ggttcacgta gtgggccatc gccctgatag acggtttttc gcccttttgac gttggagtcc 3900
acgttcttta atagtggact cttgttccaa actggaacaa cactcaaccc tatctcggtc 3960
tattctttg atttataagg gattttgccg atttcggcct attggttaaa aaatgagctg 4020
atttaacaaa aatttaacgc gaattaattc tgtggaatgt gtgtcagtta gggtgtggaa 4080
agtccccagg ctccccagca ggcagaagta tgcaaagcat gcatctcaat tagtcagcaa 4140
ccaggtgtgg aaagtcccca ggctccccag caggcagaag tatgcaaagc atgcatctca 4200
attagtcagc aaccatagtc ccgcccctaa ctccgcccat cccgccccta actccgccca 4260
gttccgccca ttctccgccc catggctgac taatttttt tatttatgca gaggccgagg 4320
ccgcctctgc ctctgagcta ttccagaagt agtgaggagg ctttttttgga ggcctaggct 4380
tttgcaaaaa gctcccggga gcttgtatat ccattttcgg atctgatcaa gagacaggat 4440
gaggatcgtt tcgcatgatt gaacaagatg gattgcacgc aggttctccg gccgcttggg 4500
tggagaggct attcggctat gactgggcac aacagacaat cggctgctct gatgccgccg 4560
tgttccggct gtcagcgcag gggcgcccgg ttctttttgt caagaccgac ctgtccggtg 4620
ccctgaatga actgcaggac gaggcagcgc ggctatcgtg ctggccacg acgggcgttc 4680
cttgcgcagc tgtgctcgac gttgtcactg aagcgggaag ggactggctg ctattgggcg 4740
aagtgccggg gcaggatctc ctgtcatctc accttgctcc tgccgagaaa gtatccatca 4800
tggctgatgc aatgcggcgg ctgcatacgc ttgatccggc tacctgccca ttcgaccacc 4860
aagcgaaaca tcgcatcgag cgagcacgta ctcggatgga agccggtctt gtcgatcagg 4920
atgatctgga cgaagagcat caggggctcg cgccagccga actgttcgcc aggctcaagg 4980
cgcgcatgcc cgacggcgag gatctcgtcg tgacccaata ggtgcctggc ttgccgaata 5040
tcatggtgga aaatggccgc ttttctggat tcatcgactg tggccggctg ggtgtggcgg 5100
accgctatca ggacatagcg ttggctaccg tgatattgc tgaagagctt ggcggcgaat 5160
gggctgaccg cttcctcgtg ctttacggta tcgccgctcc cgattcgcag cgcatcgcct 5220
tctatcgcct tcttgacgag ttcttctgag cgggactctg gggttcgaaa tgaccgacca 5280
agcgacgccc aacctgccat cacgagattt cgattccacc acgagatgat ccgaaaggt 5340
gggcttcgga atcgttttcc gggacgccgg ctggatgatc ctccagcgcg gggatctcat 5400
gctggagttc ttcgcccacc ccaacttgtt tattgcagct tataatggtt acaaataaag 5460
caatagcatc acaaatttca caaataaagc attttttttca ctgcattcta gttgtggttt 5520
gtccaaactc atcaatgtat cttatcatgt ctgtataccg tcgacctcta gctagagctt 5580
ggcgtaatca tggtcatagc tgtttcctgt gtgaaattgt tatccgctca caattccaca 5640
```

-continued

```
caacatacga gccggaagca taaagtgtaa agcctggggt gcctaatgag tgagctaact   5700
cacattaatt gcgttgcgct cactgcccgc tttccagtcg ggaaacctgt cgtgccagct   5760
gcattaatga atcggccaac gcgcggggag aggcggtttg cgtattgggc gctcttccgc   5820
ttcctcgctc actgactcgc tgcgctcggt cgttcggctg cggcgagcgg tatcagctca   5880
ctcaaaggcg gtaatacggt tatccacaga atcaggggat aacgcaggaa agaacatgtg   5940
agcaaaaggc cagcaaaagg ccaggaaccg taaaaaggcc gcgttgctgg cgttttttcca  6000
taggctccgc cccctgacg agcatcacaa aaatcgacgc tcaagtcaga ggtggcgaaa    6060
cccgacagga ctataaagat accaggcgtt tcccccctgga agctccctcg tgcgctctcc   6120
tgttccgacc ctgccgctta ccggatacct gtccgccttt ctcccttcgg gaagcgtggc   6180
gctttctcat agctcacgct gtaggtatct cagttcggtg taggtcgttc gctccaagct   6240
gggctgtgtg cacgaacccc ccgttcagcc cgaccgctgc gccttatccg gtaactatcg   6300
tcttgagtcc aacccggtaa gacacgactt atcgccactg gcagcagcca ctggtaacag   6360
gattagcaga gcgaggtatg taggcggtgc tacagagttc ttgaagtggt ggcctaacta   6420
cggctacact agaagaacag tatttggtat ctgcgctctg ctgaagccag ttaccttcgg   6480
aaaaagagtt ggtagctctt gatccggcaa acaaaccacc gctggtagcg gtggtttttt   6540
tgtttgcaag cagcagatta cgcgcagaaa aaaaggatct caagaagatc ctttgatctt   6600
ttctacgggg tctgacgctc agtggaacga aaactcacgt taagggattt tggtcatgag   6660
attatcaaaa aggatcttca cctagatcct tttaaattaa aaatgaagtt ttaaatcaat   6720
ctaaagtata tatgagtaaa cttggtctga cagttaccaa tgcttaatca gtgaggcacc   6780
tatctcagcg atctgtctat ttcgttcatc catagttgcc tgactccccg tcgtgtagat   6840
aactacgata cgggagggct taccatctgg ccccagtgct gcaatgatac cgcgagaccc   6900
acgctcaccg gctccagatt tatcagcaat aaaccagcca gccggaaggg ccgagcgcag   6960
aagtggtcct gcaactttat ccgcctccat ccagtctatt aattgttgcc gggaagctag   7020
agtaagtagt tcgccagtta atagtttgcg caacgttgtt gccattgcta caggcatcgt   7080
ggtgtcacgc tcgtcgtttg gtatggcttc attcagctcc ggttcccaac gatcaaggcg   7140
agttacatga tcccccatgt tgtgcaaaaa agcggttagc tccttcggtc ctccgatcgt   7200
tgtcagaagt aagttggccg cagtgttatc actcatggtt atggcagcac tgcataattc   7260
tcttactgtc atgccatccg taagatgctt ttctgtgact ggtgagtact caaccaagtc   7320
attctgagaa tagtgtatgc ggcgaccgag ttgctcttgc ccggcgtcaa tacgggataa   7380
taccgcgcca catagcagaa ctttaaaagt gctcatcatt ggaaaacgtt cttcggggcg   7440
aaaactctca aggatcttac cgctgttgag atccagttcg atgtaaccca ctcgtgcacc   7500
caactgatct tcagcatctt ttactttcac cagcgtttct gggtgagcaa aaacaggaag   7560
gcaaaatgcc gcaaaaaagg gaataagggc gacacgaaa tgttgaatac tcatactctt    7620
ccttttttcaa tattattgaa gcatttatca gggttattgt ctcatgagcg gatacatatt   7680
tgaatgtatt tagaaaaata aacaaatagg ggttccgcgc acatttcccc gaaaagtgcc   7740
acctgacgtc                                                         7750
```

```
SEQ ID NO: 31        moltype = AA  length = 383
FEATURE              Location/Qualifiers
REGION               1..383
                     note = NB33-meGFP-GSGGSGG-hRas
source               1..383
                     mol_type = protein
                     organism = synthetic construct
SEQUENCE: 31
MSSRAQVQLV ESGGGLVRPG GSRRLSCVDS ERTSYPMGWF RRAPGKEREF VASITWSGID   60
PTYADSVADR FTISRDVANN TLYLQMNSLK HEDTAVYYCA ARAPVGQSSS PYDYDYWGQG   120
TQVTVSSAAR GKGEELFTGV VPILVELDGD VNGHKFSVSG EGEGDATYGK LTLKFICTTG   180
KLPVPWPTLV TTLTYGVQCF SRYPDHMKRH DFFKSAMPEG YVQERTIFFK DDGNYKTRAE   240
VKFEGDTLVN RIELKGIDFK EDGNILGHKL EYNYNSHNVY IMADKQKNGI KANFKIRHNI   300
ESGGVQLADH YQQNTPIGDG PVLLPDNHYL STQSKLSKDP NEKRDHMVLK ERVTAAGITH   360
GMDELYKGSG GSGGCMSCKC VLS                                          383
```

```
SEQ ID NO: 32        moltype = DNA  length = 6562
FEATURE              Location/Qualifiers
misc_feature         1..6562
                     note = NB33-meGFP-GSGGSGG-hRas
source               1..6562
                     mol_type = other DNA
                     organism = synthetic construct
SEQUENCE: 32
gacggatcgg gagatctccc gatccctat ggtgcactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggag tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta acaactccgc cccattgacg caaatgggcg   780
gtaggcgtgt acggtgggag gtctatataa gcagagctct ctggctaact agagaaccca   840
ctgcttactg gcttatcgaa attaatacga ctcactatag gagacccaa gctggctagc     900
ggtaccgagc tcgatcact agtccagtgt ggtggaattc acgcggacca tgtcttctag     960
agcacaggt cagctggtgg agtctggggg aggattggtg cggcctgggg gctctcggag      1020
actctcctgt gtggactctg agcgcaccag ctatcccatg ggctggttcc gccgggcccc     1080
```

-continued

```
agggaaggag cgggagtttg tggcatctat tacctggagt ggtattgacc caacatatgc   1140
agactccgtg gccgaccgat tcaccatctc cagagatgtc gcgaataaca cgctgtatct   1200
gcaaatgaac agcctgaaac atgaggacac ggccgtttat tattgtgcag ctcgtgcccc   1260
cgtggggcaa tcctcttccc catatgacta tgactactgg ggccagggga cccaggtcac   1320
cgtctcctca gcggccgctc gaggtaaagg agaagaactt ttcactggag ttgtcccaat   1380
tcttgttgaa ttagatggtg atgttaatgg gcacaaattt tctgtcagtg gagagggtga   1440
aggtgatgca acatacggaa aacttaccct taaatttatt tgcactactg gaaaactacc   1500
tgttccttgg ccaacacttg tcactacttt aacttatggt gttcaatgct tttcaagata   1560
cccagatcat atgaaacggc atgacttttt caagagtgcc atgcccgaag gttatgtaca   1620
ggaaagaact atatttttca aagatgacgg gaactacaag acacgtgctg aagtcaagtt   1680
tgaaggtgat acccttgtta atagaatcga gttaaaaggt attgatttta aagaagatgg   1740
aaacattctt ggacacaaat tggaatacaa ctataactca cacaatgtat acatcatggc   1800
agacaaacaa aagaatggaa tcaaagctaa cttcaaaatt agacacaaca ttgagtccgg   1860
aggcgttcaa ctagcagacc attatcaaca aaatactcca attggcgatg gccctgtcct   1920
tttaccagac aaccattacc tgtccacaca atctaagctt tcgaaagatc ccaacgaaaa   1980
gagagaccac atggtcctta aagagagggt aacagctgct gggattacac atggcatgga   2040
cgagctgtac aagggatccg gtggaagtgg aggctgcatg agctgcaagt gtgtgctgtc   2100
ctaatgagcg gccgcactag agggcccggg cccgtttaaa cccgctgatc agcctcgact   2160
gtgccttcta gttgccagcc atctgttgtt tgcccctccc ccgtgccttc cttgaccctg   2220
gaaggtgcca ctcccactgt cctttcctaa taaaatgagg aaattgcatc gcattgtctg   2280
agtaggtgtc attctattct ggggggtggg gtggggcagg acagcaaggg ggaggattgg   2340
gaagacaata gcaggcatgc tggggatgcg gtgggctcta tggcttctga ggcggaaaga   2400
accagctggg gctctagggg gtatccccac gcgccctgta gcggcgcatt aagcgcggcg   2460
ggtgtggtgg ttacgcgcag cgtgaccgct acacttgcca gcgccctagc gcccgctcct   2520
ttcgctttct tcccttcctt tctcgccacg ttcgccggct ttccccgtca agctctaaat   2580
cggggggctcc ctttagggtt ccgatttagt gctttacggc acctcgaccc caaaaaactt   2640
gattagggtg atggttcacg tagtgggcca tcgccctgat agacggtttt tcgccctttg   2700
acgttggagt ccacgttctt taatagtgga ctcttgttcc aaactggaac aacactcaac   2760
cctatctcgg tctattcttt tgatttataa gggattttgc cgatttcggc ctattggtta   2820
aaaaatgagc tgatttaaca aaaatttaac gcgaattaat tctgtggaat gtgtgtcagt   2880
tagggtgtgg aaagtcccca ggctccccag caggcagaag tatgcaaagc atgcatctca   2940
attagtcagc aaccaggtgt ggaaagtccc caggctcccc agcaggcaga agtatgcaaa   3000
gcatgcatct caattagtca gcaaccatag tcccgcccct aactccgccc atcccgcccc   3060
taactccgcc cagttccgcc cattctccgc cccatggctg actaatttttt tttatttatg   3120
cagaggccga ggccgcctct gcctctgagc tattccagaa gtagtgagga ggcttttttg   3180
gaggcctagg cttttgcaaa aagctcccgg gagcttgtat atccatttttc ggatctgatc   3240
aagagacagg atgaggatcg tttcgcatga ttgaacaaga tggattgcac gcaggttctc   3300
cggccgcttg ggtggagagg ctattcggct atgactgggc acaacagaca atcggctgct   3360
ctgatgccgc cgtgttccgg ctgtcagcgc aggggcgccc ggttcttttt gtcaagaccg   3420
acctgtccgg tgccctgaat gaactgcagg acgaggcagc gcggctatcg tggctggcca   3480
cgacgggcgt tccttgcgca gctgtgctcg acgttgtcac tgaagcggga agggactggc   3540
tgctattggg cgaagtgccg gggcaggatc tcctgtcatc tcaccttgct cctgccgaga   3600
aagtatccat catggctgat gcaatgcggc ggctgcatac gcttgatccg gctacctgcc   3660
cattcgacca ccaagcgaaa catcgcatcg agcgagcacg tactcggatg gaagccggtc   3720
ttgtcgatca ggatgatctg gacgaagagc atcaggggct cgcgccagcc gaactgttcg   3780
ccaggctcaa ggcgcgcatg cccgacggcg aggatctcgt cgtgacccat ggcgatgcct   3840
gcttgccgaa tatcatggtg gaaaatggcc gcttttctgg attcatcgac tgtggccggc   3900
tgggtgtggc ggaccgctat caggacatag cgttggctac ccgtgatatt gctgaagagc   3960
ttggcggcga atgggctgac cgcttcctcg tgctttacgg tatcgccgct cccgattcgc   4020
agcgcatcgc cttctatcgc cttcttgacg agttcttctg agcgggactc tggggttcga   4080
aatgaccgac caagcgacgc ccaacctgcc atcacgagat ttcgattcca ccgccgcctt   4140
ctatgaaagg ttgggcttcg gaatcgtttt ccgggacgcc ggctggatga tcctccagcg   4200
cggggatctc atgctggagt tcttcgccca ccccaacttg tttattgcag cttataatgg   4260
ttacaaataa agcaatagca tcacaaattt cacaaataaa gcattttttt cactgcattc   4320
tagttgtggt ttgtccaaac tcatcaatgt atcttatcat gtctgtatac cgtcgacctc   4380
tagctagagc ttggcgtaat catggtcata gctgtttcct gtgtgaaatt gttatccgct   4440
cacaattcca cacaacatac gagccggaag cataaagtgt aaagcctggg gtgcctaatg   4500
agtgagctaa ctcacattaa ttgcgttgcg ctcactgccc gctttccagt cgggaaacct   4560
gtcgtgccag ctgcattaat gaatcggcca acgcgcgggg agaggcggtt tgcgtattgg   4620
gcgctcttcc gcttcctcgc tcactgactc gctgcgctcg gtcgttcggc tgcggcgagc   4680
ggtatcagct cactcaaagg cggtaatacg gttatccaca gaatcagggg ataacgcagg   4740
aaagaacatg tgagcaaaag gccagcaaaa ggccaggaac cgtaaaaagg ccgcgttgct   4800
ggcgtttttc cataggctcc gccccctga cgagcatcac aaaaatcgac gctcaagtca   4860
gaggtggcga aacccgacag gactataaag ataccaggcg tttccccctg gaagctccct   4920
cgtgcgctct cctgttccga ccctgccgct taccggatac ctgtccgcct ttctcccttc   4980
gggaagcgtg gcgctttctc atagctcacg ctgtaggtat ctcagttcgg tgtaggtcgt   5040
tcgctccaag ctgggctgtg tgcacgaacc ccccgttcag cccgaccgct gcgccttatc   5100
cggtaactat cgtcttgagt ccaacccggt aagacacgac ttatcgccac tggcagcagc   5160
cactggtaac aggattagca gagcgaggta tgtaggcggt gctacagagt tcttgaagtg   5220
gtggcctaac tacggctaca ctagaagaac agtatttggt atctgcgctc tgctgaagcc   5280
agttaccttc ggaaaaagag ttggtagctc ttgatccggc aaacaaacca ccgctggtag   5340
cggtggtttt tttgtttgca agcagcagat tacgcgcaga aaaaaaggat ctcaagaaga   5400
tcctttgatc ttttctacgg ggtctgacgc tcagtggaac gaaaactcac gttaagggat   5460
tttggtcatg agattatcaa aaaggatctt cacctagatc ctttttaaatt aaaaatgaag   5520
ttttaaatca atctaaagta tatatgagta aacttggtct gacagttacc aatgcttaat   5580
cagtgaggca cctatctcag cgatctgtct atttcgttca tccatagttg cctgactccc   5640
cgtcgtgtag ataactacga tacgggaggg cttaccatct ggccccagtg ctgcaatgat   5700
accgcgagac ccacgctcac cggctccaga tttatcagca ataaaccagc cagccggaag   5760
ggccgagcgc agaagtggtc ctgcaacttt atccgcctcc atccagtcta ttaattgttg   5820
```

-continued

```
ccgggaagct agagtaagta gttcgccagt taatagtttg cgcaacgttg ttgccattgc   5880
tacaggcatc gtggtgtcac gctcgtcgtt tggtatggct tcattcagct ccggttccca   5940
acgatcaagg cgagttacat gatcccccat gttgtgcaaa aaagcggtta gctccttcgg   6000
tcctccgatc gttgtcagaa gtaagttggc cgcagtgtta tcactcatgg ttatggcagc   6060
actgcataat tctcttactg tcatgccatc cgtaagatgc ttttctgtga ctggtgagta   6120
ctcaaccaag tcattctgag aatagtgtat gcggcgaccg agttgctctt gcccggcgtc   6180
aatacgggat aataccgcgc cacatagcag aactttaaaa gtgctcatca ttggaaaacg   6240
ttcttcgggg cgaaaactct caaggatctt accgctgttg agatccagtt cgatgtaacc   6300
cactcgtgca cccaactgat cttcagcatc ttttactttc accagcgttt ctgggtgagc   6360
aaaaacagga aggcaaaatg ccgcaaaaaa gggaataagg gcgacacgga aatgttgaat   6420
actcatactc ttcctttttc aatattattg aagcatttat cagggttatt gtctcatgag   6480
cggatacata tttgaatgta tttagaaaaa taaacaaata ggggttccgc gcacatttcc   6540
ccgaaaagtg ccacctgacg tc                                            6562
```

```
SEQ ID NO: 33              moltype = AA  length = 400
FEATURE                    Location/Qualifiers
REGION                     1..400
                           note = opioid receptor
source                     1..400
                           mol_type = protein
                           organism = synthetic construct
SEQUENCE: 33
MDSSAAPTNA SNCTDALAYS SCSPAPSPGS WVNLSHLDGN LSDPCGPNRT DLGGRDSLCP   60
PTGSPSMITA ITIMALYSIV CVVGLFGNFL VMYVIVRYTK MKTATNIYIF NLALADALAT   120
STLPFQSVNY LMGTWPFGTI LCKIVISIDY YNMFTSIFTL CTMSVDRYIA VCHPVKALDF   180
RTPRNAKIIN VCNWILSSAI GLPVMFMATT KYRQGSIDCT LTFSHPTWYW ENLLKICVFI   240
FAFIMPVLII TVCYGLMILR LKSVRMLSGS KEKDRNLRRI TRMVLVVVAV FIVCWTPIHI   300
YVIIKALVTI PETTFQTVSW HFCIALGYTN SCLNPVLYAF LDENFKRCFR EFCIPTSSNI   360
EQQNSTRIRQ NTRDHPSTAN TVDRTNHQLE NLEAETAPLP                         400
```

```
SEQ ID NO: 34              moltype = DNA  length = 6679
FEATURE                    Location/Qualifiers
misc_feature               1..6679
                           note = opioid receptor
source                     1..6679
                           mol_type = other DNA
                           organism = synthetic construct
SEQUENCE: 34
gacggatcgg gagatctccc gatcccctat ggtcgactct cagtacaatc tgctctgatg   60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttaggggttag gcgttttgcg ctgcttcgcg atgtacgggc cagatatacg cgttgacatt   240
gattattgac tagttattaa tagtaatcaa ttacgggatc attagttcat agcccatata   300
tggagttccg cgttacataa cttacggtaa atggcccgcc tggctgaccg cccaacgacc   360
cccgcccatt gacgtcaata atgacggtatg ttcccatagt aacgccaata gggactttcc   420
attgacgtca atgggtggac tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta acaactccgc cccattgacg caaatgggcg   780
gtaggcgtgt acggtgggag gtctatataa gcagagctct ctggctaact agagaaccca   840
ctgcttactg gcttatcgaa attaatacga ctcactatag ggagacccaa gcttggtacc   900
gagctcggat ccactagtaa cggccgccag tgtgctggaa ttctgcagat aaacgaattc   960
gcccttctcc tggctacctc gcacagcggt gcccgcccgg cgtcagtac catggacagc   1020
agcgctgccc ccacgaacgc cagcaattgc actgatgcct tggcgtactc aagttgctcc   1080
ccagcaccca gccccggttc ctgggtcaac ttgtcccact tagatggcaa cctgtccgac   1140
ccatgcggtc cgaaccgcac cgacctgggc gggagagaca gcctgtgccc tccgaccggc   1200
agtccctcca tgatcacggc catcacgatc atggccctct actccatcgt gtgcgtggtg   1260
gggctcttcg gaaacttcct ggtcatgtat gtgattgtca gatacaccaa gatgaagact   1320
gccaccaaca tctacatttt caaccttgct ctggcagatg ccttagccac cagtaccctg   1380
cccttccaga gtgtgaatta cctaatggga acatggccat ttggaaccat cctttgcaag   1440
atagtgatct ccatagatta ctataacatg ttcaccagca tattcaccct ctgcaccatg   1500
agtgttgatc gatacattgc agtctgccac cctgtcaagg ccttagattt ccgtactccg   1560
cgaaatgcca aaattatcaa tgtctgcaac tggatcctct cttcagccat tggtcttcct   1620
gtaatgttca tggctacaac aaaatacagg caaggttcca tagattgtac actaacattc   1680
tctcatccaa cctggtactg ggaaaacctg ctgaagatct gtgtttcat cttcgccttc   1740
attatgccag tgctcatcat taccgtgtgc tatggactga tgatcttgcg cctcaagagt   1800
gtccgcatgc tctctggctc caaagaaaag gacaggaatc ttcgaaggat caccaggatg   1860
gtgctggtgg tggtggctgt gttcatcgtc tgctggactc ccattcacat ttacgtcatc   1920
attaaagcct tggttacaat cccagaaact acgttccaga ctgtttcttg cacttctgc   1980
attgctctag gttacacaaa cagctgcctc aacccagtcc tttatgcatt tctggatgaa   2040
aacttcaaac gatgcttcag agagttctgt atcccaacct cttccaacat tgagcaacaa   2100
aactccactc gaattcgtca gaacactaga gaccacccct caaccgccaa tacagtggat   2160
agaactaatc atcagctaga aaatctggaa gcagaaactg ctccgttgcc cctcgactag   2220
agggccctat tctatagtgt cacctaaatg ctagagctcg ctgatcagcc tcgactgtgc   2280
cttctagttg ccagccatct gttgtttgcc cctcccccgt gccttccttg accctggaag   2340
gtgccactcc cactgtcctt tcctaataaa atgaggaaat tgcatcgcat tgtctgagta   2400
ggtgtcattc tattctgggg ggtggggtgg gcaggacag caaggggag gattgggaag   2460
```

```
acaatagcag gcatgctggg gatgcggtgg gctctatggc ttctgaggcg gaaagaacca    2520
gctgggctc tagggggtat ccccacgcgc cctgtagcgg cgcattaagc gcggcgggtg     2580
tggtggttac gcgcagcgtg accgctacac ttgccagcgc cctagcgccc gctcctttcg    2640
ctttcttccc ttcctttctc gccacgttcg ccggctttcc ccgtcaagct ctaaatcggg    2700
gcatcccttt agggttccga tttagtgctt tacggcacct cgaccccaaa aaacttgatt    2760
agggtgatgg ttcacgtagt gggccatcgc cctgatagac ggttttttcgc cctttgacgt   2820
tggagtccac gttctttaat agtggactct tgttccaaac tggaacaaca ctcaaccta     2880
tctcggtcta ttcttttgat ttataaggga ttttggggat ttcggcctat tggttaaaaa    2940
atgagctgat ttaacaaaaa tttaacgcga attaattctg tggaatgtgt gtcagttagg    3000
gtgtggaaag tccccaggct ccccaggcag gcagaagtat gcaaagcatg catctcaatt    3060
agtcagcaac caggtgtgga aagtccccag gctccccagc aggcagaagt atgcaaagca    3120
tgcatctcaa ttagtcagca accatagtcc cgcccctaac tccgcccatc ccgcccctaa    3180
ctccgcccag ttccgcccat tctccgcccc atggctgact aatttttttt atttatgcag    3240
aggccgaggc cgcctctgcc tctgagctat tccagaagta gtgaggaggc tttttttggag   3300
gcctaggctt ttgcaaaaag ctcccggag cttgtatatc cattttcgga tctgatcaag     3360
agacaggatg aggatcgttt cgcatgattg aacaagatgg attgcacgca ggttctccgg     3420
ccgcttgggt ggagaggcta ttcggctatg actgggcaca acagacaatc ggctgctctg    3480
atgccgccgt gttccggctg tcagcgcagg ggcgcccggt tcttttttgtc aagaccgacc   3540
tgtccggtgc cctgaatgaa ctgcaggacg aggcagcgcg gctatcgtgg ctggccacga    3600
cgggcgttcc ttgcgcagct gtgctcgacg ttgtcactga agcgggaagg gactggctgc     3660
tattgggcga agtgccgggg caggatctcc tgtcatctca ccttgctcct gccgagaaag    3720
tatccatcat ggctgatgca atgcggcggc tgcatacgct tgatccggct acctgcccat    3780
tcgaccacca agcgaaacat cgcatcgagc gagcacgtac tcggatggaa gccggtcttg    3840
tcgatcagga tgatctggac gaagagcatc aggggctcgc gccagccgaa ctgttcgcca    3900
ggctcaaggc gcgcatgccc gacggcgagg atctcgtcgt gacccatggc gatgcctgct    3960
tgccgaatat catggtggaa aatggccgct tttctggatt catcgactgt ggccggctgg    4020
gtgtggcgga ccgctatcag gacatagcgt tggctacccg tgatattgct gaagagcttg    4080
gcggcgaatg ggctgaccgc ttcctcgtgc tttacggtat cgccgctccc gattcgcagc     4140
gcatcgcctt ctatcgcctt cttgacgagt tcttctgagc gggactctgg ggttcgaaat     4200
gaccgaccaa gcgacgccca acctgccatc acgagatttc gattccaccg ccgccttcta    4260
tgaaaggttg ggcttcggaa tcgttttccg gacgccggc tggatgatcc tccagcgcgg     4320
ggatctcatg ctggagttct tcgcccaccc caacttgttt attgcagctt ataatggtta    4380
caaataaagc aatagcatca caaatttcac aaataaagca ttttttttcac tgcattctag    4440
ttgtggtttg tccaaactca tcaatgtatc ttatcatgtc tgtataccgt cgacctgtca    4500
ctagagcttg gcgtaatcat ggtcatagct gtttcctgtg tgaaattgtt atccgctcac    4560
aattccacac aacatacgag ccggaagcat aaagtgtaaa gcctggggtg cctaatgagt    4620
gagctaactc acattaattg cgttgcgctc actgcccgct ttccagtcgg gaaacctgtc    4680
gtgccagctg cattaatgaa tcggccaacg cgcggggaga ggcggtttgc gtattgggcg    4740
ctcttccgct tcctcgctca ctgactcgct gcgctcggtc gttcggctgc ggcgagcggt    4800
atcagctcac tcaaaggcgg taatacggtt atccacagaa tcaggggata acgcaggaaa    4860
gaacatgtga gcaaaaggcc agcaaaaggc caggaaccgt aaaaaggccg cgttgctggc    4920
gttttttccat aggctccgcc cccctgacga gcatcacaaa aatcgacgct caagtcagag    4980
gtggcgaaac ccgacaggac tataaagata ccaggcgttt ccccctggaa gctccctcgt    5040
gcgctctcct gttccgaccc tgccgcttac cggatacctg tccgcctttc tcccttcggg    5100
aagcgtggcg ctttctcaat gctcacgctg taggtatctc agttcggtgt aggtcgttcg    5160
ctccaagctg ggctgtgtgc acgaaccccc cgttcagccc gaccgctgcg ccttatccgg    5220
taactatcgt cttgagtcca acccggtaag acacgactta tcgccactgg cagcagccac    5280
tggtaacagg attagcagag cgaggtatgt aggcggtgct acagagttct tgaagtggtg    5340
gcctaactac ggctacacta gaaggacagt atttggtatc tgcgctctgc tgaagccagt    5400
taccttcgga aaaagagttg gtagctcttg atccggcaaa caaaccaccg ctggtagcgg    5460
tggtttttttt gtttgcaagc agcagattac gcgcagaaaa aaaggatctc aagaagatcc    5520
tttgatcttt tctacggggt ctgacgctca gtggaacgaa aactcacgtt aagggatttt    5580
ggtcatgaga ttatcaaaaa ggatcttcac ctagatcctt ttaaattaaa aatgaagttt    5640
taaatcaatc taaagtatat atgagtaaac ttggtctgac agttaccaat gcttaatcag    5700
tgaggcacct atctcagcga tctgtctatt tcgttcatcc atagttgcct gactccccgt    5760
cgtgtagata actacgatac gggagggctt accatctggc cccagtgctg caatgatacc    5820
gcgagaccca cgctcaccgg ctccagattt atcagcaata aaccagccag ccggaagggc    5880
cgagcgcaga agtggtcctg caactttatc cgcctccatc cagtctatta attgttgccg    5940
ggaagctaga gtaagtagtt cgccagttaa tagtttgcgc aacgttgttg ccattgctac    6000
aggcatcgtg gtgtcacgct cgtcgtttgg tatggcttca ttcagctccg gttcccaacg    6060
atcaaggcga gttacatgat cccccatgtt gtgcaaaaaa gcggttagct ccttcggtcc    6120
tccgatcgtt gtcagaagta agttggccgc agtgttatca ctcatggtta tggcagcact    6180
gcataattct cttactgtca tgccatccgt aagatgcttt tctgtgactg gtgagtactc    6240
aaccaagtca ttctgagaat agtgtatgcg gcgaccgagt tgctcttgcc cggcgtcaat    6300
acgggataat accgcgccac atagcagaac tttaaaagtg ctcatcattg gaaaacgttc    6360
ttcggggcga aaactctcaa ggatcttacc gctgttgaga tccagttcga tgtaacccac    6420
tcgtgcaccc aactgatctt cagcatcttt tactttcacc agcgtttctg ggtgagcaaa    6480
aacaggaagg caaaatgccg caaaaaaggg aataagggcg acacggaaat gttgaatact    6540
catactcttc ctttttcaat attattgaag catttatcag ggttattgtc tcatgagcgg    6600
atacatattt gaatgtattt agaaaaataa acaaataggg gttccgcgca catttccccg    6660
aaaagtgcca cctgacgtc                                                 6679
```

SEQ ID NO: 35          moltype = AA  length = 395
FEATURE                Location/Qualifiers
REGION                 1..395
                       note = GAP43-SSGSSGTG-meGFP-NB33
source                 1..395
                       mol_type = protein
                       organism = synthetic construct

```
SEQUENCE: 35
MLCCMRRTKQ VEKNDEDQNS SGSSGTGSKG EELFTGVVPI LVELGDGVNG HKFSVSGEGE  60
GDATYGKLTL KFICTTGKLP VPWPTLVTTL TYGVQCFSRY PDHMKRHDFF KSAMPEGYVQ  120
ERTIFFKDDG NYKTRAEVKF EGDTLVNRIE LKGIDFKEDG NILGHKLEYN YNSHNVYIMA  180
DKQKNGIKAN FKIRHNIESG GVQLADHYQQ NTPIGDGPVL LPDNHYLSTQ SKLSKDPNEK  240
RDHMVLKERV TAAGITHGMD ELYKGSSRAQ VQLVESGGGL VRPGGSRRLS CVDSERTSYP  300
MGWFRRAPGK EREFVASITW SGIDPTYADS VADRFTISRD VANNTLYLQM NSLKHEDTAV  360
YYCAARAPVG QSSSPYDYDY WGQGTQVTVS SAARG                             395

SEQ ID NO: 36          moltype = DNA  length = 6583
FEATURE                Location/Qualifiers
misc_feature           1..6583
                       note = GAP43-SSGSSGTG-meGFP-NB33
source                 1..6583
                       mol_type = other DNA
                       organism = synthetic construct
SEQUENCE: 36
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttaggggttag gcgtttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
gtttaaactt aagcttggta ccgacggacc atgctgtgct gtatgagaag aaccaaacag  960
gttgaaaaga atgatgagga ccagaattcc tccggatcgt ctggaaccgg ttctaaagga  1020
gaagaacttt tcactggagt tgtcccaatt cttgttgaat tagatggtga tgttaatgga  1080
cacaaatttt ctgtcagtgg agagggtgaa ggtgatgcaa catacggaaa acttaccctt  1140
aaatttattt gcactactgg aaaactacct gttccttggc caacacttgt cactacttta  1200
acttatggtt ttcaatgctt ttcaagatac ccagatcata tgaaacggca tgactttttc  1260
aagagtgcca tgcccgaagg ttatgtacag gaaagaacta tatttttcaa agatgacggg  1320
aactacaaga cacgtgctga agtcaagttt gaaggtgata cccttgttaa tagaatcgag  1380
ttaaaaggta ttgattttaa agaagatgga aacattcttg gacacaaatt ggaatacaac  1440
tataactcac acaatgtata catcatggca gacaaacaaa agaatggaat caaagctaac  1500
ttcaaaatta gacacaacat tgagtccgga ggcgttcaac tagcagacca ttatcaacaa  1560
aatactccaa ttggcgatgg ccctgtcctt ttaccagaca accattacct gtccacacaa  1620
tctaagcttt cgaaagatcc caacgaaaag agagaccaca tggtccttaa agagagggta  1680
acagctgctg ggattacaca tggcatggac gagctgtaca agggatcctc tagagcacag  1740
gtgcagctgg tggagtctgg gggaggattg gtgcggcctg gggctctcg gagactctcc  1800
tgtgtggact ctgagcgcac cagctatccc atgggctggt tccgccgggc cccagggaag  1860
gagcgggagt ttgtggcatc tattacctgg agtggtattg acccaacata tgcagactcc  1920
gtggccgacc gattcaccat ctccagagat gtcgcgaata acacgctgta tctgcaaatg  1980
aacagcctga aacatgagga cacggccgtt tattattgag cagctcgtgc ccccgttaag  2040
caatcctctt ccccatatga ctatgactac tggggccagg ggaccaggt caccgtctcc  2100
tcagcggccg ctcgaggata atgaaggtgg cggccgctcg aaactagagg gcccgtttaa  2160
acccgctgat cagcctcgac tgtgccttct agttgccagc catctgttgt ttgcccctcc  2220
cccgtgcctt ccttgaccct ggaaggtgcc actcccactg tcctttccta ataaaatgag  2280
gaaattgcat cgcattgtct gagtaggtgt cattctattc tggggggtgg ggtggggcag  2340
gacagcaagg gggaggattg ggaagacaat agcaggcatg ctggggatgc ggtgggctct  2400
atggcttctg aggcggaaag aaccagctgg ggctctaggg ggtatcccca cgcgccctgt  2460
agcggcgcat taagcgcggc gggtgtggtg gttacgcgca gcgtgaccgc tacacttgcc  2520
agcgccctag cgcccgctcc tttcgctttc ttcccttcct tctcgccac gttcgccggc  2580
tttccccgtc aagctctaaa tcggggggctc cctttagggt tccgatttag tgctttacgg  2640
cacctcgacc ccaaaaaact tgattagggt gatggttcac gtagtgggcc atcgccctga  2700
tagacggttt ttcgcccttt gacgttggag tccacgttct ttaatagtgg actcttgttc  2760
caaactggaa caacactcaa ccctatctcg gtctattctt ttgatttata agggattttg  2820
ccgatttcgg cctattggtt aaaaaatgag ctgatttaac aaaaatttaa cgcgaattaa  2880
ttctgtggaa tgtgtgtcag ttagggtgtg gaaagtcccc aggctcccca gcaggcagaa  2940
gtatgcaaag catgcatctc aattagtcag caaccaggtg tggaaagtcc ccaggctccc  3000
cagcaggcag aagtatgcaa agcatgcatc tcaattagtc agcaaccata gtcccgcccc  3060
taactccgcc catcccgccc ctaactccgc ccagttccgc ccattctccg ccccatggct  3120
gactaatttt ttttatttat gcagaggccg aggccgcctc tgcctctgag ctattccaga  3180
agtagtgagg aggcttttttt ggaggcctag gcttttgcaa aaagctcccg ggagcttgta  3240
tatccatttt cggatctgat caagagacag gatgaggatc gtttcgcatg attgaacaag  3300
atggattgca cgcaggttct ccggccgctt gggtggagag gctattcggc tatgactggg  3360
cacaacagac aatcggctgc tctgatgccg ccgtgttccg gctgtcagcg caggggcgcc  3420
cggttctttt tgtcaagacc gacctgtccg gtgccctgaa tgaactgcag gacgaggcag  3480
cgcggctatc gtggctggcc acgacgggcg ttccttgcgc agctgtgctc gacgttgtca  3540
ctgaagcggg aagggactgg ctgctattgg gcgaagtgcc ggggcaggat ctcctgtcat  3600
ctcaccttgc tcctgccgag aaagtatcca tcatggctga tgcaatgcgg cggctgcata  3660
cgcttgatcc ggctacctgc ccattcgacc accaagcgaa acatcgcatc gagcgagcac  3720
```

```
gtactcggat ggaagccggt cttgtcgatc aggatgatct ggacgaagag catcaggggc   3780
tcgcgccagc cgaactgttc gccaggctca aggcgcgcat gcccgacggc gaggatctcg   3840
tcgtgaccca tggcgatgcc tgcttgccga atatcatggt ggaaaatggc cgcttttctg   3900
gattcatcga ctgtggccgg ctgggtgtgg cggaccgcta tcaggacata gcgttggcta   3960
cccgtgatat tgctgaagag cttggcggcg aatgggctga ccgcttcctc gtgctttacg   4020
gtatcgccgc tcccgattcg cagcgcatcg ccttctatcg ccttcttgac gagttcttct   4080
gagcgggact ctggggttcg aaatgaccga ccaagcgacg cccaacctgc catcacgaga   4140
tttcgattcc accgccgcct tctatgaaag gttgggcttc ggaatcgttt tccgggacgc   4200
cggctggatg atcctccagc gcggggatct catgctggag ttcttcgccc accccaactt   4260
gtttattgca gcttataatg gttacaaata aagcaatagc atcacaaatt tcacaaataa   4320
agcatttttt tcactgcatt ctagttgtgg tttgtccaaa ctcatcaatg tatcttatca   4380
tgtctgtata ccgtcgacct ctagctagag cttggcgtaa tcatggtcat agctgtttcc   4440
tgtgtgaaat tgttatccgc tcacaattcc acacaacata cgagccggaa gcataaagtg   4500
taaagcctgg ggtgcctaat gagtgagcta actcacatta ttgcgttgc gctcactgcc   4560
cgctttccag tcgggaaacc tgtcgtgcca gctgcattaa tgaatcggcc aacgcgcggg   4620
gagaggcggt ttgcgtattg ggcgctcttc cgcttcctcg ctcactgact cgctgcgctc   4680
ggtcgttcgg ctgcggcgag cggtatcagc tcactcaaag gcggtaatac ggttatccac   4740
agaatcaggg gataacgcag gaaagaacat gtgagcaaaa ggccagcaaa aggccaggaa   4800
ccgtaaaaag gccgcgttgc tggcgttttt ccataggctc cgcccccctg acgagcatca   4860
caaaaatcga cgctcaagtc agaggtggcg aaacccgaca ggactataaa gataccaggc   4920
gtttccccct ggaagctccc tcgtgcgctc tcctgttccg accctgccgc ttaccggata   4980
cctgtccgcc tttctccctt cgggaagcgt ggcgctttct catagctcac gctgtaggta   5040
tctcagttcg gtgtaggtcg ttcgctccaa gctgggctgt gtgcacgaac cccccgttca   5100
gcccgaccgc tgcgccttat ccggtaacta tcgtcttgag tccaacccgg taagacacga   5160
cttatcgcca ctggcagcag ccactggtaa caggattagc agagcgaggt atgtaggcgg   5220
tgctacagag ttcttgaagt ggtggcctaa ctacggctac actagaagaa cagtatttgg   5280
tatctgcgct ctgctgaagc cagttacctt cggaaaaaga gttggtagct cttgatccgg   5340
caaacaaacc accgctggta gcggtggttt ttttgtttgc aagcagcaga ttacgcgcag   5400
aaaaaaagga tctcaagaag atcctttgat cttttctacg gggtctgacg ctcagtggaa   5460
cgaaaactca cgttaaggga ttttggtcat gagattatca aaaaggatct tcacctagat   5520
ccttttaaat taaaaatgaa gttttaaatc aatctaaagt atatatgagt aaacttggtc   5580
tgacagttac caatgcttaa tcagtgaggc acctatctca gcgatctgtc tatttcgttc   5640
atccatagtt gcctgactcc ccgtcgtgta gataactacg atacgggagg gcttaccatc   5700
tggccccagt gctgcaatga taccgcgaga cccacgctca ccggctccag atttatcagc   5760
aataaaccag ccagccggaa gggccgagcg cagaagtggt cctgcaactt tatccgcctc   5820
catccagtct attaattgtt gccgggaagc tagagtaagt agttcgccag ttaatagttt   5880
gcgcaacgtt gttgccattg ctacaggcat cgtggtgtca cgctcgtcgt ttggtatggc   5940
ttcattcagc tccggttccc aacgatcaag gcgagttaca tgatccccca tgttgtgcaa   6000
aaaagcggtt agctccttcg gtcctccgat cgttgtcaga agtaagttgg ccgcagtgtt   6060
atcactcatg gttatggcag cactgcataa ttctcttact gtcatgccat ccgtaagatg   6120
cttttctgtg actggtgagt actcaaccaa gtcattctga atagtgtat gcggcgaccg   6180
gagttgctct tgcccggcgt caatacggga taataccgcg ccacatagca gaactttaaa   6240
agtgctcatc attggaaaac gttcttcggg gcgaaaactc tcaaggatct taccgctgtt   6300
gagatccagt tcgatgtaac ccactcgtgc acccaactga tcttcagcat cttttacttt   6360
caccagcgtt tctgggtgag caaaaacagg aaggcaaaat gccgcaaaaa agggaataag   6420
ggcgacacgg aaatgttgaa tactcatact cttcctttttt caatattatt gaagcattta   6480
tcagggttat tgtctcatga gcggatacat atttgaatgt atttagaaaa ataaacaaat   6540
aggggttccg cgcacatttc cccgaaaagt gccacctgac gtc                     6583
```

```
SEQ ID NO: 37              moltype = AA  length = 453
FEATURE                    Location/Qualifiers
REGION                     1..453
                           note = GAP43-SSGSSGTG-meGFP-GRK2ct
source                     1..453
                           mol_type = protein
                           organism = synthetic construct
SEQUENCE: 37
MLCCMRRTKQ VEKNDEDQNS SGSSGTGSKG EELFTGVVPI LVELDGDVNG HKFSVSGEGE   60
GDATYGKLTL KFICTTGKLP VPWPTLVTTL TYGVQCFSRY PDHMKRHDFF KSAMPEGYVQ   120
ERTIFFKDDG NYKTRAEVKF EGDTLVNRIE LKGIDFKEDG NILGHKLEYN YNSHNVYIMA   180
DKQKNGIKAN FKIRHNIESG GVQLADHYQQ NTPIGDGPVL LPDNHYLSTQ SKLSKDPNEK   240
RDHMVLKERV TAAGITHGMD ELYKGSSRNF PLVISERWQQ EVAETVYEAV NADTDKIEAR   300
KRAKNKQLGH EEDYALGRDC IVHGYMLKLG NPFLTQWQRR YFYLFPNRLE WRGEGESRQS   360
LLTMEQIVSV EETQIKDKKC ILLRIKGGKQ FVLQCESDPE FVQWKKELTE TFMEAQRLLR   420
RAPKFLNKSR SAVVELSKPP LCHRNSNGLG SRG                                453
```

```
SEQ ID NO: 38              moltype = DNA  length = 6754
FEATURE                    Location/Qualifiers
misc_feature               1..6754
                           note = GAP43-SSGSSGTG-meGFP-GRK2ct
source                     1..6754
                           mol_type = other DNA
                           organism = synthetic construct
SEQUENCE: 38
gacggatcgg agatctccc gatccctat ggtgcactct cagtacaatc tgctctgatg   60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
```

-continued

```
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggtttttggc agtacatcaa tgggcgtgga tagcggtttg  660
actcacgggg atttccaagt ctccaccoca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
gtttaaactt aagcttggta ccgacggacc atgctgtgct gtatgagaag aaccaaacag  960
gttgaaaaga atgatgagga ccagaattcc tccggatcgt ctggaaccgg ttctaaagga 1020
gaagaacttt tcactggagt tgtcccaatt cttgttgaat tagatggtga tgttaatggg 1080
cacaaatttt ctgtcagtgg agagggtgaa ggtgatgcaa catacggaaa acttacccttt 1140
aaatttattt gcactactgg aaaactacct gttccttggc caacacttgt cactacttta 1200
acttatggtt ttcaatgctt ttcaagatac ccagatcata tgaaacggca tgactttttc 1260
aagagtgcca tgcccgaagg ttatgtacag gaaagaacta tatttttcaa agatgacggg 1320
aactacaaga cacgtgctga agtcaagttt gaaggtgata cccttgttaa tagaatcgag 1380
ttaaaaggta ttgattttaa agaagatgga aacattcttg gacacaaatt ggaatacaac 1440
tataactcac acaatgtata catcatggca gacaaacaaa agaatggaat caaagctaac 1500
ttcaaaatta gacacaacat tgagtccgga ggcgttcaac tagcagacca ttatcaacaa 1560
aatactccaa ttggcgatgg ccctgtcctt ttaccagaca accattacct gtccacacaa 1620
tctaagcttt cgaaagatcc caacgaaaag agagaccaca tggtccttaa agagagggta 1680
acagctgctg ggattacaca tggcatggac gagctgtaca agggatcctc tagaaacttc 1740
cctctggtga tctctgagcg ctggcagcag gaagtggcgg aaacagttta tgaagcagta 1800
aatgcagaca cggataaaat cgaggccaga aagagagcta aaaataagca gcttggccac 1860
gaagaagatt acgccctggg aagagactgc atcgtgcacg ggtacatgct gaagctgggg 1920
aacccttttcc tgacccagtg gcagcgccgc tattttttacc tctttccgaa cagacttgag 1980
tggagaggag aaggcgagtc gcgacaaagt ttactgacaa tggaacagat tgtgtccgtg 2040
gaagaaactc agattaaaga caaaaagtgc attttgttga gaataaaagg agggaagcag 2100
ttcgtttttgc agtgtgagag tgacccagag tttgtgcagt ggaagaaaga gctgacggag 2160
acattcatgg aggcccagcg gctgctacgg cgagcccca agttcctcaa caaatcccgc 2220
tcagccgtcg tggaactctc aaagcctccc ctctgccata ggaacagcaa cggcctcgga 2280
tctcgaggat aatgaaggtg gcggccgctc gaaactagag ggcccgttta aacccgctga 2340
tcagcctcga ctgtgccttc tagttgccag ccatctgttg tttgcccctc cccgtgcct 2400
tccttgaccc tggaaggtgc cactcccact gtccttcct aataaaatga ggaaattgca 2460
tcgcattgtc tgagtaggtg tcattctatt ctggggggtg gggtggggca ggacagcaag 2520
ggggaggatt gggaagacaa tagcaggcat gctggggatg cggtggctc tatggcttct 2580
gaggcggaaa gaaccagctg gggctctagg gggtatcccc acgcgcctg tagcggcgca 2640
ttaagcgcgg cgggtgtggt ggttacgcgc agcgtgaccg ctacacttgc cagcgcccta 2700
gcgcccgctc ctttcgcttt cttccctcc tttctcgcca cgttcgcgg ctttccccgt 2760
caagctctaa atcggggggct cccttaggg ttccgattta gtgctttacg gcacctcgac 2820
cccaaaaaac ttgattaggg tgatggttca cgtagtgggc catcgcccctg atagacggtt 2880
tttcgccctt tgacgttgga gtccacgttc tttaatagtg gactcttgtt ccaaactgga 2940
acaacactca accctatctc ggtctattct tttgatttat aagggatttt gccgatttcg 3000
gcctattggt taaaaaatga gctgatttaa caaaaattta acgcgaatta attctgtgga 3060
atgtgtgtca gttagggtgt ggaaagtccc caggctcccc agcaggcaga agtatgcaaa 3120
gcatgcatct caattagtca gcaaccaggt gtggaaagtc cccaggctcc ccagcaggca 3180
gaagtatgca aagcatgcat ctcaattagt cagcaaccat agtcccgccc ctaactccgc 3240
ccatcccgcc cctaactccg cccagttccg cccattctcc gccccatggc tgactaattt 3300
ttttattta tgcagaggcc gaggccgcct ctgcctctga gctattccag aagtagtgag 3360
gaggctttt tggaggccta ggcttttgca aaaagctccc gggagcttgt atatccattt 3420
tcggatctga tcaagagaca ggatgaggat cgtttcgcat gattgaacaa gatggattgc 3480
acgcaggttc tccggccgct tgggtggaga ggctattcgg ctatgactgg gcacaacaga 3540
caatcggctg ctctgatgcc gccgtgttcc ggctgtcagc gcaggggcgc ccggttcttt 3600
ttgtcaagac cgacctgtcc ggtgccctga tgaactgca ggacgaggca gcgcggctat 3660
cgtggctggc cacgacgggc gttccttgcg cagctgtgct cgacgttgtc actgaagcgg 3720
gaagggactg gctgctattg ggcgaagtgc cggggcagga tctcctgtca tctcaccttg 3780
ctcctgccga gaaagtatcc atcatggctg atgcaatgcg gcggctgcat acgcttgatc 3840
cggctacctg cccattcgac caccaagcga aacatcgcat cgagcgagca cgtactcgga 3900
tggaagccgg tcttgtcgat caggatgatc tggacgaaga gcatcagggg ctcgcgccag 3960
ccgaactgtt cgccaggctc aaggcgcgca tgcccgacgg cgaggatctc gtcgtgaccc 4020
atggcgatgc ctgcttgccg aatatcatgg tggaaaatgg ccgcttttct ggattcatcg 4080
actgtggccg gctgggtgtg gcggaccgct atcaggacat agcgttggct acccgtgata 4140
ttgctgaaga gcttggcggc gaatgggctg accgcttcct cgtgctttac ggtatcgccg 4200
ctcccgattc gcagcgcatc gccttctatc gccttcttga cgagttcttc tgagcgggac 4260
tctggggttc gaaatgaccg accaagcgac gcccaacctg ccatcacgag atttcgattc 4320
caccgccgcc ttctatgaaa ggttgggctt cggaatcgtt ttccgggacg ccggctggat 4380
gatcctccag cgcgggggatc tcatgctgga gttcttcgcc caccccaact gtttattgcg 4440
agcttataat ggttacaaat aaagcaatag catcacaaat ttcacaaata aagcattttt 4500
ttcactgcat tctagttgtg gtttgtccaa actcatcaat gtatcttatc atgtctgtat 4560
accgtcgacc tctagctaga gcttggcgta atcatggtca tagctgtttc ctgtgtgaaa 4620
ttgttatccg ctcacaattc cacacaacat acgagccgga agcataaagt gtaaagcctg 4680
gggtgcctaa tgagtgagct aactcacatt aattgcgttg cgctcactgc ccgctttcca 4740
gtcgggaaac ctgtcgtgcc agctgcatta atgaatcggc caacgcgcgg ggagaggcgg 4800
tttgcgtatt gggcgctctt ccgcttcctc gctcactgac tcgctgcgct cggtcgttcg 4860
gctgcggcga gcggtatcag ctcactcaaa ggcggtaata cggttatcca cagaatcagg 4920
ggataacgca ggaaagaaca tgtgagcaaa aggccagcaa aaggccagga accgtaaaaa 4980
ggccgcgttg ctggcgtttt tccataggct ccgcccccct gacgagcatc acaaaaatcg 5040
```

```
acgctcaagt cagaggtggc gaaacccgac aggactataa agataccagg cgtttccccc   5100
tggaagctcc ctcgtgcgct ctcctgttcc gaccctgccg cttaccggat acctgtccgc   5160
ctttctccct tcgggaagcg tggcgctttc tcatagctca cgctgtaggt atctcagttc   5220
ggtgtaggtc gttcgctcca agctgggctg tgtgcacgaa ccccccgttc agcccgaccg   5280
ctgcgcctta tccggtaact atcgtcttga gtccaacccg gtaagacacg acttatcgcc   5340
actggcagca gccactggta acaggattag cagagcgagg tatgtaggcg gtgctacaga   5400
gttcttgaag tggtgtaggt actacggcta cactagaaga acagtatttg gtatctgcgc   5460
tctgctgaag ccagttacct tcggaaaaag agttggtagc tcttgatccg gcaaacaaac   5520
caccgctggt agcggtggtt tttttgtttg caagcagcag attacgcgca gaaaaaaagg   5580
atctcaagaa gatcctttga tcttttctac ggggtctgac gctcagtgga acgaaaactc   5640
acgttaaggg attttggtca tgagattatc aaaaaggatc ttcacctaga tccttttaaa   5700
ttaaaaatga agttttaaat caatctaaag tatatatgag taaacttggt ctgacagtta   5760
ccaatgctta atcagtgagg cacctatctc agcgatctgt ctatttcgtt catccatagt   5820
tgcctgactc cccgtcgtgt agataactac gatacgggag ggcttaccat ctggccccag   5880
tgctgcaatg ataccgcgag acccacgctc accggctcca gatttatcag caataaacca   5940
gccagccgga agggccgagc gcagaagtgg tcctgcaact ttatccgcct ccatccagtc   6000
tattaattgt tgccgggaag ctagagtaag tagttcgcca gttaatagtt tgcgcaacgt   6060
tgttgccatt gctacaggca tcgtggtgtc acgctcgtcg tttggtatgg cttcattcag   6120
ctccggttcc caacgatcaa ggcgagttac atgatccccc atgttgtgca aaaaagcggt   6180
tagctccttc ggtcctccga tcgttgtcag aagtaagttg gccgcagtgt tatcactcat   6240
ggttatggca gcactgcata attctcttac tgtcatgcca tccgtaagat gcttttctgt   6300
gactggtgag tactcaacca agtcattctg agaatagtgt atgcggcgac cgagttgctc   6360
ttgcccggcg tcaatacggg ataataccgc gccacatagc agaactttaa aagtgctcat   6420
cattggaaaa cgttcttcgg ggcgaaaact ctcaaggatc ttaccgctgt tgagatccag   6480
ttcgatgtaa cccactcgtg cacccaactg atcttcagca tctttttactt tcaccagcgt   6540
ttctgggtga gcaaaaacag gaaggcaaaa tgccgcaaaa aagggaataa gggcgacacg   6600
gaaatgttga atactcatac tcttcctttt tcaatattat tgaagcattt atcagggtta   6660
ttgtctcatg agcggataca tatttgaatg tatttagaaa aataaacaaa tagggttcc   6720
gcgcacattt ccccgaaaag tgccacctga cgtc                                6754
```

```
SEQ ID NO: 39           moltype = AA  length = 512
FEATURE                 Location/Qualifiers
REGION                  1..512
                        note = GAP43-SSGSSGTG-HALO-GRK2ct
source                  1..512
                        mol_type = protein
                        organism = synthetic construct
SEQUENCE: 39
MLCCMRRTKQ VEKNDEDQNS SGSSGTGAEI GTGFPFDPHY VEVLGERMHY VDVGPRDGTP   60
VLFLHGNPTS SYVWRNIIPH VAPTHRCIAP DLIGMGKSDK PDLGYFFDDH VRFMDAFIEA   120
LGLEEVVLVI HDWGSALGFH WAKRNPERVK GIAFMEFIRP IPTWDEWPEF ARETFQAFRT   180
TDVGRKLIID QNVFIEGTLP MGVVRPLTEV EMDHYREPPL NPVDREPLWR FPNELPIAGE   240
PANIVALVEE YMDWLHQSPV PKLLFWGTPG VLIPPAEAAR LAKSLPNCKA VDIGPGLNLL   300
QEDNPDLIGS EIARWLSTLE ISGGSSRNFP LVISERWQQE VAETVYEAVN ADTDKIEARK   360
RAKNKQLGHE EDYALGRDCI VHGYMLKLGN PFLTQWQRRY FYLFPNRLEW RGEGESRQSL   420
LTMEQIVSVE ETQIKDKKCI LLRIKGGKQF VLQCESDPEF VQWKKELTET FMEAQRLLRR   480
APKFLNKSRS AVVELSKPPL CHRNSNGLGS RG                                 512
```

```
SEQ ID NO: 40           moltype = DNA  length = 6931
FEATURE                 Location/Qualifiers
misc_feature            1..6931
                        note = GAP43-SSGSSGTG-HALO-GRK2ct
source                  1..6931
                        mol_type = other DNA
                        organism = synthetic construct
SEQUENCE: 40
gacggatcgg gagatctccc gatccctat ggtgcactct cagtacaatc tgctctgatg   60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggag tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta acaactccgc cccattgacg caaatgggcg   780
gtaggcgtgt acggtgggag gtctatataa gcagagctct ctggctaact agagaaccca   840
ctgcttactg gcttatcgaa attaatacga ctcactatag ggagacccaa gctggctagc   900
gtttaaactt aagcttggta ccgacggacc atgctgtgct gtatgagaag aaccaaacag   960
gttgaaaaga atgatgagga ccagaattcc tccggatcgt ctggaaccgg tgcagaaatc   1020
ggtactggct tccattcga cccccattat gtggaagtcc tgggcgagcg catgcactac   1080
gtcgatgttg tccgcgcga tggcacccct gtgctgttcc tgcacggtaa cccgacctcc   1140
tcctacgtgt ggcgcaacat catcccgcat gttgcaccga cccatcgctg cattgctcca   1200
gacctgatcg gtatgggcaa atccgacaaa ccagacctgg gttatttctt cgacgaccac   1260
gtccgcttca tggatgcctt catcgaagcc ctgggtctga agaggtcgt cctggtcatt   1320
cacgactggg gctccgctct gggttttccac tgggccaagc gcaatccaga gcgcgtcaaa   1380
```

-continued

```
ggtattgcat ttatggagtt catccgccct atcccgacct gggacgaatg gccagaattt   1440
gcccgcgaga ccttccaggc cttccgcacc accgacgtcg gccgcaagct gatcatcgat   1500
cagaacgttt ttatcgaggg tacgctgccg atgggtgtcg tccgcccgct gactgaagtc   1560
gagatggacc attaccgcga gccgttcctg aatcctgttg accgcgagcc actgtggcgc   1620
ttcccaaacg agctgccaat cgccggtgag ccagcgaaca tcgtcgcgct ggtcgaagaa   1680
tacatggact ggctgcacca gtcccctgtc ccgaagctgc tgttctgggg cacccccaggc   1740
gttctgatcc caccggccga agccgctcgc ctggccaaaa gcctgcctaa ctgcaaggct   1800
gtggacatcg gcccgggtct gaatctgctg caagaagaca acccggacct gatcggcagc   1860
gagatcgcgc gctggctgtc gacgctcgag atttccggcg gatcctctag aaacttccct   1920
ctggtgatct ctgagcgctg gcagcaggaa gtggcggaaa cagtttatga agcagtaaat   1980
gcagacacgg ataaaatcga ggccaggaag agagctaaaa ataagcagct tggccacgaa   2040
gaagattacg ccctgggaag agactgcatc gtgcacgggt acatgctgaa gctgggggaac   2100
cctttcctga cccagtggca gcgccgctat ttttacctct ttccgaacag acttgagtgg   2160
agaggagaag gcgagtcgcg acaaagttta ctgacaatgg aacagattgt gtccgtggaa   2220
gaaactcaga ttaaagacaa aaagtgcatt ttgttgagaa taaaaggagg gaagcagttc   2280
gttttgcagt gtgagagtga cccagagttt gtgcagtgga agaaagagct gacggagaca   2340
ttcatggagg cccagcggct gctacggcga gcccccaagt tcctcaacaa atcccgctca   2400
gccgtcgtgg aactctcaaa gcctcccctc tgccatagga acagcaacgg cctcggatct   2460
cgaggataat gaaggtggcg gccgctcgaa actagagggc ccgtttaaac ccgctgatca   2520
gcctcgactg tgccttctag ttgccagcca tctgttgttt gcccctcccc cgtgccttcc   2580
ttgaccctgg aaggtgccac tcccactgtc ctttcctaat aaaatgagga aattgcatcg   2640
cattgtctga gtaggtgtca ttctattctg gggggtgggg tggggcagga cagcaagggg   2700
gaggattggg aagacaatag caggcatgct ggggatgcgg tgggctctat ggcttctgag   2760
gcggaaagaa ccagctgggg ctctaggggg tatccccacg cgccctgtag cggcgcatta   2820
agcgcggcgg gtgtggtggt tacgcgcagc gtgaccgcta cacttgccag cgccctagcg   2880
cccgctcctt tcgctttctt cccttccttt ctcgccacgt tcgccggctt tccccgtcaa   2940
gctctaaatc gggggctccc tttagggttc cgatttagtg ctttacggca cctcgacccc   3000
aaaaaacttg attagggtga tggttcacgt agtgggccat cgccctgata gacggttttt   3060
cgccctttga cgttggagtc cacgttcttt aatagtggac tcttgttcca aactggaaca   3120
acactcaacc ctatctcggt ctattctttt gatttataag ggattttgcc gatttcggcc   3180
tattggttaa aaaatgagct gatttaacaa aaatttaacg cgaattaatt ctgtggaatg   3240
tgtgtcagtt agggtgtgga aagtccccag gctccccagc aggcagaagt atgcaaagca   3300
tgcatctcaa ttagtcagca accaggtgtg gaaagtcccc aggctcccca gcaggcagaa   3360
gtatgcaaag catgcatctc aattagtcag caaccatagt cccgccccta actccgccca   3420
tcccgcccct aactccgccc agttccgccc attctccgcc ccatggctga ctaatttttt   3480
ttatttatgc agaggccgag gccgcctctg cctctgagct attccagaag tagtgaggag   3540
gctttttttgg aggcctaggc ttttgcaaaa agctcccggg agcttgtata tccatttttcg   3600
gatctgatca agagacagga tgaggatcgt ttcgcatgat tgaacaagat ggattgcacg   3660
caggttctcc ggccgcttgg gtggagaggc tattcggcta tgactggcca caacagacaa   3720
tcggctgctc tgatgccgcc gtgttccggc tgtcagcgca ggggcgcccg gttctttttg   3780
tcaagaccga cctgtccggt gccctgaatg aactgcagga cgaggcagcg cggctatcgt   3840
ggctggccac gacgggcgtt ccttgcgcag ctgtgctcga cgttgtcact gaagcgggaa   3900
gggactggct gctattgggc gaagtgccgg ggcaggatct cctgtcatct caccttgctc   3960
ctgccgagaa agtatccatc atggctgatg caatgcggcg gctgcatacg cttgatccgg   4020
ctacctgccc attcgaccac caagcgaaac atcgcatcga gcgagcacgt actcggatgg   4080
aagccggtct tgtcgatcag gatgatctgg acgaagagca tcaggggctc gcgccagccg   4140
aactgttcgc caggctcaag gcgcgcatgc ccgacgggcga ggatctcgtc gtgacccatg   4200
gcgatgcctg cttgccgaat atcatggtgg aaaatggccg cttttctgga ttcatcgact   4260
gtggccggct gggtgtggcg gaccgctatc aggacatagc gttggctacc cgtgatattg   4320
ctgaagagct tggcggcgaa tgggctgacc gcttcctcgt gctttacggt atcgccgctc   4380
ccgattcgca gcgcatcgcc ttctatcgcc ttcttgacga gttcttctga gcgggactct   4440
ggggttcgaa atgaccgacc aagcgacgcc caacctgcca tcacgagatt cgattccac   4500
cgccgccttc tatgaaaggt tgggcttcgg aatcgttttc cgggacgccg gctggatgat   4560
cctccagcgc ggggatctca tgctggagtt cttcgcccac cccaacttgt ttattgcagc   4620
ttataatggt tacaaataaa gcaatagcat cacaaatttc acaaataaag catttttttc   4680
actgcattct agttgtggtt tgtccaaact catcaatgta tcttatcatg tctgtatacc   4740
gtcgacctct agctagagct tggcgtaatc atggtcatag ctgtttcctg tgtgaaattg   4800
ttatccgctc acaattccac acaacatacg agccggaagc ataaagtgta aagcctgggg   4860
tgcctaatga gtgagctaac tcacattaat tgcgttgcgc tcactgcccg ctttccagtc   4920
gggaaacctg tcgtgccagc tgcattaatg aatcggccaa cgcgcgggga gaggcggttt   4980
gcgtattggg cgctcttccg cttcctcgct cactgactcg ctgcgctcgg tcgttcggct   5040
gcggcgagcg gtatcagctc actcaaaggc ggtaatacgg ttatccacag aatcagggga   5100
taacgcagga aagaacatgt gagcaaaagg ccagcaaaag gccaggaacc gtaaaaaggc   5160
cgcgttgctg gcgtttttcc ataggctccg cccccctgac gagcatcaca aaaatcgacg   5220
ctcaagtcag aggtggcgaa acccgacagg actataaaga taccaggcgt ttccccctgg   5280
aagctccctc gtgcgctctc ctgttccgac cctgccgctt accggatacc tgtccgcctt   5340
tctcccttcg ggaagcgtgg cgctttctca tagctcacgc tgtaggtatc tcagttcggt   5400
gtaggtcgtt cgctccaagc tgggctgtgt gcacgaaccc cccgttcagc ccgaccgctg   5460
cgccttatcc ggtaactatc gtcttgagtc caacccggta agacacgact tatcgccact   5520
ggcagcagcc actggtaaca ggattagcag agcgaggtat gtaggcggtg ctacagagtt   5580
cttgaagtgg tggcctaact acggctacac tagaagaaca gtatttggta tctgcgctct   5640
gctgaagcca gttaccttcg gaaaaagagt tggtagctct tgatccggca aacaaaccac   5700
cgctggtagc ggtggttttt ttgtttgcaa gcagcagatt acgcgcagaa aaaaaggatc   5760
tcaagaagat cctttgatct tttctacggg gtctgacgct cagtggaacg aaaactcacg   5820
ttaagggatt ttggtcatga gattatcaaa aaggatcttc acctagatcc ttttaaatta   5880
aaaatgaagt tttaaatcaa tctaaagtat atatgagtaa acttggtctg acagttacca   5940
atgcttaatc agtgaggcac ctatctcagc gatctgtcta tttcgttcat ccatagttgc   6000
ctgactcccg tcgtgtaga taactacgat acgggagggc ttaccatctg gccccagtgc   6060
tgcaatgata ccgcgagacc cacgctcacc ggctccagat ttatcagcaa taaaccagcc   6120
```

```
agccggaagg gccgagcgca gaagtggtcc tgcaacttta tccgcctcca tccagtctat  6180
taattgttgc cgggaagcta gagtaagtag ttcgccagtt aatagtttgc gcaacgttgt  6240
tgccattgct acaggcatcg tggtgtcacg ctcgtcgttt ggtatggctt cattcagctc  6300
cggttcccaa cgatcaaggc gagttacatg atcccccatg ttgtgcaaaa aagcggttag  6360
ctccttcggt cctccgatcg ttgtcagaag taagttgacg gcagtgttat cactcatggt  6420
tatggcagca ctgcataatt ctcttactgt catgccatcc gtaagatgct tttctgtgac  6480
tggtgagtac tcaaccaagt cattctgaga atagtgtatg cggcgaccga gttgctcttg  6540
cccggcgtca atacgggata ataccgcgcc acatagcaga actttaaaag tgctcatcat  6600
tggaaaacgt tcttcggggc gaaaactctc aaggatctta ccgctgttga gatccagttc  6660
gatgtaaccc actcgtgcac ccaactgatc ttcagcatct tttactttca ccagcgtttc  6720
tgggtgagca aaaacaggaa ggcaaaatgc cgcaaaaaag ggaataaggg cgacacggaa  6780
atgttgaata ctcatactct tcctttttca atattattga agcatttatc agggttattg  6840
tctcatgagc ggatacatat ttgaatgtat ttagaaaaat aaacaaatag gggttccgcg  6900
cacatttccc cgaaaagtgc cacctgacgt c                                 6931

SEQ ID NO: 41             moltype = AA  length = 472
FEATURE                   Location/Qualifiers
REGION                    1..472
                          note = GAP43-SSGSSGTG-meGFP-PRGrh
source                    1..472
                          mol_type = protein
                          organism = synthetic construct
SEQUENCE: 41
MLCCMRRTKQ VEKNDEDQNS SGSSGTGSKG EELFTGVVPI LVELDGDVNG HKFSVSGEGE   60
GDATYGKLTL KFICTTGKLP VPWPTLVTTL TYGVQCFSRY PDHMKRHDFF KSAMPEGYVQ  120
ERTIFFKDDG NYKTRAEVKF EGDTLVNRIE LKGIDFKEDG NILGHKLEYN YNSHNVYIMA  180
DKQKNGIKAN FKIRHNIESG GVQLADHYQQ NTPIGDGPVL LPDNHYLSTQ SKLSKDPNEK  240
RDHMVLKERV TAAGITHGMD ELYKGSSREL IIGPEEDYDP GYFNNESDII FQDLEKLKSH  300
PAYLVVFLRY ILSQADPGPL LFYLCSEVYQ QTNPKDSRSL GKDIWNIFLE KNAPLRVKIP  360
EMLQAEIDLR LRNNEDPRNV LCEAQEAVML EIQEQINDYR SKRTLGLGSL YGENDLLGLD  420
GDPLRERQMA EKQLAALGDI LSKYEEDRSA PMDFAVNTFM SHAGIRLRES RG          472

SEQ ID NO: 42             moltype = DNA  length = 6811
FEATURE                   Location/Qualifiers
misc_feature              1..6811
                          note = GAP43-SSGSSGTG-meGFP-PRGrh
source                    1..6811
                          mol_type = other DNA
                          organism = synthetic construct
SEQUENCE: 42
gacggatcgg gagatctccc gatccctat ggtgcactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacgggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggag tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta acaactccgc cccattgacg caaatgggcg   780
gtaggcgtgt acggtgggag gtctatataa gcagagctct ctggctaact agagaaccca   840
ctgcttactg gcttatcgaa attaatacga ctcactatag ggagacccaa gctggctagc   900
gtttaaactt aagcttggta ccgacgacc atgctgtgct gtatgagaag aaccaaacag   960
gttgaaaaga atgatgagga ccagaattcc tccggatcgt ctggaaccgg ttctaaagga  1020
gaagaacttt tcactggagt tgtcccaatt cttgttgaat tagatggtga tgttaatggg  1080
cacaaatttt ctgtcagtgg agagggtgaa ggtgatgcaa catacggaaa acttaccctt  1140
aaatttattt gcactactgg aaaactacct gttccttggc caacacttgt cactacttta  1200
acttatggtt tcaatgcttt ttcaagatac ccagatcata tgaaacggca tgactttttc  1260
aagagtgcca tgcccgaagg ttatgtacag gaaagaacta tatttttcaa agatgacggg  1320
aactacaaga cacgtgctga agtcaagttt gaaggtgata cccttgttaa tagaatcgag  1380
ttaaaaggta ttgattttaa agaagatgga aacattcttg gacacaaatt ggaatacaac  1440
tataactcac acaatgtata catcatggca gacaaacaaa agaatggaat caaagctaac  1500
ttcaaaatta gacacaacat tgagtccgga ggcgttcaac tagcagacca ttatcaacaa  1560
aatactccaa ttggcgatgg ccctgtcctt ttaccagaca accattacct gtccacacaa  1620
tctaagctttt cgaaagatcc caacgaaaag agagaccaca tggtccttaa agagagggta  1680
acagctgctg ggattacaca tggcatggac gagctgtaca aggatcctc tagagagctg  1740
attattggcc cagaggaaga ttatgaccca ggttatttca acaatgagag tgacatcatc  1800
ttccaagatc ttgaaaaact gaagtcacat ccagcttact tggtagtttt tctacgttac  1860
atcctctctc aggcagaccc tggccccctg ctttttttatt tgtgttcaga agtttatcaa  1920
cagacaaatc ccaaagattc cgaagtctg gggaaagaca tctggaacat tttcctggag  1980
aaaaatgcgc ctcagagt gaagatccct gagatgttga acatgcaagc gtaccctacgc  2040
ctgcggaaca atgaggaccc tcgcaatgtg ctctgtgaag ctcaggaggc agtcatgctg  2100
gaaatccagg agcagatcaa cgactacaga tccaagcgta ctctgggcct gggcagcctc  2160
tatggtgaaa atgacctgct aggcctggat ggggaccctc ttcgagaacg ccaaatggct  2220
gagaagcagc tggctgccct tggagatatc ttgtccaaat atgaggaaga tcggagtgcc  2280
cccatggact ttgctgttaa tacctttatg agccacgctg ggatccgtct tcgggagtct  2340
```

```
cgaggataat gaaggtggcg gccgctcgaa actagagggc ccgtttaaac ccgctgatca   2400
gcctcgactg tgccttctag ttgccagcca tctgttgttt gcccctcccc cgtgccttcc   2460
ttgaccctgg aaggtgccac tcccactgtc ctttcctaat aaaatgagga aattgcatcg   2520
cattgtctga gtaggtgtca ttctattctg ggggtggggg tggggcagga cagcaagggg   2580
gaggattggg aagacaatag caggcatgct ggggatgcgg tgggctctat ggcttctgag   2640
gcggaaagaa ccagctgggg ctctaggggg tatccccacg cgccctgtag cggcgcatta   2700
agcgcggcgg gtgtggtggt tacgcgcagc gtgaccgcta cacttgccag cgccctagcg   2760
cccgctcctt tcgctttctt cccttccttt ctcgccacgt tcgccggctt tccccgtcaa   2820
gctctaaatc gggggctccc tttagggttc cgatttagtg ctttacggca cctcgacccc   2880
aaaaaacttg attagggtga tggttcacgt agtgggccat cgccctgata gacggttttt   2940
cgccctttga cgttggagtc cacgttcttt aatagtggac tcttgttcca aactggaaca   3000
acactcaacc ctatctcggt ctattctttt gatttataag ggattttgcc gatttcggcc   3060
tattggttaa aaaatgagct gatttaacaa aaatttaacg cgaattaatt ctgtggaatg   3120
tgtgtcagtt agggtgtgga aagtccccag gctccccagc aggcagaagt atgcaaagca   3180
tgcatctcaa ttagtcagca accaggtgtg gaaagtcccc aggctcccca gcaggcagaa   3240
gtatgcaaag catgcatctc aattagtcag caaccatagt cccgcccta actccgccca   3300
tcccgcccct aactccgccc agttccgccc attctccgcc ccatggctga ctaattttttt   3360
ttatttatgc agaggccgag gccgcctctg cctctgagct attccagaag tagtgaggag   3420
gcttttttgg aggcctaggc ttttgcaaaa agctcccggg agcttgtata tccattttcg   3480
gatctgatca agagacagga tgaggatcgt ttcgcatgat tgaacaagat ggattgcacg   3540
caggttctcc ggccgcttgg gtggagaggc tattcggcta tgactgggca caacagacaa   3600
tcggctgctc tgatgccgcc gtgttccggc tgtcagcgca ggggcgcccg gttctttttg   3660
tcaagaccga cctgtccggt gccctgaatg aactgcagga cgaggcagcg cggctatcgt   3720
ggctggccac gacgggcgtt ccttgcgcag ctgtgctcga cgttgtcact gaagcgggaa   3780
gggactggct gctattgggc gaagtgccgg ggcaggatct cctgtcatct caccttgctc   3840
ctgccgagaa agtatccatc atggctgatg caatgcggcg gctgcatacg cttgatccgg   3900
ctacctgccc attcgaccac caagcgaaac atcgcatcga gcgagcacgt actcggatgg   3960
aagccggtct tgtcgatcag gatgatctgg acgaagagca tcaggggctc gcgccagccg   4020
aactgttcgc caggctcaag gcgcgcatgc ccgacggcga ggatctcgtc gtgacccatg   4080
gcgatgcctg cttgccgaat atcatggtgg aaaatggccg cttttctgga ttcatcgact   4140
gtggccgct gggtgtggcg gaccgctatc aggacatagc gttggctacc cgtgatattg   4200
ctgaagagct tggcggcgaa tgggctgacc gcttcctcgt gctttacggt atcgccgctc   4260
ccgattcgca gcgcatcgcc ttctatcgcc ttcttgacga gttcttctga gcgggactct   4320
ggggttcgaa atgaccgacc aagcgacgcc caacctgcca tcacgagatt tcgattccac   4380
cgccgccttc tatgaaaggt tgggcttcgg aatcgttttc cgggacgccg gctggatgat   4440
cctccagcgc ggggatctca tgctggagtt cttcgcccac cccaacttgt ttattgcagc   4500
ttataatggt tacaaataaa gcaatagcat cacaaatttc acaaataaag catttttttc   4560
actgcattct agttgtggtt tgtccaaact catcaatgta tcttatcatg tctgtatacc   4620
gtcgacctct agctagagct tggcgtaatc atggtcatag ctgtttcctg tgtgaaattg   4680
ttatccgctc acaattccac acaacatacg agccggaagc ataaagtgta aagcctgggg   4740
tgcctaatga gtgagctaac tcacattaat tgcgttgcgc tcactgcccg ctttccagtc   4800
gggaaacctg tcgtgccagc tgcattaatg aatcggccaa cgcgcgggga gaggcggttt   4860
gcgtattggg cgctcttccg cttcctcgct cactgactcg ctgcgctcgg tcgttcggct   4920
gcggcgagcg gtatcagctc actcaaaggc ggtaatacgg ttatccacag aatcagggga   4980
taacgcagga aagaacatgt gagcaaaagg ccagcaaaag gccaggaacc gtaaaaaggc   5040
cgcgttgctg gcgtttttcc ataggctccg ccccctgac gagcatcaca aaatcgacg   5100
ctcaagtcag aggtggcgaa acccgacagg actataaaga taccaggcgt ttcccctag   5160
aagctccctc gtgcgctctc ctgttccgac cctgccgctt accggatacc tgtccgcctt   5220
tctcccttcg ggaagcgtgg cgctttctca tagctcacgc tgtaggtatc tcagttcggt   5280
gtaggtcgtt cgctccaagc tgggctgtgt gcacgaaccc cccgttcagc ccgaccgctg   5340
cgccttatcc ggtaactatc gtcttgagtc caacccggta agacacgact tatcgccact   5400
ggcagcagcc actggtaaca ggattagcag agcgaggtat gtaggcggtg ctacagagtt   5460
cttgaagtgg tggcctaact acggctacac tagaagaaca gtatttggta tctgcgctct   5520
gctgaagcca gttaccttcg gaaaaagagt tggtagctct tgatccggca aacaaaccac   5580
cgctggtagc ggtggttttt ttgtttgcaa gcagcagatt acgcgcagaa aaaaaggatc   5640
tcaagaagat cctttgatct tttctacggg gtctgacgct cagtggaacg aaaactcacg   5700
ttaagggatt ttggtcatga gattatcaaa aaggatcttc acctagatcc ttttaaatta   5760
aaaatgaagt tttaaatcaa tctaaagtat atatgagtaa acttggtctg acagttacca   5820
atgcttaatc agtgaggcac ctatctcagc gatctgtcta tttcgttcat ccatagttgc   5880
ctgactcccc gtcgtgtaga taactacgat acgggagggc ttaccatctg gccccagtgc   5940
tgcaatgata ccgcgagacc cacgctcacc ggctccagat ttatcagcaa taaaccagcc   6000
agccggaagg gccgagcgca gaagtggtcc tgcaacttta tccgcctcca tccagtctat   6060
taattgttgc cgggaagcta gagtaagtag ttcgccagtt aatagtttgc gcaacgttgt   6120
tgccattgct acaggcatcg tggtgtcacg ctcgtcgttt ggtatggctt cattcagctc   6180
cggttcccaa cgatcaaggc gagttacatg atcccccatg ttgtgcaaaa aagcggttag   6240
ctccttcggt cctccgatcg ttgtcagaag taagttggcc gcagtgttat cactcatggt   6300
tatggcagca ctgcataatt ctcttactgt catgccatcc gtaagatgct tttctgtgac   6360
tggtgagtac tcaaccaagt cattctgaga atagtgtatg cggcgaccga gttgctcttg   6420
cccggcgtca atacgggata ataccgcgcc acatagcaga actttaaaag tgctcatcat   6480
tggaaaacgt tcttcggggc gaaaactctc aaggatctta ccgctgttga tccagttc   6540
gatgtaaccc actcgtgcac ccaactgatc ttcagcatct tttactttca ccagcgtttc   6600
tgggtgagca aaaacaggaa ggcaaaatgc cgcaaaaaag gaataaggg cgacacggaa   6660
atgttgaata ctcatactct tcctttttca atattattga agcatttatc agggttattg   6720
tctcatgagc ggatacatat ttgaatgtat ttagaaaaat aaacaaatag gggttccgcg   6780
cacatttccc cgaaaagtgc cacctgacgt c                                 6811
```

```
SEQ ID NO: 43       moltype = AA  length = 377
FEATURE             Location/Qualifiers
REGION              1..377
```

```
                          note = G 13(Q226L)
source                    1..377
                          mol_type = protein
                          organism = synthetic construct
SEQUENCE: 43
MADFLPSRSV LSVCFPGCLL TSGEAEQQRK SKEIDKCLSR EKTYVKRLVK ILLLGAGESG  60
KSTFLKQMRI IHGQDFDQRA REEFRPTIYS NVIKGMRVLV DAREKLHIPW GDNSNQQHGD  120
KMMSFDTRAP MAAQGMVETR VFLQYLPAIR ALWADSGIQN AYDRRREFQL GESVKYFLDN  180
LDKLGEPDYI PSQQDILLAR RPTKGIHEYD FEIKNVPFKM VDVGGLRSER KRWFECFDSV  240
TSILFLVSSS EFDQVLMEDR LTNRLTESLN IFETIVNNRV FSNVSIILFL NKTDLLEEKV  300
QIVSIKDYFL EFEGDPHCLR DVQKFLVECF RNKRRDQQQK PLYHHFTTAI NTENIRLVFR  360
DVKDTILHDN LKQLMLQ                                                377

SEQ ID NO: 44            moltype = DNA   length = 6507
FEATURE                  Location/Qualifiers
misc_feature             1..6507
                         note = Galfa13(Q226L)
source                   1..6507
                         mol_type = other DNA
                         organism = synthetic construct
SEQUENCE: 44
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacgggtac attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
gtttaaactt aagcttggta ccaccatggc ggacttcctg ccgtcgcggt ccgtgctgtc  960
cgtgtgcttc cccggctgcc tgctgacgag tggcgaggcc gagcagcaac gcaagtccaa  1020
ggagatcgac aaatgcctgt ctcgggaaaa gacctatgtg aagcggctgg tgaagatcct  1080
gctgctgggc gcgggcgaga gcggcaagtc caccttcctg aagcagatgc ggatcatcca  1140
cgggcaggac ttcgaccagc gcgcgcgcga ggagttccgc cccaccatct acagcaacgt  1200
gatcaaaggt atgagggtgc tggttgatgc tcgagagaag cttcatattc cctgggggaga  1260
caactcaaac caacaacatg gagataagat gatgtcgttt gatacccggg cccccatggc  1320
agcccaagga atggtggaaa caaggggtttt cttacaatat cttcctgcta taagagcatt  1380
atgggcagac agcggcatac agaatgccta tgaccggcgt cgagaatttc aactgggtga  1440
atctgtaaaa tatttcctgg ataacttgga taaacttgga gaaccagatt atattccatc  1500
acaacaagat attctgcttg ccagaagacc caccaaaggc atccatgaat acgactttga  1560
aataaaaaat gttcctttca aaatggttga tgtaggtggt ctgagatcag aaaggaaacg  1620
ttggtttgaa tgtttcgaca gtgtgacatc aatacttttc cttgtttcct caagtgaatt  1680
tgaccaggtg cttatggaag atcgactgac caatcgcctt acagagtctc tgaacatttt  1740
tgaaacaatc gtcaataacc gggttttcag caatgtctct ataattctgt tcttaaacaa  1800
gacagacttg cttgaggaga aggtgcaaat tgtgagcatc aaagactatt tcctagaatt  1860
tgaaggggat ccccactgct taagagacgt ccaaaaattc ctggtggaat gtttccggaa  1920
caaacgccgg gaccagcaac agaagccctt ataccaccac ttcaccactg ctatcaacac  1980
ggagaacatc cgccttgttt tccgtgacgt gaaggatact attctgcatg acaacctcaa  2040
gcagcttatg ctacagtgat ctagagatct ctagagggcc cgtttaaacc cgctgatcag  2100
cctcgactgt gccttctagt tgccagccat ctgttgtttg cccctccccc gtgccttcct  2160
tgaccctgga aggtgccact cccactgtcc tttcctaata aaatgaggaa attgcatcgc  2220
attgtctgag taggtgtcat tctattctgg ggggtgggg ggggcaggac agcaaggggg  2280
aggattggga agacaatagc aggcatgctg gggatgcggt gggctctatg gcttctgagg  2340
cggaaagaac cagctggggc tctagggggg atccccacgc gccctgtagc ggcgcattaa  2400
gcgcggcggg tgtggtggtt acgcgcagcg tgaccgctac acttgccagc gccctagcgc  2460
ccgctccttt cgctttcttc ccttcctttc tcgccacgtt cgccggcttt ccccgtcaag  2520
ctctaaatcg ggggctccct ttagggttcc gatttagtgc tttacggcac ctcgacccca  2580
aaaaacttga ttagggtgat ggttcacgta gtgggccatc gccctgatag acggtttttc  2640
gccctttgac gttggagtcc acgttcttta atagtggact cttgttccaa actggaacaa  2700
cactcaaccc tatctcggtc tattcttttg atttataagg gattttgccg atttcggcct  2760
attggttaaa aaatgagctg atttaacaaa aatttaacgc gaattaattc tgtggaatgt  2820
gtgtcagtta gggtgtggaa agtccccagg ctccccagca ggcagaagta tgcaaagcat  2880
gcatctcaat agtcagcaa ccaggtgtgg aaagtcccca ggctccccag caggcagaag  2940
tatgcaaagc atgcatctca attagtcagc aaccatagtc ccgcccctaa ctccgcccat  3000
cccgccccta actccgccca gttccgccca ttctccgccc catggctgac taatttttttt  3060
tatttatgca gaggccgagg ccgcctctgc ctctgagcta ttccagaagt agtgaggagg  3120
cttttttgga ggcctaggct tttgcaaaaa gctcccggga gcttgtatat ccattttcgg  3180
atctgatcaa agacaggat gaggatcgtt tcgcatgatt gaacaagatg gattgcacgc  3240
aggttctccg gccgcttggg tggagaggct attcggctat gactgggcac aacagacaat  3300
cggctgctct gatgccgccg tgttccggct gtcagcgcag gggcgcccgg ttctttttgt  3360
caagaccgac ctgtccggtg ccctgaatga actgcaggac gaggcagcgc ggctatcgtg  3420
gctggccacg acgggcgttc cttgcgcagc tgtgctcgac gttgtcactg aagcgggaag  3480
```

```
ggactggctg ctattgggcg aagtgccggg gcaggatctc ctgtcatctc accttgctcc   3540
tgccgagaaa gtatccatca tggctgatgc aatgcggcgg ctgcatacgc ttgatccggc   3600
tacctgccca ttcgaccacc aagcgaaaca tcgcatcgag cgagcacgta ctcggatgga   3660
agccggtctt gtcgatcagg atgatctgga cgaaagagcat caggggctcg cgccagccga   3720
actgttcgcc aggctcaagg cgcgcatgcc cgacggcgag gatctcgtcg tgacccatgg   3780
cgatgcctgc ttgccgaata tcatggtgga aaatggccgc ttttctggat tcatcgactg   3840
tggccggctg ggtgtggcgg accgctatca ggacatagcg ttggctaccc gtgatattgc   3900
tgaagagctt ggcggcgaat gggctgaccg cttcctcgtg ctttacggta tcgccgctcc   3960
cgattcgcag cgcatcgcct tctatcgcct tcttgacgag ttcttctgag cgggactctg   4020
gggttcgaaa tgaccgacca agcgacgccc aacctgccat cacgagattt cgattccacc   4080
gccgccttct atgaaaggtt gggcttcgga atcgttttcc gggacgccgg ctggatgatc   4140
ctccagcgcg gggatctcat gctggagttc ttcgcccacc ccaacttgtt tattgcagct   4200
tataatggtt acaaataaag caatagcatc acaaatttca caaataaagc atttttttca   4260
ctgcattcta gttgtggttt gtccaaactc atcaatgtat cttatcatgt ctgtataccg   4320
tcgacctcta gctagagctt ggcgtaatca tggtcatagc tgtttcctgt gtgaaattgt   4380
tatccgctca caattccaca caacatacga gccggaagca taaagtgtaa agcctggggt   4440
gcctaatgag tgagctaact cacattaatt gcgttgcgct cactgcccgc tttccagtcg   4500
ggaaacctgt cgtgccaact gcattaatga atcggccaac gcgcggggag aggcggtttg   4560
cgtattgggc gctcttccgc ttcctcgctc actgactcgc tgcgctcggt cgttcggctg   4620
cggcgagcgg tatcagctca ctcaaaggcg gtaatacggt tatccacaga atcaggggat   4680
aacgcaggaa agaacatgtg agcaaaaggc cagcaaaagg ccaggaaccg taaaaaggcc   4740
gcgttgctgg cgtttttcca taggctccgc ccccctgacg agcatcacaa aaatcgacgc   4800
tcaagtcaga ggtggcgaaa cccgacagga ctataaagat accaggcgtt ccccctgga   4860
agctccctcg tgcgctctcc tgttccgacc ctgccgctta ccggatacct gtccgccttt   4920
ctcccttcgg gaagcgtggc gctttctcat agctcacgct gtaggtatct cagttcggtg   4980
taggtcgttc gctccaagct gggctgtgtg cacgaacccc ccgttcagcc cgaccgctgc   5040
gccttatccg gtaactatcg tcttgagtcc aacccggtaa gacacgactt atcgccactg   5100
gcagcagcca ctggtaacag gattagcaga gcgaggtatg taggcggtgc tacagagttc   5160
ttgaagtggt ggcctaacta cggctacact agaagaacag tatttggtat ctgcgctctg   5220
ctgaagccag ttaccttcgg aaaaagagtt ggtagctctt gatccggcaa acaaaccacc   5280
gctggtagcg gtttttttgt ttgcaagcag cagattacgc gcagaaaaaa aggatctcaa   5340
gaagatcctt tgatctttc tacggggtct gacgctcagt ggaacgaaaa ctcacgttaa   5400
gggattttgg tcatgagatt atcaaaaagg atcttcacct agatccttt aaattaaaaa   5460
tgaagtttta aatcaatcta aagtatatat gagtaaactt ggtctgacag ttaccaatgc   5520
ttaatcagtg aggcacctat ctcagcgatc tgtctatttc gttcatccat agttgcctga   5580
ctccccgtcg tgtagataac tacgatacgg gagggcttac catctggccc cagtgctgca   5640
atgataccgc gagacccacg ctcaccggct ccagatttat cagcaataaa ccagccagcc   5700
ggaagggccg agcgcagaag tggtcctgca actttatccg cctccatcca gtctattaat   5760
tgttgccggg aagctagagt aagtagttcg ccagttaata gtttgcgcaa cgttgttgcc   5820
attgctacag gcatcgtggt gtcacgctcg tcgtttggta tggcttcatt cagctccggt   5880
tcccaacgat caaggcgagt tacatgatcc cccatgttgt gcaaaaaagc ggttagctcc   5940
ttcggtcctc cgatcgttgt cagaagtaag ttggccgcag tgttatcact catggttatg   6000
gcagcactgc ataattctct tactgtcatg ccatccgtaa gatgcttttc tgtgactggt   6060
gagtactcaa ccaagtcatt ctgagaatag tgtatgcggc gaccgagttg ctcttgcccg   6120
gcgtcaatac gggataatac cgcgccacat agcagaactt aaaagtgct catcattgga   6180
aaacgttctt cggggcgaaa actctcaagg atcttaccgc tgttgagatc cagttcgatg   6240
taacccactc gtgcacccaa ctgatcttca gcatctttta cttcaccag cgtttctggg   6300
tgagcaaaaa caggaaggca aaatgccgca aaaaagggaa taagggcgac acggaaatgt   6360
tgaatactca tactcttcct ttttcaatat tattgaagca tttatcaggg ttattgtctc   6420
atgagcggat acatatttga atgtatttag aaaaataaac aaataggggt tccgcgcaca   6480
tttccccgaa aagtgccacc tgacgtc                                         6507
```

```
SEQ ID NO: 45          moltype = AA  length = 342
FEATURE                Location/Qualifiers
REGION                 1..342
                       note = rhotekin-meGFP-GSGGSGG-hRas
source                 1..342
                       mol_type = protein
                       organism = synthetic construct
SEQUENCE: 45
MSSRGILEDL NMLYIRQMAL SLEDTELQRK LDHEIRMRDG ACKLLAACSQ REQALEATKS   60
LLVCNSRILS YMGELQRRKE AQVLEKTSRG KGEELFTGVV PILVELDGDV NGHKFSVSGE   120
GEGDATYGKL TLKFICTTGK LPVPWPTLVT TLTYGVQCFS RYPDHMKRHD FFKSAMPEGY   180
VQERTIFFKD DGNYKTRAEV KFEGDTLVNR IELKGIDFKE DGNILGHKLE YNYNSHNVYI   240
MADKQKNGIK ANFKIRHNIE SGGVQLADHY QQNTPIGDGP VLLPDNHYLS TQSKLSKDPN   300
EKRDHMVLKE RVTAAGITHG MDELYKGSGG SGGCMSCKCV LS                       342
```

```
SEQ ID NO: 46          moltype = DNA  length = 6436
FEATURE                Location/Qualifiers
misc_feature           1..6436
                       note = rhotekinRBD-meGFP-GSGGSGG-hRas
source                 1..6436
                       mol_type = other DNA
                       organism = synthetic construct
SEQUENCE: 46
gacggatcgg gagatctccc gatccctat ggtgcactct cagtacaatc tgctctgatg   60
ccgcatagtt aagccagtat ctgctccctg cttgtgtgtt ggaggtcgct gagtagtgcg   120
cgagcaaaat ttaagctaca caaggcaag gcttgaccga caattgcatg aagaatctgc   180
ttagggttag gcgttttgcg ctgcttcgcg atgtacgggc cagatatacg cgttgacatt   240
```

-continued

```
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggag tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta acaactccgc cccattgacg caaatgggcg   780
gtaggcgtgt acggtgggag gtctatataa gcagagctct ctggctaact agagaaccca   840
ctgcttactg gcttatcgaa attaatacga ctcactatag ggagacccaa gctggctagc   900
ggtaccgagc tcggatcact agtccagtgt ggtggaattc acgcggacca tgtcttctag   960
aggaatcctg gaggacctca atatgctcta catccggcag atggcactca gcctggagga  1020
cacagagctg cagaggaaac tagatcatga gatccggatg aggatggggg cctgcaagct  1080
gctggcagcc tgctcccagc gagaacaggc tctggaagcc accaagagcc tgctggtgtg  1140
caacagccgt attctcagct acatgggtga gctgcagcgg cgaaaggagg cccaggtgct  1200
ggagaagaca tctcgaggta aaggagaaga actttttcact ggagttgtcc caattcttgt  1260
tgaattagat ggtgatgtta atgggcacaa attttctgtc agtggagagg gtgaaggtga  1320
tgcaacatac ggaaaactta cccttaaatt tatttgcact actggaaaac tacctgttcc  1380
ttggccaaca cttgtcacta ctttaactta tggtgttcaa tgcttttcaa gatacccaga  1440
tcatatgaaa cggcatgact tttttcaagag tgccatgccc gaaggttatg tacaggaaag  1500
aactatattt ttcaaagatg acgggaacta caagacacgt gctgaagtca agtttgaagg  1560
tgatacccct gttaatagaa tcgagttaaa aggtattgat tttaaagaag atggaaacat  1620
tcttggacac aaattggaat acaactataa ctcacacaat gtatacatca tggcagacaa  1680
acaaaagaat ggaatcaaag ctaacttcaa aattagacac aacattgagt ccggaggcgt  1740
tcaactagca gaccattatc aacaaaatac tccaattgac gatggccctg tccttttacc  1800
agacaaccat tacctgtcca cacaatctaa gctttcgaaa gatcccaacg aaaagagaga  1860
ccacatggtc cttaaagaga gggtaacagc tgctgggatt acacatggca tggacgagct  1920
gtacaaggga tccggtggaa gtggaggctg catgagctgc aagtgtgtgc tgtcctaatg  1980
agcggccgca ctagagggcc cgggcccgtt taaacccgct gatcagcctc gactgtgcct  2040
tctagttgcc agccatctgt tgtttgcccc tcccccgtgc cttccttgac cctggaaggt  2100
gccactccca ctgtcctttc ctaataaaat gaggaaattg catcgcattg tctgagtagg  2160
tgtcattcta ttctgggggg tggggtgggg caggacagca agggggagga ttgggaagac  2220
aatagcaggc atgctgggga tgcggtgggc tctatggctt ctgaggcgga aagaaccagc  2280
tggggctcta gggggtatcc ccacgcgccc tgtagcggcg cattaagcgc ggcgggtgtg  2340
gtggttacgc gcagcgtgac cgctacactt gccagcgccc tagcgcccgc tcctttcgct  2400
ttcttccctt cctttctcgc cacgttcgcc ggctttcccc gtcaagctct aaatcggggg  2460
ctccctttag ggttccgatt tagtgcttta cggcacctcg acccccaaaaa acttgattag  2520
ggtgatggtt cacgtagtgg gccatcgccc tgatagacgg tttttcgccc tttgacgttg  2580
gagtccacgt tctttaatag tggactcttg ttccaaactg gaacaacact caaccctatc  2640
tcggtctatt cttttgattt ataagggatt ttgccgattt cggcctattg gttaaaaaat  2700
gagctgattt aacaaaaatt taacgcgaat taattctgtg gaatgtgtgt cagttagggt  2760
gtggaaagtc cccaggctcc ccagcaggca gaagtatgca aagcatgcat ctcaattagt  2820
cagcaaccag gtgtggaaag tccccaggct ccccagcagg cagaagtatg caaagcatgc  2880
atctcaatta gtcagcaacc atagtcccgc ccctaactcc gcccatcccg cccctaactc  2940
cgcccagttc cgcccattct ccgccccatg gctgactaat ttttttttatt tatgcagagg  3000
ccgaggccgc ctctgcctct gagctattcc agaagtagtg aggaggcttt tttggaggcc  3060
taggcttttg caaaaagctc ccgggagctt gtatatccat tttcggatct gatcaagaga  3120
caggatgagg atcgtttcgc atgattgaac aagatggatt gcacgcaggt tctccggccg  3180
cttgggtgga gaggctattc ggctatgact gggcacaaca gacaatcggc tgctctgatg  3240
ccgccgtgtt ccggctgtca gcgcagggc gcccggttct ttttgtcaag accgacctgt  3300
ccggtgccct gaatgaactg caggacgagg cagcgcggct atcgtggctg gccacgacgg  3360
gcgttccttg cgcagctgtg ctcgacgttg tcactgaagc gggaagggac tggctgctat  3420
tgggcgaagt gccggggcag gatctcctgt catctcacct tgctcctgcc gagaaagtat  3480
ccatcatggc tgatgcaatg cggcggctgc atacgcttga tccggctacc tgcccattcg  3540
accaccaagc gaaacatcgc atcgagcgag cacgtactcg gatggaagcc ggtcttgtcg  3600
atcaggatga tctggacgaa gagcatcagg ggctcgcgcc agccgaactg ttcgccaggc  3660
tcaaggcgcg catgcccgac ggcgaggatc tcgtcgtgac ccatggcgat gcctgcttgc  3720
cgaatatcat ggtggaaaat ggccgctttt ctggattcat cgactgtggc cggctgggtg  3780
tggcggaccg ctatcaggac atagcgttgg ctacccgtga tattgctgaa gagcttggcg  3840
gcgaatgggc tgaccgcttc ctcgtgcttt acggtatcgc cgctcccgat tcgcagcgca  3900
tcgccttcta tcgccttctt gacgagttct tctgagcggg actctggggt tcgaaatgac  3960
cgaccaagcg acgcccaacc tgccatcacg agatttcgat tccaccgccg ccttctatga  4020
aaggttgggc ttcggaatcg ttttccggga cgccgggttc ggatcctcc atggacgggg  4080
tctcatgctg gagttcttcg cccaccccaa cttgtttatt gcagcttata atggttacaa  4140
ataaagcaat agcatcacaa atttcacaaa taaagcattt tttcactgc attctagttg  4200
tggtttgtcc aaactcatca atgtatctta tcatgtctgt ataccgtcga cctctagcta  4260
gagcttggcg taatcatggt catagctgtt tcctgtgtga aattgttatc cgctcacaat  4320
tccacacaac atacgagccg gaagcataaa gtgtaaagcc tggggtgcct aatgagtgag  4380
ctaactcaca ttaattgcgt tgcgctcact gcccgctttc cagtcgggaa acctgtcgtg  4440
ccagctgcat taatgaatcg gccaacgcgc ggggagaggc ggtttgcgta ttgggcgctc  4500
ttccgcttcc tcgctcactg actcgctgcg ctcggtcgtt cggctgcggc gagcggtatc  4560
agctcactca aaggcggtaa tacggttatc cacagaatca ggggataacg caggaaagaa  4620
catgtgagca aaaggccagc aaaaggccag gaaccgtaaa aaggccgcgt tgctggcgtt  4680
tttccatagg ctccgccccc ctgacgagca tcacaaaaat cgacgctcaa gtcagaggtg  4740
gcgaaacccg acaggactat aaagatacca ggcgtttccc cctggaagct ccctcgtgcg  4800
ctctcctgtt ccgaccctgc cgcttaccgg atacctgtcc gcctttctcc cttcgggaag  4860
cgtggcgctt tctcatagct cacgctgtag gtatctcagt tcggtgtagg tcgttcgctc  4920
caagctgggc tgtgtgcacg aacccccccgt tcagcccgac cgctgcgcct tatccggtaa  4980
```

-continued

```
ctatcgtctt gagtccaacc cggtaagaca cgacttatcg ccactggcag cagccactgg   5040
taacaggatt agcagagcga ggtatgtagg cggtgctaca gagttcttga agtggtggcc   5100
taactacggc tacactagaa gaacagtatt tggtatctgc gctctgctga agccagttac   5160
cttcggaaaa agagttggta gctcttgatc cggcaaacaa accaccgctg gtagcggtgg   5220
tttttttgtt tgcaagcagc agattacgcg cagaaaaaaa ggatctcaag aagatccttt   5280
gatcttttct acggggtctg acgctcagtg gaacgaaaac tcacgttaag ggattttggt   5340
catgagatta tcaaaaagga tcttcaccta gatcctttta aattaaaaat gaagttttaa   5400
atcaatctaa agtatatatg agtaaacttg gtctgacagt taccaatgct taatcagtga   5460
ggcacctatc tcagcgatct gtctatttcg ttcatccata gttgcctgac tccccgtcgt   5520
gtagataact acgatacggg agggcttacc atctggcccc agtgctgcaa tgataccgcg   5580
agacccacgc tcaccggctc cagatttatc agcaataaac cagccagccg gaagggccga   5640
gcgcagaagt ggtcctgcaa ctttatccgc ctccatccag tctattaatt gttgccggga   5700
agctagagta agtagttcgc cagttaatag tttgcgcaac gttgttgcca ttgctacagg   5760
catcgtggtg tcacgctcgt cgtttggtat ggcttcattc agctccggtt cccaacgatc   5820
aaggcgagtt acatgatccc ccatgttgtg caaaaaagcg gttagctcct tcggtcctcc   5880
gatcgttgtc agaagtaagt tggccgcagt gttatcactc atggttatgg cagcactgca   5940
taattctctt actgtcatgc catccgtaag atgcttttct gtgactggtg agtactcaac   6000
caagtcattc tgagaatagt gtatgcggcg accgagttgc tcttgcccgg cgtcaatacg   6060
ggataatacc gcgccacata gcagaacttt aaaagtgctc atcattggaa aacgttcttc   6120
ggggcgaaaa ctctcaagga tcttaccgct gttgagatcc agttcgatgt aacccactcg   6180
tgcacccaac tgatcttcag catcttttac tttcaccagc gtttctgggt gagcaaaaac   6240
aggaaggcaa aatgccgcaa aaaagggaat aagggcgaca cggaaatgtt gaatactcat   6300
actcttcctt tttcaatatt attgaagcat ttatcaggggt tattgtctca tgagcggata   6360
catatttgaa tgtatttaga aaaataaaca aataggggtt ccgcgcacat ttccccgaaa   6420
agtgccacct gacgtc                                                    6436
```

```
SEQ ID NO: 47         moltype = AA   length = 193
FEATURE               Location/Qualifiers
REGION                1..193
                      note = RhoA(Q63L)
source                1..193
                      mol_type = protein
                      organism = synthetic construct
SEQUENCE: 47
MAAIRKKLVI VGDGACGKTC LLIVFSKDQF PEVYVPTVFE NYVADIEVDG KQVELALWDT   60
AGLEDYDRLR PLSYPDTDVI LMCFSIDSPD SLENIPEKWT PEVKHFCPNV PIILVGNKKD   120
LRNDEHTRRE LAKMKQEPVK PEEGRDMANR IGAFGYMECS AKTKDGVREV FEMATRAALQ   180
ARRGKKKSGC LVL                                                      193
```

```
SEQ ID NO: 48         moltype = DNA   length = 6565
FEATURE               Location/Qualifiers
misc_feature          1..6565
                      note = RhoA(Q63L)
source                1..6565
                      mol_type = other DNA
                      organism = synthetic construct
SEQUENCE: 48
tagttattaa tagtaatcaa ttacggggtc attagttcat agcccatata tggagttccg   60
cgttacataa cttacggtaa atggcccgcc tggctgaccg cccaacgacc cccgcccatt   120
gacgtcaata atgacgtatg ttcccatagt aacgccaata gggactttcc attgacgtca   180
atgggtggag tatttacggt aaactgccca cttggcagta catcaagtgt atcatatgcc   240
aagtacgccc cctattgacg tcaatgacgg taaatggccc gcctggcatt atgcccagta   300
catgacctta tgggactttc ctacttggca gtacatctac gtattagtca tcgctattac   360
catggtgatg cggttttggc agtacatcaa tgggcgtgga tagcggtttg actcacgggg   420
atttccaagt ctccacccca ttgacgtcaa tgggagtttg ttttggcacc aaaatcaacg   480
ggactttcca aaatgtcgta acaactccgc cccattgacg caaatgggcg gtaggcgtgt   540
acggtgggag gtctatataa gcagagctgg tttagtgaac cgtcagatcc gctagcctcg   600
acttgagctc ggatccggtg gttctggttc tggtggtacc atggctgcca tccggaagaa   660
actggtgatt gttggtgatg gagcctgtgg aaagacatgc ttgctcatag tcttcagcaa   720
ggaccagttc ccagaggtgt atgtgccac agtgtttgag aactatgtg cagatatcga   780
ggtggatgga aagcaggtag agttggcttt gtgggacaca gctgggctgg aagattatga   840
tcgcctgagc ccctctcct acccagatac cgatgttata ctgatgtgtt tttccatcga   900
cagccctgat agtttagaaa acatcccaga aaagtggacc ccagaagtca agcatttctg   960
tcccaacgtg cccatcatcc tggttgggaa taagaacgat cttcggaatg atgagcacac   1020
aaggcgggag ctagccaaga tgaagcagga gccggtgaaa cctgaagaag cagagatat   1080
ggcaaacagg attggcgctt ttgggtacat ggagtgttca gcaaagacca aagatggagt   1140
gagagaggtt tttgaaatgg ctacgagagc tgctctgcaa gctagacgtg gaagaaaaa   1200
atctgggtgc cttgtcttgt aaaagcttgc ggccgctcga gtctagaact agtttgagtc   1260
gagccgcgcc aattccgccc ccccccccc ccctctcct ccccccccc taacgttact   1320
ggccgaagcc gcttggaata aggccggtgt gcgtttgtct atatgttatt ttccaccata   1380
ttgccgtctt ttggcaatgt gagggcccgg aaacctggcc ctgtcttctt gacgagcatt   1440
cctaggggtc tttcccctct cgccaaagga atgcaaggtc tgttgaatgt cgtgaaggaa   1500
gcagttcctc tggaagcttc ttgaagacaa acaacgtctg tagcgaccct ttgcaggcag   1560
cggaacccc cacctggcaa caggtgcctc tgcggccaaa agccacgtgt ataagataca   1620
cctgcaaagg cggcacaacc ccagtgccac gttgtgagtt ggatagttgt ggaaagagtc   1680
aaatggctct cctcaagcgt attcaacaag ggctgaagg atgcccagaa ggtaccccat   1740
tgtatgggat ctgatctggg gcctcggtgc acatgcttta catgtgttta gtcgaggtta   1800
aaaaaacgtc taggcccccc gaaccacggg gacgtggttt tcctttgaaa aacacgatga   1860
taatatggtg agcaagggcg aggaggataa catggccatc atcaaggagt tcatgcgctt   1920
```

-continued

```
caaggtgcac atggagggct ccgtgaacgg ccacgagttc gagatcgagg gcgaggcga     1980
gggccgcccc tacgagggca cccagaccgc caagctgaag gtgaccaagg gtggccccct     2040
gcccttcgcc tgggacatcc tgtcccctca gttcatgtac ggctccaagg cctacgtgaa     2100
gcaccccgcc gacatccccg actacttgaa gctgtccttc cccgagggct tcaagtggga     2160
gcgcgtgatg aacttcgagg acggcggcgt ggtgaccgtg acccaggact cctccctgca     2220
ggacggcgag ttcatctaca aggtgaagct gcgcggcacc aacttcccct ccgacggccc     2280
cgtaatgcag aagaagacca tgggctggga ggcctcctcc gagcggatgt accccgagga     2340
cggcgccctg aagggcgaga tcaagcagag gctgaagctg aaggacggcg gccactacga     2400
cgctgaggtc aagaccacct acaaggccaa gaagcccgtg cagctgcccg gcgcctacaa     2460
cgtcaacatc aagttggaca tcacctccca caacgaggac tacaccatcg tggaacagta     2520
cgaacgcgcc gagggccgcc actccaccgg cggcatggac gagctgtaca agtaaccgcg     2580
gtcgacggta ccgcgggccc gggatctaag cttatcgata tcaacctct ggattacaaa     2640
atttgtgaaa gattgactgg tattcttaac tatgttgctc cttttacgct atgtggatac     2700
gctgctttaa tgcctttgta tcatgctatt gcttcccgta tggctttcat tttctcctcc     2760
ttgtataaat cctggttgct gtctctttat gaggagttgt ggcccgttgt caggcaacgt     2820
ggcgtggtgt gcactgtgtt tgctgacgca accccccactg gttggggcat tgccaccacc     2880
tgtcagctcc tttccgggac tttcgctttc cccctccccta ttgccacggc ggaactcatc     2940
gccgcctgcc ttgccccgctg ctggacaggg gctcggctgt tgggcactga caattccgtg     3000
gtgttgtcgg ggaaatcatc gtcctttcct tggctgctcg cctgtgttgc cacctggatt     3060
ctgcgcggga cgtccttctg ctacgtccct tcggccctca atccagcgga ccttccttcc     3120
cgcggcctgc tgccggctct gcggcctctt ccgcgtcttc gccttcgccc tcagacgagt     3180
cggatctccc tttgggccgc ctccccgcat cgataccgat gatcgatcca ccggatctag     3240
ataactgatc ataatcagcc ataccacatt tgtagaggtt ttacttgctt taaaaaacct     3300
cccacacctc cccctgaacc tgaaacataa aatgaatgca attgttgttg ttaacttgtt     3360
tattgcagct tataatggtt acaaataaag caatagcatc acaaatttca caaataaagc     3420
attttttca ctgcattcta gttgtggttt gtccaaactc atcaatgtat cttaacgcgt     3480
aaattgtaag cgttaatatt ttgttaaaat tcgcgttaaa tttttgttaa atcagctcat     3540
tttttaacca ataggccgaa atcggcaaaa tcccttataa atcaaaagaa tagaccgaga     3600
tagggttgag tgttgttcca gtttggaaca agagtccact attaaagaac gtggactcca     3660
acgtcaaagg gcgaaaaacc gtctatcagg gcgatggccc actacgtgaa ccatcaccct     3720
aatcaagttt tttgggggtcg aggtgccgta aagcactaaa tcggaaccct aaagggagcc     3780
cccgatttag agcttgacgg ggaaagccgg cgaacgtggc gagaaaggaa gggaagaaag     3840
cgaaaggagc gggcgctagg gcgctggcaa gtgtagcggt cacgctgcgc gtaaccacca     3900
cacccgccgc gcttaatgcg ccgctacagg gcgcgtcagg tggcacttt cggggaaatg     3960
tgcgcggaac ccctatttgt ttatttttct aaatacattc aaatatgtat ccgctcatga     4020
gacaataacc ctgataaatg cttcaataat attgaaaaag gaagagtcct gaggcggaaa     4080
gaaccagctg tggaatgtgt gtcagttagg gtgtggaaa tccccaggct ccccagcagg     4140
cagaagtatg caaagcatgc atctcaatta gtcagcaacc aggtgtggaa agtccccagg     4200
ctccccagca ggcagaagta tgcaaagcat gcatctcaat tagtcagcaa ccatagtccc     4260
gcccctaact ccgcccatcc cgcccctaac tccgcccagt tccgcccatt ctccgcccca     4320
tggctgacta atttttttta tttatgcaga ggccgaggcc gcctcggcct ctgagctatt     4380
ccagaagtag tgaggaggct tttttggagg cctaggcttt tgcaaagatc gatcaagaga     4440
caggatgagg atcgtttcgc atgattgaac aagatggatt gcacgcaggt tctccggccg     4500
cttgggtgga gaggctattc ggctatgact gggcacaaca gacaatcggc tgctctgatg     4560
ccgccgtgtt ccggctgtca gcgcagggg gcccggttct ttttgtcaag accgacctgt     4620
ccggtgccct gaatgaactg caagacgagg cagcgcggct atcgtggctg gccacgacg     4680
gcgttccttg cgcagctgtg ctcgacgttg tcactgaagc gggaagggac tggctgctat     4740
tgggcgaagt gccggggcag gatctcctgt catctcacct tgctcctgcc gagaaagtat     4800
ccatcatggc tgatgcaatg cggcggctgc atacgcttga tccggctacc tgcccattcg     4860
accaccaagc gaaacatcgc atcgagcgag cacgtactcg gatggaagcc ggtcttgtcg     4920
atcaggatga tctggacgaa gagcatcagg ggctcgcgcc agccgaactg ttcgccaggt     4980
tcaaggcgag catgcccgac ggcgaggatc tcgtcgtgac ccatggcgat gcctgcttgc     5040
cgaatatcat ggtggaaaat ggccgctttt ctggattcat cgactgtggc cggctgggtg     5100
tggcggaccg ctatcaggac atagcgttgg ctacccgtga tattgctgaa gagcttggcg     5160
gcgaatgggc tgaccgcttc ctcgtgcttt acggtatcgc cgctcccgat tcgcagcgca     5220
tcgccttcta tcgccttctt gacgagttct tctgagcggg actctggggt tcgaaatgac     5280
cgaccaagcg acgcccaacc tgccatcacg agatttcgat tccaccgccg ccttctatga     5340
aaggttgggc ttcggaatcg ttttccggga cgccggctgg atgatcctcc agcgcgggga     5400
tctcatgctg gagttcttcg cccacccctag ggggaggcta actgaaacac ggaaggagac     5460
aataccggaa ggaacccgcg ctatgacggc aataaaaaga cagaataaaa cgcacggtgt     5520
tgggtcgttt gttcataaac gcggggttcg gtcccagggc tggcactctg tcgatacccc     5580
accgagaccc cattggggcc aatacgcccg cgtttcttcc ttttcccac cccaccccc     5640
aagttcgggt gaaggcccag ggctcgcagc caacgtcggg gcggcaggcc ctgccatagc     5700
ctcaggttac tcatatatac tttagattga tttaaaactt cattttttaa ttaaaaggat     5760
ctaggtgaag atccttttg ataatctcat gaccaaaatc ccttaacgtg agttttcgtt     5820
ccactgagcg tcagacccgc tagaaaagat caaaggatct tcttgagatc cttttttct     5880
gcgcgtaatc tgctgcttgc aaacaaaaaa accaccgcta ccagcggtgg tttgtttgcc     5940
ggatcaagag ctaccaactc tttttccgaa ggtaactggc ttcagcagag cgcagatacc     6000
aaatactgtc cttctagtgt agccgtagtt aggccaccac ttcaagaact ctgtagcacc     6060
gcctacatac ctcgctctgc taatcctgtt accagtggct gctgccagtg gcgataagtc     6120
gtgtcttacc gggttggact caagacgata gttaccggat aaggcgcagc ggtcgggctg     6180
aacgggggt tcgtgcacac agcccagctt ggagcgaacg acctacaccg aactgagata     6240
cctacagcgt gagctatgag aaagcgccac gcttcccgaa gggagaaagg cggacaggta     6300
tccggtaagc ggcagggtcg gaacaggaga gcgcacgagg gagcttccag ggggaaacgc     6360
ctggtatctt tatagtcctg tcgggtttcg ccacctctga cttgagcgtc gatttttgtg     6420
atgctcgtca ggggggcgga gcctatgaa aaacgccagc aacgcggcct ttttacggtt     6480
cctggccttt tgctggcctt ttgctcacat gttctttcct gcgttatccc ctgattctgt     6540
ggataaccgt attaccgcca tgcat                                          6565
```

-continued

```
SEQ ID NO: 49          moltype = AA  length = 351
FEATURE                Location/Qualifiers
REGION                 1..351
                       note = GAP43-SSGSSGTG-meGFP-PAK1
source                 1..351
                       mol_type = protein
                       organism = synthetic construct
SEQUENCE: 49
MLCCMRRTKQ VEKNDEDQNS SGSSGTGSKG EELFTGVVPI LVELDGDVNG HKFSVSGEGE    60
GDATYGKLTL KFICTTGKLP VPWPTLVTTL TYGVQCFSRY PDHMKRHDFF KSAMPEGYVQ   120
ERTIFFKDDG NYKTRAEVKF EGDTLVNRIE LKGIDFKEDG NILGHKLEYN YNSHNVYIMA   180
DKQKNGIKAN FKIRHNIESG GVQLADHYQQ NTPIGDGPVL LPDNHYLSTQ SKLSKDPNEK   240
RDHMVLKERV TAAGITHGMD SRNKKKEKER PEISLPSDFE HTIHVGFDAV TGEFTGMPEQ   300
WARLLQTSNI TKSEQKKNPQ AVLDVLEFYN SKKTSNSQKY MSFTDKSPSR G            351

SEQ ID NO: 50          moltype = DNA  length = 6448
FEATURE                Location/Qualifiers
misc_feature           1..6448
                       note = GAP43-SSGSSGTG-meGFP-PAK1
source                 1..6448
                       mol_type = other DNA
                       organism = synthetic construct
SEQUENCE: 50
gacggatcgg gagatctccc gatccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggacttttcc   420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgacggacc atgctgtgct gtatgagaag aaccaaacag    960
gttgaaaaga atgatgagga ccagaattcc tccggatcgt ctggaaccgg ttctaaagga   1020
gaagaacttt tcactggagt tgtcccaatt cttgttgaat tagatggtga tgttaatggg   1080
cacaaatttt ctgtcagtgg agagggtgaa ggtgatgcaa catacggaaa acttacccctt  1140
aaatttattt gcactactgg aaaactacct gttccttggc caacacttgt cactactttta  1200
acttatggtg ttcaatgctt ttcaagatac ccagatcata tgaaacggca tgactttttc   1260
aagagtgcca tgcccgaagg ttatgtacag gaaagaacta tatttttcaa agatgacggg   1320
aactacaaga cacgtgctga agtcaagttt gaaggtgata cccttgttaa tagaatcgag   1380
ttaaaaggta ttgattttaa agaagatgga aacattcttg gacacaaatt ggaatacaac   1440
tataactcac acaatgtata catcatggca gacaaacaaa agaatggaat caaagctaac   1500
ttcaaaatta gacacaacat tgagtccgga ggcgttcaac tagcagacca ttatcaacaa   1560
aatactccaa ttggcgatgg ccctgtcctt ttaccagaca accattacct gtccacacaa   1620
tctaagcttt cgaaagatcc caacgaaaag agagaccaca tggtccttaa agagagggta   1680
acagctgctg ggattacaca tggcatggac tctagaaata agaagaaaga gaaagagcgg   1740
ccagagattt ctctcccttc agattttgaa cacacaattc atgtcggttt tgatgctgtc   1800
acaggggagt ttacgggaat gccagagcag tgggcccgct tgcttcagac atcaaatatc   1860
actaagtcgg agcagaagaa aaacccgcag gctgttctga atgtgttgga gtttacaac    1920
tcgaagaaga catccaacag ccagaaatac atgagcttta cagataagtc accttctcga   1980
ggataatgaa ggtggcggcc gctcgaaact agagggcccg tttaaacccg ctgatcagcc   2040
tcgactgtgc cttctagttg ccagccatct gttgtttgcc cctccccgt gccttccttg     2100
accctggaag gtgccactcc cactgtcctt tcctaataaa atgaggaaat tgcatcgcat   2160
tgtctgagta ggtgtcattc tattctgggg ggtggggtgg gcaggacag caagggggga    2220
gattgggaag acaatagcag gcatgctggg gatgcggtgg gctctatggc ttctgaggcg   2280
gaaagaacca gctggggctc tagggggtat ccccacgcgc cctgtagcgg cgcattaagc   2340
gcggcgggtg tggtggttac gcgcagcgtg accgctacac ttgccagcgc cctagcgccc   2400
gctcctttcg ctttcttccc ttcctttctc gccacgttcg ccggctttcc ccgtcaagct   2460
ctaaatcggg ggctcccttt agggttccga tttagtgctt tacggcacct cgaccccaaa   2520
aaacttgatt agggtgatgg ttcacgtagt gggccatcgc cctgatagac ggtttttcgc   2580
cctttgacgt tggagtccac gttctttaat agtggactct tgttccaaac tggaacaaca   2640
ctcaacccta tctcggtcta ttcttttgat ttataaggga ttttgccgat ttcggcctat   2700
tggttaaaaa atgagctgat ttaacaaaaa tttaacgcga attaattctg tggaatgtgt   2760
gtcagttagg gtgtggaaag tccccaggct ccccagcagg cagaagtatg caaagcatgc   2820
atctcaatta gtcagcaacc aggtgtggaa agtccccagg ctccccagca ggcagaagta   2880
tgcaaagcat gcatctcaat tagtcagcaa ccatagtccc gccctaact ccgcccatcc    2940
cgcccctaac tccgcccagt tccgcccatt ctccgcccca tggctgacta atttttttta   3000
tttatgcaga ggccgaggcc gcctctgcct ctgagctatt ccagaagtag tgaggaggct   3060
tttttggagg cctaggcttt tgcaaaaagc tcccgggagc ttgtatatcc attttcggat   3120
ctgatcaaga caggatga ggatcgtttc gcatgattga acaagatgga ttgcacgcag     3180
gttctccggc cgcttgggtg gagaggctat tcggctatga ctgggcacaa cagacaatcg   3240
gctgctctga tgccgccgtg ttccggctgt cagcgcaggg gcgcccggtt cttttttgtca  3300
agaccgacct gtccggtgcc ctgaatgaac tgcaggacga ggcagcgcgg ctatcgtggc   3360
```

-continued

```
tggccacgac gggcgttcct tgcgcagctg tgctcgacgt tgtcactgaa gcgggaaggg   3420
actggctgct attgggcgaa gtgccggggc aggatctcct gtcatctcac cttgctcctg   3480
ccgagaaagt atccatcatg gctgatgcaa tgcggcggct gcatacgctt gatccggcta   3540
cctgcccatt cgaccaccaa gcgaaacatc gcatcgagcg agcacgtact cggatggaag   3600
ccggtcttgt cgatcaggat gatctggacg aagagcatca ggggctcgcg ccagccgaac   3660
tgttcgccag gctcaaggcg cgcatgcccg acgcgcgagga tctcgtcgtg acccatggcg   3720
atgcctgctt gccgaatatc atggtggaaa atggccgctt ttctggattc atcgactgtg   3780
gccggctggg tgtggcggac cgctatcagg acatagcgtt ggctaccgt gatattgctg   3840
aagagcttgg cggcgaatgg gctgaccgct tcctcgtgct ttacggtatc gccgctcccg   3900
attcgcagcg catcgccttc tatcgccttc ttgacgagtt cttctgagcg ggactctgag   3960
gttcgaaatg accgaccaag cgacgcccaa cctgccatca cgagatttcg attccaccgc   4020
cgccttctat gaaaggttgg gcttcggaat cgttttccgg gacgccggct ggatgatcct   4080
ccagcgcggg gatctcatgc tggagttctt cgccccaccc aacttgttta ttgcagctta   4140
taatggttac aaataaagca atagcatcac aaatttcaca aataaagcat ttttttcact   4200
gcattctagt tgtggtttgt ccaaactcat caatgtatct tatcatgtct gtataccgtc   4260
gacctctagc tagagcttgg cgtaatcatg gtcatagctg tttcctgtgt gaaattgtta   4320
tccgctcaca attccacaca acatacgagc cggaagcata aagtgtaaag cctggggtgc   4380
ctaatgagtg agctaactca cattaattgc gttgcgctca ctgcccgctt tccagtcggg   4440
aaacctgtcg tgccagctgc attaatgaat cggccaacgc gcggggagag gcggtttgcg   4500
tattgggcgc tcttccgctt cctcgctcac tgactcgctg cgctcggtcg ttcggctgcg   4560
gcgagcggta tcagctcact caaaggcggt aatacggtta tccacagaat caggggataa   4620
cgcaggaaag aacatgtgag caaaaggcca gcaaaaggcc aggaaccgta aaaaggccgc   4680
gttgctggcg tttttccata ggctccgccc cctgacgag catcacaaaa atcgacgctc   4740
aagtcagagg tggcgaaacc cgacaggact ataaagatac caggcgtttc ccctggaag   4800
ctccctcgtg cgctctcctg ttccgaccct gccgcttacc ggatacctgt ccgcctttct   4860
ccttcgggga agcgtggcgc tttctcatag ctcacgctgt aggtatctca gttcggtgta   4920
ggtcgttcgc tccaagctgg gctgtgtgca cgaacccccc gttcagcccg accgctgcgc   4980
cttatccggt aactatcgtc ttgagtccaa cccggtaaga cacgacttat cgccactggc   5040
agcagccact ggtaacagga ttagcagagc gaggtatgta ggcggtgcta cagagttctt   5100
gaagtggtgg cctaactacg gctacactag aagaacagta tttggtatct gcgctctgct   5160
gaagccagtt accttcggaa aaagagttgg tagctcttga tccggcaaac aaaccaccgc   5220
tggtagcggt ggtttttttg tttgcaagca gcagattacg cgcagaaaaa aaggatctca   5280
agaagatcct ttgatctttt ctacggggtc tgacgctcag tggaacgaaa actcacgtta   5340
agggattttg gtcatgagat tatcaaaaag gatcttcacc tagatccttt taaattaaaa   5400
atgaagtttt aaatcaatct aaagtatata tgagtaaact tggtctgaca gttaccaatg   5460
cttaatcagt gaggcaccta tctcagcgat ctgtctattt cgttcatcca tagttgcctg   5520
actccccgtc gtgtagataa ctacgatacg ggagggctta ccatctggcc ccagtgctgc   5580
aatgataccg cgagacccac gctcaccggc tccagattta tcagcaataa accagccagc   5640
cggaagggcc gagcgcagaa gtggtcctgc aactttatcc gcctccatcc agtctattaa   5700
ttgttgccgg gaagctagag taagtagttc gccagttaat agtttgcgca acgttgttgc   5760
cattgctaca ggcatcgtgg tgtcacgctc gtcgtttggt atggcttcat tcagctccgg   5820
ttcccaacga tcaaggcgag ttacatgatc ccccatgttg tgcaaaaaag cggttagctc   5880
cttcggtcct ccgatcgttg tcagaagtaa gttggccgca gtgttatcac tcatggttat   5940
ggcagcactg cataattctc ttactgtcat gccatccgta agatgctttt ctgtgactgg   6000
tgagtactca accaagtcat tctgagaata gtgtatgcgg cgaccgagtt gctcttgccc   6060
ggcgtcaata cgggataata ccgcgccaca tagcagaact ttaaaagtgc tcatcattgg   6120
aaaacgttct cggggcgaa aactctcaag gatcttaccg ctgttgagat ccagttcgat   6180
gtaacccact cgtgcaccca actgatcttc agcatctttt actttcacca gcgtttctgg   6240
gtgagcaaaa acaggaaggc aaaatgccgc aaaaaaggga ataagggcga cacggaaatg   6300
ttgaatactc atactcttcc ttttttcaata ttattgaagc atttatcagg gttattgtct   6360
catgagcgga tacatatttg aatgtattta gaaaaataaa caaataggg ttccgcgcac   6420
atttccccga aaagtgccac ctgacgtc   6448
```

```
SEQ ID NO: 51            moltype = AA  length = 202
FEATURE                  Location/Qualifiers
REGION                   1..202
                         note = Rac1(Q61L)
source                   1..202
                         mol_type = protein
                         organism = synthetic construct
SEQUENCE: 51
MGYPYDVPDY AQAIKCVVVG DGAVGKTCLL ISYTTNAFPG EYIPTVFDNY SANVMVDGKP   60
VNLGLWDTAG LEDYDRLRPL SYPQTDVFLI CFSLVSPASF ENVRAKWYPE VRHHCPNTPI   120
ILVGTKLDLR DDKDTIEKLK EKKLTPITYP QGLAMAKEIG AVKYLECSAL TQRGLKTVFD   180
EAIRAVLCPP PVKKRKRKCL LL   202

SEQ ID NO: 52            moltype = DNA  length = 6586
FEATURE                  Location/Qualifiers
misc_feature            1..6586
                         note = Rac1(Q61L)
source                   1..6586
                         mol_type = other DNA
                         organism = synthetic construct
SEQUENCE: 52
tagttattaa tagtaatcaa ttacggggtc attagttcat agcccatata tggagttccg   60
cgttacataa cttacggtaa atggcccgcc tggctgaccg cccaacgacc cccgcccatt   120
gacgtcaata atgacgtatg ttcccatagt aacgccaata gggactttcc attgacgtca   180
atgggtggag tatttacggt aaactgccca cttggcagta catcaagtgt atcatatgcc   240
aagtacgccc cctattgacg tcaatgacgg taaatggccc gcctggcatt atgcccagta   300
```

-continued

```
catgacctta tgggactttc ctacttggca gtacatctac gtattagtca tcgctattac   360
catggtgatg cggttttggc agtacatcaa tgggcgtgga tagcggtttg actcacgggg   420
atttccaagt ctccacccca ttgacgtcaa tgggagtttg ttttggcacc aaaatcaacg   480
ggactttcca aaatgtcgta acaactccgc cccattgacg caaatgggcg gtaggcgtgt   540
acggtgggag gtctatataa gcagagctgg tttagtgaac cgtcagatcc gctagcctcg   600
acttgagctc ggatccacgg tggaattcct gcagcccggg ggatccgcca ccatgggcta   660
cccatacgat gttcctgact atgctcaggc catcaagtgt gtggtggtgg gagacggagc   720
tgttggtaaa acctgcctgc tcatcagtta cacgaccaat gcatttcctg gagagtacat   780
ccccaccgtc tttgacaact attctgccaa tgttatggta gatggaaaac cagtgaatct   840
gggcctatgg gacacagctg gactagaaga ttatgacaga ttgcgtcccc tctcctaccc   900
gcagacagac gtgttcttaa tttgcttttc ccttgtgagt cctgcatcat ttgaaaatgt   960
ccgtgcaaag tggtatcctg aagtgcgaca ccactgtccc aatactccta tcatcctcgt  1020
ggggacgaag cttgatctta gggatgataa ggacaccatt gagaagctga aggagaagaa  1080
gctgactccc atcacctacc cgcaggggct ggccatgggc aaagagatcg gtgctgtcaa  1140
atacctggag tgctcagctc tcacacagcg aggactcaag acagtgtttg acgaagctat  1200
ccgagcggtt ctctgtcccc ctcctgtcaa gaagaggaag agaaaatgcc tgctgttgta  1260
agcggccgct cgagtctaga actagtttga gtcgagccgc ggcaattccg ccctctccc  1320
tccccccccc ctaacgttac tggccgaagc cgcttgaaat aaggccggtg tgcgtttgtc  1380
tatatgttat tttccaccat attgccgtct tttggcaatg tgagggcccg gaaacctggc  1440
cctgtcttct tgacgagcat cctagggggt cttttccctc tcgccaaagg aatgcaaggt  1500
ctgttgaatg tcgtgaagga agcagttcct ctggaagctt cttgaagaca aacaacgtct  1560
gtagcgaccc tttgcaggca gcggaacccc ccacctggca acaggtgcct ctgcggccaa  1620
aagccacgtg tataagatac acctgcaaag gcggcacaac cccagtgcca cgttgtgagt  1680
tggatagttg tggaaagagt caaatggctc tcctcaagcg tattcaacaa ggggctgaag  1740
gatgcccaga aggtacccca ttgtatggga tctgatctgg ggcctcggtg cacatgcttt  1800
acatgtgttt agtcgaggtt aaaaaaacgt ctaggcccc cgaaccacgg ggacgtggtt  1860
ttcctttgaa aaacacgatg ataatatggt gagcaaggc gaggaggata acatggccat  1920
catcaaggag ttcatgcgct tcaaggtgca catggagggc tccgtgaacg gccacgagtt  1980
cgagatcgag ggcgagggcg agggccgccc ctacgagggc acccagaccg ccaagctgaa  2040
ggtgaccaag ggtggccccc tgcccttcgc ctgggacatc ctgtccctc agttcatgta  2100
cggctccaag gcctacgtga agcacccgc cgacatcccc gactacttga agctgtcctt  2160
ccccgagggc ttcaagtggg agcgcgtgat gaacttcgag gacggcggcg tggtgaccgt  2220
gacccaggac tcctccctgc aggacggcga gttcatctac aaggtgaagc tgcgcggcac  2280
caacttcccc tccgacggcc ccgtaatgca gaagaagacc atgggctggg aggcctcctc  2340
cgagcggatg taccccgagg acggcgccct gaagggcgag atcaagcaga ggctgaagct  2400
gaaggacggc ggccactacg acgctgaggt caagaccacc tacaaggcca agaagcccgt  2460
gcagctgccc ggcgcctaca acgtcaacat caagttggac atcacctccc acaacgagga  2520
ctacaccatc gtgaacagt acgaacgcgc cgagggccgc cactccaccg gcggcatgga  2580
cgagctgtac aagtaaccgc ggtcgacggt accgcgggcc cgggatctaa gcttatcgat  2640
aatcaacctc tggattacaa aatttgtgaa agattgactg gtattcttaa ctatgttgct  2700
ccttttacgc tatgtggata cgctgcttta atgcctttgt atcatgctat tgcttcccgt  2760
atggctttca ttttctcctc cttgtataaa tcctggttgc tgtctcttta tgaggagttg  2820
tggcccgttg tcaggcaacg tggcgtggtg tgcactgtgt ttgctgacgc aacccccact  2880
ggttggggca ttgccaccac ctgtcagctc ctttccggga ctttcgcttt ccccctccct  2940
attgccacgg cggaactcat cgccgcctgc cttgcccgct gctggacagg ggctcggctg  3000
ttgggcactg acaattccgt ggtgttgtcg gggaaatcat cgtcctttcc ttggctgctc  3060
gcctgtgttg ccacctggat tctgcgcggg acgtccttct gctacgtccc ttcggccctc  3120
aatccagcgg accttccttc ccgcggcctg ctgccggctc tgcggcctct tccgcgtctt  3180
cgccttcgcc ctcagacgag tcggatctcc ctttgggccg cctccccgca tcgataccgt  3240
ggatcgatcc accggatcta gataactgat cataatcagc cataccacat ttgtagaggt  3300
tttacttgct ttaaaaaacc tcccacacct ccccctgaac ctgaaacata aaatgaatgc  3360
aattgttgtt gttaacttgt ttattgcagc ttataatggt tacaaataaa gcaatagcat  3420
cacaaatttc acaaataaag cattttttttc actgcattct agttgtggtt tgtccaaact  3480
catcaatgta tcttaacgcg taaattgtaa gcgttaatat tttgttaaaa ttcgcgttaa  3540
atttttgtta aatcagctca ttttttaacc aataggccga aatcggcaaa atcccttata  3600
aatcaaaaga atagaccgag atagggttga gtgttgttcc agtttggaac aagagtccac  3660
tattaaagaa cgtggactcc aacgtcaaag ggcgaaaaac cgtctatcag ggcgatggcc  3720
cactacgtga accatcaccc taatcaagtt ttttggggtc gaggtgccgt aaagcactaa  3780
atcggaaccc taaagggagc ccccgattta gagcttgacg gggaaagccg cgaacgtgg  3840
cgagaaagga agggaagaaa gcgaaaggag cgggcgctag ggcgctggca agtgtagcgg  3900
tcacgctgcg cgtaaccacc acacccgccg cgcttaatgc gccgctacag ggcgcgtcag  3960
gtggcacttt cgggggaaat gtgcgcggaa cccctatttg tttatttttc taaatacatt  4020
caaatatgta tccgctcatg agacaataac cctgataaat gcttcaataa tattgaaaaa  4080
ggaagagtat tgaggcggaa agaaccagct gtggaatgtg tgtcagttag ggtgtggaaa  4140
gtccccaggc tccccagcag gcagaagtat gcaaagcatg catctcaatt agtcagcaac  4200
caggtgtgga aagtccccag gctccccagc aggcagaagt atgcaaagca tgcatctcaa  4260
ttagtcagca accatagtcc cgcccctaac tccgcccatc ccgcccctaa ctccgcccag  4320
ttccgcccat tctccgcccc atggctgact aatttttttt atttatgcag aggccgaggc  4380
cgcctcggcc tctgagctat tccagaagta gtgaggaggc ttttttggag gcctaggctt  4440
ttgcaaagat cgatcaagag acaggatgag gatcgtttcg catgattgaa caagatggat  4500
tgcacgcagg ttctccggcc gcttgggtgg agaggctatt cggctatgac tgggcacaac  4560
agacaatcgg ctgctctgat gccgccgtgt tccggctgtc agcgcagggg cgcccggttc  4620
tttttgtcaa gaccgacctg tccggtgccc tgaatgaact gcaagacgag gcagcgcggc  4680
tatcgtggct ggccacgacg ggcgttcctt gcgcagctgt gctcactgaa  4740
cgggaaggga ctggctgcta ttgggcgaag tgccggggca ggatctcctg tcatctcacc  4800
ttgctcctgc cgagaaagta tccatcatgg ctgatgcaat gcggcggctg catacgcttg  4860
atccggctac ctgcccattc gaccaccaag cgaaacatcg catcgagcga gcacgtactc  4920
ggatggaagc cggtcttgtc gatcaggatg atctggacga agagcatcag gggctcgcgc  4980
cagccgaact gttcgccagg ctcaaggcga gcatgcccga cggcgaggat ctcgtcgtga  5040
```

-continued

```
cccatggcga tgcctgcttg ccgaatatca tggtggaaaa tggccgcttt tctggattca   5100
tcgactgtgg ccggctgggt gtggcggacc gctatcagga catagcgttg gctaccgtg   5160
atattgctga agagcttggc ggcgaatggg ctgaccgctt cctcgtgctt tacggtatcg   5220
ccgctcccga ttcgcagcgc atcgccttct atcgccttct tgacgagttc ttctgagcgg   5280
gactctgggg ttcgaaatga ccgaccaagc gacgcccaac ctgccatcac gagatttcga   5340
ttccaccgcc gccttctatg aaaggttggg cttcggaatc gttttccggg acgccggctg   5400
gatgatcctc cagcgcgggg atctcatgct ggagttcttc gcccaccctaa gggggaggct   5460
aactgaaaca cggaaggaga caataccgga aggaacccgc gctatgacgg caataaaaag   5520
acagaataaa acgcacggtg ttgggtcgtt tgttcataaa cgcggggttc ggtcccaggg   5580
ctggcactct gtcgataccc caccgagacc ccattggggc caatacgccc gcgtttcttc   5640
cttttcccca ccccacccccc caagttcggg tgaaggccca gggctcgcag ccaacgtcgg   5700
ggcggcaggc cctgccatag cctcaggtta ctcatatata ctttagattg atttaaaact   5760
tcatttttaa tttaaaagga tctaggtgaa gatcctttttt gataatctca tgaccaaaat   5820
cccttaacgt gagtttttcgt tccactgagc gtcagacccc gtagaaaaga tcaaaggatc   5880
ttcttgagat cctttttttc tgcgcgtaat ctgctgcttg caaacaaaaa aaccaccgct   5940
accagcggtg gtttgtttgc cggatcaaga gctaccaact ctttttccga aggtaactgg   6000
cttcagcaga gcgcagatac caaatactgt ccttctagtg tagccgtagt taggccacca   6060
cttcaagaac tctgtagcac cgcctacata cctcgctctg ctaatcctgt taccagtggc   6120
tgctgccagt ggcgataagt cgtgtcttac cgggttggac tcaagacgat agttaccgga   6180
taaggcgcag cggtcgggct gaacggggggg ttcgtgcaca cagcccagct tggagcgaac   6240
gacctacacc gaactgagat acctacacgc tgagctatga aaagcgcca cgcttcccga   6300
agggagaaag gcggacaggt atccggtaag cggcaggggtc cggcaggag acgcacgag   6360
ggagcttcca gggggaaacg cctggtatct ttatagtcct gtcgggtttc gccacctctg   6420
acttgagcgt cgatttttgt gatgctcgtc aggggggcgg agcctatgga aaaacgccag   6480
caacgcggcc tttttacggt tcctggcctt ttgctggcct tttgctcaca tgttctttcc   6540
tgcgttatcc cctgattctg tggataaccg tattaccgcc atgcat   6586
```

SEQ ID NO: 53          moltype = AA  length = 1500
FEATURE                Location/Qualifiers
REGION                 1..1500
                       note = GAP43-SSGSSGTG-meGFP-IRS1
source                 1..1500
                       mol_type = protein
                       organism = synthetic construct SEQUENCE: 53
```
MLCCMRRTKQ VEKNDEDQNS SGSSGTGSKG EELFTGVVPI LVELDGDVNG HKFSVSGEGE    60
GDATYGKLTL KFICTTGKLP VPWPTLVTTL TYGVQCFSRY PDHMKRHDFF KSAMPEGYVQ   120
ERTIFFKDDG NYKTRAEVKF EGDTLVNRIE LKGIDFKEDG NILGHKLEYN YNSHNVYIMA   180
DKQKNGIKAN FKIRHNIESG GVQLADHYQQ NTPIGDGPVL LPDNHYLSTQ SKLSKDPNEK   240
RDHMVLKERV TAAGITHGMD ELYKDIMCPP DTDGFSDVRK VGYLRKPKSM HKRFFVLRAA   300
SEAGGPARLE YYENEKKWRH KSSAPKRSIP LESCFNINKR ADSKNKHLVA LYTRDEHFAI   360
AADSEAEQDS WYQALLQLHN RAKAHHDGAG GGCGGSCSGS SGVGEAGEDL SYDTGPGPAF   420
KEVWQVILKP KGLGQTKNLI GIYRLCLTSK TISFVKLNSE AAAVVLQLMN IRRCGHSENF   480
FFIEVGRSAV TGPGEFWMQV DDSVVAQNMH ETILEAMRAM SDEFRPRTKS QSSSSCSNPI   540
SVPLRRHHLN NPPPSQVGLT RRSRTESITA TSPASMVGGK PGSFRVRASS DGEGTMSRPA   600
SVDGSPVSPS TNRTHAHRHR GSSRLHPPLN HSRSIPMPSS RCSPSATSPV SLSSSSTSGH   660
GSTSDCLFPR RSSASVSGSP SDGGFISSDE YGSSPCDFRS SFRSVTPDSL GHTPPARGEE   720
ELSNYICMGG KGASTLTAPN GHYILSRGGN GHRYIPGATM GTSPALTGDE AAGAADLDNR   780
FRKRTHSAGT SPTISHQKTP SQSSVVSIEE YTEMMPAAYP PGGGSGGRLP GYRHSAFVPT   840
HSYPEEGLEM HHLERRGGHH RPDSSNLHTD DGYMPMSPGV APVPSNRKGN GDYMPMSPKS   900
VSAPQQIINP IRRHPQRVDP NGYMMMSPSG SCSPDIGGGS CSSSSISAAP SGSSYGKPWT   960
NGVGGHHTHA LPHAKPPVES GGGKLLPCTG DYMNMSPVGD SNTSSPSECY YGPEDPQHKP  1020
VLSYYSLPRS FKHTQRPGEP EEGARHQHLR LSSSSGRLRY TATAEDSSSS TSSDSLGGGY  1080
CGARPESSVT HPHHHALQPH LPRKVDTAAQ TNSRLARPTR LSLGDPKAST LPRVREQQQQ  1140
QQQQQQSSLH PPEPKSPGEY VNIEFGSGQP GYLAGPATSR SSPSVRCLPQ LHPAPREETG  1200
SEEYMNMDLG PGRRATWQES GGVELGRVGP APPGAASICR PTRSVPNSRG DYMTMQIGCP  1260
RQSYVDTSPV APVSYADMRT GIAAEKVSLP RTTGAAPPPS STASASASVT PQGAAEQAAH  1320
SSLLGGPQGP GGMSAFTRVN LSPNHNQSAK VIRADTQGCR RRHSSETFSA PTRAANTVSF  1380
GAGAAGGGSG GGSEDVKRHS SASFENVWLR PGDLGGASKE SAPGCGAAGG LEKSLNYIDL  1440
DLVKDVKQHP QDCPSQQQSL PPPPPHQPLG SNEGSSPRRS SEDLSTYASI NFQKQPEDRQ  1500
```

SEQ ID NO: 54          moltype = DNA  length = 9892
FEATURE                Location/Qualifiers
misc_feature           1..9892
                       note = GAP43-SSGSSGTG-meGFP-IRS1
source                 1..9892
                       mol_type = other DNA
                       organism = synthetic construct SEQUENCE: 54
```
gacggatcgg gagatctccc gatcccctat ggtgcactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggag tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
```

-continued

```
tcgctattac catggtgatg cggtttttggc agtacatcaa tgggcgtgga tagcggtttg      660
actcacgggg atttccaagt ctccacccca ttgacgtcaa tgggagtttg ttttggcacc      720
aaaatcaacg ggactttcca aaatgtcgta acaactccgc cccattgacg caaatgggcg      780
gtaggcgtgt acggtgggag gtctatataa gcagagctct ctggctaact agagaaccca      840
ctgcttactg gcttatcgaa attaatacga ctcactatag ggagacccaa gctggctagc      900
gtttaaactt aagcttggta ccgacggacc atgctgtgct gtatgagaag aaccaaacag      960
gttgaaaaga atgatgagga ccagaattcc tccggatcgt ctggaaccgg ttctaaagga     1020
gaagaacttt tcactggagt tgtcccaatt cttgttgaat tagatggtga tgttaatggg     1080
cacaaatttt ctgtcagtgg agagggtgaa ggtgatgcaa catacggaaa acttaccctt     1140
aaatttattt gcactactgg aaaactacct gttccttggc caacacttgt cactacttta     1200
acttatggtg ttcaatgctt ttcaagatac ccagatcata tgaaacggca tgactttttc     1260
aagagtgcca tgcccgaagg ttatgtacag gaaagaacta tattttttcaa agatgacggg     1320
aactacaaga cacgtgctga agtcaagttt gaaggtgata cccttgttaa tagaatcgag     1380
ttaaaaggta ttgattttaa agaagatgga aacattcttg gacacaaatt ggaatacaac     1440
tataactcac acaatgtata catcatggca gacaaacaaa agaatggaat caaagctaac     1500
ttcaaaatta gacacaacat tgagtccgga ggcgttcaac tagcagacca ttatcaacaa     1560
aatactccaa ttggcgatgg ccctgtcctt ttaccagaca accattacct gtccacacaa     1620
tctaagcttt cgaaagatcc caacgaaaag agagaccaca tggtccttaa agagagggta     1680
acagctgctg ggattacaca tggcatggac gagctgtaca aggatatcat gtgccctccg     1740
gataccgatg gcttctcaga cgtgcgcaag gtgggttacc tgcgcaaacc caagagtatg     1800
cataagcgct ttttcgtgct gcgggcggcc agcgaggccg ggggcccggc gcgcctggag     1860
tattatgaga acgagaagaa gtggcggcac aagtcgagcg ccccaaacg ctcgatcccc     1920
ctcgagagct gtttcaacat caacaagcgg gctgactcca agaacaagca cctggtggct     1980
ctctacaccc gagacgaaca cttgtgccatt gcggcggata gcgaggctga acaagacagc     2040
tggtaccagg ctcttctgca gctgcataat cgggcaaagg cccaccatga cggggctgga     2100
ggaggctgcg gtggtagctg cagcggcagc tctggcgtag gagagcgagg ggaggacttg     2160
agctatgaca cgggcccagg acccgcgttc aaggaggtct ggcaggttat cctgaaaccc     2220
aagggcttag gtcagacaaa gaacttgatt ggtatctacc gcctctgcct gaccagcaag     2280
accatcagct ttgtgaagct caactctgag gctgccgctg tggtgctgca gctgatgaac     2340
atcagacgct gtggccactc agagaacttc ttcttcatcg aggtgggcg gtcagctgtg     2400
accgggcccg gcgagttcgt gatgcaagtg gatgactccg tggtggccca gaacatgcat     2460
gagaccattc tagaggccat gcgggccatg agcgatgagt ttcgcccgcg cacgaaaagc     2520
caatcttcat ccagttgctc caaccccatc agtgttcccc tgcgcaggca ccatctcaac     2580
aatcctccgc ccagccaagt ggggctgact cggagatctc gaactgagag catcactgcc     2640
acctcccctg ccagtatggt gggtgggaaa ccaggttcct tcagggtgcg tgcctccagc     2700
gatggcgaag gcaccatgtc ccgtccagca tcagtggatg gcagtcctgt gagccctagc     2760
accaacagga cccacgccca tcggcatcga ggcagctcca ggttgcaccc cccactcaac     2820
cacagccgct ccatccctat gccttcttca cgatgctccc cttcagccac cagcccagtg     2880
agcctgtcat ccagtagtac cagtggccac ggctccactt cagactgtct cttcccgagg     2940
cgctctagtg cttccgtgtc cggttctcct agcgatggcg gtttcatctc ttctgatgag     3000
tatggctcta gtccctgcga tttccgaagt tccttccgca gtgtcacccc agattccctg     3060
ggccacaccc caccagccag gggtgaggag gagctgagca actatatctg catgggtggc     3120
aagggagcct ccaccttgac agctcccaat ggtcactaca ttttgtctag gggtggcaac     3180
ggccatcgct acatcccagg tgctaccatg gggacaagac cggcgctgac tggagacgaa     3240
gccgctggtg cagcagatct ggataaccgg tttcggaaga gaactcactc ggctggcacg     3300
tcccccacca tatcccacca gaagacccc tcgcagtcct cagtggtttc tattgaggaa     3360
tatacagaga tgatgcccgc tgcctaccca ccaggaggtg gcagtggagg ccgactgccc     3420
ggctaccggc attccgcctt cgtgcccacc cactcctatc ccgaggaggg tctagagatg     3480
caccacttgg aacgtcgtgg gggccaccac cgtccagact cctccaacct ccacaccgat     3540
gatggctaca tgcccatgtc tcccggagtg gctccagtgc ccagcaaccg caaaggaaat     3600
ggggactata tgcccatgag ccccaagagt gtatctgccc cccagcagat cattaaccac     3660
atcaggcgcc acccacagag agtggacccc aatggctaca tgatgatgtc tcccagtggt     3720
agttgctctc ctgacattgg aggtgggtct tgcagcagta gcagcatcag cgcagcccct     3780
tctgggagca gctatgggaa gccatggaca aacggagtag gggggcacca tacccatgcc     3840
cttccccatg ccaaacctcc tgttgagagc ggtggtgata agctcttgcc ttgcactggt     3900
gactacatga acatgtcgcc agtgggagat tccaacacca gcagccctc agaatgctac     3960
tatggcccag aagatcccca gcacaagcct gtcctctcct actactcatt accaaggtcc     4020
tttaagcaca cccagcgccc tggggagcca gaggagggtg ccaggcacca gcatcttcgt     4080
ctctcttcaa gctctggacg ccttcgctat accgcaactg ctgaagattc ctcctcttcc     4140
accagcagcg acagcctggg tggggggttac tgtgtggggcta ggccagagtc tagcgtcaca     4200
catccccacc accatgcctt gcagcccat ctgcctcgaa aggtagacac agctgcacag     4260
accaacagcc gcctggctcg acccacaagg ctgtccttgg gggatcccaa ggcaagcact     4320
ttaccccggg tacgagagca acagcagcag cagcaacagc agcagcagtc ttccctgcac     4380
cctcccgagc ccaaaagccc aggagaatat gtgaatattg aattcgggag tggccagcca     4440
ggctatttag ctggccctgc aacttcccgt agctcccctt cagttcgatg tctacccag     4500
ctccacccag ctcccagaga agagactggc tcggaagagt acatgaacat ggacttgggg     4560
ccaggccgga gggcaacctg gcaggagagt ggtggagttg agttgggcag agtaggccct     4620
gcacctccag gggctgcttc catttgtagg ccaaccgg cggtgccaaa tagccgtggt     4680
gattacatga ccatgcagat aggttgtcct cgtcaaagct atggatac ctcaccagtg     4740
gccccagtca gctatgctga catgcggaca ggcattgctg cagagaaggt gagcctgccc     4800
agaaccacag gagctgcccc ccctccatcc tccacagcct ctgcttctgc ttctgttaca     4860
cctcaagggg ccgctgagca ggccgctcac tcttccttgc tgggaggccc tcaggacct     4920
gggggcatga gcgcattcac cagggtgaac ctaagtccca accataacca gagtgccaaa     4980
gtgattcgtg cagacactca aggctgccgg aggaggcaca gctccgaac cttctcggcg     5040
cctacgcggg ctgccaacac agtgtctttt ggagcagggg ctgcaggagg gggcagcggt     5100
ggtggcagtg aggatgtgaa acgccacagc tctgcatcct ttgagaatgt gtggctgaga     5160
cccgggatc taggggggagc atccaaggag tcggctccag ggtgcgggc tgccggggga     5220
ttggagaaga gtcttaacta tatagacttg gatttggtca aggatgttaa gcagcaccct     5280
caagactgcc cctctcaaca gcagtccctg ccaccccctc ccctcacca acccttaggc     5340
```

```
agcaatgagg gcagctcccc aagacgctcc agtgaggatt taagcaccta tgccagcatc   5400
aacttccaga agcaaccaga ggaccgtcaa tagaggtggc ggccgctcga gtctagaggg   5460
cccgtttaaa cccgctgatc agcctcgact gtgccttcta gttgccagcc atctgttgtt   5520
tgcccctccc ccgtgccttc cttgaccctg gaaggtgcca ctcccactgt cctttcctaa   5580
taaaatgagg aaattgcatc gcattgtctg agtaggtgtc attctattct gggggggtgg   5640
gtggggcagg acagcaaggg ggaggattgg gaagacaata gcaggcatgc tggggatgcg   5700
gtgggctcta tggcttctga ggcggaaaga accagctggg gctctagggg gtatccccac   5760
gcgccctgta gcggcgcatt aagcgcggcg ggtgtggtgg ttacgcgcag cgtgaccgct   5820
acacttgcca gcgccctagc gcccgctcct ttcgctttct tcccttcctt tctcgccacg   5880
ttcgccggct ttccccgtca agctctaaat cggggggctcc ctttagggtt ccgatttagt   5940
gctttacggc acctcgaccc caaaaaactt gattagggtg atggttcacg tagtgggcca   6000
tcgccctgat agacggtttt tcgccctttg acgttggagt ccacgttctt taatagtgga   6060
ctcttgttcc aaactggaac aacactcaac cctatctcgg tctattcttt tgatttataa   6120
gggattttgc cgatttcggc ctattggtta aaaaatgagc tgatttaaca aaaatttaac   6180
gcgaattaat tctgtggaat gtgtgtcagt tagggtgtgg aaagtcccca ggctccccag   6240
caggcagaag tatgcaaagc atgcatctca attagtcagc aaccaggtgt ggaaagtccc   6300
caggctcccc agcaggcaga agtatgcaaa gcatgcatct caattagtca gcaaccatag   6360
tcccgcccct aactccgccc atcccgcccc taactccgcc cagttccgcc cattctccgc   6420
cccatggctg actaatttttt tttatttatg cagaggccga ggccgcctct gcctctgagc   6480
tattccagaa gtagtgagga ggcttttttg gaggcctagg cttttgcaaa aagctcccgg   6540
gagcttgtat atccattttc ggatctgatc aagagacagg atgaggatcg tttcgcatga   6600
ttgaacaaga tggattgcac gcaggttctc cggccgcttg ggtggagagg ctattcggct   6660
atgactgggc acaacagaca atcggctgct ctgatgccgc cgtgttccgg ctgtcagcgc   6720
aggggcgccc ggttctttttt gtcaagaccg acctgtccgg tgccctgaat gaactgcagg   6780
acgaggcagc gcggctatcg tggctggcca cgacgggcgt tccttgcgca gctgtgctcg   6840
acgttgtcac tgaagcggga aagggactggc tgctattggg cgaagtgccg gggcaggatc   6900
tcctgtcatc tcaccttgct cctgccgaga aagtatccat catggctgat gcaatgcggc   6960
ggctgcatac gcttgatccg gctacctgcc cattcgacca ccaagcgaaa catcgcatcg   7020
agcgagcacg tactcggatg gaagccggtc ttgtcgatca ggatgatctg gacgaagagc   7080
atcaggggct cgcgccagcc gaactgttcg ccaggctcaa ggcgcgcatg cccgacggcg   7140
aggatctcgt cgtgacccat ggcgatgcct gcttgccgaa tatcatggtg gaaaatggcc   7200
gcttttctgg attcatcgac tgtggccggc tgggtgtggc ggaccgctat caggacatag   7260
cgttggctac ccgtgatatt gctgaagagc ttggcggcga tgggctgac cgcttcctcg   7320
tgctttacgg tatcgccgct cccgattcgc agcgcatcgc cttctatcgc cttcttgacg   7380
agttcttctg agcgggactc tggggttcga atgaccgacc aagcgacgc ccaacctgct   7440
atcacgagat ttcgattcca ccgccgcctt ctatgaaagg ttgggcttcg gaatcgtttt   7500
ccgggacgcc ggctggatga tcctccagcg cggggatctc atgctggagt tcttcgccca   7560
ccccaacttg tttattgcag cttataatgg ttacaaataa agcaatagca tcacaaattt   7620
cacaaataaa gcatttttttt cactgcattc tagttgtggt ttgtccaaac tcatcaatgt   7680
atcttatcat gtctgtatac cgtcgacctc tagctagagc ttggcgtaat catggtcata   7740
gctgtttcct gtgtgaaatt gttatccgct cacaattcca cacaacatac gagccggaag   7800
cataaagtgt aaagcctggg gtgcctaatg agtgagctaa ctcacattaa ttgcgttgcg   7860
ctcactgccc gctttccagt cgggaaacct gtcgtgccag ctgcattaat gaatcggcca   7920
acgcgcgggg agaggcggtt tgcgtattgg gcgctcttcc gcttcctcgc tcactgactc   7980
gctgcgctcg gtcgttcggc tgcggcgagc ggtatcagct cactcaaagg cggtaatacg   8040
gttatccaca gaatcagggg ataacgcagg aaagaacatg tgagcaaaag gccagcaaaa   8100
ggccaggaac cgtaaaaagg ccgcgttgct ggcgtttttc cataggctcc gcccccctga   8160
cgagcatcac aaaaatcgac gctcaagtca gaggtggcga aacccgacag gactataaag   8220
ataccaggcg tttccccctg gaagctccct cgtgcgctct cctgttccga ccctgccgct   8280
taccggatac ctgtccgcct ttctcccttc gggaagcgtg gcgctttctc atagctcacg   8340
ctgtaggtat ctcagttcgg tgtaggtcgt tcgctccaag ctgggctgtg tgcacgaacc   8400
ccccgttcag cccgaccgct gcgccttatc cggtaactat cgtcttgagt ccaacccggt   8460
aagacacgac ttatcgccac tggcagcagc cactggtaac aggattagca gagcgaggta   8520
tgtaggcggt gctacagagt tcttgaagtg gtggcctaac tacggctaca ctagaagaac   8580
agtatttggt atctgcgctc tgctgaagcc agttaccttc ggaaaaagag ttggtagctc   8640
ttgatccggc aaacaaacca ccgctggtag cggtggtttt tttgtttgca agcagcagat   8700
tacgcgcaga aaaaaaggat ctcaagaaga tcctttgatc ttttctacgg ggtctgacgc   8760
tcagtggaac gaaaactcac gttaagggat tttggtcatg agattatcaa aaaggatctt   8820
cacctagatc ctttttaaatt aaaaatgaag ttttaaatca atctaaagta tatatgagta   8880
aacttggtct gacagttacc aatgcttaat cagtgaggca cctatctcag cgatctgtct   8940
atttcgttca tccatagttg cctgactccc cgtcgtgtag ataactacga tacgggaggg   9000
cttaccatct ggccccagtg ctgcaatgat accgcgagac ccacgctcac cggctccaga   9060
tttatcagca ataaaccagc cagccggaag ggccgagcgc agaagtggtc ctgcaacttt   9120
atccgcctcc atccagtcta ttaattgttg ccgggaagct agagtaagta gttcgccagt   9180
taatagtttg cgcaacgttg ttgccattgc tacaggcatc gtggtgtcac gctcgtcgtt   9240
tggtatggct tcattcagct ccggttccca acgatcaagg cgagttacat gatccccat   9300
gttgtgcaaa aaagcggtta gctccttcgg tcctccgatc gttgtcagaa gtaagttggc   9360
cgcagtgtta tcactcatgg ttatggcagc actgcataat tctcttactg tcatgccatc   9420
cgtaagatgc ttttctgtga ctggtgagta ctcaaccaag tcattctgag aatagtgtat   9480
gcggcgaccg agttgctctt gcccggcgtc aatacgggat aataccgcgc cacatagcag   9540
aactttaaaa gtgctcatca ttggaaaacg ttcttcgggg cgaaaactct caaggatctt   9600
accgctgttg agatccagtt cgatgtaacc cactcgtgca cccaactgat cttcagcatc   9660
ttttactttc accagcgttt ctgggtgagc aaaaacagga aggcaaaatg ccgcaaaaaa   9720
gggaataagg gcgacacgga aatgttgaat actcatactc ttcctttttc aatattattg   9780
aagcatttat cagggttatt gtctcatgag cggatacata tttgaatgta tttagaaaaa   9840
taaacaaata ggggttccgc gcacatttcc ccgaaaagtg ccacctgacg tc            9892
```

SEQ ID NO: 55          moltype = AA  length = 1391
FEATURE                Location/Qualifiers -continued

```
REGION                  1..1391
                        note = insulin receptor IR1-His6
source                  1..1391
                        mol_type = protein
                        organism = synthetic construct
SEQUENCE: 55
MCCPGCCATG GRRGAAAAPL LVAVAALLLG AAGHLYPGEV CPGMDIRNNL TRLHELENCS    60
VIEGHLQILL MFKTRPEDFR DLSFPKLIMI TDYLLLFRVY GLESLKDLFP NLTVIRGSRL   120
FFNYALVIFE MVHLKELGLY NLMNITRGSV RIEKNNELCY LATIDWSRIL DSVEDNYIVL   180
NKDDNEECGD ICPGTAKGKT NCPATVINGQ FVERCWTHSH CQKVCPTICK SHGCTAEGLC   240
CHSECLGNCS QPDDPTKCVA CRNFYLDGRC VETCPPPYYH FQDWRCVNFS FCQDLHHKCK   300
NSRRQGCHQY VIHNNKCIPE CPSGYTMNSS NLLCTPCLGP CPKVCHLLEG EKTIDSVTSA   360
QELRGCTVIN GSLIINIRGG NNLAAELEAN LGLIEEISGY LKIRRSYALV SLSFFRKLRL   420
IRGETLEIGN YSFYALDNQN LRQLWDWSKH NLTITQGKLF FHYNPKLCLS EIHKMEEVSG   480
TKGRQERNDI ALKTNGDQAS CENELLKFSY IRTSFDKILL RWEPYWPPDF RDLLGFMLFY   540
KEAPYQNVTE FDGQDACGSN SWTVVDIDPP LRSNDPKSQN HPGWLMRGLK PWTQYAIFVK   600
TLVTFSDERR TYGAKSDIIY VQTDATNPSV PLDPISVSNS SSQIILKWKP PSDPNGNITH   660
YLVFWERQAE DSELFELDYC LKGLKLPSRT WSPPFESEDS QKHNQSEYED SAGECCSCPK   720
TDSQILKELE ESSFRKTFED YLHNVVFVPR PSRKRRSLGD VGNVTVAVPT VAAFPNTSST   780
SVPTSPEEHR PFEKVVNKES LVISGLRHFT GYRIELQACN QDTPEERCSV AAYVSARTMP   840
EAKADDIVGP VTHEIFENNV VHLMWQEPKE PNGLIVLYEV SYRRYGDEEL HLCVSRKHFA   900
LERGCRLRGL SPGNYSVRIR ATSLAGNGSW TEPTYFYVTD YLDVPSNIAK IIIGPLIFVF   960
LFSVVIGSIY LFLRKRQPDG PLGPLYASSN PEYLSASDVF PCSVYVPDEW EVSREKITLL  1020
RELGQGSFGM VYEGNARDII KGEAETRVAV KTVNESASLR ERIEFLNEAS VMKGFTCHHV  1080
VRLLGVVSKG QPTLVVMELM AHGDLKSYLR SLRPEAENNP GRPPPTLQEM IQMAAEIADG  1140
MAYLNAKKFV HRDLAARNCM VAHDFTVKIG DFGMTRDIYE TDYYRKGGKG LLPVRWMAPE  1200
SLKDGVFTTS SDMWSFGVVL WEITSLAEQP YQGLSNEQVL KFVMDGGYLD QPDNCPERVT  1260
DLMRMCWQFN PKMRPTFLEI VNLLKDDLHP SFPEVSFFHS EENKAPESEE LEMEFEDMEN  1320
VPLDRSSHCQ REEAGGRDGG SSLGFKRSYE EHIPYTHMNG GKKNGRILTL PRSNPSGGGG  1380
SHHHHHHHHH H                                                       1391

SEQ ID NO: 56           moltype = DNA  length = 10124
FEATURE                 Location/Qualifiers
misc_feature            1..10124
                        note = IR1
source                  1..10124
                        mol_type = other DNA
                        organism = synthetic construct
SEQUENCE: 56
gacggatcgg gagatctccc gatcccctat ggtgcactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgtttttgcg ctgcttcgcg agtacattta tattggctca tgtccaatat   240
gaccgccatg ttgacattga ttattgacta gttattaata gtaatcaatt acggggtcat   300
tagttcatag cccatatatg gagttccgcg ttacataact tacggtaaat ggcccgcctg   360
gctgaccgcc caacgacccc cgcccattga cgtcaataat gacgtatgtt cccatagtaa   420
cgccaatagg gactttccat tgacgtcaat gggtggagta ttacggtaa actgcccact   480
tggcagtaca tcaagtgtat catatgccaa gtccgccccc tattgacgtc aatgacggta   540
aatggcccgc ctggcattat gcccagtaca tgaccttacg ggactttcct acttggcagt   600
acatctacgt attagtcatc gctattacca tggtgatgcg gttttggcag tacaccaatg   660
ggcgtggata gcggtttgac tcacggggat ttccaagtct ccaccccatt gacgtcaatg   720
ggagtttgtt ttggcaccaa aatcaacggg actttccaaa atgtcgtaat aaccccgccc   780
cgttgacgca aatgggcggt aggcgtgtac ggtgggaggt ctatataagc agagctcgtt   840
tagtgaaccg tcagatcctc actctcttcc gcatcgctgt ctgcgagggc cagctgttgg   900
gctcgcggtt gaggacaaac tcttcgcggt ctttccagta ctcttggatc ggaaaaccgt   960
cggcctccga acggtactcc gccaccgagg gacctgagcg agtccgcatc gaccggatcg  1020
gaaaacctct cgagaaaggc gtctaaccag tcacagtcgc aaggtaggct gagcaccgtg  1080
gcgggcggca gcgggtggcg gtcggggttg tttctggcgg aggtgctgct gatgatgtaa  1140
ttaaagtagg cggtcttgag acggcggatg gtcgaggtga ggtggtggca gcttgagatc  1200
cagctgttgg ggtgagtact ccctctcaaa agcgggcatt acttctgcgc taagattgtc  1260
agtttccaaa aacgaggagg atttgatatt cacctggccc gatctggcca tacacttgag  1320
tgacaatgac atccactttg cctttctctc cacaggtgtc cactcccagg tccaagttta  1380
aactttaata cgactcacta tagggccgc caccaagctt ggtaccatgt gctgtcccgg  1440
ctgttgcgcc accggggggcc ggcgggggggc ggcggccgcg ccgctgctgg tggcggtggc  1500
cgcgctgcta ctgggcgccg cgggccacct gtacccggga gaggtgtgtc ccggcatgga  1560
tatccggaac aacctcacta ggttgcatga gctggagaat tgctctgtca tcgaaggaca  1620
cttgcagata ctcttgatgt tcaaaacgag gcccgaagat ttccgagacc tcagtttccc  1680
caaactcatc atgatcactg attacttgct gctcttccgg gtctctatggc tcgagagctt  1740
gaaggacctg ttccccaacc tcacggtcat ccggggatca cgactgttct ttaactacgc  1800
gctggtcatc ttcgagatgg ttcacctcaa ggaactcggc ctctacaacc tgatgaacat  1860
cacccggggt tctgagtccgca tcgagaagaa caatgagctc tgttacttgg ccactatcga  1920
ctggtcccgt atcctggatt ccgtggagga taattacatc gtgttgaaca agatgacaa  1980
cgaggagtgt ggagacatct gtccgggtac cgcgaagggc aagaccaact gccccgccac  2040
cgtcatcaac gggcagtttg tcgaacgatg ttggactcat agcactgcc agaaagtttg  2100
cccgaccatc tgtaagtcac acggctgcac cgccgaaggc ctctgttgcc acagcgagtg  2160
cctgggcaac tgttctcagc ccgacgaccc caccaagtgc gtggcctgcc gcaacttcta  2220
cctggacggc aggtgtgtgg agacctgccc gcccccgtac taccacttcc aggactggcg  2280
ctgtgtgaac ttcagcttct gccaggacct gcaccacaaa tgcaagaact cgcggaggca  2340
gggctgccac cagtacgtca ttcacaacaa caagtgcatc cctgagtgtc cctccgggta  2400
```

```
cacgatgaat tccagcaact tgctgtgcac cccatgcctg ggtccctgtc ccaaggtgtg   2460
ccacctccta gaaggcgaga agaccatcga ctcggtgacg tctgcccagg agctccgagg   2520
atgcaccgtc atcaacggga gtctgatcat caacattcga ggaggcaaca atctggcagc   2580
tgagctagaa gccaacctcg gcctcattga agaaatttca gggtatctaa aaatccgccg   2640
atcctacgct ctggtgtcac tttccttctt ccggaagtta cgtctgattc gaggagagac   2700
cttggaaatt gggaactact ccttctatgc cttggacaac cagaacctaa ggcagctctg   2760
ggactggagc aaaacacaac tcaccatcac tcaggggaaa ctcttcttcc actataaccc   2820
caaactctgc ttgtcagaaa tccacaagat ggaagaagtt tcaggaacca aggggcgcca   2880
ggagagaaac gacattgccc tgaagaccaa tggggaccag gcatcctgtg aaaatgagtt   2940
acttaaattt tcttacattc ggacatcttt tgacaagatc ttgctgagat gggagccgta   3000
ctggcccccc gacttccgag acctcttggg gttcatgctg ttctacaaag aggcccctta   3060
tcagaatgtg acggagttcg acgggcagga tgcatgtggt tccaacagtt ggacggtggt   3120
agacattgac ccacccctga ggtccaacga ccccaaatca cagaaccacc cagggtggct   3180
gatgcggggt ctcaagccct ggacccagta tgccatcttt gtgaagaccc tggtcacctt   3240
ttcggatgaa cgccggacct atggggccaa gagtgacatc atttatgtcc agacagatgc   3300
caccaacccc tctgtgcccc tggatccaat ctcagtgtct aactcatcat cccagattat   3360
tctgaagtgg aaaccaccct ccgacccaa tggcaacatc acccactacc tggttttctg   3420
ggagaggcag gcggaagaca gtgagctgtt cgagctggat tattgcctca aagggctgaa   3480
gctgccctcg aggacctggt ctccaccatt cgagtctgaa gattctcaga agcacaacca   3540
gagtgagtat gaggattcgg ccggcgaatg ctgctcctgt ccaaagacag actctcagat   3600
cctgaaggag ctggaggagt cctcgtttag gaagacgttt gaggattacc tgcacaacgt   3660
ggtttttcgtc cccaggccat ctcggaaacg caggtccctt gcgatgttg ggaatgtgac   3720
ggtggccgtg cccacggtgg cagctttccc caacacttcc tcgaccagcg tgcccacgag   3780
tccgaggagg cacaggcctt ttgagaaggt ggtgaacaag gagtcgctgg tcatctccgg   3840
cttgcgcacac ttcacgggct atcgcatcga gctgcaggct tgcaaccagg acaccctga   3900
ggaacggtgc agtgtggcag cctacgtcag tgcgaggacc atgcctgaag ccaaggctga   3960
tgacattgtt ggccctgtga cgcatgaaat ctttgagaac aacgtcgtcc acttgatgtg   4020
gcaggagccg aaggagccca atggtctgat cgtgctgtat gaagtgagtt atcggcgata   4080
tggtgatgag gagctgcatc tctgcgtctc ccgcaagcac ttcgctctgg aacggggctg   4140
caggctgcgt gggctgtcac cggggaacta cagcgtgcga atccgggcca cctccettgc   4200
gggcaacggc tcttggacgg aacccaccta tttctacgtg acagactatt tagacgtccc   4260
gtcaaatatt gcaaaaatta tcatcggccc cctcatcttt gtctttctct tcagtgttgt   4320
gattggaagt atttatctat tcctgagaaa gaggcagcca gatgggccgc tgggaccgct   4380
ttacgcttct tcaaaccctg agtatctcag tgccagtgat gtgtttccat gctctgtgta   4440
cgtgccggat gagtgggagg tgtctcgaga gaagatcacc ctccttcgag agctggggca   4500
gggctccttc ggcatggtgt atgagggcaa tgccaggggac atcatcaagg gtgaggcaga   4560
gacccgcgtg gcggtgaaga cggtcaacga gtcagccagt ctccgagagc ggattgagtt   4620
cctcaatgag gcctcggtca tgaagggctt cacctgccat catgtggtgc gcctcctggg   4680
agtggtgtcc aagggccagc ccacgctggt ggtgatggag ctgatggctc acggagacct   4740
gaagagctac ctccgttctc tgcggccaga ggctgagaat aatcctggcc gccctccccc   4800
tacccttcaa gagatgattc agatggcggc agagattgct gacgggatgg cctacctgaa   4860
cgccaagaag tttgtgcatc gggacctggc agcgagaaac tgcatggtcg cccatgattt   4920
tactgtcaaa attggagact ttggaatgac cagagacatc tatgaaacgg attactaccg   4980
gaaagggggc aagggtctgc tccctgtacg gtggatggca ccggagtccc tgaaggatgg   5040
ggtcttcacc acttcttctg acatgtggtc ctttggcgtg gtcctttggg aaatcaccag   5100
cttggcagaa cagcccttacc aaggcctgtc taatgaacag gtgttgaaat ttgtcatgga   5160
tggagggtat ctggatcaac ccgacaactg tccagagaga gtcactgacc tcatgcgcat   5220
gtgctggcaa ttcaacccca agatgaggcc aaccttcctg gagattgtca acctgctcaa   5280
ggacgacctg caccccagct ttccagaggt gtcgttcttc cacagcgagg agaacaaggc   5340
tcccgagagt gaggagctgg agatggagtt tgaggacatg gagaatgtgc ccctggaccg   5400
ttcctcgcac tgtcagaggg aggaggcggg gggccgggat ggaggtgtct cgctgggttt   5460
caagcggagc tacgaggaac acatcccctta cacacacatg aacggaggca agaaaaacgg   5520
gcggattctg accttgcctc ggtccaatcc ttccgggggt ggaggctctc accatcacca   5580
ccatcatcac caccatcact aaactcgagt ctagagcggc cgccgaattc gggcccgttt   5640
aaacccgctg atcagcctcg actgtgcctt ctagttgcca gccatctgtt gtttgcccct   5700
cccccgtgcc ttccttgacc ctggaaggtg ccactcccac tgtccttcc taataaaatg   5760
aggaaattgc atcgcattgt ctgagtaggt gtcattctat tctggggggt ggggtggggc   5820
aggacagcaa gggggaggat tgggaagaca atagcaggca tgctggggat gcggtgggct   5880
ctatggcttc tgaggcggaa agaaccagct ggggctctag ggggtatccc cacgcgccct   5940
gtagcggcgc attaagcgcg gcgggtgtgg tggttacgcg cagcgtgacc gctacacttg   6000
ccagcgccct agcgcccgct cctttcgctt tcttcccttc ctttctcgcc acgttcgcag   6060
gctttccccg tcaagctcta aatcgggggc tccctttagg gttccgattt agtgctttac   6120
ggcacctcga ccccaaaaaa cttgattagg gtgatggttc acgtagtggg ccatcgccct   6180
gatagacggt ttttcgccct ttgacgttgg agtccacgtt ctttaatagt ggactctagg   6240
tccaaactgg aacaacactc aaccctatct cggtctattc ttttgattta taagggattt   6300
tgccgatttc ggcctattgg ttaaaaaatg agctgattta acaaaaattt aacgcgaatt   6360
aattctgtgg aatgtgtgtc agttagggtg tggaaagtcc ccaggctccc cagcaggcag   6420
aagtatgcaa agcatgcatc tcaattagtc agcaaccagg tgtggaaagt ccccaggctc   6480
cccagcaggc agaagtatgc aaagcatgca tctcaattag tcagcaacca tagtcccgcc   6540
cctaactccg cccatcccgc ccctaactcc gcccagttcc gcccattctc cgccccatgg   6600
ctgactaatt tttttattt atgcagaggc cgaggccgcc tctgcctctg agctattcca   6660
gaagtagtga ggaggctttt ttggaggcct aggcttttgc aaaaagctct cgggagcttg   6720
tatatccatt ttcggatctg atcagcacgt gatgaaaaag cctgaactca ccgcgacgtc   6780
tgtcgagaag tttctgatcg aaaagttcga tgctctccga cctgatgc agctctcgga   6840
gggcgaagaa tctcgtgctt tcagcttcga gtaggaggg cgtggatatg tcctgcgggt   6900
aaatagctgc gccgatggtt tctacaaaga tcgttatgtt tatcggcact ttgcatcggc   6960
cgcgctcccg attccggaag tgcttgacat tggggaattc agcgagagcc tgacctattg   7020
catctcccgc cgtgcacagg gtgtcacgtt gcaagacctg cctgaaaccg aactgcccgc   7080
tgttctgcag ccggtcgcgg aggccatgga tgcgatcgct gcggccgatc ttagccagac   7140
```

```
gagcgggttc ggcccattcg gaccgcaagg aatcggtcaa tacactacat ggcgtgattt   7200
catatgcgcg attgctgatc cccatgtgta tcactggcaa actgtgatgg acgacaccgt   7260
cagtgcgtcc gtcgcgcagg ctctcgatga gctgatgctt tgggccgagg actgccccga   7320
agtccggcac ctcgtgcacg cggatttcgg ctccaacaat gtcctgacgg acaatggccg   7380
cataacagcg gtcattgact ggagcgaggc gatgttcggg gattcccaat acgaggtcgc   7440
caacatcttc ttctggaggc cgtggttggc ttgtatggag cagcagacgc gctacttcga   7500
gcggaggcat ccggagcttg caggatcgcc gcggctccgg gcgtatatgc tccgcattgg   7560
tcttgaccaa ctctatcaga gcttggttga cggcaatttc gatgatgcag cttgggcgca   7620
gggtcgatgc gacgcaatcg tccgatccgg agccgggact gtcgggcgta cacaaatcgc   7680
ccgcagaagc gcggccgtct ggaccgatgg ctgtgtagaa gtactcgccg atagtggaaa   7740
ccgacgcccc agcactcgtc cgagggcaaa ggaatagcac gtgctacgag atttcgattc   7800
caccgccgcc ttctatgaaa ggttgggctt cggaatcgtt ttccgggacg ctggctggat   7860
gatcctccag cgcggggatc tcatgctgga gttcttcgcc caccccaact tgtttattgc   7920
agcttataat ggttacaaat aaagcaatag catcacaaat ttcacaaata aagcatttt   7980
ttcactgcat tctagttgtg gtttgtccaa actcatcaat gtatcttatc atgtctgtat   8040
accgtcgacc tctagctaga gcttggcgta atcatggtca tagctgtttc ctgtgtgaaa   8100
ttgttatccg ctcacaattc cacacaacat acgagccgga agcataaagt gtaaagcctg   8160
gggtgcctaa tgagtgagct aactcacatt aattgcgttg cgctcactgc ccgctttcca   8220
gtcgggaaac ctgtcgtgcc agctgcatta atgaatcggc caacgcgcgg ggagaggcgg   8280
tttgcgtatt gggcgctctt ccgcttcctc gctcactgac tcgctgcgct cggtcgttcg   8340
gctgcggcga gcggtatcag ctcactcaaa ggcggtaata cggttatcca cagaatcagg   8400
ggataacgca ggaaagaaca tgtgagcaaa aggccagcaa aaggccagga accgtaaaaa   8460
ggccgcgttg ctggcgtttt tccataggct ccgcccccct gacgagcatc acaaaaatcg   8520
acgctcaagt cagaggtggc gaaacccgac aggactataa agataccagg cgtttccccc   8580
tggaagctcc ctcgtgcgct ctcctgttcc gaccctgccg cttaccggat acctgtccgc   8640
ctttctccct tcgggaagcg tggcgctttc tcatagctca cgctgtaggt atctcagttc   8700
ggtgtaggtc gttcgctcca agctgggctg tgtgcacgaa ccccccgttc agcccgaccg   8760
ctgcgcctta tccggtaact atcgtcttga gtccaacccg gtaagacacg acttatcgcc   8820
actggcagca gccactggta acaggattag cagagcgagg tatgtaggcg gtgctacaga   8880
gttcttgaag tggtggccta actacggcta cactagaaga acagtatttg gtatctgcgc   8940
tctgctgaag ccagttacct tcggaaaaag agttggtagc tcttgatccg gcaaacaaac   9000
caccgctggt agcggtggtt ttttgtttg caagcagcag attacgcgca gaaaaaaagg   9060
atctcaagaa gatcctttga tcttttctac ggggtctgag cgcggaaccc ctatttgttt   9120
attttctaa atacattcaa atatgtatcc gctcatgaat taattcttag aaaaactcat   9180
cgagcatcaa atgaaactgc aatttattca tatcaggatt atcaatacca tatttttgaa   9240
aaagccgttt ctgtaatgaa ggagaaaact caccgaggca gttccatagg atggcaagat   9300
cctggtatcg gtctgcgatt ccgactcgtc caacatcaat acaacctatt aatttcccct   9360
cgtcaaaaat aaggttatca agtgagaaat caccatgagt gacgactgaa tccggtgaga   9420
atggcaaaag tttatgcatt tctttccaga cttgttcaac aggccagcca ttacgctcgt   9480
catcaaaatc actcgcatca accaaaccgt tattcattcg tgattgcgcc tgagcgagac   9540
gaaatacgcg atcgctgtta aaaggacaat tacaaacagg aatcgaatgc aaccggcgca   9600
ggaacactgc cagcgcatca acaatatttt cacctgaatc aggatattct tctaatacct   9660
ggaatgctgt tttcccaggg atcgcagtgg tgagtaacca tgcatcatca ggagtacgga   9720
taaaatgctt gatggtcgga gaggcataaa attccgtcag ccagtttagt ctgaccatct   9780
catctgtaac atcattggca acgctacctt tgccatgttt cagaaacaac tctggcgcat   9840
cgggcttccc atacaatcga tagattgtcg cacctgattg cccgacatta tcgcgagccc   9900
atttataccc atataaatca gcatccatgt tggaatttaa tcgcggccta gagcaagacg   9960
tttcccgttg aatatggctc ataacacccc ttgtattact gtttatgtaa gcagacagtt  10020
ttattgttca tgaccaaaat cccttaacgt gagttttcgt tccactgagc gtcagacccc  10080
gtagaaatcc gcgcacattt ccccgaaaag tgccacctga cgtc                   10124
```

```
SEQ ID NO: 57          moltype = AA   length = 354
FEATURE                Location/Qualifiers
REGION                 1..354
                       note = Galfa-i1
source                 1..354
                       mol_type = protein
                       organism = synthetic construct
SEQUENCE: 57
MGCTLSAEDK AAVERSKMID RNLREDGEKA AREVKLLLLG AGESGKSTIV KQMKIIHEAG   60
YSEEECKQYK AVVYSNTIQS IIAIIRAMGR LKIDFGDSAR ADDARQLFVL AGAAEEGFMT  120
AELAGVIKRL WKDSGVQACF NRSREYQLND SAAYYLNDLD RIAQPNYIPT QQDVLRTRVK  180
TTGIVETHFT FKDLHFKMFD VGGQRSERKK WIHCFEGVTA IIFCVALSDY DLVLAEDEEM  240
NRMHESMKLF DSICNNKWFT DTSIILFLNK KDLFEEKIKK SPLTICYPEY AGSNTYEEAA  300
AYIQCQFEDL NKRKDTKEIY THFTCATDTK NVQFVFDAVT DVIIKNNLKD CGLF         354
```

```
SEQ ID NO: 58          moltype = DNA   length = 5771
FEATURE                Location/Qualifiers
misc_feature           1..5771
                       note = Galfa-i1
source                 1..5771
                       mol_type = other DNA
                       organism = synthetic construct
SEQUENCE: 58
tagttattaa tagtaatcaa ttacgggggtc attagttcat agcccatata tggagttccg   60
cgttacataa cttacggtaa atggcccgcc tggctgaccg cccaacgacc cccgcccatt  120
gacgtcaata atgacgtatg ttcccatagt aacgccaata gggactttcc attgacgtca  180
atgggtggag tatttacggt aaactgccca cttggcagta tcaagtgt atcatatgcc  240
aagtacgccc cctattgacg tcaatgacgg taaatggccc gcctggcatt atgcccagta  300
```

-continued

```
catgacccta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cgtcagatcc gctagcctcg    600
acttgagctc tctggctaac tagagaaccc actgcttact ggcttatcga aattaatacg    660
actcactata gggagaccca agctggctag cgtttaaact taagcttggt accaccatgg    720
gctgcacgct gagcgccgag gacaaggcgg cggtggagcg gagtaagatg atcgaccgca    780
acctccgtga ggacggcgag aaggcggcgc gcgaggtcaa gctgctgctg ctcggtgctg    840
gtgaatctgg taaaagtaca attgtgaagc agatgaaaat tatccatgca gctggttatt    900
cagaagagga gtgtaaacaa tacaaagcag tggtctacag taacaccatc cagtcaatta    960
ttgctatcat tagggctatg gggaggttga agatagactt tggtgactca gcccgggcgg   1020
atgatgcacg ccaactcttt gtgctagctg gagctgctga agaaggcttt atgactgcag   1080
aacttgctgg agttataaag agattgtgga aagatagtgg tgtacaagcc tgtttcaaca   1140
gatcccgaga gtaccagctt aatgattctg cagcatacta tttgaatgac ttggacagaa   1200
tagctcaacc aaattacatc ccgactcaac aagatgttct cagaactaga gtgaaaacta   1260
caggaattgt tgaaacccat tttactttca aagatcttca tttttaaaatg tttgatgtgg   1320
gaggtcagag atctgagcgg aagaagtgga ttcattgctt cgaaggagtg acggcgatca   1380
tcttctgtgt agcactgagt gactacgacc tggttctagc tgaagatgaa gaaatgaacc   1440
gaatgcatga aagcatgaaa ttgtttgaca gcatatgtaa caacaagtgg tttacagata   1500
catccattat acttttttcta aacaagaagg atctctttga agaaaaaatc aaaaagagcc   1560
ctctcactat atgctatcca gaatatgcag gatcaaacac atatgaagag gcagctgcat   1620
atattcaatg tcagtttgaa gacctcaata aaagaaagga cacaaaggaa atatacaccc   1680
acttcacatg tgccacagat actaagaatg tgcagtttgt ttttgatgct gtaacagatg   1740
tcatcataaa aaataatcta aaagattgtg gtctctttta accgcggtcg acggtaccgc   1800
gggcccggga tctaagctta tcgataatca acctctggat tacaaaattt gtgaaagatt   1860
gactggtatt cttaactatg ttgctccttt tacgctatgt ggatacgctg ctttaatgcc   1920
tttgtatcat gctattgctt cccgtatggc tttcattttc tcctccttgt ataaatcctg   1980
gttgctgtct ctttatgagg agttgtggcc cgttgtcagg caacgtggcg tggtgtgcac   2040
tgtgtttgct gacgcaaccc ccactggttg gggcattgcc accacctgtc agctcctttc   2100
cgggactttc gctttcccccc tccctattgc cacggcggaa ctcatcgccg cctgccttgc   2160
ccgctgctgg acaggggctc ggctgttggg cactgacaat tccgtggtgt tgtcggggaa   2220
atcatcgtcc tttccttggc tgctcgcctg tgttgccacc tggattctgc gcgggacgtc   2280
cttctactac gtcccttcgg ccctcaatcc agcggacctt ccttcccgcg gcctgctgcc   2340
ggctctgcgg cctcttccgc gtcttcgcct tcgccctcag acgagtcgga tctccctttg   2400
ggccgcctcc ccgcatcgat accgtggatc gatccaccgg atctagataa ctgatcataa   2460
tcagccatac cacatttgta gaggttttac ttgctttaaa aaacctccca cacctccccc   2520
tgaacctgaa acataaaatg aatgcaattg ttgttgttaa cttgtttatt gcagcttata   2580
atggttacaa ataaagcaat agcatcacaa atttcacaaa taaagcattt ttttcactgc   2640
attctagttg tggtttgtcc aaactcatca atgtatctta acgcgtaaat tgtaagcgtt   2700
aatattttgt taaaattcgc gttaaatttt tgttaaatca gctcattttt taaccaatag   2760
gccgaaatcg gcaaaatccc ttataaatca aaagaataga ccgagatagg gttgagtgtt   2820
gttccagttt ggaacaagag tccactatta agaacgtgg atccaacgt caaagggcga   2880
aaaaccgtct atcagggcga tggcccacta cgtgaaccat caccctaatc aagttttttg   2940
gggtcgaggt gccgtaaagc actaaatcgg aaccctaaag ggagccccg atttagagct   3000
tgacggggaa agccggcgaa cgtggcgaga aggaaggga agaaagcgaa aggagcgggc   3060
gctagggcgc tggcaagtgt agcggtcacg ctgcgcgtaa ccaccacacc gccgcgctt   3120
aatgcgccgc tacagggcgc gtcaggtggc acttttcggg gaaatgtgcg cggaacccct   3180
atttgtttat ttttctaaat acattcaaat atgtatccgc tcatgagaca ataaccctga   3240
taaatgcttc aataatattg aaaaaggaag agtcctgagg cggaaagaac cagctgtgga   3300
atgtgtgtca gttagggtgt ggaaagtccc caggctcccc agcaggcaga agtatgcaaa   3360
gcatgcatct caattagtca gcaaccaggt gtggaaagtc cccaggctcc ccagcaggca   3420
gaagtatgca aagcatgcat ctcaattagt cagcaaccat agtcccgccc ctaactccgc   3480
ccatcccgcc cctaactccg cccagttccg cccattctcc gccccatggc tgactaattt   3540
ttttatttta tgcagaggcc gaggccgcct cggcctctga gctattccag aagtagtgag   3600
gaggcttttt tggaggccta ggcttttgca aagatcgatc aagagacagg atgaggatcg   3660
tttcgcatga ttgaacaaga tggattgcac gcaggttctc cggccgcttg ggtggagagg   3720
ctattcggct atgactgggc acaacagaca atcggctgct ctgatgccgc cgtgttccgg   3780
ctgtcagcgc aggggcgccc ggttcttttt gtcaagaccg acctgtccgg tgccctgaat   3840
gaactgcaag acgaggcagc gcggctatcg tggctggcca cgacgggcgt tccttgcgca   3900
gctgtgctcg acgttgtcac tgaagcggga agggactggc tgctattggg cgaagtgccg   3960
gggcaggatc tcctgtcatc tcaccttgct cctgccgaga agtatccat catggctgat   4020
gcaatgcggc ggctgcatac gcttgatccg gctacctgcc cattcgacca ccaagcgaaa   4080
catcgcatcg agcgagcacg tactcggatg gaagccggtc ttgtcgatca ggatgatctg   4140
gacgaagagc atcaggggct cgcgccagcc gaactgttcg ccaggctcaa ggcgagcatg   4200
cccgacggcg aggatctcgt cgtgacccat ggcgatgcct gcttgccgaa tatcatggtg   4260
gaaaatggcc gcttttctgg attcatcgac tgtggccggc tgggtgtggc ggaccgctat   4320
caggacatag cgttggctac ccgtgatatt gctgaagagc ttggcggcga atgggctgac   4380
cgcttcctcg tgctttacgg tatcgccgct cccgattcgc agcgcatcgc cttctatcgc   4440
cttcttgacg agttcttctg agcgggactc tggggttcga atgaccgac caagcgacgc   4500
ccaacctgcc atcacgagat ttcgattcca ccgccgcctt ctatgaaagg ttgggcttcg   4560
gaatcgtttt ccgggacgcc ggctggatga tcctccagcg cggggatctc atgctggagt   4620
tcttcgccca cctagggggg aggctaactg aaacacggaa ggagacaata ccggaaggaa   4680
cccgcgctat gacggcaata aaaagacaga ataaaacgca cggtgttggg tcgtttgttc   4740
ataaacgcgg ggttcggtcc cagggctggc actctgtcga taccccaccg agaccccatt   4800
ggggccaata cgcccgcgtt tcttcctttt ccccacccca ccccccaagt tcgggtgaag   4860
gcccagggct cgcagccaac gtcggggcgg caggccctgc catagcctca ggttactcat   4920
atatacttta gattgattta aaacttcatt tttaattta aaggatctag gtgaagatcc   4980
ttttgataa tctcatgacc aaaatccctt aacgtgagtt ttcgttccac tgagcgtcag   5040
```

-continued

```
acccccgtaga aaagatcaaa ggatcttctt gagatccttt tttctgcgc gtaatctgct    5100
gcttgcaaac aaaaaaacca ccgctaccag cggtggtttg tttgccggat caagagctac    5160
caactctttt tccgaaggta actggcttca gcagagcgca gataccaaat actgtccttc    5220
tagtgtagcc gtagttaggc caccacttca agaactctgt agcaccgcct acatacctcg    5280
ctctgctaat cctgttacca gtggctgctg ccagtgcga taagtcgtgt cttaccgggt     5340
tggactcaag acgatagtta ccggataagg cgcagcggtc gggctgaacg gggggttcgt    5400
gcacacagcc cagcttggag cgaacgacct acaccgaact gagataccta cagcgtgagc    5460
tatgagaaag cgccacgctt cccgaaggga gaaaggcgga caggtatccg gtaagcggca    5520
gggtcggaac aggagagcgc acgagggagc ttccagggg aaacgcctgg tatctttata     5580
gtcctgtcgg gtttcgccac ctctgacttg agcgtcgatt tttgtgatgc tcgtcagggg    5640
ggcggagcct atggaaaaac gccagcaacg cggcctttt acggttcctg gccttttgct     5700
ggccttttgc tcacatgttc tttcctgcgt tatcccctga ttctgtggat aaccgtatta    5760
ccgccatgca t                                                         5771
```

```
SEQ ID NO: 59            moltype = AA   length = 340
FEATURE                  Location/Qualifiers
REGION                   1..340
                         note = Gbeta1
source                   1..340
                         mol_type = protein
                         organism = synthetic construct
SEQUENCE: 59
MSELDQLRQE AEQLKNQIRD ARKACADATL SQITNNIDPV GRIQMRTRRT LRGHLAKIYA    60
MHWGTDSRLL VSASQDGKLI IWDSYTTNKV HAIPLRSSWV MTCAYAPSGN YVACGGLDNI   120
CSIYNLKTRE GNVRVSRELA GHTGYLSCCR FLDDNQIVTS SGDTTCALWD IETGQQTTTF   180
TGHTGDVMSL SLAPDTRLFV SGACDASAKL WDVREGMCRQ TFTGHESDIN AICFFPNGNA   240
FATGSDDATC RLFDLRADQE LMTYSHDNII CGITSVSFSK SGRLLLAGYD DFNCNVWDAL   300
KADRAGVLAG HDNRVSCLGV TDDGMAVATG SWDSFLKIWN                         340
```

```
SEQ ID NO: 60            moltype = DNA   length = 6390
FEATURE                  Location/Qualifiers
misc_feature            1..6390
                         note = Gbeta1
source                   1..6390
                         mol_type = other DNA
                         organism = synthetic construct
SEQUENCE: 60
gacggatcgg gagatctccc gatcccctat ggtgcactct cagtacaatc tgctctgatg    60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag gctagcgttt aaacttaagc    900
ttggtaccga gctcggatcc accatgagtg agcttgacca gttacggcag gaggccgagc    960
aacttaagaa ccagattcga gacgccagga agcatgtgc agatgcaact ctctctcaga    1020
tcacaaacaa catcgaccca gtgggaagaa tccaaatgcg cacgagagga cactgcggg    1080
ggcacctggc caagatctac gccatgcact ggggcacaga ctccaggctt ctcgtcagtg    1140
cctcgcagga tggtaaactt atcatctggg acagctacac caccaacaag gtccacgcca    1200
tccctctgcg ctcctcctgg gtcatgacct gtgcatatgc cccttctggg aactatgtgg    1260
cctgcggtgg cctggataac atttgctcca tttacaatct gaaaactcgt gagggggaacg    1320
tgcgcgtgag tcgtgagctg gcaggacaca caggttacct gtcctgctgc cgattcctga    1380
atgacaatca gatcgtcacc agctctggag acaccacgtg tgccctgtgg gacatcgaga    1440
ccggccagca gacgaccacg tttaccggac acactggaga tgtcatgagc ctttctcttg    1500
ctcctgacac cagactgttc gtctctggtg cttgtgatgc ttcagccaaa ctctgggatg    1560
tgcgagaagg catgtgccgg cagaccttca ctggccacga gtctgacatc aatgccattt    1620
gcttctttcc aaatggcaat gcatttgcca ctggctcaga cgacgccacc tgcaggctgt    1680
ttgaccttcg tgctgaccag gagctcatga cttactccca tgacaacatc atctgcggga    1740
tcacctctgt ctccttctcc aagagcgggc gcctcctcct tgctgggtac gacgacttca    1800
actgcaacgt ctgggatgca ctcaaagccg accgggcagg tgtcttggct gggcatgaca    1860
accgcgtcag ctgcctgggc gtgactgacg atggcatggc tgtggcgaca gggtcctggg    1920
atagcttcct caagatctgg aactaactcg agtctagagg gcccgtttaa acccgctgat    1980
cagcctcgac tgtgccttct agttgccagc catctgttgt ttgcccctcc cccgtgcctt    2040
ccttgaccct ggaaggtgcc actcccactg tcctttccta ataaaatgag gaaattgcat    2100
cgcattgtct gagtaggtgt cattctattc tggggggtgt ggtggggcag gacagcaagg    2160
gggaggattg ggaagacaat agcaggcatg ctggggatgc ggtgggctct atggcttctg    2220
aggcggaaag aaccagctgg ggctctaggg ggtatcccca cgcgccctgt agcggcgcat    2280
taagcgcggc gggtgtggtg gttacgcgca gcgtgaccgc tacacttgcc agcgccctag    2340
cgcccgctcc tttcgctttc ttcccttcct ttctcgccac gttcgccggc tttccccgtc    2400
aagctctaaa tcgggggctc cctttagggt tccgatttag tgctttacgg cacctcgacc    2460
ccaaaaaact tgattagggt gatggttcac gtagtgggcc atcgccctga tagacggttt    2520
```

```
ttcgcccttt gacgttggag tccacgttct ttaatagtgg actcttgttc caaactggaa    2580
caacactcaa ccctatctcg gtctattctt ttgatttata agggattttg ccgatttcgg    2640
cctattggtt aaaaaatgag ctgatttaac aaaaatttaa cgcgaattaa ttctgtggaa    2700
tgtgtgtcag ttagggtgtg gaaagtcccc aggctcccca gcaggcagaa gtatgcaaag    2760
catgcatctc aattagtcag caaccaggtg tggaaagtcc ccaggctccc cagcaggcag    2820
aagtatgcaa agcatgcatc tcaattagtc agcaaccata gtcccgcccc taactccgcc    2880
catcccgccc ctaactccgc ccagttccgc ccattctccg ccccatggct gactaatttt    2940
ttttatttat gcagaggccg aggccgcctc tgcctctgag ctattccaga agtagtgagg    3000
aggcttttt ggaggcctag gcttttgcaa aaagctcccg ggagcttgta tatccatttt     3060
cggatctgat caagagacag gatgaggatc gtttcgcatg attgaacaag atggattgca    3120
cgcaggttct ccggccgctt gggtggagag gctattcggc tatgactggg cacaacagac    3180
aatcggctgc tctgatgccg ccgtgttccg gctgtcagcg caggggcgcc cggttctttt    3240
tgtcaagacc gacctgtccg gtgccctgaa tgaactgcag gacgaggcag cgcggctatc    3300
gtggctggcc acgacgggcg ttccttgcgc agctgtgctc gacgttgtca ctgaagcggg    3360
aagggactgg ctgctattgg gcgaagtgcc ggggcaggat ctcctgtcat ctcaccttgc    3420
tcctgccgag aaagtatcca tcatggctga tgcaatgcgg cggctgcata cgcttgatcc    3480
ggctacctgc ccattcgacc accaagcgaa acatcgcatc gagcgagcac gtactcggat    3540
ggaagccggt cttgtcgatc aggatgatct ggacgaagag catcagggc tcgcgccagc     3600
cgaactgttc gccaggctca aggcgcgcat gcccgacggc gaggatctcg tcgtgaccca    3660
tggcgatgcc tgcttgccga atatcatggt ggaaaatggc cgcttttctg gattcatcga    3720
ctgtggccgc ctgggtgtgg cggaccgcta tcaggacata gcgttggcta cccgtgatat    3780
tgctgaagag cttggcggcg aatgggctga ccgcttcctc gtgctttacg gtatcgccgc    3840
tcccgattcg cagcgcatcg ccttctatcg ccttcttgac gagttcttct gagcgggact    3900
ctggggttcg aaatgaccga ccaagcgacg cccaacctgc catcacgaga tttcgattcc    3960
accgccgcct tctatgaaag gttgggcttc ggaatcgttt tccgggacgc cggctggatg    4020
atcctccagc gcggggatct catgctggag ttcttcgccc acccaacttt gtttattgca    4080
gcttataatg gttacaaata aagcaatagc atcacaaatt tcacaaataa agcattttt     4140
tcactgcatt ctagttgtgg tttgtccaaa ctcatcaatg tatcttatca tgtctgtata    4200
ccgtcgacct ctagctagag cttggcgtaa tcatggtcat agctgtttcc tgtgtgaaat    4260
tgttatccgc tcacaattcc acacaacata cgagccggaa gcataaagtg taaagcctgg    4320
ggtgcctaat gagtgagcta actcacatta attgcgttgc gctcactgcc cgctttccag    4380
tcgggaaacc tgtcgtgcca gctgcattaa tgaatcggcc aacgcgcggg gagaggcggt    4440
ttgcgtattg ggcgctcttc cgcttcctcg ctcactgact cgctgcgctc ggtcgttcgg    4500
ctgcggcgag cggtatcagc tcactcaaag gcggtaatac ggttatccac agaatcaggg    4560
gataacgcag gaaagaacat gtgagcaaaa ggccagcaaa aggccaggaa ccgtaaaaag    4620
gccgcgttgc tggcgttttt ccataggctc cgcccccctg acgagcatca caaaaatcga    4680
cgctcaagtc agaggtggcg aaacccgaca ggactataaa gataccaggc gtttcccct     4740
ggaagctccc tcgtgcgctc tcctgttccg accctgccgc ttaccggata cctgtccgcc    4800
tttctccctt cgggaagcgt ggcgctttct catagctcac gctgtaggta tctcagttcg    4860
gtgtaggtcg ttcgctccaa gctgggctgt gtgcacgaac cccccgttca gcccgaccgc    4920
tgcgccttat ccggtaacta tcgtcttgag tccaacccgg taagacacga cttatcgcca    4980
ctggcagcag ccactggtaa caggattagc agagcgaggt atgtaggcgg tgctacagag    5040
ttcttgaagt ggtggcctaa ctacggctac actagaagaa cagtatttgg tatctgcgct    5100
ctgctgaagc cagttacctt cggaaaaaga gttggtagct cttgatccgg caaacaaacc    5160
accgctggta gcggtttttt tgtttgcaag cagcagatta cgcgcagaaa aaaaggatct    5220
caagaagatc ctttgatctt ttctacgggg tctgacgctc agtggaacga aaactcacgt    5280
taagggattt tggtcatgag attatcaaaa aggatcttca cctagatcct tttaaattaa    5340
aaatgaagtt ttaaatcaat ctaaagtata tatgagtaaa cttggtctga cagttaccaa    5400
tgcttaatca gtgaggcacc tatctcagcg atctgtctat ttcgttcatc catagttgcc    5460
tgactccccg tcgtgtagat aactacgata cgggagggct taccatctgg ccccagtgct    5520
gcaatgatac cgcgagaccc acgctcaccg gctccagatt tatcagcaat aaaccagcca    5580
gccggaaggg ccgagcgcag aagtggtcct gcaactttat ccgcctccat ccagtctatt    5640
aattgttgcc gggaagctag agtaagtagt tcgccagtta atagtttgcg caacgttgtt    5700
gccattgcta caggcatcgt ggtgtcacgc tcgtcgtttg gtatggcttc attcagctcc    5760
ggttcccaac gatcaaggcg agttacatga tcccccatgt tgtgcaaaaa agcggttagc    5820
tccttcggtc ctccgatcgt tgtcagaagt aagttggccg cagtgttatc actcatggtt    5880
atggcagcac tgcataattc tcttactgtc atgccatccg taagatgctt ttctgtgact    5940
ggtgagtact caaccaagtc attctgagaa tagtgtatgc ggcgaccgag ttgctcttgc    6000
ccggcgtcaa tacgggataa taccgcgcca catagcagaa ctttaaaagt gctcatcatt    6060
ggaaaacgtt cttcgggggcg aaaactctca aggatcttac cgctgttgag atccagttcg    6120
atgtaaccca ctcgtgcacc caactgatct tcagcatctt ttactttcac cagcgtttct    6180
gggtgagcaa aaacaggaag gcaaaatgcc gcaaaaaagg aataagggc gacacggaaa      6240
tgttgaatac tcatactctt cctttttcaa tattattgaa gcatttatca gggttattgt    6300
ctcatgagcg gatacatatt tgaatgtatt tagaaaaata aacaaatagg ggttccgcgc    6360
acatttcccc gaaaagtgcc acctgacgtc                                      6390
```

```
SEQ ID NO: 61            moltype = AA  length = 71
FEATURE                  Location/Qualifiers
REGION                   1..71
                         note = Ggamma2
source                   1..71
                         mol_type = protein
                         organism = synthetic construct
SEQUENCE: 61
MASNNTASIA QARKLVEQLK MEANIDRIKV SKAAADLMAY CEAHAKEDPL LTPVPASENP    60
FREKKFFCAI L                                                          71

SEQ ID NO: 62            moltype = DNA  length = 6340
FEATURE                  Location/Qualifiers
```

```
misc_feature        1..6340
                    note = Ggamma2
source              1..6340
                    mol_type = other DNA
                    organism = synthetic construct
SEQUENCE: 62
gacggatcgg gagatctccc gatcccctat ggtgcactct cagtacaatc tgctctgatg   60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccaccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctcg tttagtgacc gtcagatcac  840
tagaagcttt attgcggtag tttatcacag ttaaattgct aacgcagtca gtgcttctga  900
cacaacagtc tcgaacttaa gctgcagaag ttggtcgtga ggcactgggc aggtaagtat  960
caaggttaca agacaggttt aaggagacca atagaaactg ggcttgtcga gacagagaag 1020
actcttgcgt ttctgatagg cacctattgg tcttactgac atccactttg cctttctctc 1080
cacaggtgtc cactcccagt tcaattacag ctcttaaggc tagagtactt aatacgactc 1140
actataggct agcctcgagg tcgacggtat cgataagctt gatatcgaat tccgggagtg 1200
caggcgagct ccggcgcagc ccgcccagcc cagccccggg agccaagcca gatctgccag 1260
tgagcctcag gctttgggaa ttgaagagtg tatctgaaac ctacccagca ttccaatggc 1320
cagcaacaac accgccagca tagcacaagc caggaaactg gtagaacagc tgaagatgga 1380
agccaacatc gataggataa aggtgtccaa ggcagctgca gatttgatgg cctactgtga 1440
agcgcatgcc aaggaagatc ccctcctgac acctgttccg gcttcagaaa acccatttag 1500
ggagaagaag tttttctgtg ctatccttta agtcttcagg aggaacctga ggagcctcgg 1560
ggctccaggg acactgatgt agagttttta gcaaagtggg cgcctttcta gtccacagca 1620
tttaaagaga gggaggaaaa ccatcctgga gtctccaggc ttatgcatgt ttaaagaacc 1680
cggaattcct gcagcccggg ggatccacta gttctagagc ggccgcttcg agcagacatg 1740
ataagataca ttgatgagt ttggacaaac cacaactaga atgcagtgaa aaaaatgctt 1800
tatttgtgaa atttgtgatg ctattgcttt atttgtaacc attataagct gcaataaaca 1860
agttaacaac aacaattgca ttcttttatg tttcaggtcg agtctagagg gcccgtttaa 1920
acccgctgat cagcctcgac tgtgccttct agttgccagc catctgttgt ttgcccctcc 1980
cccgtgcctt ccttgaccct ggaaggtgcc actcccactg tcctttccta ataaaatgag 2040
gaaattgcat cgcattgtct gagtaggtgt cattctattc tggggggtgg ggtggggcag 2100
gacagcaagg gggaggattg ggaagacaat agcaggcatg ctggggatgc ggtgggctct 2160
atggcttctg aggcggaaag aaccagctgg ggctctaggg ggtatcccca cgcgccctgt 2220
agcggcgcat taagcgcggc gggtgtggtg gttacgcgca gcgtgaccgc tacacttgcc 2280
agcgccctag cgcccgctcc tttcgctttc ttcccttcct ttctcgccac gttcgccggc 2340
tttccccgtc aagctctaaa tcggggctc cctttagggt tccgatttag tgctttacgg 2400
cacctcgacc ccaaaaaact tgattagggt gatggttcac atcgccctga 2460
tagacggttt ttcgcccttt gacgttggag tccacgttct ttaatagtgg actcttgttc 2520
caaactggaa caacactcaa ccctatctcg gtctattctt ttgatttata agggatttg 2580
ccgatttcgg cctattggtt aaaaaatgag ctgatttaac aaaaatttaa cgcgaattaa 2640
ttctgtggaa tgtgtgtcag ttagggtgtg aaagtcccc aggctcccca gcaggcagaa 2700
gtatgcaaag catgcatctc aattagtcag caaccaggtg tggaaagtcc ccaggctccc 2760
cagcaggcag aagtatgcaa agcatgcatc tcaattagtc agcaaccata gtcccgcccc 2820
taactccgcc catcccgccc ctaactccgc ccagttccgc ccattctccg ccccatggct 2880
gactaatttt ttttatttat gcagaggccg aggccgcctc tgcctctgag ctattccaga 2940
agtagtgagg aggctttttt ggaggcctag gcttttgcaa aaagctcccg ggagcttgta 3000
tatccatttt cggatctgat caagagacag gatgaggatc gtttcgcatg attgaacaag 3060
atggattgca cgcaggttct ccggccgctt gggtggagag gctattcggc tatgactggg 3120
cacaacagac aatcggctgc tctgatgccg ccgtgttccg gctgtcagcg caggggcgcc 3180
cggttctttt tgtcaagacc gacctgtccg gtgccctgaa tgaactgcag gacgaggcag 3240
cgcggctatc gtggctggcc acgacgggcg ttccttgcgc agctgtgctc gacgttgtca 3300
ctgaagcggg aagggactgg ctgctattgg gcgaagtgcc ggggcaggat ctcctgtcat 3360
ctcaccttgc tcctgccgag aaagtatcca tcatggctga tgcaatgcgg cggctgcata 3420
cgcttgatcc ggctacctgc ccattcgacc accaagcgaa acatcgcatc gagcgagcac 3480
gtactcggat ggaagccggt cttgtcgatc aggatgatct ggacgaagag catcaggggc 3540
tcgcgccagc cgaactgttc gccaggctca aggcgcgcat gcccgacggc gaggatctcg 3600
tcgtgaccca tggcgatgcc tgcttgccga atatcatggt ggaaaatggc cgcttttctg 3660
gattcatcga ctgtggccgg ctgggtgtgg cggaccgcta tcaggacata gcgttggcta 3720
cccgtgatat tgctgaagag cttggcggcg aatgggctga ccgcttcctc gtgctttacg 3780
gtatcgccgc tcccgattcg cagcgcatcg ccttctatcg ccttcttgac gagttcttct 3840
gagcgggact ctggggttcg aaatgaccga ccaagcgacg cccaacctgc catcacgaga 3900
tttcgattcc accgccgcct tctatgaaag gttgggcttc ggaatcgttt tccgggacgc 3960
cggctggatg atcctccagc gcggggatct catgctggag ttcttcgccc accccaactt 4020
gtttattgca gcttataatg gttacaaata aagcaatagc atcacaaatt tcacaaataa 4080
agcatttttt tcactgcatt ctagttgtgg tttgtccaaa ctcatcaatg tatcttatca 4140
tgtctgtata ccgtcgacct ctagctagag cttggcgtaa tcatggtcat agctgtttcc 4200
tgtgtgaaat tgttatccgc tcacaattcc acacaacata cgagccggaa gcataaagtg 4260
taaagcctgg ggtgcctaat gagtgagcta actcacatta attgcgttgc gctcactgcc 4320
cgctttccag tcgggaaacc tgtcgtgcca gctgcattaa tgaatcggcc aacgcgcggg 4380
```

```
gagaggcggt ttgcgtattg ggcgctcttc cgcttcctcg ctcactgact cgctgcgctc   4440
ggtcgttcgg ctgcggcgag cggtatcagc tcactcaaag gcggtaatac ggttatccac   4500
agaatcaggg gataacgcag gaaagaacat gtgagcaaaa ggccagcaaa aggccaggaa   4560
ccgtaaaaag gccgcgttgc tggcgttttt ccataggctc cgcccccctg acgagcatca   4620
caaaaatcga cgctcaagtc agaggtggcg aaacccgaca ggactataaa gataccaggc   4680
gtttccccct ggaagctccc tcgtgcgctc tcctgttccg accctgccgc ttaccggata   4740
cctgtccgcc tttctccctt cgggaagcgt ggcgctttct catagctcac gctgtaggta   4800
tctcagttcg gtgtaggtcg ttcgctccaa gctgggctgt gtgcacgaac cccccgttca   4860
gcccgaccgc tgcgccttat ccggtaacta tcgtcttgag tccaacccgg taagacacga   4920
cttatcgcca ctggcagcag ccactggtaa caggattagc agagcgaggt atgtaggcgg   4980
tgctacagag ttcttgaagt ggtggcctaa ctacggctac actagaagaa cagtatttgg   5040
tatctgcgct ctgctgaagc cagttacctt cggaaaaaga gttggtagct cttgatccgg   5100
caaacaaacc accgctggta gcggtttttt tgtttgcaag cagcagatta cgcgcagaaa   5160
aaaaggatct caagaagatc ctttgatctt ttctacgggg tctgacgctc agtggaacga   5220
aaactcacgt taagggattt tggtcatgag attatcaaaa aggatcttca cctagatcct   5280
tttaaattaa aaatgaagtt ttaaatcaat ctaaagtata tatgagtaaa cttggtctga   5340
cagttaccaa tgcttaatca gtgaggcacc tatctcagcg atctgtctat ttcgttcatc   5400
catagttgcc tgactccccg tcgtgtagat aactacgata cgggagggct taccatctgg   5460
ccccagtgct gcaatgatac cgcgagaccc acgctcaccg gctccagatt tatcagcaat   5520
aaaccagcca gccggaaggg ccgagcgcag aagtggtcct gcaactttat ccgcctccat   5580
ccagtctatt aattgttgcc gggaagctag agtaagtagt tcgccagtta atagtttgcg   5640
caacgttgtt gccattgcta caggcatcgt ggtgtcacgc tcgtcgtttg gtatggcttc   5700
attcagctcc ggttcccaac gatcaaggcg agttacatga tcccccatgt tgtgcaaaaa   5760
agcggttagc tccttcggtc ctccgatcgt tgtcagaagt aagttggccg cagtgttatc   5820
actcatggtt atggcagcac tgcataattc tcttactgtc atgccatccg taagatgctt   5880
ttctgtgact ggtgagtact caaccaagtc attctgagaa tagtgtatgc ggcgaccgag   5940
ttgctcttgc ccggcgtcaa tacgggataa taccgcgcca catagcagaa ctttaaaagt   6000
gctcatcatt ggaaaacgtt cttcggggcg aaaactctca aggatcttac cgctgttgag   6060
atccagttcg atgtaaccca ctcgtgcacc caactgatct tcagcatctt ttactttcac   6120
cagcgtttct gggtgagcaa aaacaggaag gcaaaatgcc gcaaaaaagg gaataagggc   6180
gacacggaaa tgttgaatac tcatactctt cctttttcaa tattattgaa gcatttatca   6240
gggttattgt ctcatgagcg gatacatatt tgaatgtatt tagaaaaata aacaaatagg   6300
ggttccgcgc acatttcccc gaaaagtgcc acctgacgtc                         6340
```

```
SEQ ID NO: 63          moltype = AA  length = 449
FEATURE                Location/Qualifiers
REGION                 1..449
                       note = alfa2-adrenergic receptor
source                 1..449
                       mol_type = protein
                       organism = synthetic construct
SEQUENCE: 63
MGSLQPDAGN SSWNGTEAPG GGTRATPYSL QVTLTLVCLA GLLMLFTVFG NVLVIIAVFT    60
SRALKAPQNL FLVSLASADI LVATLVIPFS LANEVMGYWY FGKVWCEIYL ALDVLFCTSS   120
IVHLCAISLD RYWSITQAIY NLKRTPRRIK AIIITVWVIS AVISFPPLIS IEKKGGGGGP   180
QPAEPRCEIN DQKWYVISSC IGSFFAPCLI MILVYVRIYQ IAKRRTRVPP SRRGPDAVAA   240
PPGGTERRPN GLGPERSAGP GGAEAEPLPT QLNGAPGEPA PAGPRDTDAL DLEESSSSDH   300
AERPPGPRRP ERGPRGKGKA RASQVKPGDS LPRRGPGATG IGTPAAGPGE ERVGAAKASR   360
WRGRQNREKR FTFVLAVVIG VFVVCWFPFF FTYTLTAVGC SVPRTLFKFF FWFGYCNSSL   420
NPVIYTIFNH DFRRAFKKIL CRGDRKRIV                                     449
```

```
SEQ ID NO: 64          moltype = DNA  length = 6980
FEATURE                Location/Qualifiers
misc_feature           1..6980
                       note = alfa2-adrenergic receptor
source                 1..6980
                       mol_type = other DNA
                       organism = synthetic construct
SEQUENCE: 64
gacggatcgg agatctccc gatccctat ggtcgactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacgggggt attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gcttccatgg    900
gctacccata cgacgtccca gactacgcca gcatgggctc actgcagccg gatgccggca    960
acagcagctg gaacgggacc gaagcgcccg gaggcggcac ccgagccacc ccttactccc   1020
tgcaggtgac actgacgctg gtttgcctgg ctggcctgct catgctgttc acagatttg    1080
gcaacgtgct ggttattatc gcggtgttca ccagtcgcgc gctcaaagct ccccaaaacc   1140
tcttcctggt gtccctggcc tcagcggaca tcctggtggc cacgctggtc attcccttt   1200
```

-continued

```
ctttggccaa cgaggttatg ggttactggt actttggtaa ggtgtggtgt gagatctatt   1260
tggctctcga cgtgctcttt tgcacgtcgt ccatagtgca cctgtgcgcc atcagccttg   1320
accgctactg gtccatcacg caggccatcg agtacaacct gaagcgcacg ccgcgccgca   1380
tcaaggccat catcatcacc gtgtgggtca tctcggccgt catctccttc ccgccgctca   1440
tctccatcga gaagaagggc ggcggcggcg gcccgcacgc ggccgagccg cgctgcgaga   1500
tcaacgacca gaagtggtac gtcatctcgt cgtgcatcgg ctccttcttc gctccctgcc   1560
tcatcatgat cctggtctac gtgcgcatct accagatcgc caagcgtcgc acccgcgtgc   1620
cacccagccg ccggggtccg gacgccgtcg ccgcgccgcc ggggggcacc gagcgcaggc   1680
ccaacggtct gggccccgag cgcagcgcgg gcccggggg cgcagaggcc gaaccgctgc    1740
ccacccagct caacggcgcc cctggcgagc ccgcgccgac cggggccgcgc gacaccgacg   1800
cgctggacct ggaggagagc tcgtcttccg accacgccga gcggcctcca gggccccgca   1860
gacccgagcg cggtccccgg ggcaaaggca aggcccgagc gagccaggtg aagccgggcg   1920
acagcctgcc gcggcgcggg ccggggggcga cggggatcgg gacgccggct gcagggccgg   1980
gggaggacgg cgtcggggct gccaaggcgt cgcgctggcg cgggcggcag aaccgcgaga   2040
agcgcttcac gttcgtgctg gccgtggtca tcggagtcgt cgtggtgtgc tggttcccct   2100
tcttcttcac ctacacgctc acggccgtcg ggtgctccgt gccacgcacg ctcttcaaat   2160
tcttcttctg gttcggctac tgcaacagct cgttgaaccc ggtcatctac accatcttca   2220
accacgattt ccgccgcgcc ttcaagaaga tcctctgtcg ggggacaag aagcggatcg    2280
tgtgacgcat gggccttgcc ctgcgtgcag acaatggtca gacgcaggcc ctgggcttcg   2340
aggggggtgcg tctacgcatg cagcccctag cactctgaaa ccccggacct acccagctgg   2400
gagggagctc caccgcggtg gcggccgctc tagaactagt ggatccacta gtaacggccg   2460
ccagtgtgct ggaattctgc agatatccat cacactgggt gccgctcgag catgcatcta   2520
gagggcccta ttctatagtg tcacctaaat gctagagctc gctgatcagc ctcgactgtg   2580
ccttctagtt gccagccatc tgttgtttgc ccctcccccg tgccttcctt gaccctggaa   2640
ggtgccactc ccactgtcct ttcctaataa aatgaggaaa ttgcatcgca ttgtctgagt   2700
aggtgtcatt ctattctggg gggtggggtg gggcaggaca gcaagggga ggattgggaa    2760
gacaatagca ggcatgctgg ggatgcggtg ggctctatgg cttctgaggc ggaaagaacc   2820
agctggggct ctaggggta tccccacgcg ccctgtagcg gcgcattaag cgcggcgggt    2880
gtggtggtta cgcgcagcgt gaccgctaca cttgccagcg ccctagcgcc cgctcctttc   2940
gctttcttcc cttcctttct cgccacgttc gccggctttc cccgtcaagc tctaaatcgg   3000
ggcatccctt tagggttccg atttagtgct ttacggcacc tcgacccaa aaaacttgat    3060
tagggtgatg gttcacgtag tgggccatcg ccctgataga cggtttttcg ccctttgacg   3120
ttggagtcca cgttctttaa tagtggactc ttgttccaaa ctggaacaac actcaaccct   3180
atctcggtct attctttga tttataaggg attttgggga tttcggccta ttggttaaaa    3240
aatgagctga tttaacaaaa atttaacgcg aattaattct gtggaatgtg tgtcagttag   3300
ggtgtggaaa gtccccaggc tccccaggca ggcagaagta tgcaaagcat gcatctcaat   3360
tagtcagcaa ccaggtgtgg aaagtcccca ggctccccag caggcagaag tatgcaaagc   3420
atgcatctca attagtcagc aaccatagtc ccgcccctaa ctccgcccat cccgccccta   3480
actccgccca gttccgccca ttctccgccc catggctgac taattttttt tatttatgca   3540
gaggccgagg ccgcctctgc ctctgagcta ttccagaagt agtgaggagg ctttttttgga   3600
ggcctaggct tttgcaaaaa gctcccggga gcttgtatat ccattttcgg atctgatcaa   3660
gagacaggat gaggatcgtt tcgcatgatt gaacaagatg gattgcacgc aggttctccg   3720
gccgcttggg tggagaggct attcggctat gactgggcac aacagacaat ggctgctgc    3780
gatgccgccg tgttccggct gtcagcgcag gggcgcccgg ttcttttgt caagaccgac     3840
ctgtccggtg ccctgaatga actgcaggac gaggcagcgc ggctatcgtg gctggccacg   3900
acgggcgttc cttgcgcagc tgtgctcgac gttgtcactg aagcgggaag ggactggctg   3960
ctattgggcg aagtgccggg gcaggatctc ctgtcatctc accttgctcc tgccgagaaa   4020
gtatccatca tggctgatgc aatgcggcgg ctgcatacgc ttgatccggc tacctgccca   4080
ttcgaccacc aagcgaaaca tcgcatcgag cgagcacgta ctcggatgga agccggtctt   4140
gtcgatcagg atgatctgga cgaagagcat caggggctcg cgccagccga actgttcgcc   4200
aggctcaagg cgcgcatgcc cgacgcgaag gatctcgtcg tgacccatgg cgatgcctgc   4260
ttgccgaata tcatggtgga aaatggccgc ttttctggat tcatcgactg tggccggctg   4320
ggtgtggcgg accgctatca ggacatagcg ttggctaccc gtgatattgc tgaagagctt   4380
ggcggcgaat gggctgaccg cttcctcgtg ctttacggta tcgccgctcc cgattcgcag   4440
cgcatcgcct tctatcgcct tcttgacgag ttcttctgag cgggactctg gggttcgaaa   4500
tgaccgacca agcgacgccc aacctgccat cacgagattt cgattccacc gccgccttct    4560
atgaaaggtt gggcttcgga atcgttttcc gggacgccgg ctggatgatc ctccagcgcg   4620
gggatctcat gctggagttc ttcgcccacc ccaacttgtt tattgcagct tataatggtt   4680
acaaataaag caatagcatc acaaatttca caaataaagc atttttttca ctgcattcta   4740
gttgtggttt gtccaaactc atcaatgtat cttatcatgt ctgtataccg tcgacctcta   4800
gctagagctt ggcgtaatca tggtcatagc tgtttcctgt gtgaaattgt tatccgctca   4860
caattccaca acatacga gccggaagca taaagtgtaa agcctggggt gcctaatgag    4920
tgagctaact cacattaatt gcgttgcgct cactgcccgc tttccagtcg ggaaacctgt   4980
cgtgccagct gcattaatga atcggccaac gcgcggggag aggcggtttg cgtattgggc   5040
gctcttccgc ttcctcgctc actgactcgc tgcgctcggt cgttcggctg cggcgagcgg   5100
tatcagctca ctcaaaggcg gtaatacggt tatccacaga atcaggggat aacgcaggaa   5160
agaacatgtg agcaaaaggc cagcaaaagg ccaggaaccg taaaaaggcc gcgttgctgg   5220
cgtttttcca taggctccgc ccccctgacg agcatcacaa aatcgacgc tcaagtcaga    5280
ggtggcgaaa cccgacagga ctataaagat accaggcgtt tccccctgga agctccctcg   5340
tgcgctctcc tgttccgacc ctgccgctta ccggatacct gtccgccttt ctcccttcgg   5400
gaagcgtggc gctttctcaa tgctcacgct gtaggtatct cagttcggtg taggtcgttc   5460
gctccaagct gggctgtgtg cacgaacccc cgttcagcc cgaccgctgc gccttatccg     5520
gtaactatcg tcttgagtcc aacccggtaa gacacgactt atcgccactg gcagcagcca   5580
ctggtaacag gattagcaga gcgaggtatg taggcggtgc tacagagttc ttgaagtggt   5640
ggcctaacta cggctacact agaaggacag tatttggtat ctgcgctctg ctgaagccag   5700
ttaccttcgg aaaaagagtt ggtagctctt gatccggcaa acaaaccacc gctggtagcg   5760
gtggtttttt tgtttgcaag cagcagatta cgcgcagaaa aaaaggatct caagaagatc   5820
ctttgatctt ttctacgggg tctgacgctc agtggaacga aaactcacgt taagggattt   5880
tggtcatgag attatcaaaa aggatcttca cctagatcct tttaaattaa aaatgaagtt   5940
```

-continued

```
ttaaatcaat ctaaagtata tatgagtaaa cttggtctga cagttaccaa tgcttaatca   6000
gtgaggcacc tatctcagcg atctgtctat ttcgttcatc catagttgcc tgactccccg   6060
tcgtgtagat aactacgata cgggagggct taccatctgg ccccagtgct gcaatgatac   6120
cgcgagaccc acgctcaccg gctccagatt tatcagcaat aaaccagcca gccggaaggg   6180
ccgagcgcag aagtggtcct gcaactttat ccgcctccat ccagtctatt aattgttgcc   6240
gggaagctag agtaagtagt tcgccagtta atagtttgcg caacgttgtt gccattgcta   6300
caggcatcgt ggtgtcacgc tcgtcgtttg gtatggcttc attcagctcc ggttcccaac   6360
gatcaaggcg agttacatga tccccatgt tgtgcaaaaa agcggttagc tccttcggtc   6420
ctccgatcgt tgtcagaagt aagttggccg cagtgttatc actcatggt atggcagcac   6480
tgcataattc tcttactgtc atgccatccg taagatgctt ttctgtgact ggtgagtact   6540
caaccaagtc attctgagaa tagtgtatgc ggcgaccgag ttgctcttgc ccggcgtcaa   6600
tacgggataa taccgcgcca catagcagaa ctttaaaagt gctcatcatt ggaaaacgtt   6660
cttcggggcg aaaactctca aggatcttac cgctgttgag atccagttcg atgtaaccca   6720
ctcgtgcacc caactgatct tcagcatctt ttactttcac cagcgtttct gggtgagcaa   6780
aaacaggaag gcaaaatgcc gcaaaaaagg gaataagggc gacacggaaa tgttgaatac   6840
tcatactctt cctttttcaa tattattgaa gcatttatca gggttattgt ctcatgagcg   6900
gatacatatt tgaatgtatt tagaaaaata aacaaatagg ggttccgcgc acatttcccc   6960
gaaaagtgcc acctgacgtc                                              6980

SEQ ID NO: 65             moltype =   length =
SEQUENCE: 65
000

SEQ ID NO: 66             moltype = AA   length = 381
FEATURE                   Location/Qualifiers
source                    1..381
                          mol_type = protein
                          organism = synthetic construct
SEQUENCE: 66
MSSRQVQLQE SGGGLVQPEG SLTLACDTSG FTMNYYAIAW FRQAPEKERE GLATISSIDG   60
RTYYADSVKG RFTISRDSAK NMVYLQMNNL RPEDTAVYYC SAGPDYSDYG DESEYWGQGT   120
QVTVSSSRGK GEELFTGVVP ILVELDGDVN GHKFSVSGEG EGDATYGKLT LKFICTTGKL   180
PVPWPTLVTT LTYGVQCFSR YPDHMKRHDF FKSAMPEGYV QERTIFFKDD GNYKTRAEVK   240
FEGDTLVNRI ELKGIDFKED GNILGHKLEY NYNSHNVYIM ADKQKNGIKA NFKIRHNIES   300
GGVQLADHYQ QNTPIGDGPV LLPDNHYLST QSKLSKDPNE KRDHMVLKER VTAAGITHGM   360
DELYKGSGGS GGCMSCKCVL S                                            381

SEQ ID NO: 67             moltype = DNA   length = 6553
FEATURE                   Location/Qualifiers
source                    1..6553
                          mol_type = other DNA
                          organism = synthetic construct
SEQUENCE: 67
gacggatcgg gagatctccc gatccctat ggtgcactct cagtacaatc tgctctgatg   60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttaggttag gcgttttgcg ctgcttcgcg atgtacggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggag tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta acaactccgc cccattgacg caaatgggcg   780
gtaggcgtgt acggtgggag gtctatataa gcagagctct ctggctaact agagaaccca   840
ctgcttactg gcttatcgaa attaatacga ctcactatag ggagacccaa gctggctagc   900
ggtaccgagc tcggatcact agtccagtgt ggtggaattc acgcggacca tgtcttctag   960
acaggtgcag ctgcaggaga gcggcggcgg cctggtgcag cccgaggggca gcctgaccct   1020
ggcctgcgac accagcggct tcaccatgaa ctactacgcc atcgcctggt tcaggcaggc   1080
ccccgagaag gagaggggagg gcctggccac catcagcagc atcgacggca ggacctacta   1140
cgccgacagc gtgaagggca ggttcaccat cagcagggac agcgccaaga acatggtgta   1200
cctgcagatg aacaacctga gccccgagga caccgccgtg tactactgca gcgccggacct   1260
cgactacagc gactacggcg acgagagcga gtactggggc caggggcacc aggtgaccgt   1320
gagcagctct cgaggtaaag gagaagaact tttcactgga gttgtcccaa ttcttgttga   1380
attagatggt gatgttaatg ggcacaaatt ttctgtcagt ggagagggtg aaggtgatgc   1440
aacatacgga aaacttaccc ttaaatttat ttgcactact ggaaaactac ctgttccttg   1500
gccaacactt gtcactactt taacttatgg tgttcaatgc ttttcaagat acccagatca   1560
tatgaaacgg catgactttt tcaagagtgc catgcccgaa ggttatgtac aggaaagaac   1620
tatatttttc aaagatgacg ggaactacaa gacacgtgct gaagtcaagt ttgaaggtga   1680
taccttgtt aatagaatcg agttaaaagg tattgatttt aaagaagatg gaaacattct   1740
tggacacaaa ttggaataca actataactc acacaatgta tacatcatgg cagacaaaca   1800
aaagaatgga atcaaagcta acttcaaaat tagacacaac attgagtccg gagcgttca   1860
actagcagac cattatcaac aaaatactcc aattggcgat ggccctgtcc ttttaccaga   1920
caaccattac ctgtccacac aatctaagct ttcgaaagat cccaacgaaa agagagacca   1980
catggtcctt aaagagaggg taacagctgc tgggattaca catggcatgg acgagctgta   2040
caagggatcc ggtggaagtg gaggctgcat gagctgcaag tgtgtgctgt cctaatgagc   2100
ggccgcacta gagggcccgg gccgtttaa acccgctgat cagcctcgac tgtgccttct   2160
```

-continued

```
agttgccagc catctgttgt ttgcccctcc cccgtgcctt ccttgaccct ggaaggtgcc   2220
actcccactg tcctttccta ataaaatgag gaaattgcat cgcattgtct gagtaggtgt   2280
cattctattc tggggggtgg ggtggggcag gacagcaagg gggaggattg ggaagacaat   2340
agcaggcatg ctgggatgc ggtgggctct atggcttctg aggcggaaag aaccagctgg   2400
ggctctaggg ggtatcccca cgcgccctgt agcggcgat taagcgcggc gggtgtggtg   2460
gttacgcgca gcgtgaccgc tacacttgcc agcgccctag cgcccgctcc tttcgctttc   2520
ttccttcct ttctcgccac gttcgccggc tttccccgtc aagctctaaa tcgggggctc   2580
cctttagggt tccgatttag tgctttacgg cacctcgacc ccaaaaaact tgattagggt   2640
gatggttcac gtagtgggcc atcgccctga tagacggttt ttcgcccttt gacgttggag   2700
tccacgttct ttaatagtgg actcttgttc caaactggaa caacactcaa ccctatctcg   2760
gtctattctt ttgatttata agggattttg ccgatttcgg cctattggtt aaaaaatgag   2820
ctgatttaac aaaaatttaa cgcgaattaa ttctgtggaa tgtgtgtcag ttagggtgtg   2880
gaaagtcccc aggctcccca gcaggcagaa gtatgcaaag catgcatctc aattagtcag   2940
caaccaggtg tggaaagtcc ccaggctccc cagcaggcag aagtatgcaa agcatgcatc   3000
tcaattagtc agcaaccata gtcccgcccc taactccgcc catcccgccc ctaactccgc   3060
ccagttccgc ccattctccg ccccatggct gactaatttt ttttatttat gcagaggccg   3120
aggccgcctc tgcctctgag ctattccaga agtagtgagg aggcttttt ggaggcctag   3180
gcttttgcaa aaagctcccg ggagcttgta tatccatttt cggatctgat caagagacag   3240
gatgaggatc gtttcgcatg attgaacaag atggattgca cgcaggttct ccggccgctt   3300
gggtggagag gctattcggc tatgactggg cacaacagac aatcggctgc tctgatgccg   3360
ccgtgttccg gctgtcagcg caggggcgcc cggttctttt tgtcaagacc gacctgtccg   3420
gtgccctgaa tgaactgcag gacgaggcag cgcggctatc gtggctggcc acgacgggcg   3480
ttccttgcgc agctgtgctc gacgttgtca ctgaagcggg aagggactgg ctgctattgg   3540
gcgaagtgcc ggggcaggat ctcctgtcat ctcaccttgc tcctgccgag aaagtatcca   3600
tcatggctga tgcaatgcgg cggctgcata cgcttgatcc ggctacctgc ccattcgacc   3660
accaagcgaa acatcgcatc gagcgagcac gtactcggat ggaagccggt cttgtcgatc   3720
aggatgatct ggacgaagag catcagggc tcgcgccagc cgaactgttc gccaggctca   3780
aggcgcgcat gcccgacggc gaggatctcg tcgtgaccca tggcgatgcc tgcttgccga   3840
atatcatggt ggaaaatggc cgcttttctg gattcatcga ctgtggccgg ctgggtgtgg   3900
cggaccgcta tcaggacata gcgttggcta cccgtgatat tgctgaagag cttggcggcg   3960
aatgggctga ccgcttcctc gtgctttacg gtatcgccgc tcccgattcg cagcgcatcg   4020
ccttctatcg ccttcttgac gagttcttct gagcgggact ctggggttcg aaatgaccga   4080
ccaagcgacg cccaacctgc catcacgaga tttcgattcc accgccgcct tctatgaaag   4140
gttgggcttc ggaatcgttt tccgggacgc cggctggatg atcctccagc gcggggatct   4200
catgctggag ttcttcgccc accccaactt gtttattgca gcttataatg gttacaaata   4260
aagcaatagc atcacaaatt tcacaaataa agcatttttt tcactgcatt ctagttgtgg   4320
tttgtccaaa ctcatcaatg tatcttatca tgtctgtata ccgtcgacct ctagctagag   4380
cttggcgtaa tcatggtcat agctgtttcc tgtgtgaaat tgttatccgc tcacaattcc   4440
acacaacata cgagccggaa gcataaagtg taaagcctgg ggtgcctaat gagtgagcta   4500
actcacatta attgcgttgc gctcactgcc cgctttccag tcgggaaacc tgtcgtgcca   4560
gctgcattaa tgaatcggcc aacgcgcggg gagaggcggt ttgcgtattg ggcgctcttc   4620
cgcttcctcg ctcactgact cgctgcgctc ggtcgttcgg ctgcggcgag cggtatcagc   4680
tcactcaaag gcggtaatac ggttatccac agaatcaggg gataacgcag gaaagaacat   4740
gtgagcaaaa ggccagcaaa aggccaggaa ccgtaaaaag gccgcgttgc tggcgttttt   4800
ccataggctc cgcccccctg acgagcatca caaaaatcga cgctcaagtc agaggtggcg   4860
aaacccgaca ggactataaa gataccaggc gtttccccct ggaagctccc tcgtgcgctc   4920
tcctgttccg accctgccgc ttaccggata cctgtccgc tttctccctt cgggaagcgt   4980
ggcgctttct catagctcac gctgtaggta tctcagttcg gtgtaggtcg ttcgctccaa   5040
gctgggctgt gtgcacgaac cccccgttca gcccgaccgc tgcgccttat ccggtaacta   5100
tcgtcttgag tccaacccgg taagacacga cttatcgcca ctggcagcag ccactggtaa   5160
caggattagc agagcgaggt atgtaggcgg tgctacagag ttcttgaagt ggtggcctaa   5220
ctacggctac actagaagaa cagtatttgg tatctgcgct ctgctgaagc cagttacctt   5280
cggaaaaaga gttggtagct cttgatccgg caaacaaacc accgctggta gcggtggttt   5340
ttttgtttgc aagcagcaga ttacgcgcag aaaaaaagga tctcaagaag atcctttgat   5400
cttttctacg gggtctgacg ctcagtggaa cgaaaactca cgttaaggga ttttggtcat   5460
gagattatca aaaaggatct tcacctagat cctttttaaat taaaaatgaa gttttaaatc   5520
aatctaaagt atatatgagt aaacttggtc tgacagttac caatgcttaa tcagtgaggc   5580
acctatctca gcgatctgtc tatttcgttc atccatagtt gcctgactcc ccgtcgtgta   5640
gataactacg atacgggagg gcttaccatc tggccccagt gctgcaatga taccgcgaga   5700
cccacgctca ccggctccag atttatcagc aataaaccag ccagccggaa gggccgagcg   5760
cagaagtggt cctgcaactt tatccgcctc catccagtct attaattgtt gccgggaagc   5820
tagagtaagt agttcgccag ttaatagttt gcgcaacgtt gttgccattg ctacaggcat   5880
cgtggtgtca cgctcgtcgt ttggtatggc ttcattcagc tccggttccc aacgatcaag   5940
gcgagttaca tgatccccca tgttgtgcaa aaaagcggtt agctccttcg gtcctccgat   6000
cgttgtcaga agtaagttgg ccgcagtgtt atcactcatg gttatggcag cactgcataa   6060
ttctcttact gtcatgccat ccgtaagatg cttttctgtg actggtgagt actcaaccaa   6120
gtcattctga atagtgtata gcggcgacc gagttgctct gcccggcgt caatacggga   6180
taataccgcg ccacatagca gaactttaaa agtgctcatc attggaaaac gttcttcggg   6240
gcgaaaactc tcaaggatct taccgctgtt gagatccagt tcgatgtaac ccactcgtgc   6300
acccaactga tcttcagcat cttttacttt caccagcgtt tctgggtgag caaaaacagg   6360
aaggcaaaat gccgcaaaaa agggaataag ggcgacacgg aaatgttgaa tactcatact   6420
cttcctttt caatattatt gaagcattta tcagggttat tgtctcatga gcggatacat   6480
atttgaatgt atttagaaaa ataaacaaat aggggttccg cgcacatttc cccgaaaagt   6540
gccacctgac gtc                                                        6553
```

```
                         organism = synthetic construct
SEQUENCE: 68
MNNSTNSSNN SLALTSPYKT FEVVFIVLVA GSLSLVTIIG NILVMVSIKV NRHLQTVNNY  60
FLFSLACADL IIGVFSMNLY TLYTVIGYWP LGPVVCDLWL ALDYVVSNAS VMNLLIISFD  120
RYFCVTKPLT YPVKRTTKMA GMMIAAAWVL SFILWAPAIL FWQFIVGVRT VEDGECYIQF  180
FSNAAVTFGT AIAAFYLPVI IMTVLYWHIS RASKSRIKKD KKEPVANQDP VSPSLVQGRI  240
VKPNNNNMPS SDDGLEHNKI QNGKAPRDPV TENCVQGEEK ESSNDSTSVS AVASNMRDDE  300
ITQDENTVST SLGHSKDENS KQTCIRIGTK TPKSDSCTPT NTTVEVVGSS GQNGDEKQNI  360
VARKIVKMTK QPAKKKPPPS REKKVTRTIL AILLAFIITW APYNVMVLIY PFCAPCIPNT  420
VWTIGYWLCY INSTINPACY ALCNATFKKT FKHLLMCHYK NIGATR                 466

SEQ ID NO: 69       moltype = DNA   length = 6805
FEATURE             Location/Qualifiers
source              1..6805
                    mol_type = other DNA
                    organism = synthetic construct
SEQUENCE: 69
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttaggggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
gtttaaactt aagcttggta ccgagctcgg atccactagt ccagtgtggt ggaattcacc  960
atgaataact caacaaactc ctctaacaat agcctggctc ttacaagtcc ttataagaca  1020
tttgaagtgg tgtttattgt cctggtggct ggatccctca gtttggtgac cattatcggg  1080
aacatcctag tcatggtttc cattaaagtc aaccgccacc tccagaccgt caacaattac  1140
ttttttattca gcttggcctg tgctgacctt atcataggtg ttttctccat gaacttgtac  1200
accctctaca ctgtgattgg ttactggcct ttgggacctg tggtgtgtga cctttggcta  1260
gccctggact atgttgtcag caatgcctca gttatgaatc tgctcatcat cagctttgac  1320
aggtacttct gtgtcacaaa acctctgacc tacccagtca agcggaccac aaaaatggca  1380
ggtatgatga ttgcagctgc ctgggtcctc tctttcatcc tctgggctcc agccattctc  1440
ttctggcagt tcattgtagg ggtgagaact gtggaggatg gggagtgcta cattcagttt  1500
ttttccaatg ctgctgtcac ctttggtacg gctattgcag ccttctattt gccagtgatc  1560
atcatgactg tgctatattg gcacatatcc cgagccagca agagcaggat aaagaaggac  1620
aagaaggagc ctgttgccaa ccaagacccc gtttctccaa gtctggtaca aggaaggata  1680
gtgaagccaa acaataacaa catgcccagc agtgacgatg gcctggagca aacaaaatc  1740
cagaatggca aagcccccag ggatcctgtg actgaaaact gttcaggga gaggagaag  1800
gagagctcca atgactccac ctcagtcagt gctgttgcct ctaatatgag agatgatgaa  1860
ataacccagg atgaaaacac agtttccact tccctgggcc attccaaaga tgagaactct  1920
aagcaaacat gcatcagaat tggcaccaag accccaaaaa gtgactcatg tacccccaact  1980
aataccaccg tggaggtagt ggggtcttca ggtcagaatg gagatgaaaa gcagaatatt  2040
gtagcccgca agattgtgaa gatgactaag cagcctgcaa aaaagaagcc tcctccttcc  2100
cgggaaaaga aagtcaccag gacaatcttg gctattctgt tggctttcat catcacttgg  2160
gccccataca atgtcatggt gctcatttac cccttttgtg caccttgcat ccccaacact  2220
gtgtggacaa ttggttactg gctttgttac atcaacagca ctatcaaccc tgcctgctat  2280
gcactttgca atgccacctt caagaagacc tttaaacacc ttctcatgtg tcattataag  2340
aacataggcg ctacaaggta actcgagtct agagggcccg tttaaacccg ctgatcagcc  2400
tcgactgtgc cttctagttg ccagccatct gttgtttgcc cctcccccgt gccttccttg  2460
accctggaag gtgccactcc cactgtcctt tcctaataaa atgaggaaat tgcatcgcat  2520
tgtctgagta ggtgtcattc tattctgggg ggtggggtgg ggcaggacag caagggggag  2580
gattgggaag acaatagcag gcatgctggg gatgcggtgg gctctatggc ttctgaggcg  2640
gaaagaacca gctggggctc tagggggtat ccccacgcgc cctgtagcgg cgcattaagc  2700
gcggcgggtg tggtggttac gcgcagcgtg accgctacac ttgccagcgc cctagcgccc  2760
gctcctttcg ctttcttccc ttcctttctc gccacgttcg ccggctttcc ccgtcaagct  2820
ctaaatcggg ggctcccttt agggttccga tttagtgctt tacggcacct cgaccccaaa  2880
aaacttgatt agggtgatgg ttcacgtagt gggccatcgc cctgatagac ggtttttcgc  2940
cctttgacgt tggagtccac gttctttaat agtggactct tgttccaaac tggaacaaca  3000
ctcaacccta tctcggtcta ttcttttgat ttataaggga ttttgccgat ttcggcctat  3060
tggttaaaaa atgagctgat ttaacaaaaa tttaacgcga attaattctg tggaatgtgt  3120
gtcagttagg gtgtggaaag tccccaggct ccccagcagg cagaagtatg caaagcatgc  3180
atctcaatta gtcagcaacc aggtgtggaa agtccccagg ctcccagca ggcagaagta  3240
tgcaaagcat gcatctcaat tagtcagcaa ccatagtccc gcccctaact ccgcccatcc  3300
cgcccctaac tccgcccagt tccgcccatt ctccgcccca tggctgacta atttttttta  3360
tttatgcaga ggccgaggcc gcctctgcct ctgagctatt ccagaagtag tgaggaggct  3420
tttttggagg cctaggcttt tgcaaaaagc tcccgggagc ttgtatatcc attttcggat  3480
ctgatcaaga caggatga ggatcgtttc gcatgattga acaagatgga ttgcacgcag  3540
gttctccggc cgcttgggtg gagaggctat tcggctatga ctgggcacaa cagacaatcg  3600
gctgctctga tgccgccgtg ttccggctgt cagcgcaggg gcgcccggtt cttttttgtca  3660
agaccgacct gtccggtgcc ctgaatgaac tgcaggacga ggcagcgcgg ctatcgtggc  3720
```

```
tggccacgac gggcgttcct tgcgcagctg tgctcgacgt tgtcactgaa gcgggaaggg   3780
actggctgct attgggcgaa gtgccggggc aggatctcct gtcatctcac cttgctcctg   3840
ccgagaaagt atccatcatg gctgatgcaa tgcggcggct gcatacgctt gatccggcta   3900
cctgcccatt cgaccaccaa gcgaaacatc gcatcgagcg agcacgtact cggatggaag   3960
ccggtcttgt cgatcaggat gatctggacg aagagcatca ggggctcgcg ccagccgaac   4020
tgttcgccag gctcaaggcg cgcatgcccg acggcgagga tctcgtcgtg acccatggcg   4080
atgcctgctt gccgaatatc atggtggaaa atggccgctt ttctggattc atcgactgtg   4140
gccggctggg tgtggcggac cgctatcagg acatagcgtt ggctaccgt gatattgctg   4200
aagagcttgg cggcgaatgg gctgaccgct tcctcgtgct ttacggtatc gccgctcccg   4260
attcgcagcg catcgccttc tatcgccttc ttgacgagtt cttctgagcg ggactctggg   4320
gttcgaaatg accgaccaag cgacgcccaa cctgccatca cgagatttcg attccaccgc   4380
cgccttctat gaaaggttgg gcttcggaat cgttttccgg gacgccggct ggatgatcct   4440
ccagcgcggg gatctcatgc tggagttctt cgcccacccc aacttgttta ttgcagctta   4500
taatggttac aaataaagca atagcatcac aaatttcaca aataaagcat tttttcact   4560
gcattctagt tgtggtttgt ccaaactcat caatgtatct tatcatgtct gtataccgtc   4620
gacctctagc tagagcttgg cgtaatcatg gtcatagctg tttcctgtgt gaaattgtta   4680
tccgctcaca attccacaca acatacgagc cggaagcata aagtgtaaag cctggggtgc   4740
ctaatgagtg agctaactca cattaattgc gttgcgctca ctgcccgctt tccagtcggg   4800
aaacctgtcg tgccagctgc attaatgaat cggccaacgc gcggggagag gcggtttgcg   4860
tattgggcgc tcttccgctt cctcgctcac tgactcgctg cgctcggtcg ttcggctgcg   4920
gcgagcggta tcagctcact caaaggcggt aatacggtta ccacagaat cagggggataa   4980
cgcaggaaag aacatgtgag caaaaggcca gcaaaaggcc aggaaccgta aaaaggccgc   5040
gttgctggcg tttttccata ggctccgccc cctgacgag catcacaaaa atcgacgctc   5100
aagtcagagg tggcgaaacc cgacaggact ataaagatac caggcgtttc ccctggaag   5160
ctccctcgtg cgctctcctg ttccgaccct gccgcttacc ggatacctgt ccgcctttct   5220
cccttcggga agcgtggcgc tttctcatag ctcacgctgt aggtatctca gttcggtgta   5280
ggtcgttcgc tccaagctgg gctgtgtgca cgaacccccc gttcagcccg accgctgcgc   5340
cttatccggt aactatcgtc ttgagtccaa cccggtaaga cacgacttat cgccactggc   5400
agcagccact ggtaacagga ttagcagagc gaggtatgta ggcggtgcta cagagttctt   5460
gaagtggtgg cctaactacg gctacactag aagaacagta tttggtatct gcgctctgct   5520
gaagccagtt accttcggaa aaagagttgg tagctcttga tccggcaaac aaaccaccgc   5580
tggtagcggt ggtttttgttt gcaagcagca gattacgcgc agaaaaaag gatctcaaga   5640
agatcctttg atctttttcta cggggtctga cgctcagtgg aacgaaaact cacgttaagg   5700
gattttggtc atgagattat caaaaaggat cttcacctag atccttttaa attaaaaatg   5760
aagttttaaa tcaatctaaa gtatatatga gtaaacttgg tctgacagtt accaatgctt   5820
aatcagtgag gcacctatct cagcgatctg tctatttcgt tcatccatag ttgcctgact   5880
ccccgtcgtg tagataacta cgatacggga gggcttacca tctggcccca gtgctgcaat   5940
gataccgcga gaccacgct caccggctcc agatttatca gcaataaacc agccagccgg   6000
aagggccgag cgcagaagtg gtcctgcaac tttatccgcc tccatccagt ctattaattg   6060
ttgccgggaa gctagagtaa gtagttcgcc agttaatagt ttgcgcaacg ttgttgccat   6120
tgctacaggc atcgtggtgt cacgctcgtc gtttggtatg gcttcattca gctccggttc   6180
ccaacgatca aggcgagtta catgatcccc catgttgtgc aaaaaagcgg ttagctcctt   6240
cggtcctccg atcgttgtca gaagtaagtt ggccgcagtg ttatcactca tggttatggc   6300
agcactgcat aattctctta ctgtcatgcc atccgtaaga tgcttttctg tgactggtga   6360
gtactcaacc aagtcattct gagaatagtg tatgcggcga ccgagttgct cttgcccggc   6420
gtcaatacgg gataataccg cgccacatag cagaacttta aaagtgctca tcattggaaa   6480
acgttcttcg gggcgaaaac tctcaaggat cttaccgctg ttgagatcca gttcgatgta   6540
acccactcgt gcacccaact gatcttcagc atcttttact ttcaccagcg tttctgggtg   6600
agcaaaaaca ggaaggcaaa atgccgcaaa aaagggaata aggcgacac ggaaatgttg   6660
aatactcata ctcttccttt ttcaatatta ttgaagcatt tatcagggtt attgtctcat   6720
gagcggatac atatttgaat gtatttagaa aaataaacaa atagggttc cgcgcacatt   6780
tccccgaaaa gtgccacctg acgtc                                          6805
```

```
SEQ ID NO: 70              moltype = AA   length = 373
FEATURE                    Location/Qualifiers
source                     1..373
                           mol_type = protein
                           organism = synthetic construct
SEQUENCE: 70
MSSRQVQLQE SGGGLVQAGG SLRLSCVVSG FFFDTVTMAW YRRAPGKHRE LVASATAGGT   60
TTYADSVKDR FTISRDNAKN TVYLQMNSLK PEDTAVYYCN TFVRSLSWGQ GTQVTVSSSR  120
GKGEELFTGV VPILVELDGD VNGHKFSVSG EGEGDATYGK LTLKFICTTG KLPVPWPTLV  180
TTLTYGVQCF SRYPDHMKRH DFFKSAMPEG YVQERTIFFK DDGNYKTRAE VKFEGDTLVN  240
RIELKGIDFK EDGNILGHKL EYNYNSHNVY IMADKQKNGI KANFKIRHNI ESGGVQLADH  300
YQQNTPIGDG PVLLPDNHYL STQSKLSKDP NEKRDHMVLK ERVTAAGITH GMDELYKGSG  360
GSGGCMSCKC VLS                                                      373
```

```
SEQ ID NO: 71              moltype = DNA   length = 6529
FEATURE                    Location/Qualifiers
source                     1..6529
                           mol_type = other DNA
                           organism = synthetic construct
SEQUENCE: 71
gacggatcgg gagatctccc gatcccctat ggtgcactct cagtacaatc tgctctgatg   60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
```

-continued

```
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
ggtaccgagc tcggatcact agtccagtgt ggtggaattc acgcggacca tgtcttctag    960
acaagttcaa ctgcaagaga gcggtggcgg tctggttcaa gcgggtggta gcctgcgtct   1020
gagctgcgtg gttagcggtt tcttttttcga caccgttacg atggcgtggt atcgtcgtgc   1080
gccgggtaaa caccgtgagc tggttgcgag cgcgaccgcg ggtggcacca ccacctacgc   1140
ggacagcgtt aaggatcgtt tcaccatcag ccgtgacaac gcgaaaaaca ccgtgtacct   1200
gcaaatgaac agcctgaagc cggaagatac cgcggtgtac tattgcaaca cctttgttcg   1260
tagcctgagc tgggggccagg gcacccaagt gaccgtgagc agctctcgag gtaaaggaga   1320
agaactttc actggagttg tcccaattct tgttgaatta gatggtgatg ttaatgggca   1380
caaattttct gtcagtggag agggtgaagg tgatgcaaca tacggaaaac ttacccttaa   1440
atttatttgc actactggaa aactacctgt tccttggcca acacttgtca ctactttaac   1500
ttatggtgtt caatgctttt caagataccc agatcatatg aaacggcatg acttttttcaa   1560
gagtgccatg cccgaaggtt atgtacagga aagaactata ttttttcaaag atgacggdaa   1620
ctacaagaca cgtgctgaag tcaagtttga aggtgataac cttgttaata gaatcgagtt   1680
aaaaggtatt gattttaaag aagatggaaa cattcttgga cacaaattgg aatacaacta   1740
taactcacac aatgtataca tcatggcaga caaacaaaag aatggaatca aagctaactt   1800
caaaattaga cacaacattg agtccggagg cgttcaacta gcagaccatt atcaacaaaa   1860
tactccaatt ggcgatggcc ctgtcctttt accagacaac cattacctgt ccacacaatc   1920
taagctttcg aaagatccca acgaaaagag agaccacatg gtccttaaag agagggtaac   1980
agctgctggg attacacatg gcatggacga gctgtacaag ggatccggtg gaagtggagg   2040
ctgcatgagc tgcaagtgtg tgctgtccta atgagcggcc gcactagagg gcccgggccc   2100
gtttaaaccc gctgatcagc ctcgactgtg ccttctagtt gccagccatc tgttgtttgc   2160
ccctcccccg tgccttcctt gaccctggaa ggtgccactc ccactgtcct ttcctaataa   2220
aatgaggaaa ttgcatcgca ttgtctgagt aggtgtcatt ctattctggg gggtggggtg   2280
gggcaggaca gcaaggggga ggattgggaa gacaatagca ggcatgctgg ggatgcggtg   2340
ggctctatgg cttctgaggc ggaaagaacc agctggggct ctagggggta tccccacgcg   2400
ccctgtagcg gcgcattaag cgcggcgggt gtggtggtta cgcgcagcgt gaccgctaca   2460
cttgccagcg ccctagcgcc cgctccttc gctttcttcc cttcctttct cgccacgttc   2520
gccggctttc cccgtcaagc tctaaatcgg gggctccctt tagggttccg atttagtgct   2580
ttacggcacc tcgacccca aaaacttgat tagggtgatg gttcacgtag tgggccatcg   2640
ccctgataga cggttttcg cccttttgacg ttggagtcca cgttctttaa tagtggactc   2700
ttgttccaaa ctggaacaac actcaaccct atctcggtct attcttttga tttataaggga   2760
attttgccga tttcggccta ttggttaaaa aatgagctga tttaacaaaa atttaacgcg   2820
aattaattct gtggaatgtg tgtcagttag ggtgtggaaa gtccccaggc tccccagcag   2880
gcagaagtat gcaaagcatg catctcaatt agtcagcaac agtcatgtgga aagtccccag   2940
gctccccagc aggcagaagt atgcaaagca tgcatctcaa ttagtcagca accatagtcc   3000
cgcccctaac tccgcccatc ccgcccctaa ctccgcccag ttccgcccat tctccgcccc   3060
atggctgact aatttttttt atttatgcag aggccgaggc cgcctctgcc tctgagctat   3120
tccagaagta gtgaggaggc ttttttggag gcctaggctt ttgcaaaaag ctcccgggag   3180
cttgtatatc cattttcgga tctgatcaag agacaggatg aggatcgttt cgcatgattg   3240
aacaagatgg attgcacgca ggttctccgg ccgcttgggt ggagaggcta ttcggctatg   3300
actgggcaca acagacaatc ggctgctctg atgccgccgt gttccggctg tcagcgcagg   3360
ggcgcccggt tcttttttgtc aagaccgacc tgtccggtgc cctgaatgaa ctgcaggacg   3420
aggcagcgcg gctatcgtgg ctggccacga cgggcgttcc ttgcgcagct gtgctcgacg   3480
ttgtcactga gcgggaagg gactggctgc tattgggcga agtgccgggg caggatctcc   3540
tgtcatctca ccttgctcct gccgagaaag tatccatcat ggctgatgca atgcggcggc   3600
tgcatacgct tgatccggct acctgcccat tcgaccacca agcgaaacat cgcatcgagc   3660
gagcacgtac tcggatggaa gccggtcttg tcgatcagga tgatctggac gaagagcatc   3720
aggggctcgc gccagccgaa ctgttcgcca ggctcaaggc gcgcatgccc gacggcgagg   3780
atctcgtcgt gacccatggc gatgcctgct tgccgaatat catggtggaa aatggccgct   3840
tttctggatt catcgactgt ggccggctgg gtgtggcgga ccgctatcag gacatagcgt   3900
tggctacccg tgatattgct gaagagcttg gcggcgaatg ggctgaccgc ttcctcgtgc   3960
tttacggtat cgccgctccc gattcgcagc gcatcgcctt ctatcgcctt cttgacgagt   4020
tcttctgagc gggactctgg ggttcgaaat gaccgaccaa gcgacgccca acctgccatc   4080
acgagatttc gattccaccg ccgccttcta tgaaaggttg ggcttcggaa tcgtttttccg   4140
ggacgccgac tggatgatcc tccagcgcgg ggatctcatg ctggagttct tcgcccacccc   4200
caacttgttt attgcagctt ataatggtta caaataaagc aatagcatca caaatttcac   4260
aaataaagca tttttttcac tgcattctag ttgtggtttg tccaaactca tcaatgtatc   4320
ttatcatgtc tgtataccgt cgacctctag ctagagcttg gcgtaatcat ggtcatagct   4380
gtttcctgtg tgaaattgtt atccgctcac aattccacac aacatacgag ccggaagcat   4440
aaagtgtaaa gcctggggtg cctaatgagt gagctaactc acattaattg cgttgcgctc   4500
actgcccgct ttccagtcgg gaaacctgtc gtgccagctg cattaatgaa tcggccaacg   4560
cgcggggaga ggcggtttgc gtattgggcg ctcttccgct tcctcgctca ctgactcgct   4620
gcgctcggtc gttcggctgc ggcgagcggt atcagctcac tcaaaggcgg taatacggtt   4680
atccacagaa tcagggggata acgcaggaaa gaacatgtga gcaaaaggcc agcaaaaggc   4740
caggaaccgt aaaaaggccg cgttgctggc gtttttccat aggctccgcc cccctgacga   4800
gcatcacaaa aatcgacgct caagtcagag gtggcgaaac ccgacaggac tataaagata   4860
ccaggcgttt ccccctggaa gctccctcgt gcgctctcct gttccgaccc tgccgcttac   4920
cggatacctg tccgcctttc tcccttcggg aagcgtggcg ctttctcata gctcacgctg   4980
taggtatctc agttcggtgt aggtcgttcg ctccaagctg ggctgtgtgc acgaacccccc   5040
cgttcagccc gaccgctgcg ccttatccgg taactatcgt cttgagtcca acccggtaag   5100
```

-continued

```
acacgactta tcgccactgg cagcagccac tggtaacagg attagcagag cgaggtatgt   5160
aggcggtgct acagagttct tgaagtggtg gcctaactac ggctacacta gaagaacagt   5220
atttggtatc tgcgctctgc tgaagccagt taccttcgga aaaagagttg gtagctcttg   5280
atccggcaaa caaaccaccg ctggtagcgg tggtttttttt gtttgcaagc agcagattac   5340
gcgcagaaaa aaaggatctc aagaagatcc tttgatcttt tctacggggt ctgacgctca   5400
gtggaacgaa aactcacgtt aagggatttt ggtcatgaga ttatcaaaaa ggatcttcac   5460
ctagatcctt ttaaattaaa aatgaagttt taaatcaatc taaagtatat atgagtaaac   5520
ttggtctgac agttaccaat gcttaatcag tgaggcacct atctcagcga tctgtctatt   5580
tcgttcatcc atagttgcct gactccccgt cgtgtagata actacgatac gggagggctt   5640
accatctggc cccagtgctg caatgatacc gcgagaccca cgctcaccgg ctccagattt   5700
atcagcaata aaccagccag ccggaagggc cgagcgcaga agtggtcctg caactttatc   5760
cgcctccatc cagtctatta attgttgccg ggaagctaga gtaagtagtt cgccagttaa   5820
tagtttgcgc aacgttgttg ccattgctac aggcatcgtg gtgtcacgct cgtcgtttgg   5880
tatggcttca ttcagctccg gttcccaacg atcaaggcga gttacatgat cccccatgtt   5940
gtgcaaaaaa gcggttagct ccttcggtcc tccgatcgtt gtcagaagta agttggccgc   6000
agtgttatca ctcatggtta tggcagcact gcataattct cttactgtca tgccatccgt   6060
aagatgcttt tctgtgactg gtgagtactc aaccaagtca ttctgagaat agtgtatgcg   6120
gcgaccgagt tgctcttgcc cggcgtcaat acgggataat accgcgccac atagcagaac   6180
tttaaaagtg ctcatcattg gaaaacgttc ttcggggcga aaactctcaa ggatcttacc   6240
gctgttgaga tccagttcga tgtaacccac tcgtgcaccc aactgatctt cagcatcttt   6300
tactttcacc agcgtttctg ggtgagcaaa aacaggaagg caaaatgccg caaaaaaggg   6360
aataaggggc acacggaaat gttgaatact catactcttc ctttttcaat attattgaag   6420
catttatcag ggttattgtc tcatgagcgg atacatattt gaatgtattt agaaaaataa   6480
acaaataggg gttccgcgca catttccccg aaaagtgcca cctgacgtc              6529
```

SEQ ID NO: 72          moltype = AA   length = 419
FEATURE                Location/Qualifiers
source                 1..419
                       mol_type = protein
                       organism = synthetic construct
SEQUENCE: 72
```
MGEKPGTRVF KKSSPNCKLT VYLGKRDFVD HLDKVDPVDG VVLVDPDYLK DRKVFVTLTC   60
AFRYGREDLD VLGLSFRKDL FIATYQAFPP MPNPPRPPTR LQDRLLKKLG QHAHPFFFTI  120
PQNLPCSVTL QPGPEDTGKA CGVDFEIRAF CAKSIEEKSH KRNSVRLIIR KVQFAPETPG  180
PQPSAETTRH FLMSDRRSLH LEASLDKELY YHGEPLNVNV HVTNNSAKTV KKIRVSVRQY  240
ADICLFSTAQ YKCPVAQLEQ DDQVSPSSTF CKVYTITPLL SDNREKRGLA LDGQLKHEDT  300
NLASSTIVKE GANKEVLGIL VSYRVKVKLV VSRGGDVSVE LPFVLMHPKP HDHITLRPRQ  360
SAPREIDIPV DTNLIEFDTN YATDDDIVFE DFARLRLKGM KDDDCDDQFC RARDPPVAT   419
```

SEQ ID NO: 73          moltype = DNA   length = 5905
FEATURE                Location/Qualifiers
source                 1..5905
                       mol_type = other DNA
                       organism = synthetic construct
SEQUENCE: 73
```
cgttacataa cttacggtaa atggcccgcc tggctgaccg cccaacgacc cccgcccatt   60
gacgtcaata atgacgtatg ttcccatagt aacgccaata gggactttcc attgacgtca  120
atgggtggag tatttacggt aaactgccca cttggcagta catcaagtgt atcatatgcc  180
aagtacgccc cctattgacg tcaatgacgg taaatggccc gcctggcatt atgcccagta  240
catgacctta tgggactttc ctacttggca gtacatctac gtattagtca tcgctattac  300
catggtgatg cggttttggc agtacatcaa tgggcgtgga tagcggtttg actcacgggg  360
atttccaagt ctccacccca ttgacgtcaa tgggagtttg ttttggcacc aaaatcaacg  420
ggactttcca aaatgtcgta caactccgc cccattgacg caaatgggcg gtaggcgtgt  480
acggtgggag gtctatataa gcagagctgg tttagtgaac cgtcagatcc gctagcgcca  540
ccatgggtga aaaacccggg accagggtct tcaagaagtc gagccctaac tgcaagctca  600
ccgtgtactt gggcaagcgt gactttgtg atcacttgga caaagtggat cctgtcgatg  660
gtgtggtgct tgtggatcct gactacttga aggaccggaa agtgtttgtg accctcacct  720
gtgccttccg ctatggccga gaagacctgg atgtactggg cctgtctttc cgcaaagatc  780
tgttcatcgc cacctaccag gccttccccc ccatgccaa cccacctcgg ccccccaccc  840
gcctacagga ccgactgctg aagaagttgg gccagcatgc ccaccccctt ttttttcacaa  900
taccccagaa tttgccttgc tccgtcacac tgcagccagg accggaggac acagggaagg  960
cctgtggagt agactttgag attgcgagcct tctgtgccaa atctatagaa gaaaaaagcc  1020
acaaaaggaa ctccgtgcgg cttatcatca gaaaggtaca gtttgctcct gagacacccg  1080
gcccccagcc atcagctgaa accacacgcc acttcctcat gtctgaccgg aggtccctgc  1140
acctagaggc ttccctggac aaaagagctgt actaccatgg gaaccccctc aatgtcaacg  1200
tccacgtcac caacaattct gccaagaccg tcaagaagat cagagtgtct gtgagacagt  1260
atgccgacat ttgcctcttc agcaccgcgc agtacaagtg tcctgtggct cagcttgaac  1320
aagatgacca ggtgtctccc agttccacat tctgcaaggt gtacaccata accccgctgc  1380
tcagtgacaa ccgagagaag cgtggccttg cccttgacgg gcaactcaag cacgaagaca  1440
ccaacctggc ttccagcacc attgtgaagg agggagccaa caaggaggtg ctgggaatcc  1500
tagtatccta cagggtcaag gtgaagctgg tggtgtctcg aggcggggat gtctccgtgg  1560
agctaccttt cgtcctaatg caccccaagc cccacgacca tcacccctt ccccgacccc  1620
agtcagcccc ccgggaaata gacatccctg tggataccaa cctcattgaa ttcgatacca  1680
actatgccac agacgacgac atcgtgtttg aggactttgg acgccttcgg ctgaagggaa  1740
tgaaggatga cgactgtgat gaccagttct gccgggcccg ggatccaccg gtcgccacca  1800
tggtgagcaa gggcgaggag gataacatgg ccatcatcaa ggagttcatg cgcttcaagg  1860
tgcacatgga gggctccgtg aacggccacg agttcgagat cgaggcgag ggcgagggc  1920
gcccctacga gggcacccag accgccaagc tgaaggtgac caagggtggc cccctgccct  1980
tcgcctggga catcctgtcc cctcagttca tgtacggctc caaggcctac gtgaagcacc  2040
```

-continued

```
ccgccgacat ccccgactac ttgaagctgt ccttccccga gggcttcaag tgggagcgcg    2100
tgatgaactt cgaggacggc ggcgtggtgta ccgtgaccca ggactcctcc ctgcaggacg    2160
gcgagttcat ctacaaggtg aagctgcgcg gcaccaactt cccctccgac ggccccgtaa    2220
tgcagaagaa gaccatgggc tgggaggcct cctccgagcg gatgtacccc gaggacggcg    2280
ccctgaaggg cgagatcaag cagaggctga agctgaagga cggcggccac tacgacgctg    2340
aggtcaagac cacctacaag gccaagaagc ccgtgcagct gcccggcgcc tacaacgtca    2400
acatcaagtt ggacatcacc tcccacaacg aggactacac catcgtggaa cagtacgaac    2460
gcgccgaggg ccgccactcc accggcggca tggacgagct gtacaagtaa agcggccgcg    2520
actctagatc ataatcagcc ataccacatt tgtagaggtt ttacttgctt taaaaaacct    2580
cccacacctc cccctgaacc tgaaacataa aatgaatgca attgttgttg ttaacttgtt    2640
tattgcagct tataatggtt acaaataaag caatagcatc acaaatttca caaataaagc    2700
atttttttca ctgcattcta gttgtggttt gtccaaactc atcaatgtat cttaaggcgt    2760
aaattgtaag cgttaatatt ttgttaaaat tcgcgttaaa tttttgttaa atcagctcat    2820
tttttaacca ataggccgaa atcggcaaaa tcccttataa atcaaaagaa tagaccgaga    2880
tagggttgag tgttgttcca gtttggaaca agagtccact attaaagaac gtggactcca    2940
acgtcaaagg gcgaaaaacc gtctatcagg gcgatggccc actacgtgaa ccatcaccct    3000
aatcaagttt tttggggtcg aggtgccgta aagcactaaa tcggaaccct aaagggagcc    3060
cccgatttag agcttgacgg ggaaagccgg cgaacgtggc gagaaaggaa gggaagaaag    3120
cgaaaggagc gggcgctagg gcgctggcaa gtgtagcggt cacgctgcgc gtaaccacca    3180
cacccgccgc gcttaatgcg ccgctacagg gcgcgtcagg tggcacttt cggggaaatg    3240
tgcgcggaac ccctatttgt ttatttttct aaatacattc aaatatgtat ccgctcatga    3300
gacaataacc ctgataaatg cttcaataat attgaaaaag gaagagtcct gaggcggaaa    3360
gaaccagctg tggaatgtgt gtcagttagg gtgtggaaag tccccaggct ccccagcagg    3420
cagaagtatg caaagcatgc atctcaatta gtcagcaacc aggtgtggaa agtccccagg    3480
ctccccagca ggcagaagta tgcaaagcat gcatctcaat tagtcagcaa ccatagtccc    3540
gcccctaact ccgcccatcc cgcccctaac tccgcccagt tccgcccatt ctccgcccca    3600
tggctgacta attttttta tttatgcaga ggccgaggcc gcctcggcct ctgagctatt    3660
ccagaagtag tgaggaggct ttttttggag gcctaggctt ttgcaaagatc gatcaagaga    3720
caggatgagg atcgtttcgc atgattgaac aagatggatt gcacgcaggt tctccggccg    3780
cttgggtgga gaggctattc ggctatgact gggcacaaca gacaatcggc tgctctgatg    3840
ccgccgtgtt ccggctgtca gcgcagggc gcccggttct ttttgtcaag accgacctg    3900
ccggtgccct gaatgaactg caagacgagg cagcgcggc atcgtggctg gccacgacgg    3960
gcgttccttg cgcagctgtg ctcgacgttg tcactgaagc gggaagggac tggctgctat    4020
tgggcgaagt gccggggcag gatctcctgt catctcacct tgctcctgcc gagaaagtat    4080
ccatcatggc tgatgcaatg cggcggctgc atacgcttga tccggctacc tgcccattcg    4140
accaccaagc gaaacatcgc atcgagcgag cacgtactcg gatggaagcc ggtcttgtcg    4200
atcaggatga tctggacgaa gagcatcagg ggctcgcgcc agccgaactg ttcgccaggc    4260
tcaaggcgag catgcccgac ggcgaggatc tcgtcgtgac ccatggcgat gcctgcttgc    4320
cgaatatcat ggtggaaaat ggccgctttt ctggattcat cgactgtggc cggctgggtg    4380
tggcggaccg ctatcaggac atagcgttgg ctacccgtga tattgctgaa gagcttggcg    4440
gcgaatgggc tgaccgcttc ctcgtgcttt acggtatcgc cgctcccgat tcgcagcgca    4500
tcgccttcta tcgccttctt gacgagttct tctgagcggg actctggggt tcgaaatgac    4560
cgaccaagcg acgcccaacc tgccatcacg agatttcgat tccaccgccg ccttctatga    4620
aaggttgggc ttcggaatcg ttttccggga cgccggctgg atgatcctcc agcgcgggga    4680
tctcatgctg gagttcttcg cccacccctag ggggaggcta actgaaacac ggaaggagac    4740
aataccggaa ggaacccgcg ctatgacggc aataaaaaga cagaataaaa cgcacggtgt    4800
tgggtctttt gttcataaac gcgggggttcg gtcccagggc tggcactctg tcgataccc    4860
accgagaccc cattgggggcc aatacgcccg cgtttcttcc tttttcccac cccacccccc    4920
aagttcgggt gaaggcccag ggctcgcagc caacgtcggg gcggcaggcc ctgccatagc    4980
ctcaggttac tcatatatac tttagattga tttaaaactt cattttaat ttaaaaggat    5040
ctaggtgaag atccttttg ataatctcat gaccaaaatc ccttaacgtg agttttcgtt    5100
ccactgagcg tcagaccccg tagaaaagat caaaggatc tcttgagatc cttttttct    5160
gcgcgtaatc tgctgcttgc aaacaaaaaa accaccgcta ccagcggtgg tttgtttgcc    5220
ggatcaagag ctaccaactc tttttccgaa ggtaactggc ttcagcagag cgcagatacc    5280
aaatactgtt cttctagtgt agccgtagtt aggccaccac ttcaagaact ctgtagcacc    5340
gcctacatac ctcgctctgc taatcctgtt accagtggct gctgccagtg gcgataagtc    5400
gtgtcttacc gggttggact caagacgata gttaccggat aaggcgcagc ggtcgggctg    5460
aacgggggt tcgtgcacac agcccagctt ggagcgaacg acctacaccg aactgagata    5520
cctacagcgt gagctatgag aaagcgccac gcttcccgaa gggagaaagg cggacaggta    5580
tccggtaagc ggcagggtcg gaacaggaga gcgcacgagg gagcttccag ggggaaacgc    5640
ctggtatctt tatagtcctg tcgggtttcg ccacctctga cttgagcgtc gatttttgtg    5700
atgctcgtca gggggggcgga gcctatggaa aaacgccagc aacgcggcct ttttacggtt    5760
cctggccttt tgctggcctt ttgctcacat gttctttcct gcgttatccc ctgattctgt    5820
ggataaccgt attaccgcca tgcattagtt attaatagta atcaattacg gggtcattag    5880
ttcatagccc atatatggag ttccg    5905
```

```
SEQ ID NO: 74              moltype = AA  length = 371
FEATURE                    Location/Qualifiers
source                     1..371
                           mol_type = protein
                           organism = synthetic construct
SEQUENCE: 74
MILVSTTSAV PGALSSPSSP SNSSQEELLD DRDPLLVRAE LALLSTIFVA VALSNGLVLG     60
ALIRRGRRGR WAPMHVFISH LCLADLAVAL FQVLPQLAWD ATDRFHGPDA LCRAVKYLQM    120
VGMYASSYMI LAMTLDRHRA ICRPMLAYRH GGGARWNRPV LVAWAFSLLL SLPQLFIFAQ    180
RDVGNGSGVF DCWARFAEPW GLRAYVTWIA LMVFVAPALG IAACQVLIFR EIHASLVPGP    240
SERAGRRRRG HRTGSPSEGA HVSAAMAKTV RMTLVIVIVY VLCWAPFFLV QLWAAWDPEA    300
PLERPPPFVLL MLLASLNSCT NPWIYASFSS SVSSELRSLL CCAQRHTTHS LGPQDESCAT    360
ASSSLMKDTP S    371
```

-continued

```
SEQ ID NO: 75            moltype = DNA  length = 6514
FEATURE                  Location/Qualifiers
source                   1..6514
                         mol_type = other DNA
                         organism = synthetic construct
SEQUENCE: 75
gacggatcgg gagatctccc gatccccttat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
gtttaaactt aagcttggta ccgacggacc atgatcctgg tgtctaccac gtctgcagtg  960
cctgggcccc tttcgtcccc tagctctccc agcaacagca gccaggagga gctactggat  1020
gaccgagacc cgctgttagt ccgggctgaa ctggccctgc tatctacaat ttttgtggct  1080
gtggccttga gcaatggcct agtgcttggg gccctaactac gacggggtcg gcgtggacgc  1140
tgggcaccca tgcacgtctt catcagtcat ttgtgcctag ctgacctggc tgtggctctg  1200
tttcaagtgc tgcccagct ggcttgggat gccaccgacc gcttccatgg ccctgatgcc  1260
ttgtgtcggg ccgtcaagta cctgcagatg gtgggcatgt atgcctcttc ctacatgatc  1320
ctggccatga cactagaccg ccatcgcgcc atctgccgcc ctatgctggc ataccgccat  1380
ggaggtgggg ctcgctggaa caggccagtg ctggtggcct gggccttctc actccttctc  1440
agcctgcctc agctcttcat ctttgctcaa cgtgatgtgg gaaatggcag tggggtattt  1500
gattgctggg cccgatttgc agagccatgg ggccttcgtg cctatgtcac ctggatcgcc  1560
ttgatggtgt ttgtggcacc tgccctaggc attgctgcct gccaggttct tatcttccgg  1620
gagatacatg ccagtctggt gccagggcca tctgaaaggg cagggaggcg ccgcagagga  1680
caccggacag gaagtcccag cgagggagcc catgtatcag cagccatggc caagaccgtg  1740
aggatgacac tagtgattgt gattgtctac gtgctgtgct gggcaccctt cttccttgtg  1800
cagctgtggg cagcgtggga tccagaagct cctctggaaa gaccccccct tgtgttgctc  1860
atgctgctgg ctagccttaa cagctgtacc aaccccctgga tctatgcttc cacacagagc  1920
agtgtctcct cggagttgcg tagcctgctt tgctgtgctc agaggcacac cacacacagc  1980
ctgggtcctc aagatgagtc ctgtgccaca gccagctcct ctctgatgaa ggatacaccc  2040
tcctgagtat aatgaaggtg gcggccgctc gaaactagag ggcccgttta aacccgctga  2100
tcagcctcga ctgtgccttc tagttgccag ccatctgttg tttgcccctc ccccgtgcct  2160
tccttgaccc tggaaggtgc cactcccact gtcctttcct aataaaatga ggaaattgca  2220
tcgcattgtc tgagtaggtg tcattctatt ctggggggtg gggtggggca ggacagcaag  2280
ggggaggatt gggaagacaa tagcaggcat gctggggatg cggtggggctc tatggcttct  2340
gaggcggaaa gaaccagctg gggctctagg gggtatcccc acgcgccctg tagcggcgca  2400
ttaagcgcgg cgggtgtggt ggttacgcgc agcgtgaccg ctacacttgc cagcgcccta  2460
gcgcccgctc ctttcgcttt cttcccttcc tttctcgcca cgttcgccgg ctttccccgt  2520
caagctctaa atcggggggct ccctttaggg ttccgattta gtgctttacg gcacctcgac  2580
cccaaaaaac ttgattaggg tgatggttca cgtagtgggc catcgccctg atagacggtt  2640
tttcgccctt tgacgttgga gtccacgttc tttaatagtg gactcttgtt ccaaactgga  2700
acaacactca accctatctc ggtctattct tttgatttat aagggatttt gccgatttcg  2760
gcctattggt taaaaaatga gctgatttaa caaaaattta acgcgaatta attctgtgga  2820
atgtgtgtca gttagggtgt ggaaagtccc caggctcccc agcaggcaga agtatgcaaa  2880
gcatgcatct caattagtca gcaaccaggt gtggaaagtc cccaggctcc ccagcaggca  2940
gaagtatgca aagcatgcat ctcaattagt cagcaaccat agtcccgccc ctaactccgc  3000
ccatcccgcc cctaactccg cccagttccg cccattctcc gccccatggc tgactaattt  3060
tttttattta tgcagaggcc gaggccgcct ctgcctctga gctattccag aagtagtgag  3120
gaggcttttt tggaggccta ggcttttgca aaaagctccc gggagcttgt atatccattt  3180
tcggatctga tcaagagaca ggatgaggat cgtttcgcat gattgaacaa gatggattgc  3240
acgcaggttc tccggccgct tgggtggaga ggctattcgg ctatgactgg gcacaacaga  3300
caatcggctg ctctgatgcc gccgtgttcc ggctgtcagc gcaggggcgc ccggttcttt  3360
ttgtcaagac cgacctgtcc ggtgccctga tgaactgcag gacgaggca gcgcggctat  3420
cgtggctggc cacgacgggc gttccttgcg cagctgtgct cgacgttgtc actgaagcgg  3480
gaagggactg gctgctattg ggcgaagtgc cggggcagga tctcctgtca tctcaccttg  3540
ctcctgccga gaaagtatcc atcatggctg atgcaatgcg gcggctgcat acgcttgatc  3600
cggctacctg cccattcgac caccaagcga aacatcgcat cgagcgagca cgtactcgga  3660
tggaagccgg tcttgtcgat caggatgatc tggacgaaga gcatcagggg ctcgcgccag  3720
ccgaactgtt cgccaggctc aaggcgcgca tgcccgacgg cgaggatctc gtcgtgaccc  3780
atggcgatgc ctgcttgccg aatatcatgg tggaaaatgg ccgcttttct ggattcatcg  3840
actgtggccg ctgggtgtg gcggaccgct atcaggacat agcgttggct acccgtgata  3900
ttgctgaaga gcttggcggc gaatgggctg accgcttcct cgtgctttac ggtatcgccg  3960
ctcccgattc gcagcgcatc gccttctatc gccttcttga cgagttcttc tgagcgggac  4020
tctgggttc gaaatgaccg accaagcgac gcccaacctg ccatcacgag atttcgattc  4080
caccgccgcc ttctatgaaa ggttgggctt cggaatcgtt ttccgggacg ccggctggat  4140
gatcctccag cgcggggatc tcatgctgga gttcttcgcc caccccaact gtttattgc  4200
agcttataat ggttacaaat aaagcaatag catcacaaat ttcacaaata aagcattttt  4260
ttcactgcat tctagttgtg gtttgtccaa actcatcaat gtatcttatc atgtctgtat  4320
```

-continued

```
accgtcgacc tctagctaga gcttggcgta atcatggtca tagctgtttc ctgtgtgaaa  4380
ttgttatccg ctcacaattc cacacaacat acgagccgga agcataaagt gtaaagcctg  4440
gggtgcctaa tgagtgagct aactcacatt aattgcgttg cgctcactgc ccgctttcca  4500
gtcgggaaac ctgtcgtgcc agctgcatta atgaatcggc caacgcgcgg ggagaggcgg  4560
tttgcgtatt gggcgctctt ccgcttcctc gctcactgac tcgctgcgct cggtcgttcg  4620
gctgcggcga gcggtatcag ctcactcaaa ggcggtaata cggttatcca cagaatcagg  4680
ggataacgca ggaaagaaca tgtgagcaaa aggccagcaa aaggccagga accgtaaaaa  4740
ggccgcgttg ctggcgtttt tccataggct ccgcccccct gacgagcatc acaaaaatcg  4800
acgctcaagt cagaggtggc gaaacccgac aggactataa agataccagg cgtttccccc  4860
tggaagctcc ctcgtgcgct ctcctgttcc gaccctgccg cttaccggat acctgtccgc  4920
ctttctccct tcgggaagcg tggcgctttc tcatagctca cgctgtaggt atctcagttc  4980
ggtgtaggtc gttcgctcca agctgggctg tgtgcacgaa ccccccgttc agcccgaccg  5040
ctgcgcctta tccggtaact atcgtcttga gtccaacccg gtaagacacg acttatcgcc  5100
actggcagca gccactggta acaggattag cagagcgagg tatgtaggcg gtgctacaga  5160
gttcttgaag tggtggccta actacggcta cactagaaga acagtatttg gtatctgcgc  5220
tctgctgaag ccagttacct tcggaaaaag agttggtagc tcttgatccg gcaaacaaac  5280
caccgctggt agcggtggtt tttttgtttg caagcagcag attacgcgca gaaaaaaagg  5340
atctcaagaa gatcctttga tcttttctac ggggtctgac gctcagtgga acgaaaactc  5400
acgttaaggg attttggtca tgagattatc aaaaaggatc ttcacctaga tccttttaaa  5460
ttaaaaatga agttttaaat caatctaaag tatatatgag taaacttggt ctgacagtta  5520
ccaatgctta atcagtgagg cacctatctc agcgatctgt ctatttcgtt catccatagt  5580
tgcctgactc cccgtcgtgt agataactac gatacggagg ggcttaccat ctggccccag  5640
tgctgcaatg ataccgcgag acccacgctc accggctcca gatttatcag caataaacca  5700
gccagccgga agggccgagc gcagaagtgg tcctgcaact ttatccgcct ccatccagtc  5760
tattaattgt tgccgggaag ctagagtaag tagttcgcca gttaatagtt tgcgcaacgt  5820
tgttgccatt gctacaggca tcgtggtgtc acgctcgtcg tttggtatgg cttcattcag  5880
ctccggttcc caacgatcaa ggcgagttac atgatccccc atgttgtgca aaaaagcggt  5940
tagctccttc ggtcctccga tcgttgtcag aagtaagttg gccgcagtgt tatcactcat  6000
ggttatggca gcactgcata attctcttac tgtcatgcca tccgtaagat gcttttctgt  6060
gactggtgag tactcaacca agtcattctg agaatagtgt atgcggcgac cgagttgctc  6120
ttgcccggcg tcaatacggg ataataccgc gccacatagc agaactttaa aagtgctcat  6180
cattggaaaa cgttcttcgg ggcgaaaact ctcaaggatc ttaccgctgt tgagatccag  6240
ttcgatgtaa cccactcgtg cacccaactg atcttcagca tcttttactt tcaccagcgt  6300
ttctgggtga gcaaaaacag gaaggcaaaa tgccgcaaaa aagggaataa gggcgacacg  6360
gaaatgttga atactcatac tcttcctttt tcaatattat tgaagcattt atcagggtta  6420
ttgtctcatg agcggataca tatttgaatg tatttagaaa aataaacaaa taggggttcc  6480
gcgcacattt ccccgaaaag tgccacctga cgtc                              6514
```

PROBE AND METHOD FOR DETECTING MEMBRANE-ASSOCIATED MOLECULES IN LIVING CELLS

SEQUENCE LISTING

This application contains a sequence listing which has been submitted electronically in ASCII format in a text file and is hereby incorporated by reference in its entirety. This ASCII text file, created on Nov. 11, 2022, is named P1939US00-SeqList.xml and is 332 kilobytes in size.

FIELD OF THE INVENTION

The invention described herein concerns detection and visualization of molecular processes taking place in living cells.

BACKGROUND ART

In order to survive and to carry out their functions within living organisms, cells receive, process, and transmit molecular signals. Many such signals involve molecules associated with, or embedded within the cell membrane (herein referred to as membrane-associated molecules). Changes in concentration of such molecules, in their chemical modifications, in their conformation, and in their mode and extent of interactions with other molecules carry information in biological sy stems. Molecular events that involve membrane-associated molecules can be observed through the use of optically detectable molecular probes, using suitable techniques of optical microscopy.

In order to observe molecular events in living cells, the target molecules are often modified to bear optically detectable labels. These labels allow specificity in observing processes pertaining to the target molecules. However, since the presence of molecular labels can affect the processes to be observed, it is of high scientific and practical interest to develop means to observe the presence or absence of a target molecule, or its particular molecular state, without modifying the target molecule by introducing an optical label.

To detect by means of optical microscopy, with specificity, a target membrane membrane-associated molecule that bears no optical label, genetically encoded optically active probes that bind specifically to the target molecule have been used. Binding of such probes to the target molecule is then detected. Four distinct means of detecting an interaction between a non-labeled target molecule and an optically active molecular probe could be identified: 1) through observations of changes in cellular localization of the probe, 2) through observations of the diffusion rate of the probe, 3) through observations of changes in resonant energy transfer within the probe, and 4) through observations of changes in molecular orientation of the probe.

However, all of these approaches bear significant disadvantages. Quantification of cellular localization is problematic due to optical overlap between the distinct cellular compartments. Quantification of rates of diffusion (achievable through fluorescence correlation spectroscopy or single molecule tracking) is experimentally challenging and time consuming. Probes relying on bioluminescence resonant energy transfer generate only low amounts of light, which generally requires integration of signal from many cells, over periods of time of seconds to minutes, precluding imaging of dynamic molecular processes. Probes relying on fluorescence resonant energy transfer generally do not allow multiplexing. Despite their potential advantages, probes relying on changes in molecular orientation for detection of processes involving membrane-associated molecules have been used only in a small number of cases (Benninger R K & al., Biophysical Journal. 2009 Jan. 21; 96(2):L13-5; Kress A & al., Biophysical Journal. 2011 Jul. 20; 101(2):468-76; Lazar J. & al., Nature Methods. 2011 August; 8(8):684-90. Bondar A. Lazar J., Journal of Biological Chemistry. 2014 Jan. 1; 289(3):1271-81; Han Z & al., PloS One. 2014 Nov. 24; 9(11):e113873; Bondar A, Lazar J., Journal of Biological Chemistry. 2017 Jul. 1; 292(23):9690-8; Bondar A & al., Communications Biology. 2021 Feb. 12; 4(1):1-2). This is due to the non-rigid character of the cell membrane, only partially restricting the orientation of the potential molecular probes, and therefore severely limiting their ability to function as probes.

DISCLOSURE OF THE INVENTION

The present invention aims to overcome the limitations of existing technologies and to enable the use of polarization microscopy-based methods using genetically encoded probes for observing and/or detecting membrane-associated processes and/or membrane-associated molecules (preferably membrane-associated proteins), by implementing a modular molecular probe design which maximizes differences in optical properties detectable by polarization microscopy, said differences conveying information on two distinct states of the target molecule (preferably target protein), such as absence and presence of the target molecule.

The molecular probes of the invention convert the two distinct states of the target membrane-associated molecule, such as presence or absence of the target molecule, into changes of molecular orientation of a fluorescent moiety of the molecular probe. These changes in molecular orientation of the fluorescent moiety are then observed by means of polarization microscopy.

The present invention thus relates in the first aspect to a protein-based probe for detecting the presence of one of two distinct states of a target membrane-associated molecule (preferably a target membrane-associated protein), such as the presence or absence of a target membrane-associated molecule, by means of polarization microscopy, wherein the probe contains or consists of a) an anchoring moiety containing or consisting of at least one lipidated peptide and/or at least one transmembrane α-helical peptide, b) a peptide linker moiety having the length of at least 5 amino acids, wherein at least 50% of the amino acids forming the linker are selected from glycine, serine, and threonine, c) a fluorescent moiety, and d) an affinity binding moiety that binds the target membrane-associated molecule, wherein the moieties are arranged in the order a-b-c-d or d-c-b-a in the direction from the N-terminus to the C-terminus.

"Target membrane-associated molecule" or "target molecule" refers to a membrane-associated molecule which is to be detected, or whose distinct state is to be observed or detected or found. The target molecule is preferably a protein. In some embodiments of the present invention, the target membrane-associated protein is selected from activated forms of G-proteins, activated forms of G-protein coupled receptors, activated forms of arrestins and activated forms of receptor tyrosine kinases. In some embodiments of the present invention, the target membrane-associated protein is selected from G proteins $G\alpha s$, $G\alpha q$, $G\alpha i1$, $G\alpha 13$, GβGγ dimers, small GTPases RhoA, Rac1, G protein coupled receptors β2-adrenergic receptor, μ-opioid receptor, arrestins, or the tyrosine kinase insulin receptor in a distinct state.

"Two distinct states" refers to two different states of the target molecule which can be distinguished from each other. Typical distinct states of the target molecule include, for example, its presence in the membrane, its absence from the membrane, or its conformational state. The conformational state may correspond to activated or inactive forms. The two distinct states may refer to an active form of the target membrane-associated molecule and an inactive form of the target membrane-associated molecule which differ by conformation, a bound ligand, or chemical modification such as phosphorylation (in particular in target proteins).

The presence of one distinct state is detected due to interaction of the target molecule, which is in this state, with the probe of the invention. The interaction (or lack of interaction) results in a signal which can be observed by means of polarization microscopy.

The term "detect" or "detecting" refers to detecting or observing or finding a distinct state of the target (membrane-associated) molecule, or distinguishing between one of possible distinct states of the target (membrane-associated) molecule. One state of the target molecule may be its presence. One state of the target molecule may be its absence. Alternatively, states of the target molecule may be its individual and distinct conformations, such as an active state and inactive state.

The term "containing" or "comprising", such as "X containing Y" or "X comprising Y", means that X contains the component/moiety Y, but may also contain other components or moieties.

The term "consisting of", such as "X consists of Y", means that X contains the component/moiety Y, and no other component or moiety.

"Sequence identity" or "identity" refers to amino acids in two amino acid sequences which are the same when aligned for maximum correspondence. The sequence identity refers to the value obtained by comparing two optimally aligned sequences over a comparison window, wherein the compared amino acid sequence in the comparison window may contain additions or deletions as compared to the reference sequence for optimum alignment. The percentage of identity is calculated by determining the number of positions at which the identical amino acids are present in both amino acid sequences, and dividing it by the total number of positions in the window of comparison and multiplying by 100.

"Peptides" are herein considered to be amino acid sequences having a length of up to 100 amino acids, preferably up to 50 amino acids, more preferably up to 30 amino acids.

The individual moieties of the probe are covalently bound in the indicated order, i.e., there is a covalent bond or a covalently bound peptide linker between each two neighboring moieties.

An anchoring moiety is a moiety which anchors the probe in the membrane (i.e., a membrane-anchoring moiety). It may contain or consist of one or more lipidated peptides, or one or more transmembrane α-helical peptides, or a combination of one or more lipidated peptides and one or more transmembrane α-helical peptides. The anchoring moieties containing lipidated peptides or transmembrane α-helical peptides may include proteins or protein fragments containing the lipidated peptide or transmembrane α-helical peptide sequence.

Lipidated peptides are peptides having amino acid sequences that bear at least one lipophilic prenyl group, fatty acyl group, and/or glycosylphosphatidylinositol group. These peptides may be synthetic or of natural origin. The lipidated peptides of natural origin are peptides which are recognized by cellular posttranslational machinery, which modifies them by attaching at least one lipophilic prenyl group, fatty acyl group or a glycosylphosphatidylinositol group. Due to the covalently attached lipid moiety interacting favorably with lipids in the cell membrane, lipidated peptides in the cell are attached to the cell membrane.

Preferred anchoring moieties containing lipidated peptides are selected from fatty acyl bearing proteins, in particular selected from the group comprising GAP43, tyrosine kinases Lck, Src and Lyn, G-proteins Gα, polyprotein GAG, and fragments thereof. Further preferred anchoring moieties containing lipidated peptides are selected from prenyl group bearing proteins, including proteins containing a CaaX motif (Cysteine—aliphatic amino acid—aliphatic amino acid—C-terminal amino acid, SEQ ID NO:65), in particular selected from the group comprising proteins hRas, kRas and nRas, G-proteins Gγ, small GTPase Rho, and fragments thereof. Yet further preferred anchoring moieties containing lipidated peptides are selected from proteins bearing the glycosylphosphatidylinositol group, such as CD24, glypicans, cadherins, GPAA attachment proteins, COBRA-like attachment proteins or fragments thereof. The fragments used as anchoring moieties containing or consisting of lipidated peptides are membrane-anchored fragments of the herein listed proteins.

Transmembrane α-helical peptides are peptides that due to their amino acid sequence interact favorably with lipid membranes. Transmembrane α-helical peptides form helical structures that traverse the lipid bilayer of a cellular membrane.

In some embodiments, transmembrane α-helical peptides are selected from peptides having a length within the range from 17 to 35 amino acids, wherein at least 50%/6 of the amino acids forming the peptide are selected from leucine, isoleucine, valine, and alanine, and up to 15% of the amino acids forming the peptides are glutamine, glutamic acid, aspartic acid, arginine, and lysine.

In some embodiments, anchoring moieties containing transmembrane α-helical peptides are selected from integral membrane proteins and fragments thereof. Preferred integral membrane proteins are selected from membrane receptor proteins, membrane transporter proteins and membrane enzymes.

Preferred membrane receptor proteins are bitopic membrane receptor proteins, more preferably selected from the group comprising receptor tyrosine kinases, such se EGF, FGF, VEGF, PDGF, NGF and HGF receptors, insulin receptors, Eph receptors, and RET proto-oncogenes. Further preferred membrane receptor proteins are bitopic receptors of the immunoglogulin receptor family, such as T-cell receptors, killer cell immunoglobulin-like receptors, leukocyte immunoglobulin-like receptors. Fc receptors, netrin receptors, and cytokine receptors. Further preferred membrane receptor proteins are scavenger proteins. Further preferred membrane receptor proteins are polytopic membrane receptor proteins, including G protein coupled receptors (GPCRs). Preferred GPCRs are receptors of rhodopsin-like receptor family, such as opsins, serotonin, dopamine, acetylcholine, histamine, adenosine, vasopressin, somatostatin, prostaglandin, chemokine, opioid, cannabinoid, adrenergic, purinergic, olfactory, taste and vomeronasal V1R receptors. Further preferred GPCRs are receptors of secretin receptor family, such as glucagon receptor, growth hormone releasing hormone receptor, secretin receptor, or parathyroid hormone receptor. Yet further preferred GPCRs are receptors of the metabotropic glutamate receptor family, such as GABA receptors, metabotropic glutamate receptors, taste receptors, or vomeronasal V2R receptors. Even further preferred GPCRs are fungal mating pheromone receptors, cyclic AMP receptors, Frizzled or Smoothened receptors.

Preferred membrane transporter proteins are channel proteins, solute carrier proteins, or active transporters. Membrane transporter proteins are preferably polytopic.

Preferred channel proteins are aquaporins or ion channel proteins. Preferred ion channel proteins are selected from chloride channels, ligand gated ion channels, and voltage gated-like ion channels. The ligand gated ion channels are preferably selected from ATP gated ion channels, glutamate cationic channels, and Cys-loop channels. The voltage gated-like ion channels are preferably selected from potassium channels, cyclic nucleotide gated ion channels, calcium activated potassium channels, transient receptor potential (TRP) channels, sodium channels, calcium channels, two-pore channels, ryanodine receptors and inositol receptors.

Preferred membrane enzymes are oxidoreductases such as NADH-ubiquinone oxidoreductase, cytochrome c or flavin containing monoxygenases. Further preferred membrane enzymes are transferases such as glycosyltransferases, sulfotransferases, acyltransferases or phosphotransferases. Yet further preferred membrane enzymes are hydrolases such as non-receptor protein tyrosine phosphatases, O- or S-glycolases, serine endopeptidases, metalloendopeptidases or nucleotide diphosphatases. Further preferred membrane enzymes are membrane-spanning lyases, membrane-spanning ligases or membrane-spanning isomerases.

Particularly preferred anchoring moieties are hRas, kRas, GAP43, interleukin 4 receptor (IL4R), β2-adrenergic receptor (β2AR) and fragments thereof.

A peptide linker moiety has a length of at least 5 amino acids, wherein at least 50% of the amino acids forming the linker are glycine, serine, and/or threonine.

The peptide linker moiety is flexible, in order to allow multiple orientations of the fluorescent moiety within the probe. Sequences of the flexible peptide linkers are composed predominantly of small and polar amino acids, namely glycine, serine and threonine. For improved solubility, flexible peptide linkers may further include charged amino acids, in particular lysine, arginine, and glutamate.

The peptide linker moiety preferably has a length between 5 and 30 amino acids, more preferably between 6 and 20 amino acids, even more preferably between 6 and 10 amino acids.

The peptide linker sequence contains at least 50% of serine and/or glycine and/or threonine. Preferably, at least 70% of the amino acids in the linker are serine and/or glycine and/or threonine. More preferably, at least 85% of the amino acids in the linker are serine and/or glycine and/or threonine. In some embodiments, all amino acids in the linker are serine and/or glycine and/or threonine.

Particularly preferably, the peptide linker sequence is selected from the sequences GSGGSGG (SEQ ID NO:1), SSGSSGTG (SEQ ID NO:2), and GSKSSGSGSESK-STGKSTGSGTETGGS (SEQ ID NO:3).

The fluorescent moiety, due to its flexible connection to the anchoring moiety and its rigid connection to the affinity binding moiety, adopts distinctly different molecular orientations with respect to the lipid membrane, wherein the different molecular orientations correspond to different states of the target protein. For example, the different molecular orientations of the fluorescent moiety occur in the absence vs. in the presence of the target membrane-associated protein. These different molecular orientations of the fluorescent moiety can be detected by polarization microscopy, taking advantage of anisotropic optical properties (linear dichroism, fluorescence polarization) of the fluorescent moieties.

The fluorescent moiety is preferably a fluorescent protein, or a protein that becomes fluorescent when covalently or non-covalently bound to a small molecule (a fluorescent or non-fluorescent ligand).

Preferred fluorescent proteins are autofluorescent proteins, more preferably, autofluorescent proteins whose structure forms an 11-strand β-barrel.

Further preferred fluorescent proteins are proteins whose amino acid sequences have at least 80% identity (or at least 90% identity, or at least 95% identity, or 100% identity) to at least one amino acid sequence selected from amino acid sequences of proteins eGFP, meGFP, mTurquoise2, mCherry, mScarlet, mRuby, mGinger1, mPapaya, mNeon-Green, mTFP, Dronpa, Dendra, SupernovaGreen, eYGFP, Gamillus, mEos4b, TagRFP, and circularly permuted versions thereof.

Further preferred fluorescent moieties are proteins that become fluorescent upon covalent binding of a fluorescent or non-fluorescent ligand, more preferably proteins whose sequences have at least 80% identity (or at least 90% identity, or at least 95% identity, or 100% identity) to at least one amino acid sequence selected from amino acid sequences of HALO tag, CLIP tag, SNAP tag, and circularly permuted versions thereof.

Further preferred fluorescent moieties are proteins that become fluorescent upon non-covalent binding of a non-fluorescent ligand. Such proteins are preferably proteins whose sequences have at least 80% identity (or at least 90% identity, or at least 95% identity, or 100% identity) to at least one amino acid sequence selected from amino acid sequences of bacteriophytochrome IFP2.0, allophycocyanin smURFP, fatty acid binding protein UnaG, photoactive yellow protein, and circularly permuted versions thereof.

Particularly preferred fluorescent moieties are eGFP, meGFP, circularly permuted mTurquoise2, mScarlet, SNAP or HALO tag.

The affinity binding moiety is a moiety which binds the target membrane-associated molecule. The affinity binding moiety is preferably selected from affinity binding peptides and affinity binding proteins.

The affinity binding peptides preferably have a length of 30 amino acids or less, preferably 10 to 30 amino acids.

The affinity binding peptides preferably contain a sequence having at least 80% identity (or at least 90% identity, or at least 95% identity, or 100% identity) to the motif Gly-Gly-Val-Trp-Leu-Gly (SEQ ID NO:4), known to bind activated forms of G proteins Gαi.

Further preferred affinity binding peptides have sequences having at least 80% identity (or at least 90% identity, or at least 95% identity, or 100% identity) to at least one sequence selected from the C-terminal amino acid sequences of G proteins Gαi, Gαs, Gαq, Gαi1, and Gα13.

The affinity binding proteins are proteins and protein fragments which bind the target membrane-associated molecule. Affinity binding proteins are selected from single domain antibodies, affinity protein scaffolds and proteins containing or consisting of a domain specifically binding the target molecule.

The single domain antibodies are single domain antibodies binding to the target membrane-associated protein. Preferred single domain antibodies are antibodies against activated forms of G-protein coupled receptors, such as NB80, NB6, NB39 or NB33. Further preferred single domain antibodies are antibodies against activated forms of G proteins, such as NB35 or NB37. Yet further preferred single domain antibodies are antibodies against activated forms of arrestins, such as IB30 or NB32.

The affinity protein scaffolds are protein scaffolds developed to bind target membrane-associated proteins. Preferred affinity protein scaffolds are fibronectins, viral Gp2 proteins, kringle domains, pyrazinamidases, DARPins, knottin miniproteins and Sso7d.

The affinity binding proteins containing or consisting of a domain specifically binding the target molecule are preferably selected from proteins containing or consisting of a pleckstrin homology (PH) domain, such as G-protein receptor kinases (e.g. GRK2ct), pleckstrin, kinases of the Act/Rac family, kinases of the Btk/Itk/Tec family, the insulin receptor substrates (including IRS1), or regulators of small G proteins (such as RhoGEFs). Further affinity binding proteins containing or consisting of a domain specifically binding the target molecule are preferably selected from proteins containing or consisting of the regulator of G-protein signaling homology (RH) domain, such as G-protein receptor kinases (e.g. GRK2) or guanine nucleotide exchange factors (e.g. PDZ-RhoGEF or LARG). Further affinity binding proteins are preferably selected from proteins containing or consisting of Rho binding domain (RBD), such as rhotekin or Rho-associated protein kinases. Further affinity binding proteins are preferably fragments of G proteins (such as C-terminal alpha-helical fragments or miniG-proteins). Further affinity binding proteins are preferably selected from proteins containing or consisting of Cdc42/Rac1 interactive binding (CRIB) domain, such as the p21-activated kinase PAK1. Further affinity binding proteins are preferably selected from proteins containing or consisting of phosphotyrosine binding (PTB) domain, such as IRS1 or tensin. Yet further affinity binding proteins are preferably selected from proteins containing or consisting of p21 binding domain (PBD), such as PAK1. Yet further affinity binding domains are preferably selected from proteins containing or consisting of the Src homology 2 domain (SH2), such as Zap70, STAT1 or AbI1.

Particularly preferred affinity binding moieties are KB1753, NB80, NB33, NB32, GRK2ct, IRS1, PRGrh, rhotekin, or PAK1.

Another aspect of the invention is the use of the probe of the present invention as a detection probe in polarization microscopy (in in vitro techniques).

Polarization microscopy allows obtaining information on molecular orientation, through measurements of fluorescence intensity as a function of polarization of the excitation light or through measurements of intensity of fluorescence of distinct polarizations, or both. Preferably, the probes of the invention are observed by excitation polarization-resolved fluorescence microscopy, using two or more excitation polarizations, preferably by using single-photon or two-photon excitation. In some preferred embodiments, the probes of the invention are observed by fluorescence polarization-resolved microscopy, by observing the intensity of two or more polarizations of the emitted fluorescence, wherein the fluorescence is excited by single-photon or two-photon excitation.

Preferably, the polarization microscopy technique is implemented as wide-field polarization microscopy or as laser-scanning polarization microscopy.

In one embodiment, the probe of the invention is intended for use in observation and/or detection, by polarization microscopy, of the presence of activated forms of G-proteins, activated forms of G-protein coupled receptors, and/or activated forms of receptor tyrosine kinases in vitro.

An advantage of the probe of the invention is that due to its protein structure it can be genetically encoded, and therefore it can be produced directly by the observed cells, or by microorganisms on industrial scale.

The present invention further provides a method of detecting presence or absence of a target membrane-associated molecule ex vivo or in vitro, said method comprising the following steps:

a) providing a probe according to the present invention:

b) contacting the probe with a reference sample comprising cells that do not contain the target membrane-associated molecule;

c) contacting the probe with a test sample comprising cells in which the presence or absence of the target membrane-associated molecule is to be detected;

d) observing the cells in the reference sample and in the test sample by means of polarization microscopy; in particular measuring the linear dichroism and/or fluorescence polarization exhibited by the probes in each sample;

e) quantifying the linear dichroism and/or fluorescence polarization exhibited by the probes in each of the reference sample and test sample;

f) determining whether the linear dichroism and/or fluorescence polarization exhibited by the probes differs between the two samples; wherein when the linear dichroism and/or fluorescence polarization exhibited by the probes differ, it is determined that the target membrane-associated molecule is present in the cells of the test sample; and when the linear dichroism and/or fluorescence polarization exhibited by the probes do not differ, it is determined that the target membrane-associated molecule is absent from the cells of the test sample.

The present invention further provides a method of detecting active or inactive form of a target membrane-associated molecule ex vivo or in vitro, said method comprising the following steps:

a) providing a probe according to the present invention;

b) contacting the probe with a reference sample comprising cells that contain the target membrane-associated molecule either in active form or in inactive form;

c) contacting the probe with a test sample comprising cells in which the active or inactive form of the target membrane-associated molecule is to be detected;

d) observing the cells in the reference sample and in the test sample by means of polarization microscopy; in particular measuring the linear dichroism and/or fluorescence polarization exhibited by the probes in each sample:

e) quantifying the linear dichroism and/or fluorescence polarization exhibited by the probes in each of the reference sample and test sample;

f) determining whether the linear dichroism and/or fluorescence polarization exhibited by the probes differs between the two samples; wherein when the linear dichroism and/or fluorescence polarization exhibited by the probes differ, it is determined that the target membrane-associated molecule is present in the cells of the test sample in a different form than in the reference sample; and when the linear dichroism and/or fluorescence polarization exhibited by the probes do not differ, it is determined that the target membrane-associated molecule is present in the cells of the test sample in the same form as in the reference sample.

The present invention further provides a method of detecting activation or inactivation of a target membrane-associated molecule ex vivo or in vitro, said method comprising the following steps:

a) providing a probe according to the present invention;

b) contacting the probe with a test sample comprising cells in which the active or inactive form of the target membrane-associated molecule is to be detected;

c) observing the cells in the test sample by means of polarization microscopy in at least two time points; in particular measuring the linear dichroism and/or fluorescence polarization exhibited by the probe in each time point;

d) quantifying the linear dichroism and/or fluorescence polarization exhibited by the probe in each time point;

e) determining whether the linear dichroism and/or fluorescence polarization exhibited by the probe differs between the time points: wherein when the linear dichroism and/or fluorescence polarization exhibited by the probes differ between the time points, it is determined that the target membrane-associated molecule in the cells of the test sample has undergone activation or inactivation: and when the linear dichroism and/or fluorescence polarization exhibited by the probes do not differ, it is determined that the target membrane-associated molecule in the cells of the test sample has not undergone activation or inactivation.

In a preferred embodiment, contacting the probe of the invention with samples comprising cells is performed by introducing into the cells a DNA that encodes the probe of invention, in a manner that causes the cells to produce the probe of the invention. This is preferably performed by a method selected from: transfecting the cells with a plasmid encoding the probe of invention, infecting the cells with a virus encoding the probe of invention, introduction of mRNA encoding the probe of invention into the cells, modifying the genomic DNA of the cells by methods of non-targeted or targeted transgenesis such as CRISPR, introduction of the probe using a vesicle.

The cells containing the probe of the invention are preferably observed by excitation polarization resolved fluorescence microscopy, using single- or two-photon excitation and two or more polarizations of excitation light.

Alternatively, the cells containing the probe of the invention are preferably observed by fluorescence polarization resolved microscopy, using single- or two-photon excitation, obtaining information on intensity of two or more polarizations of the emitted fluorescence.

Preferably, parts of the images corresponding to cell membranes are then identified, and the extent of linear dichroism and/or fluorescence polarization in said image parts is quantified by using known procedures and software tools. The extent of linear dichroism and/or fluorescence polarization exhibited by cells in the test sample is compared to the extent of linear dichroism and/or fluorescence polarization exhibited by cells in the reference sample that do not contain the target molecule. A statistically significant difference in the extent of linear dichroism and/or fluorescence polarization between the two cell populations indicates the presence of the target membrane-associated molecule or a different state of the target membrane-associated molecule in the test sample.

The polarization microscopy techniques include excitation polarization resolved fluorescence microscopy and fluorescence polarization resolved fluorescence microscopy.

The excitation polarization resolved fluorescence microscopy techniques include, e.g., excitation polarization resolved laser scanning confocal microscopy, excitation polarization resolved laser scanning two-photon fluorescence microscopy, and excitation polarization resolved wide field fluorescence microscopy.

The fluorescence polarization resolved fluorescence microscopy techniques include. e.g., fluorescence polarization resolved laser scanning confocal fluorescence microscopy and fluorescence polarization resolved wide field fluorescence microscopy.

The probe and the method of invention present several important advantages over state-of-the-art approaches for detecting the presence or absence of a non-labeled target membrane-associated molecule within living cells. Using fluorescence (rather than luminescence) allows facile imaging on individual cells and cellular assemblies. The magnitude of the observed changes in linear dichroism or fluorescence polarization allows imaging at rates allowing real time observations of dynamic molecular processes involving changes in concentration of the target molecule. Since polarization microscopy utilizes a single fluorescent label for detection of a particular molecular event, the probes and method of invention allow, through simultaneous use of multiple probes of different spectral properties, simultaneous observation of multiple molecular events (multiplexing). Implementations of polarization microscopy such as excitation polarization resolved single-photon laser scanning confocal microscopy or excitation polarization resolved two-photon laser scanning microscopy allow observations in thick specimens. Since polarization microscopy is a ratiometric technique, it allows accurate quantitation of the observed phenomena even in presence of photobleaching.

The method of the present invention is particularly useful for observing molecular events of cell signaling, which may further be used in research and developments of diagnostics and medicaments.

Figure 1:
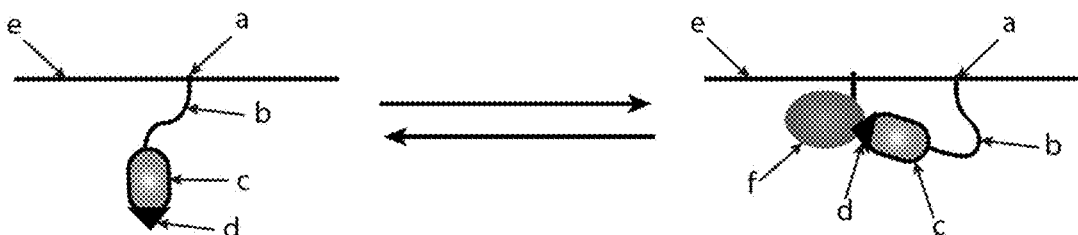
FIG. 1: Schematic illustration of the principle of function of the molecular probes of the invention. a) anchoring moiety of the probe of invention; b) peptide linker moiety of the probe of invention; c) fluorescent moiety of the probe of invention; d) affinity binding moiety of the probe of invention; e) cell membrane; f) target molecule. A change in concentration (presence/absence) or in activation state of the target molecule leads to a change of orientation of a fluorescent moiety within the molecular probe. The change in molecular orientation of the fluorescent moiety is detected by polarization microscopy.

G) Probe of Example 7. H) Probe of Example 8. I) Probe of Example 9. J) Probe of Example 10. K) Probe of Example 11. L) Probe of Example 12. M) Probe of Example 13. N) Probe of Example 14. O) Probe of Example 15. P) Probe of Example 16. Q) Probe of Example 17. R) Probe of Example 18. S) Probe of Example 19. T) Probe of Example 20. U) Probe of Example 21. V) Probe of Example 22. W) Probe of Example 23. X) Probe of Example 24.

EXAMPLES

It is understood that the specific examples of embodiments and uses of the invention described and illustrated below are meant to illustrate preferred embodiments by example, and should in no way be understood as limitations.

Example 1: A Probe for Detection of Presence of an Activated Form of the G-Protein Gαi1 (KB1753-meGFP-GSGGSGG-hRas)

A protein (SEQ ID NO:5) that includes as an anchoring moiety a fragment of the protein h-Ras, a flexible peptide linker (amino acid sequence GSGGSGG (SEQ ID NO:1)), a monomeric enhanced green fluorescent protein (meGFP) as a fluorescent moiety, and an affinity binding peptide KB1753 known to bind the activated form of the G-protein Gαi1 (Johnston C A & al., Structure. 2005 Jul. 1; 13(7):1069-80), was encoded into a DNA sequence (SEQ ID NO:6) and cloned into a mammalian expression vector (pcDNA3.1(+)) under the control of the cytomegalovirus (CMV) promoter. The resulting DNA encoding the probe of invention was transfected into HEK293 cells either alone, or along with DNA encoding the target protein of the probe.

Prior to microscopy observations, mammalian cells (HEK293) were cultured at 37° C. under an atmosphere of 95% air, 5% $CO_2$, in Dulbecco's modified Eagle's medium with Glutamax I and high glucose (Life Technologies), supplemented with 10% fetal bovine serum. Cells were plated on 8-chamber microscopy slides (p-Slides, Ibidi GmbH, Germany). Transfections were carried out using 0.2 μg of plasmid DNA and Lipofectamine 2000 (Life Technologies), according to the protocol of the manufacturer. In cotransfections, 0.2 μg of each of the plasmids were used. Microscopy experiments were carried out 48 h after transfection. Microscopy observations were performed at 37° C., maintained by a heated chamber (iBidi Heating System, iBidi).

The cells were observed by excitation polarization resolved single-photon laser scanning confocal microscopy, by excitation polarization resolved two-photon laser scanning microscopy, by excitation polarization resolved single-photon wide-field fluorescence microscopy, and by fluorescence polarization resolved single-photon laser scanning confocal microscopy.

In excitation polarization resolved single-photon laser scanning confocal microscopy, the cells (in the multi-well cover slip) were observed using a single-photon laser scanning confocal microscope Olympus FV1200, modified for excitation-polarization resolved microscopy. Specifically, the excitation laser beam was passed through an electrooptical polarization modulator (RPM-2P, Innovative Bioimaging, USA) synchronized with the function of the microscope so that the direction of polarization of the laser light was alternated between horizontal and vertical direction (within the image) between acquisition of individual pixels of the image. In order to observe the probes of invention containing the green fluorescent protein (GFP), 488 nm wavelength was used for excitation. Fluorescence of wavelengths in the range of 510-610 nm was separated from the excitation light by a long-pass dichroic mirror (DM405/488, Olympus, Japan), diffractive grating, and an adjustable slit, and detected by a photomultiplier. The samples were imaged by a 40× water immersion lens (UApoN340, NA1.15. Olympus, Japan).

The resulting images were deconvolved and quantitatively analyzed by following published procedures (Bondar A & al., Communications Biology. 2021 Feb. 12; 4(1):1-2.) that rely on publicly available software tools. Briefly, an acquired image, containing in different pixels information on fluorescence intensity excited with distinct polarizations of excitation light was deconvolved into two images, each containing fluorescence intensity excited by one polarization of the excitation light. After background subtraction, an image was generated to show, in each pixel, the base 2 logarithm of the ratio between the values of the corresponding pixels of the images containing information on fluorescence intensity excited with a horizontal and vertical polarization of excitation light. The resulting image was segmented to identify parts that correspond to the cell membrane. A value corresponding to the base 2 logarithm of the maximum dichroic ratio ($log_2(r_{max})$) was determined by fitting the observed values of the base 2 logarithm of the dichroic ratio of values ($log_2(r)$) as a function of cell membrane orientation. Observations using excitation polarization resolved two-photon laser scanning microscopy were made on the same microscopy setup as those made by excitation polarization resolved single-photon laser scanning microscopy. A femtosecond pulsed laser (MaiTai HP 1040, Newport/SpectraPhysics, USA) tuned to 960 nm was used for excitation. Fluorescence was separated from the excitation light by a long-pass dichroic mirror (DM690, Olympus, Japan), and detected by a photomultiplier. Linear dichroism was quantitated in the same fashion as for excitation polarization resolved single-photon laser scanning confocal microscopy.

Observations using excitation polarization resolved single-photon wide-field fluorescence microscopy were made on an inverted fluorescence microscope (Olympus IX83) equipped by a mercury lamp illumination unit and an EM-CCD camera (iXon 888, Andor, Ireland) attached to the side port. The microscope was adapted for polarization microscopy by adding to the optical filter cube assembly a linear polarizer (LPVISA100, Thorlabs, Germany) oriented vertically, and by inserting into the optical component compartment directly under the objective lens turret an achromatic half-wave plate (AHWP05M-580, Thorlabs, Germany) mounted in a piezo-driven motorized rotating mount (ELL14. Thorlabs, Germany). During imaging, rotating the half-wave plate in 45 degree increments allowed alternating the direction of the excitation light polarization between horizontal and vertical (within the acquired image). During microscopy observations of the probes of the invention containing the green fluorescent protein, the illuminating light passed through an excitation filter (Brightline FF02-472/30, Semrock. USA) and was reflected by a dichroic mirror (FF495-Di03-25×36) through the rotatable wave plate into an objective lens (UPLSAPO60XW/1.2, Olympus, Japan). Fluorescence collected by the objective lens passed through the half-wave plate, the dichroic mirror, and a fluorescence filter (FF01-520/35, Semrock, USA) into the camera. Images acquired with distinct excitation polarizations were aligned using the StackReg plugin (Thevenaz, P., et al. (1998). "A pyramid approach to subpixel registration based on intensity." IEEE Trans Image Process 7(1):

27-41), adjusted for bleaching, and quantitatively analyzed as described above for excitation polarization resolved single-photon laser scanning confocal microscopy.

Observations using fluorescence polarization resolved single-photon laser scanning confocal microscopy were made on an inverted laser scanning confocal microscope (Leica SP8), using an HC PLAPO CS2 objective lens (63× magnification, numerical aperture 1.20, water immersion), and 488 nm excitation illumination. Fluorescence (in the wavelength range of 497-570 nm) was detected by a HyD photon counting detector. A polarizer placed in the fluorifier disk in the emission pathway allowed imaging distinct polarizations of the emitted fluorescence. For each observed cell, a pair of images was acquired, of fluorescence polarized parallel and perpendicular to the polarization of the excitation laser beam. Each image was normalized by its average intensity, and fluorescence polarization was quantitated by determining the value of $\log_2(r_{max})$ in the same fashion as described above for linear dichroism observed by excitation polarization resolved single-photon laser scanning confocal microscopy Quantitative analysis of images acquired by all four polarization microscopy techniques shows (FIG. 2A) that in presence of its target molecule, an activated form of Gαi1 (achieved by cotransfection of a plasmid (SEQ ID NO:8) encoding the constitutively activated mutant of Gαi1, Gαi1 (Q204L) (SEQ ID NO:7), under the control of a CMV promoter), the fluorescent moiety of the probe exhibits statistically significantly higher linear dichroism and fluorescence polarization than in the absence of the target molecule.

Example 2: A Probe for Detection of Presence of an Activated Form of the G-Protein Gαi1 (KB1753-meGFP-GSGGSGG-hRas)

A protein (SEQ ID NO:5) that includes as an anchoring moiety a fragment of the protein hRas, a flexible peptide linker (amino acid sequence GSGGSGG (SEQ ID NO:1)), a monomeric enhanced green fluorescent protein (meGFP), and a peptide KB1753 which binds the activated form of the G-protein Gαi1, was encoded into a DNA sequence and cloned into a mammalian expression vector (pcDNA3.1(+)) under the control of the CMV promoter. The resulting DNA (SEQ ID NO:6), along with DNAs encoding the G protein subunits Gαi1, Gβ1, Gγ2, and the α2-adrenergic receptor (protein sequences SEQ ID NO:57, 59, 61 and 63; DNA sequences SEQ ID NO:58, 60, 62 and 64) were transfected into HEK293 cells as described in Example 1.

Figure 2:
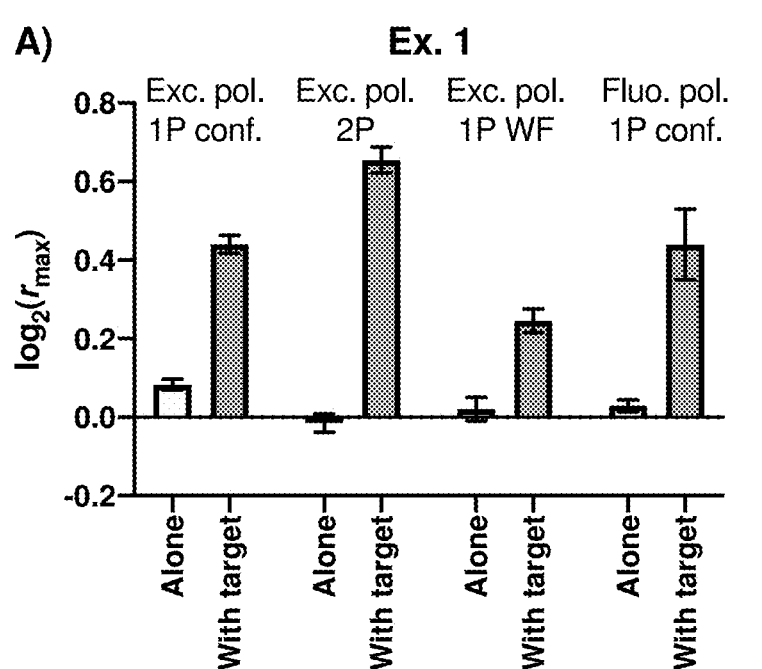
FIG. 2: Extent of linear dichroism or fluorescence polarization, expressed as $Log_2(r_{max})$, of the probes according to examples 1-22, in presence or absence of the corresponding target membrane-associated proteins. Error bars indicate 95% confidence intervals. A) Probe of Example 1, observed (from left to right) by excitation polarization resolved single-photon laser scanning confocal microscopy; by excitation polarization resolved two-photon laser scanning microscopy; by excitation polarization resolved wide field fluorescence microscopy; and by fluorescence polarization resolved single-photon laser scanning confocal microscopy. B) Probe of Example 2. C) Probe of Example 3. D) Probe of Example 4. E) Probe of Example 5. F) Probe of Example 6.
Figure 2:
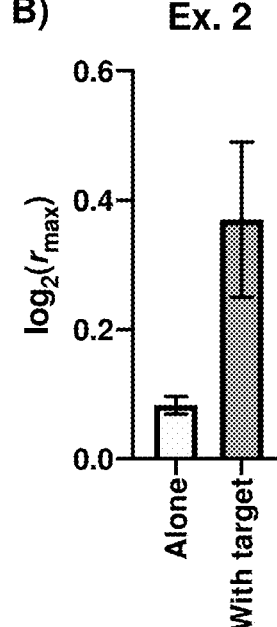
Figure 2:
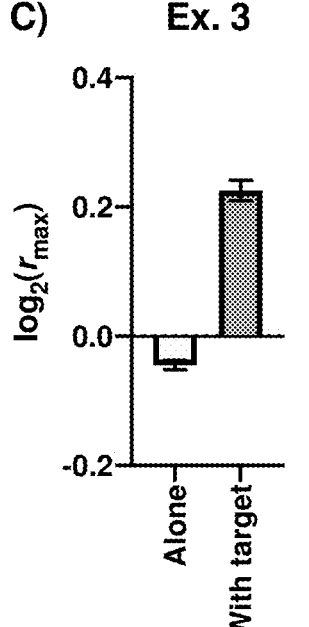
Figure 2:
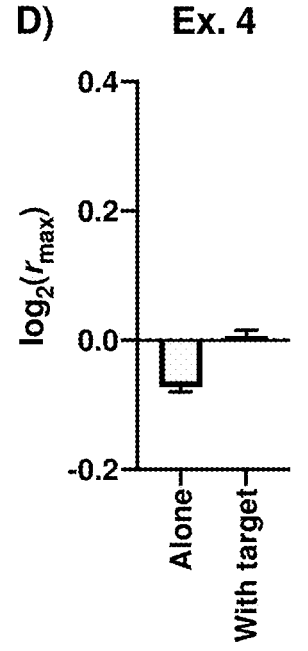
Figure 2:
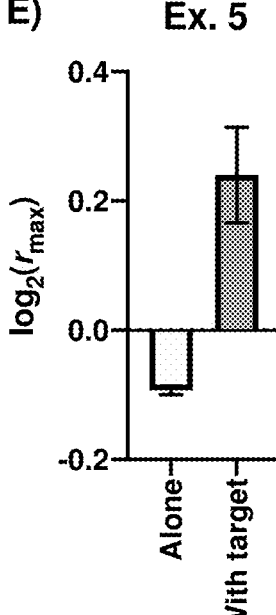

The cells were observed by excitation polarization resolved single-photon laser scanning confocal microscopy, as described in Example 1. In presence of its target molecule, an activated form of Gαi1 (achieved by application of 10 μM norepinephrine, known to activate the α2-adrenergic receptor which, in turn, activates the Gαi1 signaling pathway), the fluorescent moiety of the probe exhibits statistically significantly higher linear dichroism than in the absence of the activated form of Gαi1, the probe's target molecule (FIG. 2B).

Example 3: A Probe for Detection of Presence of an Activated Form of the G-Protein Gαi1 (KB1753-meGFP-GSGGSGG-kRas)

A protein (SEQ ID NO:9) that includes as an anchoring moiety a fragment of the protein kRas, a flexible peptide linker (amino acid sequence GSGGSGG (SEQ ID NO:1)), a monomeric enhanced green fluorescent protein (meGFP), and a peptide KB1753 which binds the activated form of the G-protein Gαi1, was encoded into a DNA sequence and cloned into a mammalian expression vector (pcDNA3.1(+)) under the control of the CMV promoter. The resulting DNA (SEQ ID NO:10) was transfected into HEK293 cells as described in Example 1. The cells were observed by excitation polarization resolved single-photon laser scanning confocal microscopy. In presence of its target molecule, an activated form of Gαi1 (achieved by cotransfection of a plasmid (SEQ ID NO:8) encoding the constitutively activated mutant of Gαi1, Gαi1(Q204L) (SEQ ID NO:7), under the control of a CMV promoter), the fluorescent moiety of the probe exhibits statistically significantly higher linear dichroism than in the absence of the target molecule (FIG. 2C).

Example 4: A Probe for Detection of Presence of an Activated Form of the G-Protein Gαi1 (GAP43-SSGSSGTG-meGFP-KB1753)

A protein (SEQ ID NO: 11) that includes as an anchoring moiety a fragment of the protein GAP43, a flexible peptide linker (amino acid sequence SSGSSGTG (SEQ ID NO:2)), a monomeric enhanced green fluorescent protein (meGFP), and a peptide KB1753 which binds the activated form of the G-protein Gαi1, was encoded into a DNA sequence and cloned into a mammalian expression vector (pcDNA3.1(+)) under the control of the CMV promoter. The resulting plasmid (SEQ ID NO:12) was transfected into HEK293 cells as described in Example 1. The cells were observed by excitation polarization resolved single-photon laser scanning confocal microscopy, as described in Example 1. In presence of its target molecule, an activated form of Gαi1 (achieved by cotransfection of a plasmid (SEQ ID NO:8) encoding the constitutively activated mutant of Gαi1, Gαi1 (Q204L) (SEQ ID NO:7), under the control of a CMV promoter), the fluorescent moiety of the probe exhibits statistically significantly higher linear dichroism than in the absence of the target molecule (FIG. 2D).

Example 5: A Probe for Detection of Presence of an Activated Form of the G-Protein Gαi1 (IL4R-SSGSSGTG-meGFP-KB1753)

A protein (SEQ ID NO:13) that includes as an anchoring moiety a transmembrane α-helix from the monotopic membrane protein interleukin 4 receptor (L4R), a flexible peptide linker (amino acid sequence SSGSSGTG, SEQ ID NO:2), a monomeric enhanced green fluorescent protein (meGFP), and a peptide KB1753 which binds the activated form of the G-protein Gαi1, was encoded into a DNA sequence and cloned into a mammalian expression vector (pcDNA3.1(+)) under the control of the CMV promoter. The resulting plasmid (SEQ ID NO:14) was transfected into HEK293 cells as described in Example 1. The cells were observed by excitation polarization resolved single-photon laser scanning confocal microscopy, as described in Example 1. In presence of its target molecule, an activated form of Gαi1 (achieved by cotransfection of a plasmid (SEQ ID NO:8) encoding the constitutively activated mutant of Gαi1, Gαi1 (Q204L) (SEQ ID NO:7), under the control of a CMV promoter), the fluorescent moiety of the probe exhibits statistically significantly higher linear dichroism than in the absence of the target molecule (FIG. 2E).

Example 6: A Probe for Detection of Presence of an Activated Form of the G-Protein Gαi1 (KB1753-meGFP-GS24-hRas)

A protein (SEQ ID NO:15) that includes as an anchoring moiety a fragment of the protein h-Ras, a flexible peptide linker (amino acid sequence GSKSSGSGSESKSTGK-STGSGTETGGS, SEQ ID NO:3), a monomeric enhanced green fluorescent protein (meGFP), and a peptide KB1753 which binds the activated form of the G-protein Gαi1, was encoded into a DNA sequence and cloned into a mammalian expression vector (pcDNA3.1(+)) under the control of the CMV promoter. The resulting DNA (SEQ ID NO:16) was transfected into HEK293 cells as described in Example 1. The cells were observed by excitation polarization resolved single-photon laser scanning confocal microscopy, as described in Example 1. In presence of its target molecule, an activated form of Gαi1 (achieved by cotransfection of a plasmid (SEQ ID NO:8) encoding the constitutively activated mutant of Gαi1, Gαi1(Q204L) (SEQ ID NO:7), under the control of a CMV promoter), the fluorescent moiety of the probe exhibits statistically significantly higher linear dichroism than in the absence of the target molecule (FIG. 2F).

Example 7: A Probe for Detection of Presence of an Activated Form of the G-Protein Gαi1 (KB1753-mScarlet-GSGGSGG-hRas)

A protein (SEQ ID NO:17) that includes as an anchoring moiety a fragment of the protein hRas, a flexible peptide linker (amino acid sequence GSGGSGG (SEQ ID NO:1)), a fluorescent protein mScarlet, and a peptide KB1753 which binds the activated form of the G-protein Gαi1, was encoded into a DNA sequence and cloned into a mammalian expression vector (pcDNA3.1(+)) under the control of the CMV promoter. The resulting plasmid (SEQ ID NO: 18) was transfected into HEK293 cells as described in Example 1. The cells were observed by excitation polarization resolved single-photon laser scanning confocal microscopy as described in Example 1, but using excitation light of 543 nm wavelength, and detecting fluorescence of wavelengths 560-600 nm. In presence of its target molecule, an activated form of Gαi1 (achieved by cotransfection of a plasmid (SEQ ID NO:8) encoding the constitutively activated mutant of Gαi1, Gαi1(Q204L) (SEQ ID NO:7), under the control of a CMV promoter), the fluorescent moiety of the probe exhibits statistically significantly higher linear dichroism than in the absence of the target molecule (FIG. 2G).

Example 8: A Probe for Detection of Presence of an Activated Form of the G-Protein Gαi1 (KB1753-mScarlet-GSGGSGG-hRas)

A protein (SEQ ID NO:17) that includes as an anchoring moiety a fragment of the protein hRas, a flexible peptide linker (amino acid sequence GSGGSGG (SEQ ID NO:1)), a fluorescent protein mScarlet, and a peptide KB1753 which binds the activated form of the G-protein Gαi1, was encoded into a DNA sequence and cloned into a mammalian expression vector (pcDNA3.1(+)) under the control of the CMV promoter. The resulting plasmid (SEQ ID NO:18), along with DNAs encoding the G protein subunits Gαi1, Gβ1, Gγ2, and the α2-adrenergic receptor (protein sequences SEQ ID NO:57, 59, 61 and 63; DNA sequences SEQ ID NO:58, 60, 62 and 64) were transfected into HEK293 cells as described in Example 1. The cells were observed by excitation polarization resolved single-photon laser scanning confocal microscopy as described in Example 1, but using excitation light of 543 nm wavelength, and detecting fluorescence of wavelengths 560-600 nm. In presence of its target molecule, an activated form of Gαi1 (achieved by application of 10 μM norepinephrine, known to activate the α2-adrenergic receptor which, in turn, activates the Gαi1 signaling pathway), the fluorescent moiety of the probe exhibits statistically significantly higher linear dichroism than in the absence of the activated form of Gαi1, the probe's target molecule (FIG. 2H).

Example 9: A Probe for Detection of Presence of an Activated Form of the G-Protein Gαi1 (KB1753-cpmTurquoise2-GSGGSGG-hRas)

A protein (SEQ ID NO:19) that includes as an anchoring moiety a fragment of the protein hRas, a flexible peptide linker (amino acid sequence GSGGSGG (SEQ ID NO:1)), a fluorescent protein circularly permuted mTurquoise2, and a peptide KB1753 which binds the activated form of the G-protein Gαi1, was encoded into a DNA sequence and cloned into a mammalian expression vector (pcDNA3.1(+)) under the control of the CMV promoter. The resulting plasmid (SEQ ID NO:20) was transfected into HEK293 cells as described in Example 1. The cells were observed by excitation polarization resolved single-photon laser scanning confocal microscopy as described in Example 1, but using excitation light of 458 nm wavelength, and detecting fluorescence of wavelengths 480-550 nm. In presence of its target molecule, an activated form of Gαi1 (achieved by cotransfection of a plasmid (SEQ ID NO:8) encoding the constitutively activated mutant of Gαi1, Gαi1(Q204L) (SEQ ID NO:7), under the control of a CMV promoter), the fluorescent moiety of the probe exhibits statistically significantly higher linear dichroism than in the absence of the target molecule (FIG. 2I).

Example 10: A Probe for Detection of Presence of an Activated Form of the G-Protein Gαi1 (KB1753-HALO-GSGGSGG-hRas)

A protein (SEQ ID NO:21) that includes as an anchoring moiety a fragment of the protein hRas, a flexible peptide linker (amino acid sequence GSGGSGG (SEQ ID NO:1)), a fluorogenic protein (HALO) based on haloalkane dehalogenase, and a peptide KB1753 which binds the activated form of the G-protein Gαi1, was encoded into a DNA sequence and cloned into a mammalian expression vector (pcDNA3.1 (+)) under the control of the CMV promoter. The resulting plasmid (SEQ ID NO:22) was transfected into HEK293 cells as described in Example 1. The fluorogenic protein tag was made fluorescent by treatment with the fluorescent dye JF-549 (purchased from Promega Corp.). The cells were observed by excitation polarization resolved single-photon laser scanning confocal microscopy as described in Example 1, but using excitation light of 543 nm wavelength, and detecting fluorescence of wavelengths 560-600 nm. In presence of its target molecule, an activated form of Gαi1 (achieved by cotransfection of a plasmid (SEQ ID NO:8) encoding the constitutively activated mutant of Gαi1, Gαi1 (Q204L) (SEQ ID NO:7), under the control of a CMV promoter), the fluorescent moiety of the probe exhibits statistically significantly lower linear dichroism than in the absence of the target molecule (FIG. 2J).

Example 11: A Probe for Detection of Presence of an Activated Form of the G-Protein Gαi1 (KB1753-HALO-GSGGSGG-hRas)

A protein (SEQ ID NO:21) that includes as an anchoring moiety a fragment of the protein hRas, a flexible peptide linker (amino acid sequence GSGGSGG (SEQ ID NO:1)), a fluorogenic protein (HALO) based on haloalkane dehalogenase, and a peptide KB1753 which binds the activated form of the G-protein Gαi1, was encoded into a DNA sequence and cloned into a mammalian expression vector (pcDNA3.1 (+)) under the control of the CMV promoter. The resulting plasmid (SEQ ID NO:22), along with DNAs encoding the G protein subunits Gαi1, Gβ1, Gγ2, and the α2-adrenergic receptor (protein sequences SEQ ID NO:57, 59, 61 and 63; DNA sequences SEQ ID NO:58, 60, 62 and 64) were transfected into HEK293 cells as described in Example 1. The fluorogenic protein tag was made fluorescent by treatment with the fluorescent dye JF-549 (purchased from Promega Corp). The cells were observed by excitation polarization resolved single-photon laser scanning confocal microscopy as described in Example 1, but using excitation light of 543 nm wavelength, and detecting fluorescence of wavelengths 560-600 nm. The cells were observed by excitation polarization resolved single-photon laser scanning confocal microscopy, as described in Example 1. In presence of its target molecule, an activated form of Gαi1 (achieved by application of 10 µM norepinephrine, known to activate the α2-adrenergic receptor which, in turn, activates the Gαi1 signaling pathway), the fluorescent moiety of the probe exhibits statistically significantly lower linear dichroism than in the absence of the activated form of Gαi1, the probe's target molecule (FIG. 2K).

Example 12: A Probe for Detection of Presence of an Activated Form of the G-Protein Gαi1 (KB1753-SNAP-GSGGSGG-hRas)

A protein (SEQ ID NO:23) that includes as an anchoring moiety a fragment of the protein hRas, a flexible peptide linker (amino acid sequence GSGGSGG (SEQ ID NO:1)), a fluorogenic protein (SNAP) based on alkylguanine-DNA alkyltransferase, and a peptide KB1753 which binds the activated form of the G-protein Gαi1, was encoded into a DNA sequence and cloned into a mammalian expression vector (pcDNA3.1(+)) under the control of the CMV promoter. The resulting plasmid (SEQ ID NO:24) was transfected into HEK293 cells as described in Example 1. The fluorogenic protein tag was made fluorescent by treatment with the fluorescent dye SNAP Cell 430 (purchased from New England Biolabs). The cells were observed by excitation polarization resolved single-photon laser scanning confocal microscopy as described in Example 1, but using excitation light of 405 nm wavelength, and detecting fluorescence of wavelengths 430-530 nm. In presence of its target molecule, an activated form of Gαi1 (achieved by cotransfection of a plasmid (SEQ ID NO:8) encoding the constitutively activated mutant of Gαi1, Gαi1(Q204L) (SEQ ID NO:7), under the control of a CMV promoter), the fluorescent moiety of the probe exhibits statistically significantly higher linear dichroism than in the absence of the target molecule (FIG. 2L).

Example 13: A Probe for Detection of Presence of an Activated Form of the β2-Adrenergic Receptor (NB80-meGFP-GSGGSGG-hRas)

A protein molecule (SEQ ID NO:25) that includes as an anchoring moiety a fragment of the protein hRas, a flexible peptide linker (amino acid sequence GSGGSGG (SEQ ID NO:1)), a monomeric enhanced green fluorescent protein (meGFP), and an affinity binding moiety (a single-domain antibody NB-80 capable of binding the activated form of β2-adrenergic receptor, was encoded into a DNA sequence and cloned into a mammalian expression vector (pcDNA3.1 (+)) under the control of the CMV promoter. The resulting plasmid (SEQ ID NO:26) was transfected into HEK293 cells as described in Example 1. The cells were observed by excitation polarization resolved single-photon laser scanning confocal microscopy as described in Example 1. In presence of its target molecule, an activated form of the β2-adrenergic receptor (achieved by cotransfection of a plasmid (SEQ ID NO:28) encoding the fp2-adrenergic receptor (SEQ ID NO:27) under the control of a CMV promoter and treatment of the observed cells by 10 µM norepinephrine), the fluorescent moiety of the probe exhibits statistically significantly lower linear dichroism than in the absence of the target molecule (FIG. 2M).

Example 14: A Molecular Probe for Detection of Presence of an Activated Form of the β2-Adrenergic Receptor (β2AR-SSGSSGTG-meGFP-NB80)

A protein molecule (SEQ ID NO:29) that includes the β2-a drenergic receptor (containing 7 transmembrane a-helical domains) as the membrane anchoring moiety, a flexible peptide linker (amino acid sequence SSGSSGTG, SEQ ID NO:2), a monomeric enhanced green fluorescent protein (meGFP), and an affinity binding moiety (a single-domain antibody termed NB-80 known to bind the activated form of the β2-adrenergic receptor, was encoded into a DNA sequence and cloned into a mammalian expression vector (pcDNA3.1(+)) under the control of the CMV promoter. The resulting plasmid (SEQ ID NO:30) was transfected into HEK293 cells as described in Example 1. The cells were observed by excitation polarization resolved single-photon laser scanning confocal microscopy as described in Example 1. In presence of its target molecule, an activated form of the β2-adrenergic receptor (achieved by application of 10 uM norepinephrine), the fluorescent moiety of the probe exhibits statistically significantly higher linear dichroism than in the absence of the target molecule. (FIG. 2N).

Example 15: a Probe for Detection of Presence of an Activated Form of the µ-Opioid Receptor (NB33-meGFP-GSGGSGG-hRas)

A protein molecule (SEQ ID NO:31) that includes as an anchoring moiety a fragment of the protein hRas, a flexible peptide linker (amino acid sequence GSGGSGG (SEQ ID NO:1)), a monomeric enhanced green fluorescent protein (meGFP), and an affinity binding moiety (a single-domain antibody NB-33 capable of binding the activated form of µ-opioid receptor, was encoded into a DNA sequence and cloned into a mammalian expression vector (pcDNA3.1(+)) under the control of the CMV promoter. The resulting plasmid (SEQ ID NO:32) was transfected into HEK293 cells as described in Example 1. The cells were observed by excitation polarization resolved single-photon laser scanning confocal microscopy as described in Example 1. In presence of its target molecule, an activated form of the µ-opioid receptor (achieved by cotransfection of a plasmid (SEQ ID NO:34) encoding the p-opioid receptor (SEQ ID NO:33) under the control of a CMV promoter and treatment of the observed cells by 10 µM DAMGO), the fluorescent moiety of the probe exhibits statistically significantly lower linear dichroism than in the absence of the target molecule (FIG. 2O).

Example 16: A Probe for Detection of Presence of an Activated Form of the μ-Opioid Receptor (GAP43-SSGSSGTG-meGFP-NB33)

A protein molecule (SEQ ID NO:35) that includes as an anchoring moiety a fragment of the protein GAP43, a flexible peptide linker (amino acid sequence SSGSSGTG (SEQ ID NO:2)), a monomeric enhanced green fluorescent protein (meGFP), and an affinity binding moiety (a single-domain antibody NB-33 capable of binding the activated form of μ-opioid receptor, was encoded into a DNA sequence and cloned into a mammalian expression vector (pcDNA3.1(+)) under the control of the CMV promoter. The resulting plasmid (SEQ ID NO:36) was transfected into HEK293 cells as described in Example 1. The cells were observed by excitation polarization resolved single-photon laser scanning confocal microscopy as described in Example 1. In presence of its target molecule, an activated form of the μ-opioid receptor (achieved by cotransfection of a plasmid (SEQ ID NO:34) encoding the μ-opioid receptor (SEQ ID NO:33) under the control of a CMV promoter and treatment of the observed cells by 10 μM DAMGO), the fluorescent moiety of the probe exhibits statistically significantly lower linear dichroism than in the absence of the target molecule (FIG. 2P).

Example 17: A Probe for Detection of Presence of GβGγ Dimer (GAP43-SSGSSGTG-meGFP-GRK2ct)

A protein (SEQ ID NO:37) that includes as an anchoring moiety a fragment of the protein GAP43, a flexible peptide linker (amino acid sequence SSGSSGTG (SEQ ID NO:2)), a monomeric enhanced green fluorescent protein (meGFP), and as an affinity binding moiety a fragment of the G-protein-coupled receptor kinase 2 containing the pleckstrin homology (PH) domain capable of binding the GβGγ dimer, was encoded into a DNA sequence and cloned into a mammalian expression vector (pcDNA3.1(+)) under the control of the CMV promoter. The resulting plasmid (SEQ ID NO:38) was transfected into HEK293 cells as described in Example 1. The cells were observed by excitation polarization resolved single-photon laser scanning confocal microscopy as described in Example 1. In presence of its target molecule, the GβGγ dimer (SEQ ID NO:59 and 61, respectively) (achieved by cotransfection of plasmids encoding the Gβ1 and Gβ2 proteins (SEQ ID NO:60 and 62, respectively) under the control of a CMV promoter), the fluorescent moiety of the probe exhibits statistically significantly lower linear dichroism than in the absence of the target molecule (FIG. 2Q).

Example 18: A Probe for Detection of Presence of GβGγ Dimer (GAP43-SSGSSGTG-HALO-GRK2ct)

A protein (SEQ ID NO:39) that includes as an anchoring moiety a fragment of the protein GAP43, a flexible peptide linker (amino acid sequence SSGSSGTG (SEQ ID NO:2)), a fluorogenic protein (HALO), and as an affinity binding moiety a fragment of the G-protein-coupled receptor kinase 2 containing the pleckstrin homology (PH) domain capable of binding the GβGγ dimer, was encoded into a DNA sequence and cloned into a mammalian expression vector (pcDNA3.1(+)) under the control of the CMV promoter. The resulting plasmid (SEQ ID NO:40) was transfected into HEK293 cells as described in Example 1. The fluorogenic protein tag was made fluorescent by treatment with the fluorescent dye JF-549 (purchased from Promega Corp.). The cells were observed by excitation polarization resolved single-photon laser scanning confocal microscopy as described in Example 10. In presence of its target molecule, the GβGγ diner (SEQ ID NO:59 and 61, respectively) (achieved by cotransfection of plasmids encoding the Gβ1 and Gβ2 proteins (SEQ ID NO:60 and 62, respectively) under the control of a CMV promoter), the fluorescent moiety of the probe exhibits statistically significantly higher linear dichroism than in the absence of the target molecule (FIG. 2R).

Example 19: A Probe for Detection of Presence of the Activated Form of the G-Protein Gα13 (GAP43-SSGSSGTG-meGFP-PRGrh)

A protein (SEQ ID NO:41) that includes as an anchoring moiety a fragment of the protein GAP43, a flexible peptide linker (amino acid sequence SSGSSGTG (SEQ ID NO:2)), a monomeric enhanced green fluorescent protein (meGFP), and as an affinity binding moiety a fragment of the PDZ-Rho guanine nucleotide exchange factor (PDZ-RhoGEF) containing the regulator of G-protein signaling homology (RH) domain capable of binding the activated form of the G-protein Gα13, was encoded into a DNA sequence and cloned into a mammalian expression vector (pcDNA3.1(+)) under the control of the CMV promoter. The resulting plasmid (SEQ ID NO:42) was transfected into HEK293 cells as described in Example 1. The cells were observed by excitation polarization resolved single-photon laser scanning confocal microscopy as described in Example 1. In presence of its target molecule, an activated form of Gα13 (achieved by cotransfection of a plasmid (SEQ ID NO:44) encoding the constitutively activated mutant of Gα13, Gα13(Q226L) (SEQ ID NO:43), under the control of a CMV promoter), the fluorescent moiety of the probe exhibits statistically significantly lower linear dichroism than in the absence of the target molecule (FIG. 2S).

Example 20: A Probe for Detection of Presence of the Activated Form of the Small GTPase RhoA (rhotekin-meGFP-GSGGSGG-hRas)

A protein molecule (SEQ ID NO:45) that includes as an anchoring moiety a fragment of the protein hRas, a flexible peptide linker (amino acid sequence GSGGSGG (SEQ ID NO:1)), a monomeric enhanced green fluorescent protein (meGFP), and a fragment of rhotekin containing the Rho-binding (RB) domain capable of binding the activated form the small GTPase Rho, was encoded into a DNA sequence and cloned into a mammalian expression vector (pcDNA3.1 (+)) under the control of the CMV promoter. The resulting plasmid (SEQ ID NO:46) was transfected into HEK293 cells as described in Example 1. The cells were observed by excitation polarization resolved single-photon laser scanning confocal microscopy as described in Example 1. In presence of its target molecule, an activated form of the small GTPase RhoA, achieved by cotransfection of a plasmid (SEQ ID NO:48) encoding the constitutively activated mutant of RhoA, RhoA(Q63L) (SEQ ID NO:47), under the control of a CMV promoter), the fluorescent moiety of the probe exhibits statistically significantly higher linear dichroism than in the absence of the target molecule (FIG. 2T).

Example 21: A Probe for Detection of Presence of the Activated Form of the Small GTPase Rac1 (GAP43-SSGSSGTG-meGFP-Δ6-PAK1)

A protein (SEQ ID NO:49) that includes as an anchoring moiety a fragment of the protein GAP43, a flexible peptide linker (amino acid sequence SSGSSGTG (SEQ ID NO:2)), a monomeric enhanced green fluorescent protein (meGFP), and as an affinity binding moiety a fragment of P21-activated kinase PAK1 containing the Cdc42/Rac1 interactive binding (CRIB) domain capable of binding the activated form of the small GTPase Rac1, was encoded into a DNA sequence and cloned into a mammalian expression vector (pcDNA3.1(+)) under the control of the CMV promoter. The resulting plasmid (SEQ ID NO:50) was transfected into HEK293 cells as described in Example 1. The cells were observed by excitation polarization resolved single-photon laser scanning confocal microscopy as described in Example 1. In presence of its target molecule, an activated form of the small GTPase Rac1 (achieved by cotransfection of a plasmid (SEQ ID NO:52) encoding the constitutively activated mutant of Rac1, Rac1(Q61L) (SEQ ID NO:51), under the control of a CMV promoter), the fluorescent moiety of the probe exhibits statistically significantly lower linear dichroism than in the absence of the target molecule (FIG. 2U).

Example 22: A Probe for Detection of Presence of the Activated Form of the Insulin Receptor 1 (GAP43-SSGSSGTG-meGFP-IRS1)

A protein (SEQ ID NO:53) that includes as an anchoring moiety a fragment of the protein GAP43, a flexible peptide linker (amino acid sequence SSGSSGTG (SEQ ID NO:2)), a monomeric enhanced green fluorescent protein (meGFP), and a protein (IRS1) capable of binding the activated form of insulin receptor 1 (type of receptor tyrosine kinase), was encoded into a DNA sequence and cloned into a mammalian expression vector (pcDNA3.1(+)) under the control of the CMV promoter. The resulting plasmid (SEQ ID NO:54) was transfected into HEK293 cells as described in Example 1. The cells were observed by excitation polarization resolved single-photon laser scanning confocal microscopy as described in Example 1. In presence of its target molecule, the activated form of the insulin receptor 1 (achieved by cotransfection of a plasmid (SEQ ID NO:56) encoding the insulin receptor 1 (SEQ ID NO:55) under the control of a CMV promoter, activated by the presence of 5% fetal bovine serum containing natural levels of insulin), the fluorescent moiety of the probe exhibits statistically significantly lower linear dichroism than in the absence of the target molecule (FIG. 2V).

Example 23: A Probe for Detection of Presence of an Activated Form of the Muscarinic Acetylcholine Receptor (NB9_20-meGFP-GSGGSGG-hRas)

A protein molecule (SEQ ID NO:66) that includes as an anchoring moiety a fragment of the protein hRas, a flexible peptide linker (amino acid sequence GSGGSGG (SEQ ID NO:1)), a monomeric enhanced green fluorescent protein (meGFP), and an affinity binding moiety (a single-domain antibody NB-9_20 capable of binding the activated form of muscarinic acetylcholine receptor, was encoded into a DNA sequence and cloned into a mammalian expression vector (pcDNA3.1(+)) under the control of the CMV promoter. The resulting plasmid (SEQ ID NO:67) was transfected into HEK293 cells as described in Example 1. The cells were observed by excitation polarization resolved single-photon laser scanning confocal microscopy as described in Example 1. In presence of its target molecule, an activated form of the muscarinic acetylcholine receptor (achieved by cotransfection of a plasmid (SEQ ID NO:69) encoding the muscarinic acetylcholine receptor (SEQ ID NO:68) under the control of a CMV promoter), the fluorescent moiety of the probe exhibits statistically significantly lower linear dichroism than in the absence of the target molecule (FIG. 2W).

Example 24: A Probe for Detection of Presence of an Activated Form of the β-Arrestin 2 (NB32-meGFP-GSGGSGG-hRas)

A protein molecule (SEQ ID NO:70) that includes as an anchoring moiety a fragment of the protein hRas, a flexible peptide linker (amino acid sequence GSGGSGG (SEQ ID NO:1)), a monomeric enhanced green fluorescent protein (meGFP), and an affinity binding moiety (a single-domain antibody NB-32 capable of binding the activated form of β-arrestins was encoded into a DNA sequence and cloned into a mammalian expression vector (pcDNA3.1(+)) under the control of the CMV promoter. The resulting plasmid (SEQ ID NO:71) was transfected into HEK293 cells as described in Example 1. The cells were observed by excitation polarization resolved single-photon laser scanning confocal microscopy as described in Example 1. In presence of its target molecule, an activated form of the β-arrestin 2 (achieved by cotransfection of a plasmid (SEQ ID NO:73) encoding β-arrestin 2 (SEQ ID NO:72) under the control of a CMV promoter and another plasmid (SEQ ID NO:75) encoding the vasopressin receptor (SEQ ID NO:74) under the control of a CMV promoter and treatment of the observed cells by 10 μM vasopressin), the fluorescent moiety of the probe exhibits statistically significantly higher dichroism than in the absence of the target molecule (FIG. 2X).

Protein Sequences Used in the Examples:

In the protein sequences of the probes listed below, bold text indicates an affinity binding moiety of claim 1, italic text indicates a fluorescent moiety of claim 1, underlined text indicates a peptide linker moiety of claim 1, and regular text indicates an anchoring moiety of claim 1. Protein sequences of molecules to be detected bear no markup.

SEQ ID NO: 5 (KB1753-meGFP-GSGGSGG-hRas):

MSSRGYYHGIWVGEEGRLSRGKGEELFTGVVPILVELDGDVNGHKFSVSGEGEGDATYGKLTL

KFICTTGKLPVPWPTLVTTLTYGVQCFSRYPDHMKRHDFFKSAMPEGYVQERTIFFKDDGNYKTRA

EVKFEGDYLVNRIELKGIDFKEDGNILGHKLEYNYNSHNVYIMADKQKNGIKANFKIRHNIESGGVQ

*LADHYQQNTPIGDGPVLLPDNHYLSTQSKLSKDPNEKRDHMVLKERVTAAGITHGMDELYKGSGG*

*SGGCMSCKCVLS*

SEQ ID NO: 7 (Gαi1(Q204L)):
MGCTLSAEDKAAVERSKMIDRNLREDGEKAAREVKLLLLGAGESGKSTIVKQMKIIHEAGYS

EEECKQYKAVVYSNTIQSIIAIIRAMGRLKIDFGDSARADDARQLFVLAGAAEEGFMTAELAG

VIKRLWKDSGVQACFNRSREYQLNDSAAYYLNDLDRIAQPNYIPTQQDVLRTRVKTTGIVET

HFTFKDLHFKMFDVGGLRSERKKWIHCFEGVTAIIFCVALSDYDLVLAEDEEMNRMHESMKL

FDSICNNKWFTDTSIILFLNKKDLFEEKIKKSPLTICYPEYAGSNTYEEAAAYIQCQFEDLNKRK

DTKEIYTHFTCATDTKNVQFVFDAVTDVIIKNNLKDCGLF

SEQ ID NO: 9 (KB1753-mcGFP-GSGGSGG-kRas):
MSSRGYYHGIWVGEEGRLSR*GKGEELFTGVVPILVELDGDVNGHKFSVSGEGEGDATYGKLTL*

*KFICTYGKLPVPWPTLVTTLTYGVQCFSRYPDHMKRHDFFKSAMPEGYVQERTIFFKDDGNYKTRA*

*EVKFEGDTLVNRIELKGIDFKEDGNILGHKLEYNYNSHNVYIMADKQKNGIKANFKIRHNIESGGVQ*

*LADHYQQNTPIGDGPVLLPDNHYLSTQSKLSKDPNEKRDHMVLKERVTAAGITHGMDELYKGSGG*

*SGGKKKKKKSKTKCVIM*

SEQ ID NO: 11 (GAP43-SSGSSGTG-mcGFP-KB1753):
MLCCMRRTKQVEKNDEDQN*SSGSSGTGSKGEELFTGVVPILVELDGDVNGHKFSVSGEGEGDA*

*TYGKLTLKFICTTGKLPVPWPTLVTTLTYGVQCFSRYPDHMKRHDFFKSAMPEGYVQERTIFFKDD*

*GNYKTRAEVKFEGDTLVNRIELKGIDFKEDGNILGHKLEYNYNSHNVYIMADKQKNGIKANFKIRH*

*NIESGGVQLADHYQQNTPIGDGPVLLPDNHYLSTQSKLSKDPNEKRDHMVLKERVTAAGITHGMD*

*ELYK*GSSRGYYHGIWVGEEGRLSRG

SEQ ID NO: 13 (IL4R-SSGSSGTG-meGFP-KB1753):
MAAGPRTSLLLAFALLCLPWTNGGVAFPAMSSDPDGTDTEQHLLLGVSVSCIVILAVCLLCY

VSITVEKNDEDQN*SSGSSGTGSKGEELFTGVVPILVELDGDVNGHKFSVSGEGEGDATYGKLTLK*

*FICTTGKLPVPWPTLVTTLTYGVQCFSRYPDHMKRHDFFKSAMPEGYVQERTIFFKDDGNYKTRAE*

*VKFEGDTLVNRIELKGIDFKEDGNILGHKLEYNYNSHNVYIMADKQKNGIKANFKIRHNIESGGVQL*

*ADHYQQNTPIGDGPVLLPDNHYLSTQSKLSKDPNEKRDHX1VLKERVTAAGITHGMDELFA*GSSR

GYYHGIWVGEEGRLSRG

SEQ ID NO: 15 (KB1753-meGFP-GS24-hRas):
MSSRGYYHGIWVGEEGRLS*RGKGEELFTGVVPILVELDGDVNGHKFSVSGEGEGDATYGKLTL*

*KFICTTGKLPVPWPTLVTTLTYGVQCFSRYPDHMKRHDFFKSAMPEGYVQERTIFFKDDGNYKTRA*

*EVKFEGDTLVNRIELKGIDFKEDGNILGHKLEYNYNSHNVYIMADKQKNGIKANFKIRHNIESGGVQ*

*LADHYQQNTPIGDGPVLLPDNHYLSTQSKLSKDPNEKRDHMVLKERVTAAGITHGMDELYKGSKS*

*SCSCSESKSTCKSTCSGTETGGSCMSCKCVLS*

SEQ ID NO: 17 (KB1753-mScarlct-GSGGSGG-hRas):
MSSRGYYHGIWVGEEGRLSR*VSKGEAVIKEFMRFKVHMEGSMNGHEFEIEGEGEGRPYEGTQ*

*TAKLKVTKGGPLPFSWDILSPQFMYGSRAFTKHPADIPDYYKQSFPEGFKWERVMNFEDGGAVTV*

*TQDTSLEDGTLIYKVKLRGTNFPPDGPVMQKKTMGWEASTERLYPEDGVLKGDIKMALRLKDGGR*

*YLADFKTTYKAKKPVQMPGAYNVDRKLDITSHNEDYFVVEQYERSEGRHSIGGMDELYKGSGGSG*

*GCMSCKCVLS*

SEQ ID NO: 19 (KB1753-cpmTurquoisc2-GSGGSGG-hRas):
MSSRGYYHGIWVGEEGRLSR*VPVPWPTLVTTLSWGVQCFARYPDHMKQHDFFKSAMPEGYV*

*QERTISFKDDGTYKTRAEVKFEGDTLVNRIELKGIDFKEDGNILGHKLEYNYFSDNVYITADKQKNG*

*IKANFKIRHNVEDGGVQLADHYQQNTPIGDGPVLLPDNHYLSTQSKLSKDPNEKRDHMVLLEFVT*

-continued

AAGITLGMDELYKGGGSGSKGEELFTGVVPILVELDGDVNGHKFSVRGEGEGDATNGKLTLKFICT

TGKLGSGGSGGCMSCKCVLS

SEQ ID NO: 21 (KB1753-HALO-GSGGSGG-hRas):
MSSRGYYHGIWVGEEGRLSRAEIGTGFPFDPHYVEVLGERMHYVDVGPRDGTPVLFLHGNPT

SSYVWRNIIPHVAPTHRCIAPDLIGMGKSDKPDLGYFFDDHVRFMDAFIEALGLEEVVLVIHDWGS

ALGFHWAKRNPERVKGIAFMEFIRPIPTWDEWPEFARETFQAFRTTDVGRKLIIDQNVFIEGTLPM

GVVRPLTEVEMDHYREPFLNPVDREPLWRFPNELPIAGEPANIVALVEEYMDWLHQSPVPKLLFW

GTPGVLIPPAEAARLAKSLPNCKAVDIGPGLNLLQEDNPDLIGSEIARWLSTLEISGGSGGSGG

CMSCKCVLS

SEQ ID NO: 23 (KB1753-SNAP-GSGGSGG-hRas):
MSSRGYYHGIWVGEEGRLSRDKDCEMKRTTLDSPLGKLELSGCEQGLHRIIFLGKGTSAADAV

EVPAPAAVLGGPEPLMQATAWLNAYFHQPEAIEEFPVPALHHPVFQQESFTRQVLWKLLKVVKFG

EVISYSHLAALAGNPAATAAVKTALSGNPVPILIPCHRVVQGDLDVGGYEGGLAVKEWLLAHEGHRL

GKPGLGSGGSGGCMSCKCVLS

SEQ ID NO: 25 (NB80-meGFP-GSGGSGG-hRas):
MSSRGQVQLQESGGGLVQAGGSLRLSCAASGSIFSINTMGWYRQAPGKQRELVAAIHSG

GSTNYANSVKGRFTISRDNAANTVYLQMNSLKPEDTAVYYCNVKDYGAVLYEYDYWGQ

GTQVTVSSRGKGEELFTGVVPILVELDGDVNGHKFSVSGEGEGDATYGKLTLKFICTTGKLPVPW

PTLVTTLTYGVQCFSRYPDHMKRHDFFKSAMPEGYVQERTIFFKDDGNYKTRAEVKFEGDTLVNRI

ELKGIDFKEDGNILGHKLEYNYNSHNVYIMADKQKNGIKANFKIRHNIESGGVQLADHYQQNTPIG

DGPVLLPDNHYLSTQSKLSKDPNEKRDHMVLKERVTAAGITHGMDELYKGSGGSGGCMSCKCVL

S

SEQ ID NO: 27 (β2-adrenergic receptor):
MGQPGNGSAFLLAPNRSHAPDHDVTQQRDEVWVVGMGIVMSLIVLAIVFGNVLVITAIAKFE

RLQTVTNYFITSLACADLVMGLAVVPFGAAHILMKMWTFGNFWCEFWTSIDVLCVTASIETL

CVIAVDRYFAITSPFKYQSLLTKNKARVIILMVWIVSGLTSFLPIQMHWYRATHQEAINCYAN

ETCCDFFTNQAYAIASSIVSFYVPLVIMVFVYSRVFQEAKRQLQKIDKSEGRFHVQNLSQVEQ

DGRTGHGLRRSSKFCLKEHKALKTLGIIMGTFTLCWLPFFIVNIVHVIQDNLIRKEVYILLNWI

GYVNSGFNPLIYCRSPDFRIAFQELLCLRRSSLKAYGNGYSSNGNTGEQSGYHVEQEKENKLL

CEDLPGTEDFVGHQGTVPSDNIDSQGRNCSTNDSLL

SEQ ID NO: 29 (β2AR-SSGSSGTG-meGFP-NB80):
MGQPGNGSAFLLAPNRSHAPDHDVTQQRDEVWVVGMGIVMSLIVLAIVFGNVLVITAIAKFE

RLQTVTNYFITSLACADLVMGLAVVPFGAAHILMKMWTFGNFWCEFWTSIDVLCVTASIETL

CVIAVDRYFAITSPFKYQSLLTKNKARVIILMVWIVSGLTSFLPIQMHWYRATHQEAINCYAN

ETCCDFFTNQAYAIASSIVSFYVPLVIMVFVYSRVFQEAKRQLQKIDKSEGRFHVQNLSQVEQ

DGRTGHGLRRSSKFCLKEHKALKTLGIIMGTFTLCWLPFFIVNIVHVIQDNLIRKEVYILLNWI

GYVNSGFNPLIYCRSPDFRIAFQELLCLRRSSLKAYGNGYSSNGNTGEQSGYHVEQEKENKLL

CEDLPGTEDFVGHQGTVPSDNIDSQGRNCSTNDSLLSSGSSGTGSKGEELFTGVVPILVELDGDV

NGHKFSVSGEGEGDATYGKLTLKFICTTGKLPVPWPTLVTTLTYGVQCFSRYPDHMKRHDFFKSA

MPEGYVQERTIFFKDDGNYKTRAEVKFEGDTLVNRIELKGIDFKEDGNILGHKLEYNYNSHNVYIM

ADKQKNGIKANFKIRHNIESGGVQLADHYQQNTPIGDGPVLLPDNHYLSTQSKLSKDPNEKRDHM

VLKERVTAAGITHGMDELYKGSSRGQVQLQESGGGLVQAGGSLRLSCAASGSIFSINTMGW

YRQAPGKQRELVAAIHSGGSTNYANSVKGRFTISRDNAANTVYLQMNSLKPEDTAVYYC

NVKDYGAVLYEYDYWGQGTQVTVS

SEQ ID NO: 31 (NB33-mcGFP-GSGGSGG-hRas):
MSSRAQVQLVESGGGLVRPGGSRRLSCVDSERTSYPMGWFRRAPGKEREFVASITWSGI

DPTYADSVADRFTISRDVANNTLYLQMNSLKHEDTAVYYCAARAPVGQSSSPYDYDYWG

QGTQVTVSSAAR*GKGEELFTGVVPILVELDGDVNGHKFSVSGEGEGDATYGKLTLKFICTTGKL*

*PVPWPTLVTTLTYGVQCFSRYPDHMKRHDFFKSAMPEGYVQERTIFFKDDGNYKTRAEVKFEGDT*

*LVNRIELKGIDFKEDGNILGHKLEYNYNSHNVYIMADKQKNGIKANFKIRHNIESGGVQLADHYQQ*

*NTPIGDGPVLLPDNHYLSTQSKLSKDPNEKRDHMVLKERVTAAGITHGMDELYK*GSGGSGGCMS

CKCVLS

SEQ ID NO: 33 (μ-opioid receptor):
MDSSAAPTNASNCTDALAYSSCSPAPSPGSWVNLSHLDGNLSDPCGPNRTDLGGRDSLCPPT

GSPSMITAITIMALYSIVCVVGLFGNFLVMYVIVRYTKMKTATNIYIFNLALADALATSTLPFQ

SVNYLMGTWPFGTILCKIVISIDYYNMFTSIFTLCTMSVDRYIAVCHPVKALDFRTPRNAKIIN

VCNWILSSAIGLPVMFMATTKYRQGSIDCTLTFSHPTWYWENLLKICVFIFAFIMPVLIITVCY

GLMILRLKSVRMLSGSKEKDRNLRRITRMVLVVVAVFIVCWTPIHIYVIIKALVTIPETTFQTVS

WHFCIALGYTNSCLNPVLYAFLDENFKRCFREFCIPTSSNIEQQNSTRIRQNTRDHPSTANTVD

RTNHQLENLEAETAPLP

SEQ ID NO: 35 (GAP43-SSGSSGTG-mcGFP-NB33):
MLCCMRRTQOVEKNDEDQN*SSGSSGTG**SKGEELFTGVVPILVELDGDVNGHKFSVSGEGEGDA*

*TYGKLTLKFICTTGKLPVPWPTLVTTLTYGVQCFSRYPDHMKRHDFFKSAMPEGYVQERTIFFKDD*

*GNYKTRAEVKFEGDTLVNRIELKGIDFKEDGNILGHKLEYNYNSHNVYIMADKQKNGIKANFKIRH*

*NIESGGVQLADHYQQNTPIGDGPVLLPDNHYLSTQSKLSKDPNEKRDHMVLKERVFAAGITHGMD*

*ELYK*GSSRAQVQLVESGGGLVRPGGSRRLSCVDSERTSYPMGWFRRAPGKEREFVASIT

WSGIDPTYADSVADRFTISRDVANNTLYLQMNSLKHEDTAVYYCAARAPVGQSSSPYDY

DYWGQGTQVTVSSAARG

SEQ ID NO: 37 (GAP43-SSGSSGTG-mcGFP-GRK2ct):
MLCCMRRTKQVEKNDEDQN*SSGSSGTG**SKGEELFTGVVPILVELDGDVNGHKFSVSGEGEGDA*

*TYGKLTLKFICTTGKLPVPWPTLVTTLTYGVQCFSRYPDHMKRHDFFKSAMPEGYVQERTIFFKDD*

*GNYKTRAEVKFEGDTLVNRIELKGIDFKEDGNILGHKLEYNYNSHNVYIMADKQKNGIKANFKIRH*

*NIESGGVQLADHYQQNTPIGDGPVLLPDNHYLSTQSKLSKDPNEKRDHMVLKERVTAAGITHGMD*

*ELYK*GSSRNFPLVISERWQQEVAETVYEAVNADTDKIEARKRAKNKQLGHEEDYALGRD

CIVHGYMLKLGNPFLTQWQRRYFYLFPNRLEWRGEGESRQSLLTMEQIVSVEETQIKD

KKCILLRIKGGKQFVLQCESDPEFVQWKKELTETFMEAQRLLRRAPKFLNKSRSAVVEL

SKPPLCHRNSNGLGSRG

SEQ ID NO: 39 (GAP43-SSGSSGTG-HALO-GRK2ct):
MLCCMRRTKQVEKNDEDQN*SSGSSGTG**AEIGTGFPFDPHYVEVLGERMHYVDVGPRDGTPVLF*

*LHGNPTSSYVWRNIIPHVAPTHRCIAPDLIGMGKSDKPDLGYFFDDHVRFMDAFIEALGLEEVVLVI*

*HDWGSALGFHWAKRNPERVKGIAFMEFIRPIPTWDEWPEFARETFQAFRTTDVGRKLIIDQNVFIE*

*GTLPMGVVRPLTEVEMDHYREPFLNPVDREPLWRFPNELPIAGEPANIVALVEEYMDWLHQSPVP*

*KLLFWGTPGVLIPPAEAARLAKSLPNCKAVDIGPGLNLLQEDNPDLIGSEIARWLSTLEIS*GGSSRSF

PLVISERYVQQEVAETVYEAVNADTDKIEARKRAKNKQLGHEEDYALGRDCIVHGYMLK

LGNPFLTQWQRRYFYLFPNRLEWRGEGESRQSLLTMEQIVSVEETQIKDKKCILLRIKG

GKQFVLQCESDPEFVQWKKELTETFMEAQRLLRRAPKFLNKSRSAVVELSKPPLCHRNS

NGLGSRG

SEQ ID NO: 41 (GAP43-SSGSSGTG-mcGFP-PRGrh):
MLCCMRRTKQVEKNDEDQNSSGSSGTGSKGEELFFGVVPILVELDGDVNGHKFSVSGEGEGDA

TYGKLTLKFICITGKLPVPWPTLVTTLTYGVQCFSRYPDHMKRHDFFKSAMPEGYVQERTIFFKDD

GNYKIRAEVKFEGDTLVNRIELKGIDFKEDGNILGHKLEYNYNSHNVYIMADKQKNGIKANFKIRH

NIESGGVQLADHYQQNTPIGDGPVLLPDNHYLSTQSKLSKDPNEKRDHMVLKERVFAAGITHGMD

ELYKGSSRELIIGPEEDYDPGYFNNESDIIFQDLEKLKSHPAYLVVFLRYILSQADPGPLLF

YLCSEVYQQTNPKDSRSLGKDIWNIFLEKNAPLRVKIPEMLQAEIDLRLRNNEDPRNVLC

EAQEAVMLEIQEQINDYRSKRTLGLGSLYGENDLLGLDGDPLRERQMAEKQLAALGDI

LSKYEEDRSAPMDFAVNTFMSHAGIRLRESRG

SEQ ID NO: 43 (Gα13(Q226L)):
MADFLPSRSVLSVCFPGCLLTSGEAEQQRKSKEIDKCLSREKTYVKRLVKILLLGAGESGKSTF

LKQMRIIHGQDFDQRAREEFRPTIYSNVIKGMRVLVDAREKLHIPWGDNSNQQHGDKMMSF

DTRAPMAAQGMVETRVFLQYLPAIRALWADSGIQNAYDRRREFQLGESVKYFLDNLDKLGE

PDYIPSQQDILLARRPTKGIHEYDFEIKNVPFKMVDVGGLRSERKRWFECFDSVTSILFLVSSSE

FDQVLMEDRLTNRLTESLNIFETIVNNRVFSNVSIILFLNKTDLLEEKVQIVSIKDYFLEFEGDP

HCLRDVQKFLVECFRNKRRDQQQKPLYHHFTTAINTENIRLVFRDVKDTILHDNLKQLMLQ

SEQ ID NO: 45 (rhotckin-mcGFP-GSGGSGG-hRas):
MSSRGILEDLNMLYIRQMALSLEDTELQRKLDHEIRMRDGACKLLAACSQREQALEAT

KSLLVCNSRILSYMGELQRRKEAQVLEKTSRGKGEELFTGVVPILVELDGDVNGHKFSVSGE

GEGDATYGKLTLKFICTTGKLPVPWPTLVTTLTYGVQCFSRYPDHMKRHDFFKSAMPEGYVQERTI

FFKDDGNYKTRAEVKFEGDTLVNRIELKGIDFKEDGNILGHKLEYNYNSHNVYIMADKQKNGIKAN

FKIRHNIESGGVQLADHYQQNTPIGDGPVLLPDNHYLSTQSKLSKDPNEKRDHMVLKERVTAAGIT

HGMDELYKGSGGSGGCMSCKCVLS

SEQ ID NO: 47 (RhoA(Q63L)):
MAAIRKKLVIVGDGACGKTCLLIVFSKDQFPEVYVPTVFENYVADIEVDGKQVELALWDTAG

LEDYDRLRPLSYPDTDVILMCFSIDSPDSLENIPEKWTPEVKHFCPNVPIILVGNKKDLRNDEH

TRRELAKMKQEPVKPEEGRDMANRIGAFGYMECSAKTKDGVREVFEMATRAALQARRGKK

KSGCLVL

SEQ ID NO: 49 (GAP43-SSGSSGTG-mcGFP-PAK1):
MLCCMRRTKQVEKNDEDQNSSGSSGTGSKGEELFTGVVPILVELDGDVNGHKFSVSGEGEGDA

TYGKLTLKFICTTGKLPVPWPTLVTTLTYGVQCFSRYPDHMKRHDFFKSAMPEGYVQERTIFFKDD

GNYKTRAEVKFEGDTLVNRIELKGIDFKEDGNILGHKLEYNYNSHNVYIMADKQKNGIKANFKIRH

NIESGGVQLADHYQQNTPIGDGPVLLPDNHYLSTQSKLSKDPNEKRDHMVLKERVTAAGITHGMD

SRNKKKEKERPEISLPSDFEHTIHVGFDAVTGEFTGMPEQWARLLQTSNITKSEQKKNP

QAVLDVLEFYNSKKTSNSQKYMSFTDKSPSRG

SEQ ID NO: 51 (Rac1(Q61L)):
MGYPYDVPDYAQAIKCVVVGDGAVGKTCLLISYTTNAFPGEYIPTVFDNYSANVMVDGKPV

NLGLWDTAGLEDYDRLRPLSYPQTDVFLICFSLVSPASFENVRAKWYPEVRHHCPNTPIILVG

TKLDLRDDKDTIEKLKEKKLTPITYPQGLAMAKEIGAVKYLECSALTQRGLKTVFDEAIRAVL

CPPPVKKRKRKCLLL

-continued

SEQ ID NO: 53 (GAP43-SSGSSGTG-mcGFP-IRSI):
MLCCMRRTKQVEKNDEDQNSSGSSGTGSKGEELFTGVVPILVELDGDVNGHKFSVSGEGEGDA

TYGKLTLKFICTTGKLPVPWPTLVTTLTYGVQCFSRYPDHMKRHDFFKSAMPEGYVQERTIFFKDD

GNYKTRAEVKFEGDTLVNRIELKGIDFKEDGNILGHKLEYNYNSHNVYIMADKQKNGIKANFKIRH

NIESGGVQLADHYQQNTPIGDGPVLLPDNHYLSTQSKLSKDPNEKRDHMVLKERVTAAGITHGMD

ELYKDIMCPPDTDGFSDVRKVGYLRKPKSMHKRFFVLRAASEAGGPARLEYYENEKKW

RHKSSAPKRSIPLESCFNINKRADSKNKHLVALYTRDEHFAIAADSEAEQDSWYQALLQL

HNRAKAHHDGAGGGCGGSCSGSSGVGEAGEDLSYDTGPGPAFKEVWQVILKPKGLGQ

TKNLIGIYRLCLTSKTISFVKLNSEAAAVVLQLMNIRRCGHSENFFFIEVGRSAVTGPGEF

WMQVDDSVVAQNMHETILEAMRAMSDEFRPRTKSQSSSSCSNPISVPLRRHHLNNPPPS

QVGLTRRSRTESITATSPASMVGGKPGSFRVRASSDGEGTMSRPASVDGSPVSPSTNRTH

AHRHRGSSRLHPPLNHSRSIPMPSSRCSPSATSPVSLSSSSTSGHGSTSDCLFPRRSSASVSG

SPSDGGFISSDEYGSSPCDFRSSFRSVTPDSLGHTPPARGEEELSNYICMGGKGASTLTAP

NGHYILSRGGNGHRYIPGATMGTSPALTGDEAAGAADLDNRFRKRTHSAGTSPTISHQK

TPSQSSVVSIEEYTEMMPAAYPPGGGSGGRLPGYRHSAFVPTHSYPEEGLEMHHLERRG

GHHRPDSSNLHTDDGYMPMSPGVAPVPSNRKGNGDYMPMSPKSVSAPQQIINPIRRHPQ

RVDPNGYMMMSPSGSCSPDIGGGSCSSSSISAAPSGSSYGKPWTNGVGGHHTHALPHAK

PPVESGGGKLLPCTGDYMNMSPVGDSNTSSPSECYYGPEDPQHKPVLSYYSLPRSFKHT

QRPGEPEEGARHQHLRLSSSSGRLRYTATAEDSSSSTSSDSLGGGYCGARPESSVTHPHH

HALQPHLPRKVDTAAQTNSRLARPTRLSLGDPKASTLPRVREQQOQQOQOQQSSLHPP

EPKSPGEYVNIEFGSGQPGYLAGPATSRSSPSVRCLPQLHPAPREETGSEEYMNMDLGPG

RRATWQESGGVELGRVGPAPPGAASICRPTRSVPNSRGDYMTMQIGCPRQSYVDTSPVA

PVSYADMRTGIAAEKVSLPRTTGAAPPPSSTASASASVTPQGAAEQAAHSSLLGGPQGPG

GMSAFTRVNLSPNHNQSAKVIRADTQGCRRRHSSETFSAPTRAANTVSFGAGAAGGGSG

GGSEDVKRHSSASFENVWLRPGDLGGASKESAPGCGAAGGLEKSLNYIDLDLVKDVKQ

HPQDCPSQQQSLPPPPPHQPLGSNEGSSPRRSSEDLSTYASINFQKQPEDRQ

SEQ ID NO: 55 (insulin receptor IR1-His6):
MCCPGCCATGGRRGAAAAPLLVAVAALLLGAAGHLYPGEVCPGMDIRNNLTRLHELENCSV

IEGHLQILLMFKTRPEDFRDLSFPKLIMITDYLLLFRVYGLESLKDLFPNLTVIRGSRLFFNYAL

VIFEMVHLKELGLYNLMNITRGSVRIEKNNELCYLATIDWSRILDSVEDNYIVLNKDDNEECG

DICPGTAKGKTNCPATVINGQFVERCWTHSHCQKVCPTICKSHGCTAEGLCCHSECLGNCSQP

DDPTKCVACRNFYLDGRCVETCPPPYYHFQDWRCVNFSFCQDLHHKCKNSRRQGCHQYVIH

NNKCIPECPSGYTMNSSNLLCTPCLGPCPKVCHLLEGEKTIDSVTSAQELRGCTVINGSLIINIR

GGNNLAAELEANLGLIEEISGYLKIRRSYALVSLSFFRKLRLIRGETLEIGNYSFYALDNQNLRQ

LWDWSKHNLTITQGKLFFHYNPKLCLSEIHKMEEVSGTKGRQERNDIALKTNGDQASCENEL

LKFSYIRTSFDKILLRWEPYWPPDFRDLLGFMLFYKEAPYQNVTEFDGQDACGSNSWTVVDI

DPPLRSNDPKSQNHPGWLMRGLKPWTQYAIFVKTLVTFSDERRTYGAKSDIIYVQTDATNPS

VPLDPISVSNSSSQIILKWKPPSDPNGNITHYLVFWERQAEDSELFELDYCLKGLKLPSRTWSPP

FESEDSQKHNQSEYEDSAGECCSCPKTDSQILKELEESSFRKTFEDYLHNVVFVPRPSRKRRSL

GDVGNVTVAVPTVAAFPNTSSTSVPTSPEEHRPFEKVVNKESLVISGLRHFTGYRIELQACNQ

DTPEERCSVAAYVSARTMPEAKADDIVGPVTHEIFENNVVHLMWQEPKEPNGLIVLYEVSYR

-continued

RYGDEELHLCVSRKHFALERGCRLRGLSPGNYSVRIRATSLAGNGSWTEPTYFYVTDYLDVP

SNIAKIIIGPLIFVFLFSVVIGSIYLFLRKRQPDGPLGPLYASSNPEYLSASDVFPCSVYVPDEWE

VSREKITLLRELGQGSFGMVYEGNARDIIKGEAETRVAVKTVNESASLRERIEFLNEASVMKG

FTCHHVVRLLGVVSKGQPTLVVMELMAHGDLKSYLRSLRPEAENNPGRPPPTLQEMIQMAA

EIADGMAYLNAKKFVHRDLAARNCMVAHDFTVKIGDFGMTRDIYETDYYRKGGKGLLPVR

WMAPESLKDGVFTTSSDMWSFGVVLWEITSLAEQPYQGLSNEQVLKFVMDGGYLDQPDNCP

ERVTDLMRMCWQFNPKMRPTFLEIVNLLKDDLHPSFPEVSFFHSEENKAPESEELEMEFEDME

NVPLDRSSHCQREEAGGRDGGSSLGFKRSYEEHIPYTHMNGGKKNGRILTLPRSNPSGGGGS

HHHHHHHHHH

SEQ ID NO: 57 (Gαi1):
MGCTLSAEDKAAVERSKMIDRNLREDGEKAAREVKLLLLGAGESGKSTIVKQMKIIHEAGYS

EEECKQYKAVVYSNTIQSIIAIIRAMGRLKIDFGDSARADDARQLFVLAGAAEEGFMTAELAG

VIKRLWKDSGVQACFNRSREYQLNDSAAYYLNDLDRIAQPNYIPTQQDVLRTRVKTTGIVET

HFTFKDLHFKMFDVGGQRSERKKWIHCFEGVTAIIFCVALSDYDLVLAEDEEMNRMHESMK

LFDSICNNKWFTDTSIILFLNKKDLFEEKIKKSPLTICYPEYAGSNTYEEAAAYIQCQFEDLNKR

KDTKEIYTHFTCATDTKNVQFVFDAVTDVIIKNNLKDCGLF

SEQ ID NO: 59 (Gβ1):
MSELDQLRQEAEQLKNQIRDARKACADATLSQITNNIDPVGRIQMRTRRTLRGHLAKIYAMH

WGTDSRLLVSASQDGKLIIWDSYTTNKVHAIPLRSSWVMTCAYAPSGNYVACGGLDNICSIY

NLKTREGNVRVSRELAGHTGYLSCCRFLDDNQIVTSSGDTTCALWDIETGQQTTTFTGHTGD

VMSLSLAPDTRLFVSGACDASAKLWDVREGMCRQTFTGHESDINAICFFPNGNAFATGSDDA

TCRLFDLRADQELMTYSHDNIICGITSVSFSKSGRLLLAGYDDFNCNVWDALKADRAGVLAG

HDNRVSCLGVTDDGMAVATGSWDSFLKIWN

SEQ ID NO: 61 (Gγ2):
MASNNTASIAQARKLVEQLKMEANIDRIKVSKAAADLMAYCEAHAKEDPLLTPVPASENPFR

EKKFFCAIL

SEQ ID NO: 63 (α2-adrenergic receptor):
MGSLQPDAGNSSWNGTEAPGGGTRATPYSLQVTLTLVCLAGLLMLFTVFGNVLVIIAVFTSR

ALKAPQNLFLVSLASADILVATLVIPFSLANEVMGYWYFGKVWCEIYLALDVLFCTSSIVHLC

AISLDRYWSITQAIYNLKRTPRRIKAIIITVWVISAVISFPPLISIEKKGGGGGPGQPAEPRCEINDQ

KWYVISSCIGSFFAPCLIMILVYVRIYQIAKRRTRVPPSRRGPDAVAAPPGGTERRPNGLGPERS

AGPGGAEAEPLPTQLNGAPGEPAPAGPRDTDALDLEESSSSDHAERPPGPRRPERGPRGKGKA

RASQVKPGDSLPRRGPGATGIGTPAAGPGEERVGAAKASRWRGRQNREKRFTFVLAVVIGVF

VVCWFPFFFTYTLTAVGCSVPRTLFKFFFWFGYCNSSLNPVIYTIFNHDFRRAFKKILCRGDRK

RIV

SEQ ID NO: 66 (NB9_20-mcGFP-GSGGSGG-hRas)
MSSRQVQLQESGGGLVQPEGSLTLACDTSGFTMNYYAIAWFRQAPEKEREGLATISSID

GRTYYADSVKGRFTISRDSAKNMVYLQMNNLRPEDTAVYYCSAGPDYSDYGDESEYWG

QGTQVTVSSSR*GKGEELFTGVVPILVELDGDVNGHKFSVSGEGEGDATYGKLTLKFICTTGKLPV*

*PWPTLVTTLTYGVQCFSRYPDHMKRHDFFKSAMPEGYVQERTIFFKDDGNYKTRAEVKFEGDTLV*

*NRIELKGIDFKEDGNILGHKLEYNYNSHNVYIMADKQKNGIKANFKIRHNIESGGVQLADHYQQNT*

*PIGDGPVLLPDNHYLSTQSKLSKDPNEKRDHMVLKERVTAAGITHGMDELYK*GSGGSGGCMSCK

CVLS

-continued

SEQ ID NO: 68 (muscarinic acetylcholine receptor protein sequence):
MNNSTNSSNNSLALTSPYKTFEVVFIVLVAGSLSLVTIIGNILVMVSIKVNRHLQTVNNYFLFS

LACADLIIGVFSMNLYTLYTVIGYWPLGPVVCDLWLALDYVVSNASVMNLLIISFDRYFCVTK

PLTYPVKRTTKMAGMMIAAAWVLSFILWAPAILFWQFIVGVRTVEDGECYIQFFSNAAVTFG

TAIAAFYLPVIIMTVLYWHISRASKSRIKKDKKEPVANQDPVSPSLVQGRIVKPNNNNMPSSD

DGLEHNKIQNGKAPRDPVTENCVQGEEKESSNDSTSVSAVASNMRDDEITQDENTVSTSLGH

SKDENSKQTCIRIGTKTPKSDSCTPTNTTVEVVGSSGQNGDEKQNIVARKIVKMTKQPAKKKP

PPSREKKVTRTILAILLAFIITWAPYNVMVLIYPFCAPCIPNTVWTIGYWLCYINSTINPACYAL

CNATFKKTFKHLLMCHYKNIGATR

SEQ ID NO: 70 (NB32-meGFP-GSGGSGG-hRas):
MSSRQVQLQESGGGLVQAGGSLRLSCVVSGFFFDTVTMAWYRRAPGKHRELVASATAG

GTTTYADSVKDRFTISRDNAKNTVYLQMNSLKPEDTAVYYCNTFVRSLSWGQGTQVTV

SSSR_GKGEELFTGVVPILVELDGDVNGHKFSVSGEGEGDATYGKLTLKFICTTGKLPVPWPTLVTT_

_LTYGVQCFSRYPDHMKRHDFFKSAMPEGYVQERTIFFKDDGNYKTRAEVKFEGDTLVNRIELKGI_

_DFKEDGNILGHKLEYNYNSHNVYIMADKQKNGIKANFKIRHNIESGGVQLADHYQQNTPIGDGPVL_

LPDNHYLSTQSKLSKDPNEKRDHMVLKERVTAAGITHGMDELYK<u>GSGGSGG</u>CMSCKCVLS

SEQ ID NO: 72 (β-arrestin 2):
MGEKPGTRVFKKSSPNCKLTVYLGKRDFVDHLDKVDPVDGVVLVDPDYLKDRKVFVTLTCA

FRYGREDLDVLGLSFRKDLFIATYQAFPPMPNPPRPPTRLQDRLLKKLGQHAHPFFFTIPQNLP

CSVTLQPGPEDTGKACGVDFEIRAFCAKSIEEKSHKRNSVRLIIRKVQFAPETPGPQPSAETTRH

FLMSDRRSLHLEASLDKELYYHGEPLNVNVHVTNNSAKTVKKIRVSVRQYADICLFSTAQYK

CPVAQLEQDDQVSPSSTFCKVYTITPLLSDNREKRGLALDGQLKHEDTNLASSTIVKEGANKE

VLGILVSYRVKVKLVVSRGGDVSVELPFVLMHPKPHDHITLPRPQSAPREIDIPVDTNLIEFDT

NYATDDDIVFEDFARLRLKGMKDDDCDDQFCRARDPPVAT

SEQ ID NO: 74 (vasopressin receptor):
MILVSTTSAVPGALSSPSSPSNSSQEELLDDRDPLLVRAELALLSTIFVAVALSNGLVLGALIRR

GRRGRWAPMHVFISHLCLADLAVALFQVLPQLAWDATDRFHGPDALCRAVKYLQMVGMY

ASSYMILAMTLDRHRAICRPMLAYRHGGGARWNRPVLVAWAFSLLLSLPQLFIFAQRDVGN

GSGVFDCWARFAEPWGLRAYVTWIALMVFVAPALGIAACQVLIFREIHASLVPGPSERAGRR

RRGHRTGSPSEGAHVSAAMAKTVRMTLVIVIVYVLCWAPFFLVQLWAAWDPEAPLERPPFV

LLMLLASLNSCTNPWIYASFSSSVSSELRSLLCCAQRHTTHSLGPQDESCATASSSLMKDTPS

The nucleic acid sequences mentioned in the Examples are contained only in the Sequence Listing which forms part of the present patent application.

INDUSTRIAL APPLICABILITY

The invention can be used for observations of molecular processes of cell signaling. Since many such processes are of pharmacological importance, the invention can be used for elucidating the mode of action of existing pharmaceutical drugs and for discovering novel pharmacological treatments of diseases.

---

What is claimed is:

1. A method of detecting a presence or an absence of a target membrane-associated molecule in cells, said method comprising the following steps:

providing a protein-based probe;

contacting the probe with a reference sample comprising cells that do not contain the target membrane-associated molecule;

contacting the probe with a test sample comprising cells in which the presence or absence of the target membrane-associated molecule is to be detected;

observing the cells in the reference sample and in the test sample by means of polarization microscopy;

quantifying the fluorescence polarization exhibited by the probes in each of the reference sample and test sample;

determining whether the fluorescence polarization exhibited by the probes differs between the two samples; wherein when the fluorescence polarization exhibited by the probes differ, it is determined that the target membrane-associated molecule is present in the cells of the test sample; and when the fluorescence polarization exhibited by the probes do not differ, it is determined that the target membrane-associated molecule is absent from the cells of the test sample; and wherein the protein-based probe comprises:

a) an anchoring moiety comprising at least one lipidated peptide and/or at least one transmembrane a-helical peptide, b) a peptide linker moiety having a length of at least 5 amino acids, wherein at least 50% of the amino acids forming the peptide linker are selected from glycine, serine, and threonine, c) a fluorescent moiety, and d) an affinity binding moiety capable of binding the target membrane-associated molecule, wherein the moieties are arranged in the order a-b-c-d or d-c-b-a in the direction from the N-terminus to the C-terminus; and wherein the step of providing a protein-based probe is performed by introducing into the cells a DNA that encodes the protein-based probe of invention, and by causing the cells to produce the protein-based probe.

2. The method according to claim 1, wherein the moieties are arranged in the order d-c-b-a in the direction from the N-terminus to the C-terminus.

3. The method according to claim 1, wherein the peptide linker moiety contains between 5 and 30 amino acids, of which at least 50% are serine and/or glycine and/or threonine, and the remaining amino acids are lysine and/or arginine and/or glutamate.

4. The method according to claim 3, wherein at least 70% of the amino acids in the peptide linker moiety are serine and/or glycine and/or threonine.

5. The method according to claim 1, wherein the fluorescent moiety is a fluorescent protein, or a protein configured to become fluorescent when covalently or non-covalently bound to a fluorescent or non-fluorescent ligand, wherein the fluorescent moiety is selected from the group consisting of fluorogenic protein tag based on haloalkane dehalogenase, a fluorogenic protein tag based on alkylguanine-DNA alkyl-transferase, bacteriophytochrome-based near-infrared fluorescent protein 2.0(IFP2.0), allophycocyanin-derived small ultra-red fluorescent protein (smURFP), fatty acid binding protein UnaG, photoactive yellow protein and circularly permuted versions thereof.

6. The method according to claim 1, wherein the polarization microscopy is selected from excitation polarization resolved fluorescence microscopy and fluorescence polarization resolved fluorescence microscopy.

7. The method of detecting active or inactive form of a target membrane-associated molecule in cells, said method comprising the following steps:

providing a protein-based probe;

contacting the probe with a reference sample comprising cells that contain the target membrane-associated molecule either in active form or in inactive form;

contacting the probe with a test sample comprising cells in which the active or inactive form of the target membrane-associated molecule is to be detected;

observing the cells in the reference sample and in the test sample by means of polarization microscopy;

quantifying the fluorescence polarization exhibited by the probes in each of the reference sample and test sample; and determining whether the fluorescence polarization exhibited by the probes differs between the two samples; wherein when the fluorescence polarization exhibited by the probes differ, it is determined that the target membrane-associated molecule is present in the cells of the test sample in a different form than in the reference sample; and when the fluorescence polarization exhibited by the probes do not differ, it is determined that the target membrane-associated molecule is present in the cells of the test sample in the same form as in the reference sample;

wherein the protein-based probe comprises:

a) an anchoring moiety comprising at least one lipidated peptide and/or at least one transmembrane α-helical peptide, b) a peptide linker moiety having a length of at least 5 amino acids, wherein at least 50% of the amino acids forming the peptide linker are selected from glycine, serine, and threonine, c) a fluorescent moiety, and d) an affinity binding moiety capable of binding the target membrane-associated molecule, wherein the moieties are arranged in the order a-b-c-d or d-c-b-a in the direction from the N-terminus to the C-terminus; and wherein the step of providing a protein-based probe is performed by introducing into the cells a DNA that encodes the protein-based probe, and by causing the cells to produce the protein-based probe.

8. The method according to claim 7, wherein the polarization microscopy is selected from excitation polarization resolved fluorescence microscopy and fluorescence polarization resolved fluorescence microscopy.

9. A method of detecting activation or inactivation of a target membrane-associated molecule in cells, said method comprising the following steps:

providing a protein-based probe;

contacting the probe with a test sample comprising cells in which the active or inactive form of the target membrane-associated molecule is to be detected;

observing the cells in the test sample by means of polarization microscopy in at least two time points;

quantifying the fluorescence polarization exhibited by the probe in each time point;

determining whether the fluorescence polarization exhibited by the probe differs between the time points; wherein when the fluorescence polarization exhibited by the probe differ between the time points, it is determined that the target membrane-associated molecule in the cells of the test sample has undergone activation or inactivation; and when the fluorescence polarization exhibited by the probes do not differ, it is determined that the target membrane-associated molecule in the cells of the test sample has not undergone activation or inactivation; and wherein the protein-based probe comprises:

a) an anchoring moiety comprising at least one lipidated peptide and/or at least one transmembrane a-helical peptide, b) a peptide linker moiety having a length of at least 5 amino acids, wherein at least 50% of the amino acids forming the peptide linker are selected from glycine, serine, and threonine, c) a fluorescent moiety, and d) an affinity binding moiety capable of binding the target membrane-associated molecule, wherein the moieties are arranged in the order a-b-c-d or d-c-b-a in the direction from the N-terminus to the C-terminus; and wherein the step of providing a protein-based probe is performed by introducing into the cells a DNA that encodes the protein-based probe, and by causing the cells to produce the protein-based probe.

10. The method according to claim 9, wherein the polarization microscopy is selected from excitation polarization resolved fluorescence microscopy and fluorescence polarization resolved fluorescence microscopy.

11. The method according to claim 3, wherein at least 85% of the amino acids in the peptide linker moiety are serine and/or glycine and/or threonine.

12. The method according to claim 7, wherein the moieties are arranged in the order d-c-b-a in the direction from the N-terminus to the C-terminus.

13. The method according to claim 7, wherein the peptide linker moiety contains between 5 and 30 amino acids, of which at least 50% are serine and/or glycine and/or threonine, and the remaining amino acids are lysine and/or arginine and/or glutamate.

14. The method according to claim 13, wherein at least 70% of the amino acids in the peptide linker moiety are serine and/or glycine and/or threonine.

15. The method according to claim 13, wherein at least 85% of the amino acids in the peptide linker moiety are serine and/or glycine and/or threonine.

16. The method according to claim 7, wherein the fluorescent moiety is a fluorescent protein, or a protein configured to become fluorescent when covalently or non-covalently bound to a fluorescent or non-fluorescent ligand, wherein the fluorescent moiety is selected from the group consisting of a fluorogenic protein tag based on haloalkane dehalogenase, a fluorogenic protein tag based on alkylguanine-DNA alkyltransferase, bacteriophytochrome-based near-infrared fluorescent protein 2.0 (IFP2.0), allophycocyanin-derived small ultra-red fluorescent protein (smURFP), fatty acid binding protein UnaG, photoactive yellow protein and circularly permuted versions thereof.

17. The method according to claim 9, wherein the moieties are arranged in the order d-c-b-a in the direction from the N-terminus to the C-terminus.

18. The method according to claim 9, wherein the peptide linker moiety contains between 5 and 30 amino acids, of which at least 50% are serine and/or glycine and/or threonine, and the remaining amino acids are lysine and/or arginine and/or glutamate.

19. The method according to claim 18, wherein at least 70% of the amino acids in the peptide linker moiety are serine and/or glycine and/or threonine.

20. The method according to claim 18, wherein at least 85% of the amino acids in the peptide linker moiety are serine and/or glycine and/or threonine.

21. The method according to claim 9, wherein the fluorescent moiety is a fluorescent protein, or a protein configured to become fluorescent when covalently or non-covalently bound to a fluorescent or non-fluorescent ligand, wherein the fluorescent moiety is selected from the group consisting of a fluorogenic protein tag based on haloalkane dehalogenase, a fluorogenic protein tag based on alkylguanine-DNA alkyltransferase, bacteriophytochrome-based near-infrared fluorescent protein 2.0 (IFP2.0), allophycocyanin-derived small ultra-red fluorescent protein (smURFP), fatty acid binding protein UnaG, photoactive yellow protein and circularly permuted versions thereof.

\* \* \* \* \*